United States Patent [19]
Frank et al.

[11] Patent Number: 5,932,470
[45] Date of Patent: Aug. 3, 1999

[54] ECTOPARASITE SALIVA PROTEINS AND APPARATUS TO COLLECT SUCH PROTEINS

[75] Inventors: Glenn R. Frank, Wellington; Shirley Wu Hunter; Lynda Wallenfels, both of Ft. Collins, all of Colo.

[73] Assignee: Heska Corporation, Ft. Collins, Colo.

[21] Appl. No.: 09/005,069

[22] Filed: Jan. 8, 1998

Related U.S. Application Data

[60] Division of application No. 08/630,822, Apr. 10, 1996, Pat. No. 5,840,695, which is a continuation-in-part of application No. PCT/US95/13200, Oct. 6, 1995, which is a continuation-in-part of application No. 08/487,001, Jun. 7, 1995, Pat. No. 5,795,862, and a continuation-in-part of application No. 08/487,608, Jun. 7, 1995, which is a continuation-in-part of application No. 08/319,590, Oct. 7, 1994, Pat. No. 5,646,115.

[51] Int. Cl.[6] .............................. C12N 1/20; C12N 1/14; C12N 15/00; C07H 21/02
[52] U.S. Cl. ................................ 435/252.3; 435/254.11; 435/320.1; 435/325; 536/23.1; 935/22
[58] Field of Search .......................... 435/252.3, 254.11, 435/325, 320.1; 536/23.1; 935/22

[56] References Cited

U.S. PATENT DOCUMENTS 5,356,622  10/1994  Heath et al. .......................... 424/265.1

FOREIGN PATENT DOCUMENTS

WO 93/18788  9/1993  WIPO .

OTHER PUBLICATIONS

Baker et al., 1975, *J. Small Anim. Pract.,* 16 (5):317–327.
Benjamin et al., 1963, *Exp. Parasitol.* 13:143–154.
Benjamin et al., 1960, *Exp. Parasitol.,* 10:214–222.
Greene et al., 1993, *Parasite Immunol.,* 15:69–74.
Greene et al., 1993, *Vet. Immunol. & Immunopathol.,* 37(1):15–23.
Halliwell et al., 1987, *Vet. Immunol. Immunopathol.,* 15:203–213.
Halliwell et al., 1985, *Vet. Immunol. & Immunopath,* 8(3):215–23.
Keep et al., 1967, *Austral. Vet. J.,* 43:425–426.
Kristensen et al., 1978, *Nord. Vet.–Med.,* 30:414–423.
Kunkle et al., 1985, *J. Amer. Vet. Medical Assn.,* 186(7):677–80.
McKeon et al., 1994, *Int. J. Parasitol.,* 24(2):259–63.
Michaeli et al., 1966, *J. Immunol.,* 97(3):402–406.
Michaeli et al., 1965, *J. Immunol.,* 95(1):162–170.
Van Winkle, 1981, *J. Amer. Anim. Hosp. Assoc.,* 17:343–354.
Wade et al., 1988, *J. Med. Entomol.,* 25(3):186–189.
Young et al., 1963, *Exp. Parasitol.,* 13:155–166.

*Primary Examiner*—Robert A. Wax
*Assistant Examiner*—Einar Stole
*Attorney, Agent, or Firm*—Sheridan Ross P.C.

[57] ABSTRACT

The present invention is directed to a novel product and method for isolating ectoparasite saliva proteins, and a novel product and method for detecting and/or treating allergic dermatitis in an animal. The present invention includes a saliva protein collection apparatus capable of collecting ectoparasite saliva proteins substantially free of contaminating material. The present invention also relates to ectoparasite saliva proteins, nucleic acid molecules having sequences that encode such proteins, and antibodies raised against such proteins. The present invention also includes methods to obtain such proteins and to use such proteins to identify animals susceptible to or having allergic dermatitis. The present invention also includes therapeutic compositions comprising such proteins and their use to treat animals susceptible to or having allergic dermatitis.

9 Claims, 16 Drawing Sheets

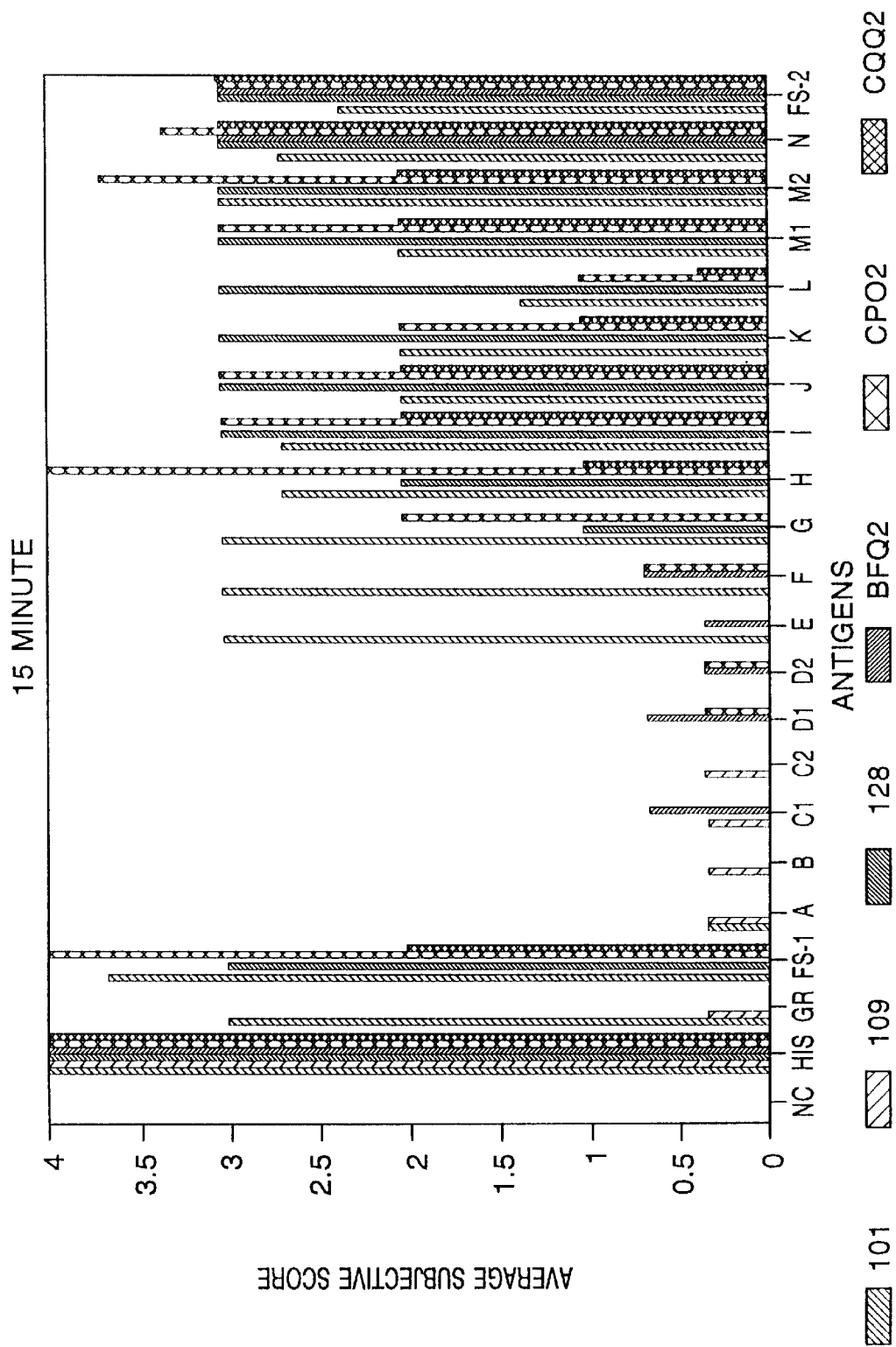

FRACTIONATED FLEA SALIVA ELISA WITH PURIFIED ALLERGIC DOG IGE

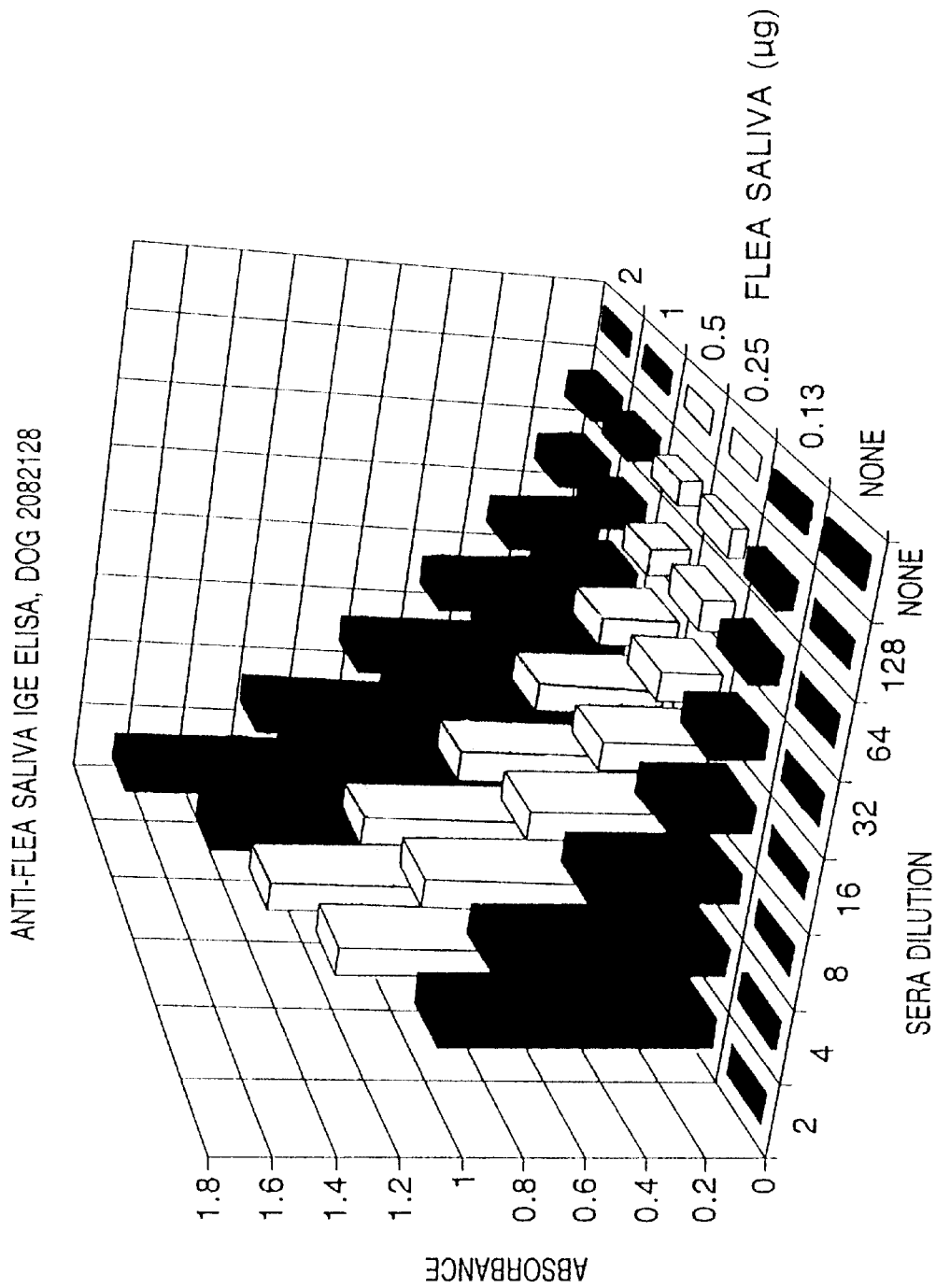

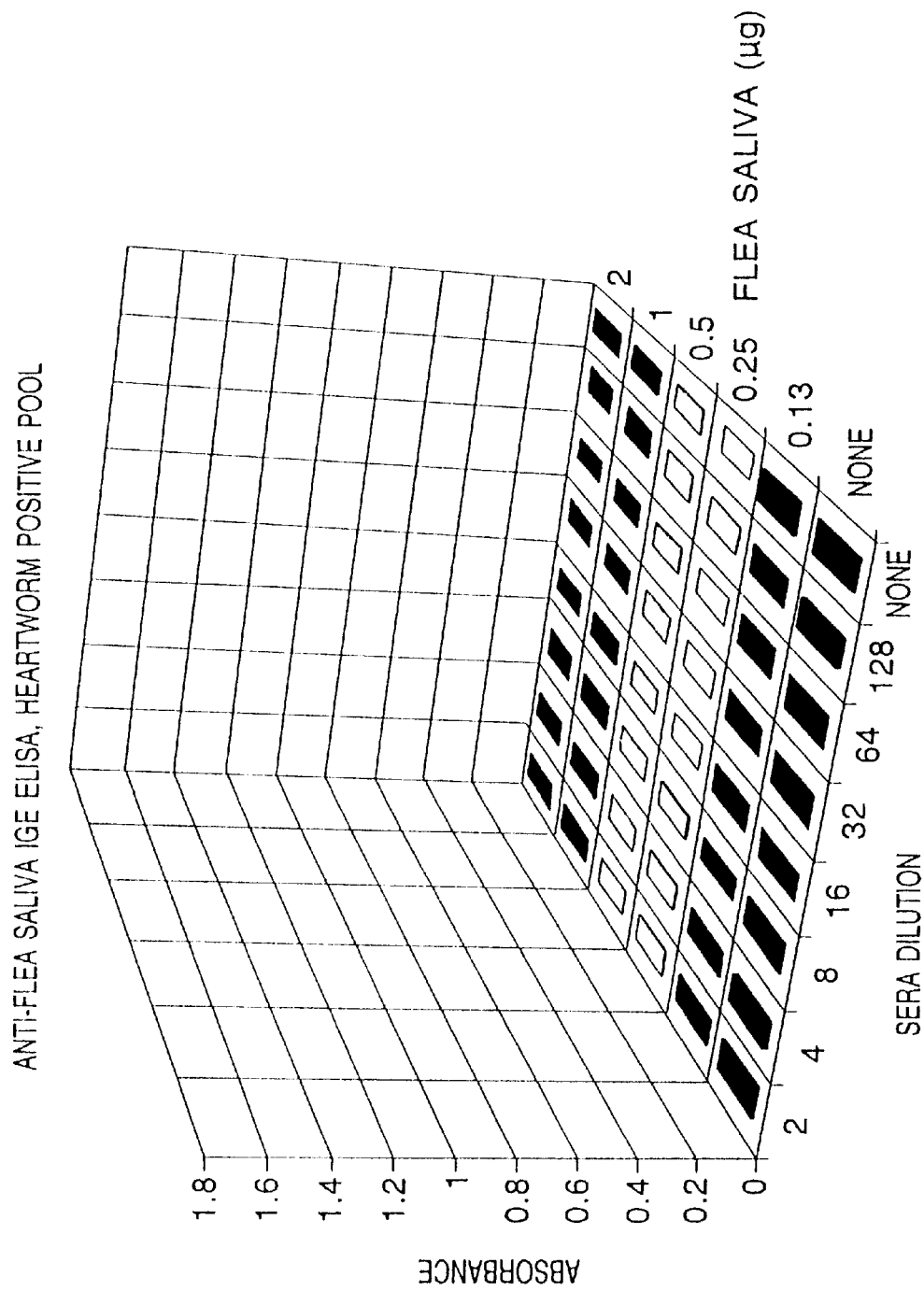

ECTOPARASITE SALIVA PROTEINS AND APPARATUS TO COLLECT SUCH PROTEINS

CROSS-REFERENCE TO RELATED APPLICATIONS

This application is a divisional application of U.S. patent application No. 08/630,822, filed Apr. 10, 1996, now U.S. Pat. No. 5,840,695, which is a continuation-in-part of PCT International Application No. PCT/US95/13200, filed Oct. 6, 1995, which is a continuation-in-part application of U.S. patent application Ser. No. 08/487,001, filed Jun. 7, 1995, now U.S. Pat. No. 5,795,862, and of U.S. patent application Ser. No. 08/487,608, filed Jun. 7, 1995, which are continuation-in-part applications of U.S. patent application Ser. No. 08/319,590, filed Oct. 7, 1994, now U.S. Pat. No. 5,646,115. Each of the patent applications referred to in this section is incorporated by reference herein in its entirety.

FIELD OF THE INVENTION

The present invention relates to a novel product and method for isolating ectoparasite saliva proteins, and a novel product and method for detecting and/or treating allergic dermatitis in an animal.

BACKGROUND OF THE INVENTION

Bites from ectoparasites, in particular fleas, can cause a hypersensitive response in animals. In particular, hypersensitive responses to fleabites is manifested in a disease called flea allergy dermatitis (FAD). Hypersensitivity refers to a state of altered reactivity in which an animal, having been previously exposed to a compound, exhibits an allergic response to the compound upon subsequent exposures. Hypersensitive responses include immediate and delayed-type hypersensitivity, and in particular Type I, Type II, Type III and Type IV hypersensitivities (described in detail in Janeway et al., *Immunobiology*, Garland Publishing, New York, 1994, which is incorporated in its entirety by this reference.).

Foreign compounds that induce symptoms of immediate and/or delayed hypersensitivity are herein referred to as allergens. The term "allergen" primarily refers to foreign compounds capable of causing an allergic response. The term can be used interchangeably with the term "antigen," especially with respect to a foreign compound capable of inducing symptoms of immediate and/or delayed hypersensitivity. Factors that influence an animal's susceptibility to an allergen can include a genetic component and/or environmental exposure to an allergen. Animals can be de-sensitized to an allergen by repeated injections of the allergen to which an animal is hypersensitive.

FAD can have manifestations of both immediate and delayed-type hypersensitivity (described in detail in Janeway et al., ibid.). Effective treatment of FAD has been difficult if not impossible to achieve. FAD afflicts about 15% of cats and dogs in flea endemic areas and the frequency is increasing each year. In a geographical area, effective flea control requires treatment of all animals. One treatment investigators have proposed includes desensitization of animals using flea allergens. However, reliable, defined preparations of flea allergens are needed for such treatments.

Until the discovery of the novel formulations of the present invention, flea allergens responsible for FAD had not been clearly defined. Whole flea antigen preparations have been used to diagnose and desensitize animals with FAD (Benjamini et al., 1960, pp. 214–222, *Experimental Parasitology*, Vol. 10; Keep et al., 1967, pp. 425–426, *Australian Veterinary Journal*, Vol. 43; Kristensen et al., 1978, pp. 414–423, *Nord. Vet-Med*, Vol. 30; Van Winkle, 1981, pp. 343–354, *J. Amer. Animal Hosp. Assoc.*, Vol. 17; Haliwell et al., 1987, pp. 203–213, *Veterinary Immunology and Immunopathology*, Vol. 15; Greene et al., 1993, pp. 69–74, *Parasite Immunology*, Vol. 15); PCT Publication No. WO 93/18788 by Opdebeeck et al.; and Van Winkle, pp. 343–354, 1981, *J. Am. Anim. Hosp. Assoc.*, vol. 32. Available commercial whole flea extracts, however, are unpredictable and, therefore, have limited usefulness.

Prior investigators have suggested that products contained in flea saliva might be involved in FAD and have also suggested methods to isolate such products: Benjamini et al., 1963, pp. 143–154, *Experimental Parasitology*, Vol. 13; Young et al., 1963, pp. 155–166, *Experimental Parasitology* 13, Vol. 13; Michaeli et al., 1965, pp. 162–170, *J. Immunol.*, Vol. 95; and Michaeli et al., 1996, pp. 402–406, *J. Immunol.*, Vol. 97. These investigators, however, have characterized the allergenic factors of flea saliva as being haptens having molecular weights of less than 6 kilodaltons (kD). That they are not proteins is also supported by the finding that they are not susceptible to degradation when exposed to strong acids (e.g., 6 N hydrochloric acid) or heat. Some of the particular low molecular weight allergenic factors have also been characterized as being a highly fluorescent aromatic fraction (Young et al., ibid.). In addition, studies by such investigators have indicated that in order to be allergenic, such factors need to be associated with adjuvants and/or carriers, such as collagen or portions of the membrane used to collect the oral secretions. Moreover, the methods described to collect flea saliva factors were difficult and unpredictable. Furthermore the factors isolated by these methods were typically contaminated with material from the fleas, their culture medium or the skin-based membranes used to allow the fleas to feed.

Thus, there remains a need to more clearly define flea saliva allergens capable of inducing a hypersensitive response in animals. In addition, there remains a need to develop a method to collect substantially pure flea saliva allergens which provide predictable and less expensive preparations of allergens useful for desensitizing animals subject to, or having, FAD.

SUMMARY OF THE INVENTION

The present invention relates to, in one embodiment, a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein present in flea saliva extract FS-1, FS-2 and/or FS-3, i.e., the portion is encoded by a nucleic acid molecule capable of hybridizing under stringent conditions with the nucleic acid strand that is complementary to the nucleic acid strand that comprises the coding strand of the nucleic acid molecule that encodes a flea saliva protein of the present invention. Preferred flea saliva proteins include fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and/or fspN(O). In addition, the flea saliva protein of the formulation can include at least a portion of an amino acid sequence represented by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:88, SEQ ID NO:90, SEQ ID NO:100, and/or SEQ ID NO:102.

Another embodiment of the present invention includes a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein represented as a protein peak in FIG. 2.

Another embodiment of the present invention includes a formulation comprising at least one isolated ectoparasite saliva protein, in which the ectoparasite saliva protein comprises at least a portion of an amino acid sequence, in which the portion is encoded by a nucleic acid molecule capable of hybridizing under stringent conditions with a nucleic acid molecule that encodes a flea saliva protein represented as a protein peak in FIG. 12.

One aspect of the present invention includes a formulation comprising an ectoparasite saliva product, in which the formulation, when submitted to Tris glycine SDS-PAGE, comprises a fractionation profile as depicted in a FIG. 1B, lane 13 and/or FIG. 1B, lane 14.

Yet another embodiment of the present invention includes a formulation comprising at least one isolated ectoparasite saliva product substantially free of contaminating material, the formulation being produced by a process comprising: (a) collecting ectoparasite saliva products on a collection means within a saliva collection apparatus containing ectoparasites, the apparatus comprising (i) a housing operatively connected to a chamber, the chamber having an ambient temperature warmer than the housing thereby forming a temperature differential between the housing and the chamber, the housing being capable of retaining ectoparasites, and (ii) an interface between the housing and the chamber, the interface comprising ((a)) a means capable of collecting at least a portion of saliva products deposited by ectoparasites retained in the apparatus and ((b)) a barrier means capable of substantially preventing contaminating material from contacting the collection means, in which the temperature differential attracts ectoparasites retained in the housing to attempt to feed through the barrier means and collection means and, thereby, deposit saliva products on the collection means; and (b) extracting the saliva products from the collection means to obtain the formulation. Also included in the present invention is such an apparatus and use such an apparatus to produce formulations comprising flea saliva products substantially free of contaminating material.

Another aspect of the present invention includes an isolated nucleic acid molecule capable of hybridizing under stringent conditions with a gene encoding a flea saliva protein present in flea saliva extract FS-1, FS-2 and/or FS-3, including, but not limited to fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and/or fspN(O). In particular, the nucleic acid molecule is capable of hybridizing under stringent conditions with nucleic acid sequence SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:79; SEQ ID NO:81; SEQ ID NO:82; SEQ ID NO:83; SEQ ID NO:84; SEQ ID NO:85; SEQ ID NO:86; SEQ ID NO:87; SEQ ID NO:89; SEQ ID NO:91; SEQ ID NO:92; SEQ ID NO:93: SEQ ID NO:94; SEQ ID NO:95; SEQ ID NO:96; SEQ ID NO:97; SEQ ID NO:98; SEQ ID NO:99; SEQ ID NO:101: as well as with the complements of any of these sequences. In a further embodiment, a nucleic acid molecule of the present invention can include a nucleic acid molecule capable of hybridizing under stringent conditions with the complement of a nucleic acid sequence encoding a flea saliva protein having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:88, SEQ ID NO:90, SEQ ID NO:100, and SEQ ID NO:102. In a still further embodiment, a nucleic acid molecule of the present invention can include a nucleic acid molecule which comprises a nucleic acid sequence selected from the group consisting of SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71; SEQ ID NO:79; SEQ ID NO:81; SEQ ID NO:82; SEQ ID NO:83; SEQ ID NO:84; SEQ ID NO:85; SEQ ID NO:86; SEQ ID NO:87; SEQ ID NO:89; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:101, SEQ ID NO:104, a complement of any of said nucleic acid sequences, or an allelic variant of any of said nucleic acid sequences. Also included in the present invention are recombinant molecules and recombinant cells having a nucleic acid molecule of the present invention.

Also included in the present invention is a method for producing at least one ectoparasite saliva protein, comprising: (a) culturing a cell transformed with at least one nucleic acid capable of hybridizing under stringent conditions with the complement a gene encoding a flea saliva protein present in flea saliva extract FS-1, FS-2, and/or FS-3 to produce the protein; and (b) recovering the ectoparasite saliva proteins.

Another aspect of the present invention includes an antibody capable of selectively binding to an ectoparasite saliva product, or mimetope thereof.

Yet another aspect of the present invention includes a therapeutic composition for treating allergic dermatitis comprising any of the formulations disclosed herein. In particular, the therapeutic composition is useful for treating flea allergy dermatitis, mosquito allergy dermatitis and/or Culicoides allergy dermatitis. The present invention also includes a method to desensitize a host animal to allergic dermatitis, comprising administering to the animal a therapeutic composition.

The present invention further relates to an assay kit for testing if an animal is susceptible to or has allergic dermatitis, the kit comprising: (a) a formulation as disclosed herein; and (b) a means for determining if the animal is susceptible to or has allergic dermatitis, in which the means comprises use of the formulation to identify animals susceptible to or having allergic dermatitis.

According to the present invention, a method can be used to identify an animal susceptible to or having allergic dermatitis, the method comprising: (a) administering to a site on the animal a formulation of the present invention and administering to a different site on the animal a control solution selected from the group consisting of positive control solutions and negative control solutions; and (b) comparing a reaction resulting from administration of the formulation with a reaction resulting from administration of the control solution. The animal is determined to be susceptible to or to have allergic dermatitis if the reaction to the formulation is at least as large as the reaction to the positive control solution. The animal is determined not to be susceptible to or not to have allergic dermatitis if the reaction to the formulation is about the same size as the reaction to the negative control solution. In particular, the method can detect immediate hypersensitivity and/or delayed hypersensitivity.

Also according to the present invention, a method can be used to identify an animal susceptible to or having allergic dermatitis by measuring the presence of antibodies indicative of allergic dermatitis in the animal, the method comprising: (a) contacting a formulation of the present invention with a body fluid from the animal under conditions sufficient for formation of an immunocomplex between the formulation and the antibodies, if present, in the body fluid; and (b) determining the amount of immunocomplex formed, in which formation of the immunocomplex indicates that the animal is susceptible to or has allergic dermatitis. In particular, the method can be used to detect IgE antibodies as an indicator of immediate hypersensitivity in the animal.

The present invention also includes a method for prescribing treatment for allergic dermatitis, comprising: (a) identifying an animal that is susceptible to or has allergic dermatitis by an in vivo or in vitro assay comprising a formulation of the present invention; and (b) prescribing a treatment comprising administering a formulation of the present invention to the animal.

BRIEF DESCRIPTION OF THE DRAWINGS

FIG. 5 illustrates the relative size of wheals produced 15 minutes after injection of various flea saliva protein formulations into flea-sensitized dogs.

FIGS. 11A and 11B depict ELISA results measuring anti-flea saliva IgE antibodies in the serum of a flea sensitized dog and the lack thereof in heartworm infected dogs.

DETAILED DESCRIPTION OF THE INVENTION

Figure 1A:
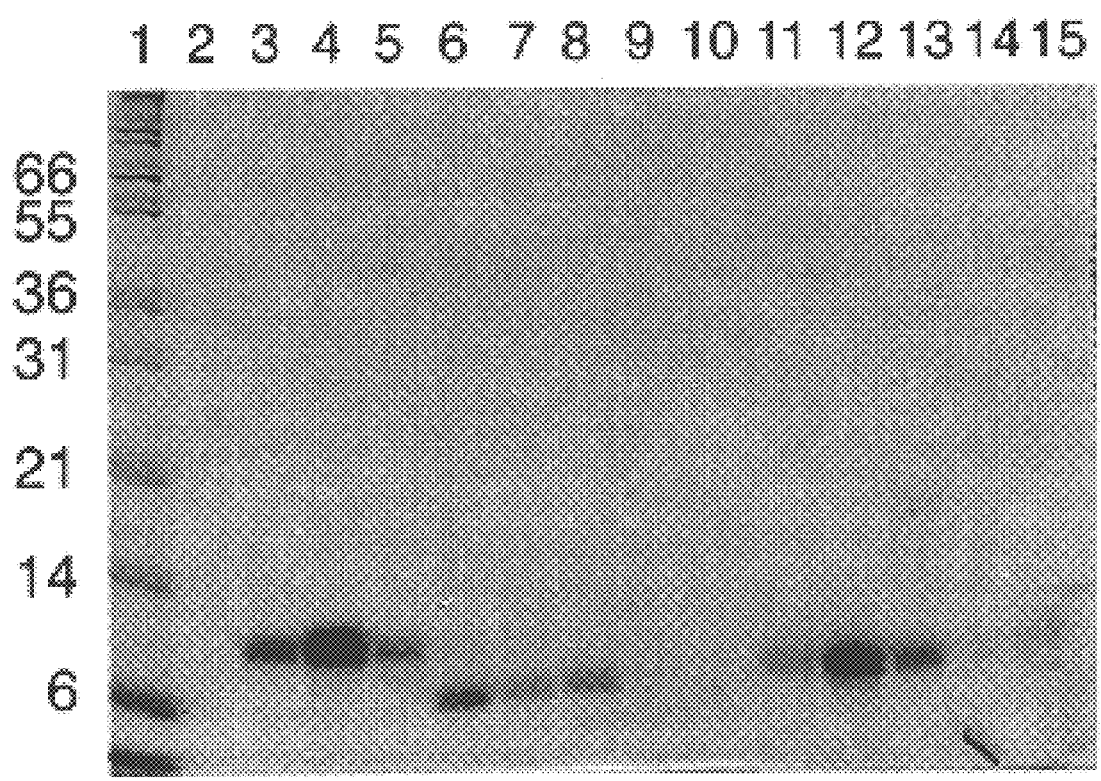
FIG. 1A illustrates the resolution of flea saliva proteins by reducing 16% Tris glycine SDS-PAGE.

The present invention includes a novel product and method for diagnosing and treating allergic dermatitis of animals to ectoparasites. The invention is particularly advantageous in that it provides for a unique formulation of ectoparasite saliva products sufficiently free of contaminants such as blood proteins, fecal material and larval culture medium, to be useful in diagnosis and therapy of allergies caused by ectoparasites. In addition, the present invention includes ectoparasite saliva products having other activities, important, for example, in a flea's ability to feed and/or counteract a host's resistance to fleas, such as products having clotting, anti-coagulant, protease, phospholipase, prostaglandin, anti-complement, other immunosuppressant, phosphatase, apyrase, vasoactive, and/or anti-inflammatory activities. Included among flea saliva products are products, such as, but not limited to, proteases, that are regurgitated by the flea that originated in other organs, such as, but not limited to, the midgut.

The invention is also particularly advantageous in that it provides an apparatus and method for reproducibly and efficiently isolating ectoparasite saliva products substantially free of contaminating material.

According to the present invention, ectoparasites are external living parasites that attach and feed through the skin of a host animal. Ectoparasites include parasites that live on a host animal and parasites that attach temporarily to an animal in order to feed. Also, according to the present invention, ectoparasite saliva refers to the material released from the mouth of an ectoparasite when the ectoparasite attempts to feed in response to a temperature differential, such as exists in an apparatus of the present invention. Ectoparasite saliva includes ectoparasite saliva products. Ectoparasite saliva products of the present invention comprise the portion of ectoparasite saliva bound to a collecting means of the present invention (described in detail below), herein referred to as ectoparasite saliva components. As such, ectoparasite saliva products also include the portion of ectoparasite saliva extracted from a collecting means of the present invention, herein referred to as ectoparasite saliva extract. Included in ectoparasite saliva extracts are ectoparasite saliva proteins which can be isolated using, for example, any method described herein. Ectoparasite saliva extracts of the present invention can also include other ectoparasite saliva products, such as, prostaglandins and other pharmacologically active molecules.

One embodiment of the present invention is a formulation that contains ectoparasite saliva products that can be used to diagnose and/or treat animals susceptible to or having (i.e., suffering from) allergic dermatitis. Preferred types of allergic dermatitis to diagnose and/or treat using ectoparasite saliva products of the present invention include flea allergy dermatitis, Culicoides allergy dermatitis and mosquito allergy dermatitis. A preferred type of allergic dermatitis to diagnose and/or treat using ectoparasite saliva products of the present invention is flea allergy dermatitis. As used herein, an animal that is susceptible to allergic dermatitis refers to an animal that is genetically pre-disposed to developing allergic dermatitis and/or to an animal that has been primed with an antigen in such a manner that re-exposure to the antigen results in symptoms of allergy that can be perceived by, for example, observing the animal or measuring antibody production by the animal to the antigen. As such, animals susceptible to allergic dermatitis can include animals having sub-clinical allergic dermatitis. Sub-clinical allergic dermatitis refers to a condition in which allergy symptoms cannot be detected by simply observing an animal (i.e., manifestation of the disease can include the presence of anti-ectoparasite saliva protein antibodies within an affected animal but no dermatitis). For example, sub-clinical allergic dermatitis can be detected using in vivo or in vitro assays of the present invention, as described in detail below. Reference to animals having allergic dermatitis includes animals that do display allergy symptoms that can be detected by simply observing an animal and/or by using in vivo or in vitro assays of the present invention, as described in detail below.

One embodiment of the present invention is a formulation that includes one or more isolated ectoparasite saliva proteins. According to the present invention, an isolated protein is a protein that has been removed from its natural milieu. An isolated ectoparasite saliva protein can, for example, be obtained from its natural source, be produced using recombinant DNA technology, or be synthesized chemically. As used herein, an isolated ectoparasite saliva protein can be a full-length ectoparasite saliva protein or any homologue of such a protein, such as an ectoparasite saliva protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol). A homologue of an ectoparasite saliva protein is a protein having an amino acid sequence that is sufficiently similar to a natural ectoparasite saliva protein amino acid sequence that a nucleic acid sequence encoding the homologue is capable of hybridizing under stringent conditions to (i.e., with) a nucleic acid molecule encoding the natural ectoparasite saliva protein (i.e., the complement of a nucleic acid sequence encoding the natural ectoparasite saliva protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an ectoparasite saliva protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an ectoparasite saliva protein homologue of the present invention is from about 4 to about 6 amino acids in length, with preferred sizes depending on whether a full-length, multivalent (i.e., fusion protein having more than one domain each of which has a function), or functional portions of such proteins are desired.

Ectoparasite saliva protein homologues can be the result of allelic variation of a natural gene encoding an ectoparasite saliva protein. A natural gene refers to the form of the gene found most often in nature. Ectoparasite saliva protein homologues can be produced using techniques known in the art including, but not limited to, direct modifications to a gene encoding a protein using, for example, classic or recombinant DNA techniques to effect random or targeted mutagenesis.

Preferred ectoparasite saliva proteins of the present invention, including homologues thereof, are capable of detecting and/or treating allergic dermatitis resulting from the bites of ectoparasites. A preferred ectoparasite saliva protein homologue includes at least one epitope capable of eliciting a hypersensitive response to the natural ectoparasite saliva protein counterpart. An ectoparasite saliva protein homologue can also include an epitope capable of hyposensitizing an animal to the natural form of the protein. The ability of an ectoparasite saliva protein homologue to detect and/or treat (i.e., immunomodulate or regulate by, for example, desensitizing) the hypersensitivity of an animal susceptible to or having allergic dermatitis, can be tested using techniques known to those skilled in the art. Such techniques include skin tests and immunoabsorbent assays as described in detail below. Additional preferred ectoparasite saliva proteins of the present invention have other activities that include activities important for feeding and survival of the ectoparasite.

In one embodiment, a formulation of the present invention can comprise a protein having at least a portion of an isolated ectoparasite saliva protein. According to the present invention, "at least a portion of an ectoparasite saliva protein" refers to a portion of an ectoparasite saliva protein encoded by a nucleic acid molecule that is capable of hybridizing, under stringent conditions, with a nucleic acid encoding a full-length ectoparasite saliva protein of the present invention. Preferred portions of ectoparasite saliva proteins are useful for detecting and/or treating allergic dermatitis resulting from the bites of ectoparasites. Additional preferred portions have activities important for flea feeding and survival. Suitable sizes for portions of an ectoparasite saliva protein of the present invention are as disclosed for saliva protein homologues of the present invention.

As will be apparent to one of skill in the art, the present invention is intended to apply to all ectoparasites. A formulation of the present invention can include saliva products from any ectoparasites. A preferred ectoparasite of the present invention from which to isolate saliva products (including proteins), and/or from which to identify proteins that can then be produced recombinantly or synthetically, include arachnids, insects and leeches. More preferred ectoparasites from which to obtain saliva products include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasite saliva products include those from fleas, mosquitos, midges, sandflies, blackflies, ticks and Rhodnius, with products from fleas, mosquitos and Culicoides being even more preferred.

A particularly preferred formulation of the present invention includes flea saliva proteins. Preferred flea saliva products include those from Ctenocephalides, Xenopsylla, Pulex, Tunga, Nosopsyllus, Diamanus, Ctopsyllus and Echidnophaga fleas, with saliva products from *Ctenocephalides canis* and *Ctenocephalides felis* fleas being even more preferred. For the purposes of illustration, many of the following embodiments discuss flea saliva proteins. Such discussion of flea saliva proteins is not intended, in any way, to limit the scope of the present invention.

In one embodiment, a formulation of the present invention is substantially free from contaminating material. Contaminating material can include, for example, ectoparasite fecal material, blood proteins from previous meals taken by an ectoparasite (e.g., fetuin, ferritin, albumin, hemoglobin and other large blood proteins), ectoparasite cuticular debris, and ectoparasite larval culture medium (e.g., blood, mouse food and sand). As used herein, a formulation that is substantially free of contaminants is a formulation that without further purification can be used as a diagnostic or therapeutic agent without causing undesired side effects. Preferably, a formulation substantially free from contaminating material comprises less than about 50 percent contaminating material, more preferably less than about 10 percent contaminating material, and even more preferably less than about 5 percent contaminating material. As such, a formulation of the present invention preferably comprises at least about 50 percent flea saliva products, more preferably at least about 90 percent flea saliva products, and even more preferably at least about 95 percent flea saliva products. A formulation of the present invention substantially free of contaminating material can include a formulation not having any blood contaminants or flea midgut contents. A formulation substantially free of contaminating material can be obtained using a saliva collection apparatus of the present invention as described in detail below.

A formulation that is substantially free of contaminating material can be identified by typical methods known to those of skill in the art. For example, the presence of contaminants can be identified by: (1) overloading and resolving a formulation by sodium dodecyl sulfate polyacrylamide gel electrophoresis (SDS-PAGE); (2) resolving a formulation by a variety of chromatography techniques; (3) screening a formulation with antibodies capable of binding to specific contaminants using, for example, immunoblot or enzyme-linked immunoassay techniques; (4) resolving a formulation by capillary electrophoresis; or (5) screening a formulation using an assay to detect hemoglobin.

One embodiment of a formulation of the present invention includes at least one or more flea saliva proteins having molecular weights ranging from about 6 kD to about 65 kD as determined by Tris-glycine SDS-PAGE, preferably using a 14% polyacrylamide gel and resolved using methods standard in the art. A preferred formulation includes one or more flea saliva proteins having molecular weights ranging from about 6 kD to about 55 kD. A more preferred formulation includes one or more proteins having elution (or migration) patterns as shown in FIG. 1.

In another embodiment, a formulation of the present invention includes at least one or more flea saliva proteins having molecular weights ranging from about 40 kD to about 300 kD as determined by Tris-glycine SDS-PAGE and resolved using methods standard in the art. Greater than 50% of the flea saliva proteins contained in such a formulation have a molecular weights ranging from about 40 kD to about 55 kD, and appear to be similar to fspN. A more preferred formulation includes one or more proteins having elution (or migration) patterns as shown in FIG. 1.

In another embodiment, a formulation of the present invention includes one or more flea saliva proteins having basic isoelectric points, or pI values. An isoelectric pH, or pI, value refers to the pH value at which a molecule has no net electric charge and fails to move in an electric field. A preferred formulation of the present invention includes proteins having a pI value of at least about pI 8.5, and more preferably of at least about pI 9.0. Flea saliva protein fspH, for example, has pI values ranging from about pI 8.5 to about pI 9.6, which may represent heterogeneity in the proteins due to allelic variation in the flea population from which the flea saliva proteins were collected.

In yet another embodiment, a formulation of the present invention includes at least a portion of one or more flea saliva products eluted from a collection means of the present invention. Examples of such formulations include flea extracts FS-1, FS-2, and FS-3. The FS-1, FS-2 and FS-3 fleas saliva extracts are produced according to the method described in detail in Example 2. According to the present invention, the terms FS-1 flea saliva extract, FS-2 flea saliva extract or FS-3 flea saliva extract can be used interchangeably with the terms FS-1 flea saliva product mixture, FS-2 flea saliva product mixture or FS-3 flea saliva product mixture, respectively.

Figure 1B:
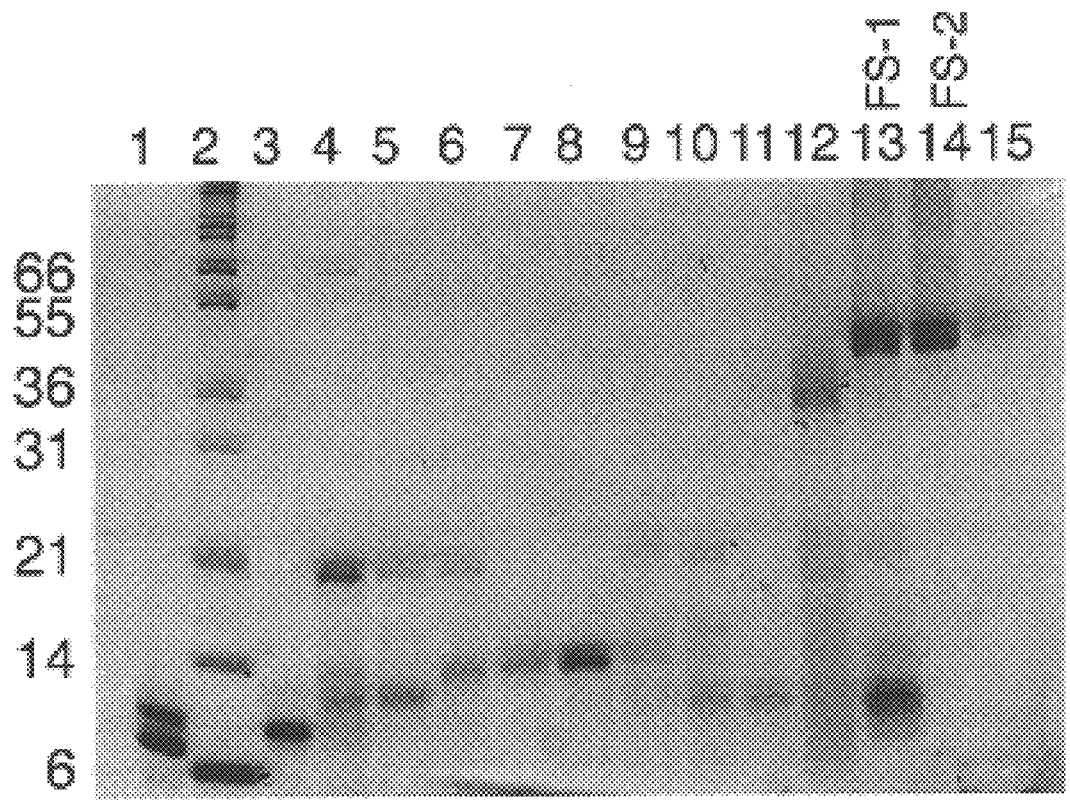
FIG. 1B illustrates the resolution of flea saliva proteins, FS-1 and FS-2 by reducing 16% Tris glycine SDS-PAGE.
Figure 2:
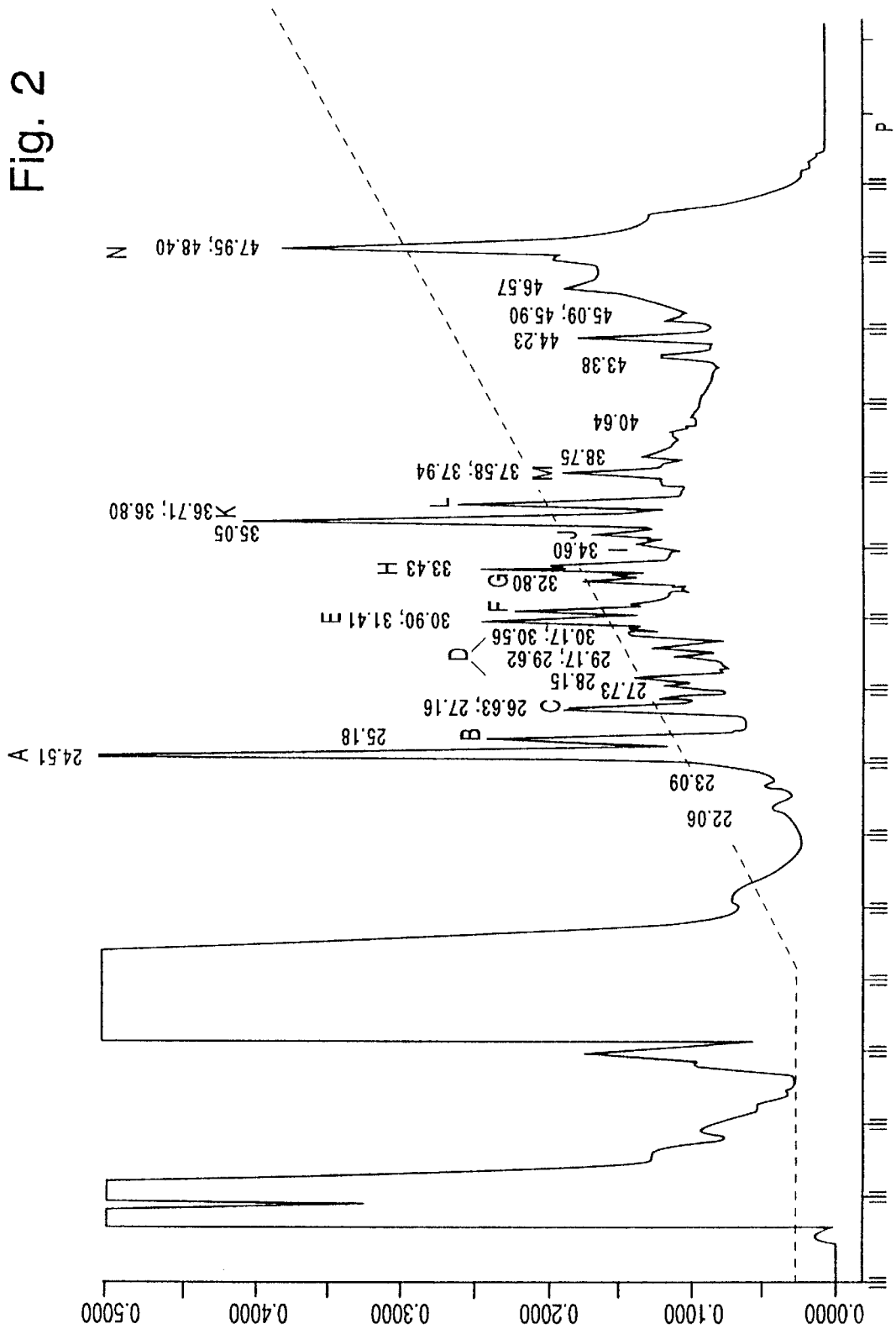
FIG. 2 illustrates the resolution of flea saliva proteins using high pressure liquid chromatography.

An FS-1 flea saliva extract includes a mixture of proteins (a) that, when submitted to reducing 16% Tris glycine SDS-PAGE, migrate as bands as are shown in FIG. 1B, lane 13; and (b) that, when submitted to reverse phase high pressure liquid chromatography (HPLC), migrate as peaks as are shown in FIG. 2. The peaks in FIG. 2 are obtained when the proteins included in FS-1 are collected using a saliva collection apparatus of the present invention as described in detail below, and further resolved into protein peaks by passing the collected proteins over a C4 HPLC column using 5% to 63% acetonitrile or 5.6% to 70% Solvent B at a flow rate of 0.8 milliliters per minute, in which Solvent A is about 0.1% TFA in water and Solvent B is about 0.085% TFA in 90% acetonitrile. Referring to FIG. 2, the peaks are referred to and depicted as peak A, peak B, peak C, peak D, peak E, peak F, peak G, peak H, peak I, peak J, peak K, peak L, peak M and peak N. Flea saliva proteins (or protein fragments) contained within such peaks are referred to as fspA, fspB, fspC, fspD, fspE, fspF, fspG, fspH, fspI, fspJ, fspK, fspL, fspM and fspN. The peaks refer to the regions marked in FIG. 2 and it is to be noted that a peak does not necessarily contain just one protein (or protein fragment). Further resolution of proteins contained within the above-referenced peaks by, for example, amino acid sequencing or SDS-PAGE gel electrophoresis, has indicated that fspC includes at least two proteins referred to as fspC1 and fspC2, fspD includes at least two proteins referred to as fspD1 and fspD2, fspG includes at least four proteins referred to as fspG1, fspG2 and fspG3, fspG4, fspJ includes at least two proteins referred to as fspJ1 and fspJ2, fspL includes at least two proteins referred to as fspL1 and fspL2, fspM includes at least two proteins referred to as fspM1 and fspM2, and fspN includes at least three proteins and/or protein fragments referred to as fspN1, fspN2 and fspN3. At least partial amino acid sequences have been obtained for a number of the flea saliva proteins as represented by SEQ ID NO:1 (a partial N- (amino-) terminal amino acid sequence of fspA), SEQ ID NO:2 (an amino acid sequence, beginning at the N-terminus, that represents most of the fspH protein), SEQ ID NO:3 (a partial N-terminal amino acid sequence of an Endoproteinase Asp-N fragment of fspH, denoted fspHe), SEQ ID NO:4 (a partial N-terminal amino acid sequence of an Endoproteinase Asp-N fragment of fspH, denoted fspHh), SEQ ID NO:5 (a partial N-terminal amino acid sequence of an Endoproteinase Asp-N fragment of fspH, denoted fspHj, which also represents a partial N-terminal amino acid sequence of fspH), SEQ ID NO:6 (a partial N-terminal amino acid sequence of fspI), SEQ ID NO:7 (a partial N-terminal amino acid sequence of fspJ1), SEQ ID NO:8 (a partial N-terminal amino acid sequence of fspJ2), SEQ ID NO:9 (a partial N-terminal amino acid sequence of fspL1), SEQ ID NO:10 (a partial N-terminal amino acid sequence of fspL2), SEQ ID NO:11 (a partial N-terminal amino acid sequence of fspN1), SEQ ID NO:12 (a partial N-terminal amino acid sequence of fspN2), SEQ ID NO:13 (a partial N-terminal amino acid sequence of fspN3), SEQ ID NO:14 (a partial N-terminal amino acid sequence of fspH), SEQ ID NO:25 (a translation of the nucleic acid sequence represented by SEQ ID NO:24, corresponding to fspI), SEQ ID NO:26 (an apparent full-length translation product of fspI), SEQ ID NO:27 (a partial N-terminal amino acid sequence of fspB), SEQ ID NO:28 (a partial N-terminal amino acid sequence of fspG1), SEQ ID NO:29 (a partial N-terminal amino acid sequence of fspG2), SEQ ID NO:30 (a partial N-terminal amino acid sequence of fspG3), SEQ ID NO:31 (a partial N-terminal amino acid sequence of an Endoproteinase Asp-N fragment of fspN, denoted fspN(100–101)), SEQ ID NO:33 (a translation product, named PfspH$_{80}$, of the partial nucleic acid sequence of nfspH$_{242}$, denoted SEQ ID NO:32), SEQ ID NO:35 (a translation product, named PfspI$_{155}$, of the partial nucleic acid sequence of nfspI$_{591}$, denoted SEQ ID NO:34), SEQ ID NO:51 (a translation product, named PfspN(A)$_{172}$, of the partial nucleic acid sequence of nfspN(A)$_{646}$, denoted SEQ ID NO:50), SEQ ID NO:53 (a translation product, named PfspN(B)$_{153}$, of the partial nucleic acid sequence of nfspN(B)$_{612}$, denoted SEQ ID NO:52), SEQ ID NO:54 (a partial apparent N-terminal amino acid sequence, named PfspN(A)$_{56}$, of PfspN(A)), SEQ ID NO:56 (an apparent full-length translation product, named PfspN(A)$_{398}$, of nfspN(A)$_{1197}$, denoted SEQ ID NO:55), SEQ ID NO:58 (an apparent full-length translation product, named PfspG4$_{90}$, of nfspG4$_{565}$, denoted SEQ ID NO:57), SEQ ID NO:60 (an apparent full-length translation product, named PfspM(A)$_{157}$, of the nucleic acid sequence of nfspM(A)$_{897}$, denoted SEQ ID NO:59), SEQ ID NO:62 (a translation product, named PfspM(B)$_{900}$, of the nucleic acid sequence of nfspM(B)$_{2706}$, denoted SEQ ID NO:61), SEQ ID NO:64 (a translation product, named PfspM(C)$_{137}$, of the nucleic acid sequence of nfspM(C)$_{414}$, denoted SEQ ID NO:63), SEQ ID NO:66 (a translation product, named PfspM(D)$_{90}$, of the nucleic acid sequence of nfspM(D)$_{273}$, denoted SEQ ID NO:65), SEQ ID NO:68 (an apparent full-length translation product, named PfspM(E)$_{461}$, of the nucleic acid sequence of nfspM(E)$_{1704}$, denoted SEQ ID NO:67), SEQ ID NO:70 (a translation product, named PfspM(F)$_{586}$, of the nucleic acid sequence of nfspM(F)$_{1758}$, denoted SEQ ID NO:69), SEQ ID NO:72 (a partial N-terminal amino acid sequence of fspM(G), denoted PfspM(G)), SEQ ID NO:73 (a partial N-terminal amino acid sequence of fspM(H), denoted PfspM(H)), SEQ ID NO:74 (a partial N-terminal amino acid sequence of fspM(I), denoted PfspM(I)), SEQ ID NO:75 (a partial N-terminal 76 acid sequence of fspM(J), denoted PfspM(J)), SEQ ID NO:76 (a partial N-terminal amino acid sequence of fspM (K), denoted PfspM(K)), SEQ ID NO:77 (a partial N-terminal amino acid sequence of fspM(L), denoted PfspM (L)) and SEQ ID NO:78 (a partial N-terminal amino acid sequence of fspM(M), denoted PfspM(M)). Details of how each protein was characterized is described in the Examples section.

An FS-2 flea saliva extract includes a mixture of proteins that, when submitted to reducing 16% Tris glycine SDS-PAGE, migrate as bands as are shown in FIG. 1B, lanes 14 and 15.

It is within the scope of the present invention that additional flea saliva products of interest remain on a collection means following the elution protocols to obtain FS-1, FS-2 and FS-3 flea saliva extracts. It is also within the scope of the invention that a formulation of the present invention can include flea saliva products removed from a collection means by eluting using other techniques, for example, by using higher concentrations of eluants.

In another embodiment, a formulation of the present invention includes at least a portion of an ectoparasite saliva protein homologue preferably having at least about 50 percent, more preferably at least about 75 percent, and even more preferably at least about 85 percent amino acid homology (identity within comparable regions) with at least a portion of at least one product contained in the saliva extracts FS-1, FS-2 or FS-3. Preferred homologues include at least a portion of an ectoparasite saliva product having at least about 50 percent, more preferably at least about 75 percent, and even more preferably at least about 85 percent amino acid homology with at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM (J), fspM(K), fspM(L), fspM(M), fspN(B), fspN(C), fspN (D), fspN(E), fspN(F), fspN(G), fspN(H), fspN(I), fspN(J), fspN(K), fspN(L), fspN(M), fspN(N) and/or fspN(O). As such, also included are proteins having at least a portion of one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80 and/or other sequences disclosed herein.

In a preferred embodiment, a formulation of the present invention includes at least a portion of an ectoparasite saliva product homologue of the present invention that is encoded by a nucleic acid molecule having at least about 50 percent, more preferably at least about 75 percent, and even more preferably at least about 85 percent homology with a nucleic acid molecule encoding at least a portion of a product contained in the saliva extracts FS-1, FS-2 or FS-3. A preferred ectoparasite saliva product homologue is encoded by a nucleic acid molecule having at least about 50 percent, more preferably at least about 75 percent, and even more preferably at least about 85 percent, homology with a nucleic acid molecule encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) or fspN(O).

Figure 3:
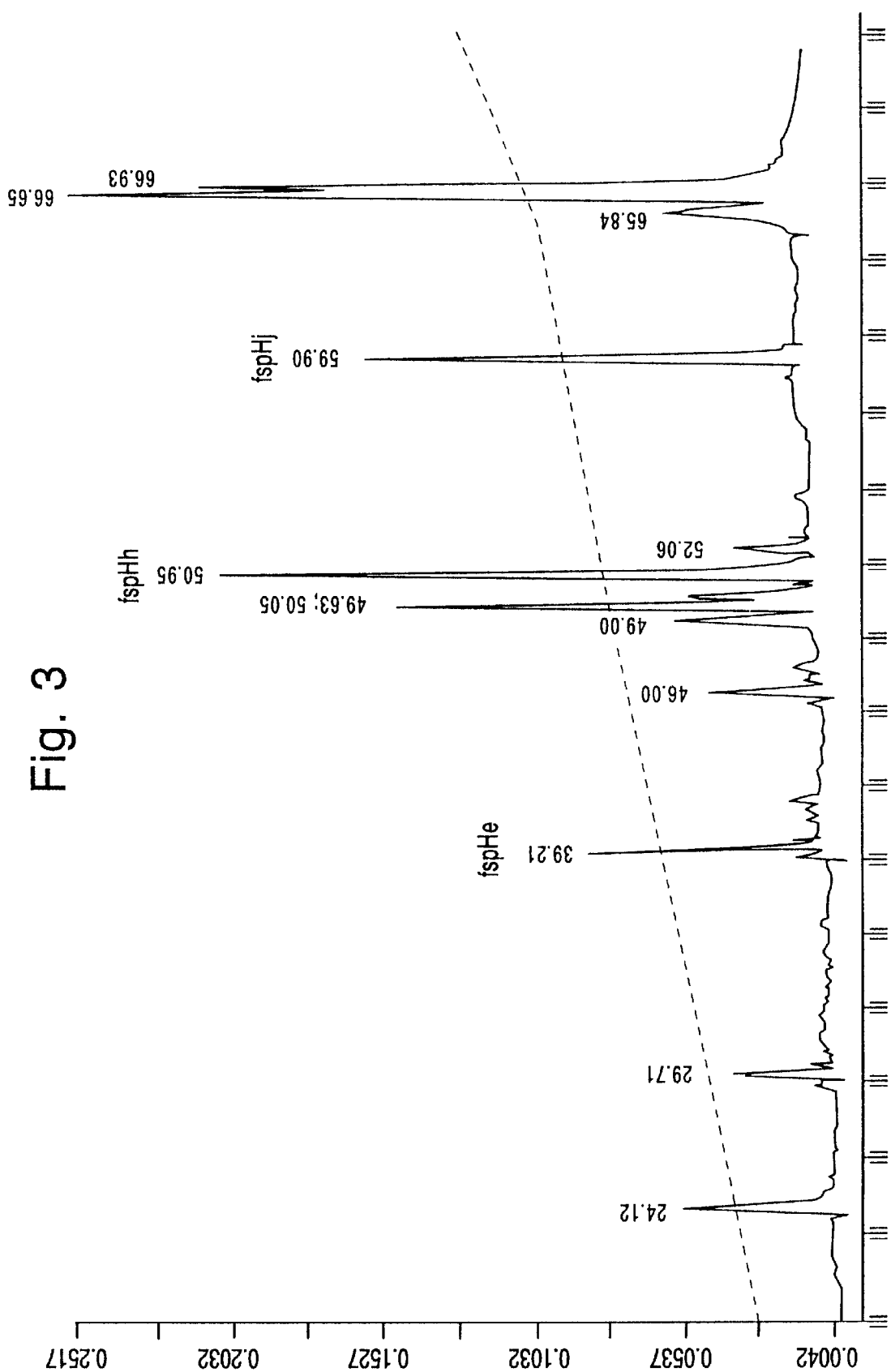
FIG. 3 illustrates the peaks obtained from reverse phase HPLC resolution of proteolytic fragments of fspH protein digested with Endoproteinase Asp-N.

In yet another embodiment, a formulation of the present invention includes a protein which, when digested with Endoproteinase Asp-N, generates proteolytic fragments that, when subjected to reverse phase HPLC, migrate with peaks as depicted in FIG. 3. The reverse phase HPLC was performed using the methods disclosed by Stone et al., Enzymatic Digestion of Proteins and HPLC Peptide Isolation, in A Practical Guide to Protein and Peptide Purification for Microsequencing, PT Matsudaira ed., Academic Press, San Diego, Calif. (i.e., Narrowbore procedure: vydac C18 reverse-phase, 300 A, 5 μm support; flow rate of 0.2 ml/min; Solvent A being 0.6% TFA in water and Solvent B being 0.052% TFA in 80% acetonitrile in water; the sample was injected at 2% B; the gradient after a hold at 2% B was 2–37.5% B over 60 min., 37.5%–75% B over 30 min., 75%–98% B over 15 min.; and detection at 214 nm). An example of such a protein is fspH, which also has the characteristics of a molecular weight of about 8613±6 daltons when determined by ESMS. A particularly preferred formulation of the present invention includes a fspH protein having the amino acid sequence represented by SEQ ID NO:2, SEQ ID NO:3, SEQ ID NO:4, SEQ ID NO:5, SEQ ID NO:14 and SEQ ID NO:33.

In preferred embodiments, formulations of the present invention can include at least one isolated protein having (i.e., including) at least a portion of one of the amino acid sequences identified in the Sequence ID Listing, and more specifically an amino acid sequence selected from the group consisting of SEQ ID NO:1; SEQ ID NO:2; SEQ ID NO:14; SEQ ID NO:3; SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:27; SEQ ID NO:28; SEQ ID NO:29; SEQ ID NO:30; SEQ ID NO:31; SEQ ID NO:33; SEQ ID NO:25; SEQ ID NO:26; SEQ ID NO:35; SEQ ID NO:31; SEQ ID NO:51; SEQ ID NO:53; SEQ ID NO:54; SEQ ID NO:56; SEQ ID NO:58; SEQ ID NO:60; SEQ ID NO:62; SEQ ID NO:64; SEQ ID NO:66; SEQ ID NO:68; SEQ ID NO:70; SEQ ID NO:72; SEQ ID NO:73; SEQ ID NO:74; SEQ ID NO:75; SEQ ID NO:76; SEQ ID NO:77; SEQ ID NO:78; SEQ ID NO:80; SEQ ID NO:88; SEQ ID NO:90; SEQ ID NO:100; SEQ ID NO:102.

It should be noted that although fspN1 and fspN2 appear to have similar, if not identical, partial N-terminal sequences (represented, respectively by SEQ ID NOS:11 and 12), the two proteins migrate differently when submitted to Tris glycine SDS-PAGE, suggesting that they are different proteins, possibly due to a carboxyl-terminal truncation of one of the proteins and/or post-translation modification, such as glycosylation. Comparison of amino acid sequence SEQ ID NO:51 with amino acid sequences reported in GenBank indicates that SEQ ID NO:51 is about 28% identical with human prostatic acid phosphatase. Comparison of amino acid sequence SEQ ID NO:53 with amino acid sequences reported in GenBank indicates that SEQ ID NO:53 is about 30% identical with human prostatic acid phosphatase. Comparison of amino acid sequence SEQ ID NO:56 with amino acid sequences reported in GenBank indicates that SEQ ID NO:56 is about 30% identical with human prostatic acid phosphatase.

It is to be appreciated that ectoparasite saliva proteins of the present invention include, but are not limited to, full-length proteins, hybrid proteins, fusion proteins, multivalent proteins, and proteins that are truncated homologues of, or are proteolytic products of, at least a portion of a protein contained in the saliva extracts FS-1, FS-2 or FS-3; and preferably at least a portion of saliva protein fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM (G), fspM(H), fspM(I), fspM(J), fspM(K), fspM(L), fspM (M), fspN(B), fspN(C), fspN(D), fspN(E), fspN(F), fspN (G), fspN(H), fspN(I), fspN(J), fspN(K), fspN(L), fspN(M), fspN(N) and fspN(O). As such, also included are proteins having at least a portion of one of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80 and/or other sequences disclosed herein. As used herein, the term hybrid protein refers to a single protein produced from two different proteins.

The foregoing SEQ ID NO's represent amino acid sequences deduced according to methods disclosed in the Examples. It should be noted that since amino acid sequencing technology is not entirely error-free, the foregoing SEQ ID NO's, at best, represent an apparent amino acid sequence of the ectoparasite saliva proteins of the present invention. In addition, the variation seen in the foregoing SEQ ID NO's can also be due, at least in part, to allelic variation since the proteins being sequenced were derived from populations of fleas.

According to the present invention, a formulation of the present invention can include flea saliva proteins that have undergone post-translational modification. Such modification can include, for example, glycosylation. Glycosylation can include addition of N-linked and/or O-linked oligosaccharides. It is to be appreciated that post-translational modification of a protein of the present invention can contribute to an epitope's ability to induce an allergic response against the protein in an immediate or delayed hypersensitivity response.

Another embodiment of the present invention is an isolated nucleic acid molecule capable of hybridizing, under stringent conditions, with an ectoparasite saliva protein gene encoding an ectoparasite saliva protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions. An isolated nucleic acid molecule of the present invention can also be produced using recombinant DNA technology (e.g., polymerase chain reaction (PCR) amplification, cloning) or chemical synthesis. Isolated ectoparasite saliva protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an ectoparasite saliva protein of the present invention or to form stable hybrids under stringent conditions with natural nucleic acid molecule isolates.

An isolated nucleic acid molecule of the present invention can include a nucleic acid sequence that encodes at least one ectoparasite saliva protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an ectoparasite saliva protein. As heretofore disclosed, ectoparasite saliva proteins of the present invention include, but are not limited to, proteins having full-length ectoparasite saliva protein coding regions, portions thereof, and other ectoparasite saliva protein homologues.

It is to be appreciated that an ectoparasite saliva protein of the present invention can be encoded by a full-length nucleic acid sequence which encodes a polyprotein. The polyprotein can be post-translationally processed into multiple proteins which are found in saliva. As used herein, an ectoparasite saliva protein gene includes all nucleic acid sequences related to a natural ectoparasite saliva protein gene such as regulatory regions that control production of an ectoparasite saliva protein encoded by that gene (such as, but not limited to, transcription, translation or post-translation control regions) as well as the coding region itself. A nucleic acid molecule of the present invention can be an isolated natural ectoparasite saliva protein nucleic acid molecule or a homologue thereof. A nucleic acid molecule of the present invention can include one or more regulatory regions, full-length or partial coding regions, or combinations thereof. The minimal size of an ectoparasite saliva protein nucleic acid molecule of the present invention is the minimal size capable of forming a stable hybrid under stringent hybridization conditions with a corresponding natural gene.

An ectoparasite saliva protein nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an allergic response in animals having allergic dermatitis or the ability of a homologue to act as an anti-coagulant) and/or by hybridization with isolated ectoparasite saliva protein nucleic acids under stringent conditions.

One embodiment of the present invention is an ectoparasite saliva protein nucleic acid molecule capable of encoding at least a portion of a flea saliva product, or a homologue thereof (e.g., saliva products of other ectoparasites), contained in the saliva extracts FS-1, FS-2 or FS-3, wherein FS-1, when submitted to HPLC, resolves into peak A, peak B, peak C, peak D, peak E, peak F, peak G, peak H, peak I, peak J, peak K, peak L, peak M and/or peak N. A preferred nucleic acid molecule is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM (H), fspM(I), fspM(J), fspM(K), fspM(L), fspM(M), fspN (B), fspN(C), fspN(D), fspN(E), fspN(F), fspN(G), fspN(H), fspN(I), fspN(J), fspN(K), fspN(L), fspN(M), fspN(N) and/ or fspN(O), or homologues thereof. As such, preferred nucleic acid molecules include, but are not limited, nucleic acid molecules that encode proteins having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:83; SEQ ID NO:84; SEQ ID NO:85; SEQ ID NO:86; SEQ ID NO:87; SEQ ID NO:89, SEQ ID NO:91, SEQ ID NO:92; SEQ ID NO:93; SEQ ID NO:94, SEQ ID NO:95, SEQ ID NO:96, SEQ ID NO:97, SEQ ID NO:98, SEQ ID NO:99, SEQ ID NO:101, SEQ ID NO:104, as well as with the complements of any of these sequences or homologues thereof. Such preferred nucleic acid molecules can hybridize to the coding and/or complementary strand.

A preferred nucleic acid molecule of the present invention is capable of hybridizing under stringent conditions to a nucleic acid molecule that encodes at least a portion of a flea saliva product, or a homologue thereof (e.g., saliva products of other ectoparasites), contained in the saliva extracts FS-1, FS-2 or FS-3. Such preferred nucleic acid molecules hybridize to the coding strand and/or to the strand complementary to the coding strand of a nucleic acid molecule that encodes at least a portion of such a flea saliva product or homologue thereof. Also preferred is an ectoparasite saliva protein nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea saliva product, or a homologue thereof (e.g., saliva products of other ectoparasites), contained in the saliva extracts FS-1, FS-2 or FS-3. A particularly preferred nucleic acid sequence is a nucleic acid sequence having at least about 65 percent, preferably at least about 75 percent, more preferably at least about 85 percent, and even more preferably at least about 95 percent homology with a nucleic acid sequence encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) and fspN(O). As such, also preferred are nucleic acid molecules having at least about 65 percent, preferably at least about 75 percent, more preferably at least about 85 percent, and even more preferably at least about 95 percent homology with a nucleic acid sequence encoding at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:83, SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:101 and/or SEQ ID NO:104.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having a nucleic acid sequence as represented by SEQ ID NO:20, SEQ ID NO:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:79, SEQ ID NO:81, SEQ ID NO:82, or other sequences disclosed herein, or complements thereof. SEQ ID NO:20, a nucleic acid sequence that includes about 60 nucleotides of the apparent gene encoding flea saliva protein fspH, includes about 25 percent of the coding region of fspH. SEQ ID NO:24, a nucleic acid sequence that includes about 573 nucleotides of the apparent gene encoding flea saliva protein fspI, encodes a protein of about 149 amino acids, represented by SEQ ID NO:25. The entire translation product of fspI is apparently about 158 amino acids and is denoted SEQ ID NO:26. SEQ ID NO:32, a 242 bp nucleic acid sequence of the apparent gene encoding flea saliva protein fspH, encodes a protein of about 80 amino acids, which is denoted SEQ ID NO:33. SEQ ID NO:34, a 591 bp nucleic acid sequence of the apparent gene encoding flea saliva protein fspI, encodes a protein of about 155 amino acids, which is denoted SEQ ID NO:35. SEQ ID NO:50, a 646 bp nucleic acid sequence of the apparent gene encoding a fspN flea saliva protein, encodes a protein of about 172 amino acids, which is denoted SEQ ID NO:51. SEQ ID NO:52, a 612 bp nucleic acid sequence of the apparent gene encoding a fspN flea saliva protein, encodes a protein of about 153 amino acids, which is denoted SEQ ID NO:53. SEQ ID NO:55, a 1197 bp nucleic acid sequence of the apparent gene encoding fspN3, encodes a protein of about 398 amino acids, which is denoted SEQ ID NO:56. SEQ ID NO:57, a 565 bp nucleic acid sequence of the apparent gene encoding a fspG4 flea saliva protein, encodes a protein of about 90 amino acids, which is denoted SEQ ID NO:58. SEQ ID NO:59, a 897 bp nucleic acid sequence of the apparent gene encoding a fspM(A) flea saliva protein, encodes a protein of about 157 amino acids, which is denoted SEQ ID NO:60. SEQ ID NO:61, a 2706 bp nucleic acid sequence of the apparent gene encoding a fspM(B) flea saliva protein, encodes a protein of about 900 amino acids, which is denoted SEQ ID NO:62. SEQ ID NO:63, a 414 bp nucleic acid sequence of the apparent gene encoding a fspM(C) flea saliva protein, encodes a protein of about 137 amino acids, which is denoted SEQ ID NO:64. SEQ ID NO:65, a 273 bp nucleic acid sequence of the apparent gene encoding a fspM(D) flea saliva protein, encodes a protein of about 90 amino acids, which is denoted SEQ ID NO:66. SEQ ID NO:67, a 1704 bp nucleic acid sequence of the apparent gene encoding a fspM(E) flea saliva protein, encodes a protein of about 461 amino acids, which is denoted SEQ ID NO:68. SEQ ID NO:69, a 1758 bp nucleic acid sequence of the apparent gene encoding a fspM(F) flea saliva protein, encodes a protein of about 586 amino acids, which is denoted SEQ ID NO:70. SEQ ID NO:71, SEQ ID NO:79, SEQ ID NO:81, SEQ ID NO:82 include the apparent coding regions of nfspM(D), nfspG4, nfspM(A) and nfspM(E), respectively.

Knowing a nucleic acid molecule of an ectoparasite saliva protein of the present invention allows one skilled in the art to make copies of that nucleic acid molecule as well as to obtain a nucleic acid molecule including additional portions of ectoparasite saliva protein-encoding genes (e.g., nucleic acid molecules that include the translation start site and/or transcription and/or translation control regions), and/or ectoparasite saliva protein nucleic acid molecule homologues. Knowing a portion of an amino acid sequence of an ectoparasite saliva protein of the present invention allows one skilled in the art to clone nucleic acid sequences encoding such an ectoparasite saliva protein. In addition, a desired ectoparasite saliva protein nucleic acid molecule can be obtained in a variety of ways including screening appropriate expression libraries with antibodies which bind to ectoparasite saliva proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea saliva protein nucleic acid molecules, preferred cDNA libraries include cDNA libraries made from unfed whole flea, fed whole flea, fed flea midgut, unfed flea midgut, and flea salivary gland. Techniques to clone and amplify genes are disclosed, for example, in Sambrook et al., ibid. The Examples section includes examples of the isolation of cDNA sequences encoding flea saliva proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea saliva product, or a homologue thereof (e.g., saliva products of other ectoparasites), contained in the saliva extracts FS-1, FS-2 or FS-3. A preferred oligonucleotide is capable of hybridizing, under stringent conditions, with a nucleic acid molecule that is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) and fspN(O), or homologues thereof. As such, certain preferred oligonucleotides are capable of hybridizing to a nucleic acid molecule capable of encoding a protein having at least a portion of one or more of the following amino acid sequences: SEQ ID NO:1, SEQ ID NO:2, SEQ ID NO:3, SEQ ID NO:4, SEQ ID NO:5, NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, SEQ ID NO:83, SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:101, SEQ ID NO:104, or homologues thereof, such oligonucleotides can hybridize to the coding or non-coding strand of a double-stranded nucleic acid molecule. Certain preferred oligonucleotides are capable of hybridizing to nucleic acid molecules including nucleic acid sequences represented by SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of saliva proteins by ectoparasites. Such therapeutic applications include the use of such oligonucleotides in, for example, antisense-, triplex formation-, ribozyme- and/or RNA drug-based technologies. The present invention, therefore, includes such oligonucleotides and methods to interfere with the production of ectoparasite saliva proteins by use of one or more of such technologies.

The present invention also includes a recombinant vector, which includes an ectoparasite saliva protein nucleic acid molecule of the present invention inserted into any vector capable of delivering the nucleic acid molecule into a host cell. Such a vector contains heterologous nucleic acid sequences, that is nucleic acid sequences that are not naturally found adjacent to ectoparasite saliva protein nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of ectoparasite saliva protein nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

A preferred nucleic acid molecule to include in a recombinant vector of the present invention is a nucleic acid molecule that encodes at least a portion of at least one flea saliva product, or a homologue thereof (e.g., saliva products of other ectoparasites), contained in the saliva extracts FS-1, FS-2 or FS-3. A particularly preferred nucleic acid molecule to include in a recombinant vector is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) and fspN(O), or homologues thereof. As such, also included are nucleic acid molecules that encode a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO: 80, or other sequences disclosed herein, or homologues thereof, and nucleic acid molecules including at least a portion of a nucleic acid sequence represented by SEQ ID NO:20, SEQ ID NO:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:79, SEQ ID NO:81, SEQ ID NO:82, or other sequences disclosed herein, or complements thereof.

In one embodiment, an isolated ectoparasite saliva protein of the present invention is produced by culturing a cell capable of expressing the protein under conditions effective to produce the protein, and recovering the protein. A preferred cell to culture is a recombinant cell that is capable of expressing the ectoparasite saliva protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell include nucleic acid molecules that encode at least a portion of a flea saliva product, or a homologue thereof (e.g., saliva products of other ectoparasites), contained in the saliva extracts FS-1, FS-2 or FS-3. Particularly preferred nucleic acid molecules with which to transform a host cell are as disclosed herein for including in recombinant vectors of the present invention.

Suitable host cells to transform include any cell that can be transformed and that can express the introduced ectoparasite saliva protein. Such cells are, therefore, capable of producing ectoparasite saliva proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., $E.$ $coli$) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, $Heliothis$ $zea$ insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an ectoparasite saliva protein.

Expression vectors of the present invention may also contain secretory signals (i.e., signal segment nucleic acid sequences) to enable an expressed ectoparasite saliva protein to be secreted from the cell that produces the protein.

Suitable signal segments include an ectoparasite saliva protein signal segment or any heterologous signal segment capable of directing the secretion of an ectoparasite saliva protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of an ectoparasite nucleic acid molecule of the present invention can enhance the stability during production, storage and/or use of the protein encoded by the nucleic acid molecule. Furthermore, a fusion segment can function as a tool to simplify purification of an ectoparasite saliva protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an ectoparasite saliva protein. Linkages between fusion segments and ectoparasite saliva proteins can be constructed to be susceptible to cleavage to enable straight-forward recovery of the ectoparasite saliva proteins. Fusion proteins are preferably produced by culturing a recombinant cell transformed with a fusion nucleic acid sequence that encodes a protein including the fusion segment attached to either the carboxyl and/or amino terminal end of an ectoparasite saliva protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules that encode at least a portion of a flea saliva product, or a homologue thereof (e.g., saliva products of other ectoparasites), contained in the saliva extracts FS-1, FS-2, or FS-3. Particularly preferred nucleic acid molecules to include in a recombinant molecule are as disclosed herein for including in a recombinant vector of the present invention.

A recombinant cell of the present invention includes any cells transformed with at least one of any nucleic acid molecules of the present invention. A preferred recombinant cell is a cell transformed with at least one nucleic acid molecule that encodes at least a portion of a flea saliva product, or a homologue thereof (e.g., saliva products of other ectoparasites), contained in the saliva extracts FS-1, FS-2 and/or FS-3. A preferred recombinant cell is transformed with at least one nucleic acid molecule that is capable of encoding at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N) and fspN(O), or homologues thereof. As such, also included are nucleic acid molecules that encode a protein having at least a portion of one or more of the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:25, SEQ ID NO:26, SEQ ID NO:27, SEQ ID NO:28, SEQ ID NO:29, SEQ ID NO:30, SEQ ID NO:31, SEQ ID NO:33, SEQ ID NO:35, SEQ ID NO:51, SEQ ID NO:53, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:73, SEQ ID NO:74, SEQ ID NO:75, SEQ ID NO:76, SEQ ID NO:77, SEQ ID NO:78, SEQ ID NO:80, or other sequences disclosed herein, or homologues thereof, and nucleic acid molecules including at least a portion of a nucleic acid sequence represented by SEQ ID NO:20, SEQ ID NO:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:79, SEQ ID NO:81, SEQ ID NO:82, or other sequences disclosed herein, or complements thereof. Particularly preferred recombinant cells include *E. coli* transformed with at least one of the aforementioned nucleic acid molecules.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce an ectoparasite saliva protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an ectoparasite saliva protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant ectoparasite saliva proteins may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Ectoparasite saliva proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

Ectoparasite saliva proteins are preferably retrieved in "substantially pure" form. As used herein, "substantially pure" refers to a purity that allows for the effective use of the protein as a therapeutic composition or diagnostic. For example, an animal being administered dosages of ectoparasite saliva protein isolated from a recombinant cell of the present invention should exhibit no substantial toxicity from contaminants mixed with the protein.

Ectoparasite saliva products substantially free of contaminating material can be isolated using a saliva collection apparatus of the present invention. A saliva collection apparatus of the present invention is designed to stimulate (i.e., cause) ectoparasites retained in the container to feed, and thereby to release saliva, which is collected separate from contaminating material.

Ectoparasites attach and feed from warm-blooded host animals. A host animal, as used herein, refers to an animal that ectoparasites can feed from or on. Without being bound by theory, it is believed that ectoparasites, such as fleas, possess heat receptors which enables the ectoparasite to sense a temperature differential between the warm skin of the host and the ambient air. The temperature differential stimulates (i.e., causes) the ectoparasite to feed from the warm surface (i.e., from the warm animal skin). It is also believed that motion, vibration and darkness can be sensed by ectoparasites, thereby encouraging them to feed. An ectoparasite feeds by penetrating the dermis of an animal with its mouthparts, the mouthparts remaining in that position while the ectoparasite secretes saliva to enhance feeding. During feeding, an ectoparasite can release contaminants such as blood proteins and fecal material.

A saliva collection apparatus of the present invention includes a chamber and housing such that a temperature differential between the chamber and housing of the apparatus is maintained which causes or promotes ectoparasites retained in the housing to attempt to feed from the chamber. When ectoparasites housed in such an apparatus attempt to feed in accordance with the present invention, the arthropods release saliva which is collected in such a manner that proteins, and other products, in the saliva are isolated substantially free of contaminating material. In order to collect saliva substantially free of contaminating material, an apparatus of the present invention also includes a collection means to capture saliva on a surface separate from the surface which captures the contaminating material.

A saliva collection apparatus of the present invention can be used to collect saliva from any ectoparasite such as those disclosed herein. Ectoparasites of the present invention can feed on any animal susceptible to ectoparasite infestation (i.e., a host animal), including but not limited to, a wide variety of vertebrates. Preferred host animals include mammals and birds. More preferred host animals include cats, dogs, humans, horses, rabbits, sheep, cattle, swine, goats, raccoons, ferrets, rats and opossums as well as other pets, economic food animals and animals that are hosts for fleas that infest pets and economic food animals. Particularly preferred host animals are cats and dogs.

Particularly preferred ectoparasites of the present invention from which to collect saliva include any suitable species of flea. Preferred fleas include fleas capable of infesting cats and dogs. Newly hatched fleas (i.e., recently emerged from a pupal state) that have not had a first blood meal are preferred for the following reasons: Because newly emerged fleas have not had a first blood meal, such fleas attempt to feed. Since newly emerged fleas have not had a blood meal, they also do not release as much contaminating material as do fed fleas. Newly emerged fleas live longer without a blood meal than do fleas which have had at least one blood meal. It should be noted that fed fleas can also be used with an apparatus of the present invention.

It will be obvious to one of skill in the art that a saliva collection apparatus of the present invention is useful for collecting saliva from any ectoparasite. For the purpose of illustration, a flea saliva collection apparatus of the present invention is described in detail below. Such description is not intended, in any way, to limit the scope of the present invention. It is within the skill of one in the art to collect saliva from other ectoparasites in a straightforward manner based on methods to collect saliva from fleas.

One embodiment of the present invention is a saliva collection apparatus that includes a chamber and a housing operatively connected to an interface in such a manner that a temperature differential is maintained between the chamber and the housing. The interface includes a collection means and a barrier means positioned such that, in order to attempt to feed, flea mouthparts penetrate the barrier means prior to the collection means. The temperature differential between the chamber and the housing is a difference in temperature suitable to attract fleas retained in the housing to attempt to feed through the interface and, thereby deposit saliva products on the collection means. Due to the relative positioning of the collection means and the barrier means, contaminating material is deposited on the barrier means.

A flea saliva collection apparatus of the present invention includes a housing. A housing can comprise any material capable of retaining fleas that provides structural support and that can be connected to a retaining means. The housing is preferably made of a material capable of withstanding cleaning and/or sterilization procedures commonly used by those skilled in the art. As such, the housing can be reused. Preferred housing materials of the present invention include, but are not limited to, plastic, metal, rubber, wood and glass materials and combinations of such materials. More preferred housing materials include plastic and metal materials with plastic materials being even more preferred. Preferred plastic materials include plexiglass, teflon, nylon and polycarbonate. A particularly preferred plastic material is plexiglass, or other durable, break-resistant plastic, preferably clear so as to allow viewing of fleas inside the container.

In accordance with the present invention, the size of a housing of the present invention is such that the housing can support a desired number of fleas without overcrowding. Both surface area and the volume of the housing can be important. The size of the housing can vary according to the number of fleas to be retained in the housing. Preferably, the size of the housing is sufficient to maintain from about 1,000 fleas to about 6,000 fleas per housing for about 72 hours, more preferably from about 2,000 fleas to about 5,000 fleas per housing for about 72 hours, and even more preferably from about 3,000 fleas to about 4,000 fleas per housing for about 72 hours.

A suitable height for a housing of the present invention is a height that is sufficiently high to allow room for fleas to move about while feeding. The height of a housing for fleas is preferably from about 1.0 centimeters (cm) to about 3.0 cm, more preferably from about 1.5 cm to about 2.5 cm, and even more preferably from about 1.8 cm to about 2.2 cm.

The shape of a housing of the present invention can be any shape having at least one flat surface suitable for feeding by fleas contained within the housing. A housing of the present invention is preferably shaped as a cylinder, a box having four or more sides, a half-dome, or a half cylinder. A particularly preferred shape is a short cylinder.

The diameter of a preferred housing of the present invention can vary widely. Different diameter containers can be used according to, for example, the number of fleas to be placed into the housing without overcrowding. The interior diameter of a rounded housing of the present invention is preferably from about 4.0 cm to about 5.5 cm, more preferably from about 4.5 cm to about 5.5 cm, and even more preferably about 5.0 cm.

According to the present invention, the size, shape, height, and diameter of the housing can vary for different ectoparasites depending upon the size and number of arthropods retained in the housing.

In accordance with the present invention, a housing is operatively connected to a retaining means and an exchange means. As used herein, "operatively connected" refers to combining portions of a saliva collection apparatus of the present invention in such a manner that fleas can be retained within the apparatus and can deposit saliva on the collection means. A retaining means of the present invention is penetrable by the mouthparts of fleas. A retaining means of the present invention can comprise any material or combination of materials that is suitable for retaining fleas and through which fleas can feed (i.e., the retaining means is penetrable by flea mouthparts). As such, the retaining means may comprise a material having openings sufficiently large (i.e., large enough) for flea mouthparts to penetrate, but sufficiently small (i.e., small enough) so as to effectively prevent loss of any fleas retained therein. Preferred retaining means comprise a material having openings of from about 0.25 millimeters (mm) to about 0.50 mm, more preferably having openings of from about 0.30 mm to about 0.50 mm, and even more preferably having openings of from about 0.35 mm to about 0.45 mm. One of skill in the art will recognize that the size of the openings can vary according to the type of ectoparasite retained in the housing of an apparatus. For example, maintenance of particularly small ectoparasites such as, but not limited to, lice may require retaining means having smaller openings. Conversely, a retaining means for hard ticks, which are ectoparasites that cement their mouthparts into the host animal, require larger openings, preferably in the range of about 1 mm.

Preferred materials for use as retaining means include, but are not limited to, metallic mesh, nylon mesh, plastic film, cloth and combinations of such materials. More preferred retaining means include nylon mesh and metal mesh, and an even more preferred retaining means includes nylon mesh. The collection apparatus can be retrofitted with a variety of retaining means. Preferred retaining means are reusable.

An exchange means of the present invention can comprise any material or combination of materials capable of maintaining a permissive environment for fleas within the housing by allowing the exchange of gas, humidity and heat between the interior environment of the housing and the environment exterior to the housing. The housing can be retrofitted with different exchange means having different gas, humidity and heat permeabilities. As used herein, the term gas refers to any atmospheric gases required for flea survival, including, but not limited to, carbon dioxide, oxygen, and nitrogen. Gas can also refer to gaseous products produced by fleas while maintained in a housing of the present invention, such as gaseous products of metabolism including expirations or gases from feces.

Exchange means of the present invention are comprised of materials having openings that are sufficiently large to allow gas, heat and humidity to escape, but sufficiently small so as to effectively prevent loss of fleas. Preferred exchange means comprise a material having openings of from about 0.10 millimeters (mm) to about 0.45 mm, more preferably having openings of from about 0.10 mm to about 0.30 mm, and even more preferably having openings of from about 0.13 mm to about 0.15 mm.

Preferred materials to use as an exchange means include, but are not limited to, metallic mesh, nylon mesh, plastic, cloth and combinations of such materials. More preferred exchange means include nylon mesh, metal mesh, and combinations of such materials and an even more preferred exchange means includes nylon mesh. Preferred exchange materials are reusable.

In accordance with the present invention, an apparatus includes a chamber operatively connected to a housing. A chamber of the present invention is capable of maintaining an internal temperature suitable to create a temperature differential between a housing and a chamber of an apparatus which promotes deposition of saliva by fleas retained in the housing on a collection means of an apparatus. A preferred chamber is also capable of maintaining an internal humidity level suitable for the survival of ectoparasites contained in the apparatus (e.g., suitable to prevent desiccation of the ectoparasites). A chamber of the present invention is also capable of being attached to an artificial feeding system as described in detail in the Examples. A chamber can comprise any material capable of maintaining suitable temperature and humidity levels within the chamber. A chamber is preferably made of a material capable of withstanding cleaning or sterilization procedures commonly used by those skilled in the art. As such, a chamber can be reused. Preferred chamber materials of the present invention include, but are not limited to, glass, plastic, metal, rubber, and wood materials and combinations of such materials. More preferred chamber materials include glass and plastic materials with glass materials being even more preferred.

In accordance with the present invention, the size of a chamber of the present invention is such that the chamber can maintain a suitable temperature level to stimulate fleas to deposit saliva on the collection means of the apparatus. The size of the chamber can vary according to the amount of blotting material (as described in detail below) to be placed in the chamber, the diameter of the collection means to be attached to the chamber or whether the chamber is to be attached to an artificial feeding system as described in detail in the Examples. Preferably, the height of a chamber of the present invention is high enough to allow a suitable amount of blotting material to be placed in the chamber, such that the blotting material maintains a humidity level in the chamber suitable for flea survival. The height of a chamber is preferably from about 1.0 cm to about 7.0 cm, more preferably from about 2.0 cm to about 6.0 cm, and even more preferably from about 3.0 cm to about 5.0 cm.

In accordance with the present invention, the shape of a chamber can be any shape having at least one open end to which an interface of the present invention can be attached. A chamber of the present invention is preferably shaped as a cylinder open at both ends or a cylinder open at one end. A particularly preferred shape is a cylinder open at both ends.

The diameter of a preferred chamber of the present invention can vary widely. Different diameter chambers can be used according to, for example, the diameter of the interface to be attached to the chamber or the diameter of the housing to be attached to the chamber. The interior diameter of a chamber of the present invention is preferably from about 2.0 cm to about 6.5 cm, more preferably from about 3.0 cm to about 5.5 cm, and even more preferably from about 4.0 cm to about 4.5 cm.

A chamber of the present invention can contain a blotting means suitable for maintaining a humidity level in the chamber suitable for flea survival. Methods for maintaining suitable humidity levels are described in detail below. A chamber of the present invention can contain food or water, but preferably is humid (i.e., damp but not wet) and does not contain food.

A saliva collection apparatus of the present invention includes an interface. An interface of the present invention includes means capable of collecting saliva products substantially free of contaminating material. As such, an interface of the present invention is penetrable by flea mouthparts but capable of keeping contaminating material, such as blood and fecal material, separate from flea saliva products secreted by fleas as they attempt to feed. An interface of the present invention comprises a means for collecting saliva products and a means for creating a barrier between contaminating material and collected saliva products.

A collection means of the present invention can be of any material capable of collecting (i.e., adsorbing) at least a portion of saliva proteins deposited (i.e., secreted) by retained fleas that are attempting to feed through the interface. In addition, a collection means of the present invention is capable of collecting saliva components other than saliva proteins deposited by fleas attempting to feed through the interface. The collection means is such that saliva products not only can bind to the collection means but also can be eluted (i.e., extracted) therefrom upon exposure to a suitable eluent (i.e., extractant). As such, preferred collection means materials of the present invention include materials that are hydrophobic and have a low binding capacity since saliva components are easily eluted from such material. The material of a collection means of the present invention should also be capable of being penetrated by the mouthparts of fleas.

Preferred collection means materials of the present invention include, but are not limited to, nylon, nitrocellulose, CM-derivatized, diethylaminoethyl (DEAE)-derivatized, paper, polysulfone, cellulose ester, polytetrafluoroethylene (PTFE) and polyvinylidene fluoride (PVDF) membranes. A particularly preferred anion exchange membrane collection means material includes DE-81 chromatography paper, which can be obtained from Whatman, Inc., Clifton, N.J. Particularly preferred collection means materials include PVDF. A preferred PVDF collection means material includes Durapore™.

The shape of a collection means of the present invention can vary according to the shape of the chamber to which the collection means is to be attached. A preferred shape of a collection means includes, but is not limited to, a round shape or a box-like shape having four or more sides, with a round shape being more preferred.

The size of a collection means of the present invention can also vary according to the size of the chamber to which the collection means is to be attached. The size of a collection means is preferably larger than the open end of a chamber, thereby preventing the collection means from passing into the chamber. The size of a collection means is preferably from about 2.2 cm to about 6.5 cm in diameter, more preferably from about 3.2 cm to about 5.7 cm, and even more preferably from about 4.2 cm to about 4.7 cm.

A saliva collection apparatus of the present invention provides for a novel barrier means which enables collection of ectoparasite saliva substantially free of contaminating material. A barrier means of the present invention can be any material capable of substantially preventing contaminating material from contacting the collection means (i.e., substantially prevents the passage of contaminating material such as flea fecal material and blood products through the collection means), but is also capable of being penetrated by the mouthparts of fleas and of allowing the passage of saliva through the barrier means. Preferably, the thickness of a barrier means material of the present invention is microns thick. Preferred barrier means materials of the present invention include, but are not limited to, very thin plastic, teflon, cloth, paper, paraffin and wax materials. More preferred barrier means materials of the present invention include stretched plastic, with Saran Wrap™ and particularly Parafilm™, stretched very thin (i.e., as thin as can be stretched by machine and/or hand), being even more preferred.

The size of a barrier means of the present invention can vary according to the size of the chamber to which the barrier means is to be attached. The size of the barrier means preferably is sufficiently large that the barrier means can extend up the sides of a chamber of the present invention, thereby enabling the barrier means to be secured to the chamber. The size of the barrier means is sufficiently small such that the barrier means does not interfere with, for example, the ability of the saliva collection apparatus containing the chamber to be attached to an artificial feeding system.

According to the present invention, a collection means and a barrier means are operatively connected to a chamber of a saliva collection apparatus in such a manner that fleas retained in the housing of such apparatus are capable of penetrating both the barrier means and the collection means to deposit saliva on the collection means. A collection means of the present invention preferably is removably attached to a site on a chamber by a barrier means. A preferred site of attachment of a collection means and a barrier means is the portion of a chamber designed to interface with a housing. A more preferred site of attachment of a collection means and a barrier means is the open end of a chamber.

A saliva collection apparatus of the present invention can also include a blotting means. A blotting means of the present invention is capable of maintaining a humidity within the apparatus suitable for flea survival and, as such, is capable of retaining liquid for the period of time fleas are retained in the apparatus. As such, a blotting means can be any suitable absorbent material. Preferred blotting means include natural and synthetic sponges, foam, paper, cloth, and agarose. More preferred blotting means material include sponges and paper, with filter paper being even more preferred. In a particularly preferred embodiment, one or more pieces of VWR Blotting Pads #320 (available from VWR Scientific, Denver, Colo.) comprise a blotting means.

As stated above, a saliva collection apparatus of the present invention is capable of maintaining a temperature differential between a housing and a chamber of the apparatus. A suitable temperature differential within an apparatus of the present invention includes a temperature differential which stimulates fleas retained in the apparatus to penetrate the interface of the apparatus and deposit saliva on the collecting means. Preferred temperatures in a chamber of the present invention range from about 20° C. to about 45° C., whereas preferred temperatures in a housing of the present invention range from about 5° C. to about 35° C. In a preferred embodiment, the temperature in the chamber ranges from about 35° C. to about 40° C. and the temperature in the housing ranges from about 10° C. to about 30° C. A particularly preferred chamber temperature ranges from about 35° C. to about 37° C.; and a particularly preferred housing chamber temperature is from about 20° C. to about 27° C.

The survival of ectoparasites can be affected by humidity. As such, the humidity level in a housing of an apparatus of the present invention is suitable for maintaining the survival of ectoparasites retained therein. Suitable relative humidity levels within an apparatus of the present invention can vary depending upon the ectoparasite contained within the apparatus. As used herein, relative humidity refers to the degree of atmospheric water vapor relative to the maximum degree of atmospheric water vapor that results in precipitation. Thus, relative humidity is expressed in percent humidity, wherein 100% humidity represents saturation of atmospheric water vapor. Preferred humidity levels in a chamber of the present invention range from about 50% to about 100%, whereas preferred humidity levels in a housing of the present invention range from about 40% to about 60%. In a preferred embodiment, the humidity levels in the chamber ranges from about 50% to about 94% and the humidity level in the housing is about 50%.

Another embodiment of the present invention is the use of contrasting colors to attract fleas. For example, at least one surface of a collection apparatus of the present invention can be of a color sufficiently dark to attract fleas to penetrate the interface of the apparatus. Without being bound by theory, it is believed that fleas are capable of sensing light from dark and preferably tend to feed towards a dark surface. Therefore, according to the present invention, a chamber can be darker than a housing, thereby attracting fleas to the interface between the chamber and the housing. Suitable dark colors include colors ranging from black to light brown, preferably black.

Figure 4A:
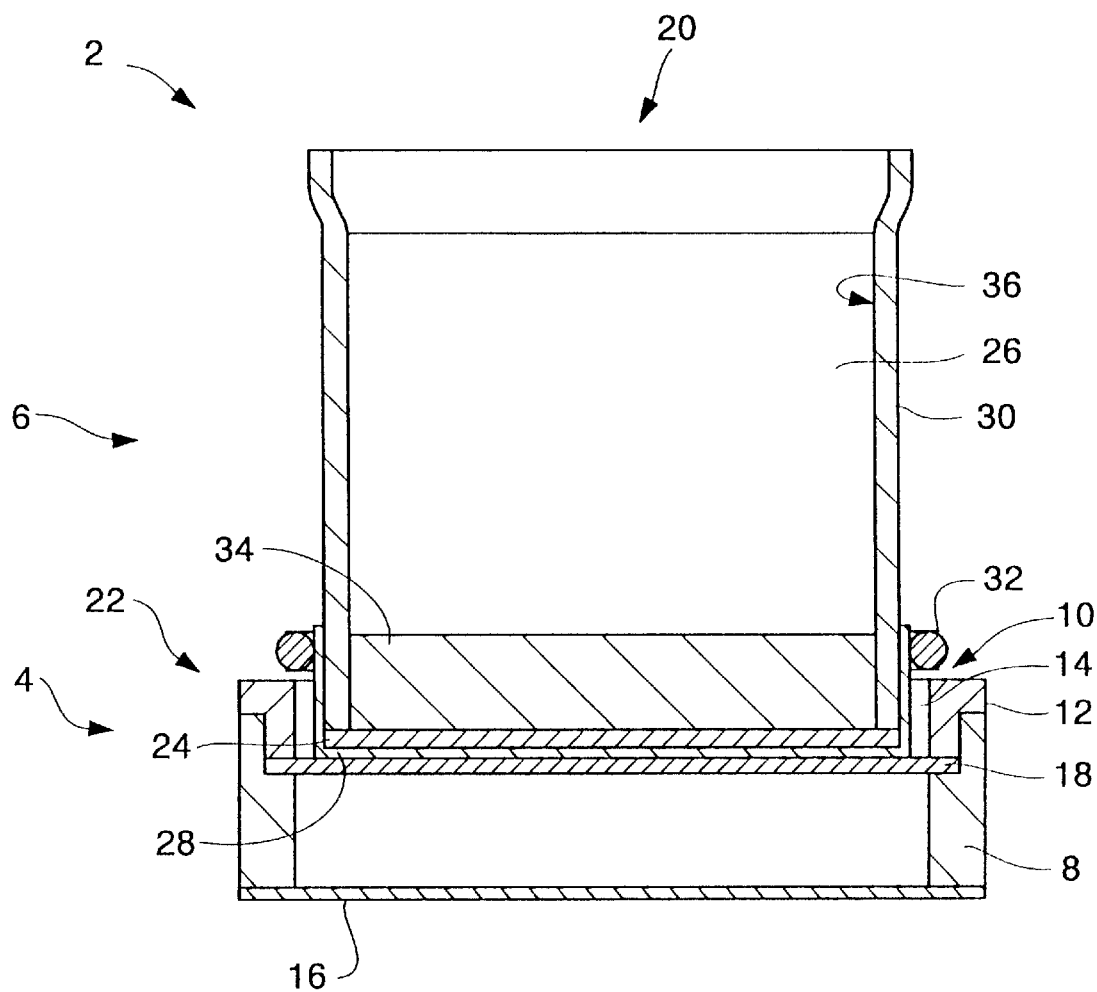
FIG. 4A illustrates a cross-section of a flea saliva collection apparatus of the present invention.
Figure 4B:
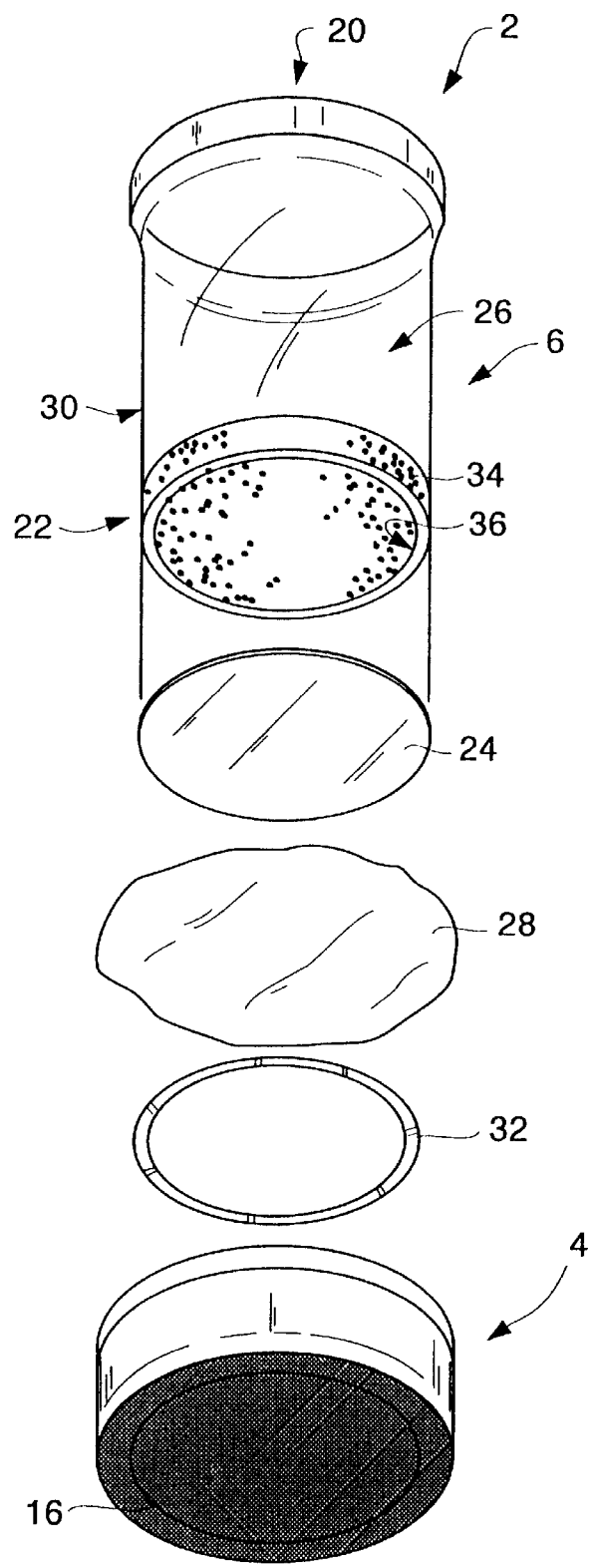
FIG. 4B illustrates a blow-out of a flea saliva collection apparatus of the present invention.

A preferred embodiment of a collection apparatus of the present invention is depicted in FIGS. 4A and 4B. A saliva collection apparatus (2) is separable into a housing (4) and a chamber (6). A cross-section of a saliva collection apparatus of the present invention (2) is shown in FIG. 4A. Referring to FIGS. 4A and 4B, the housing (4) has an open-ended cylinder having a first portion (8) and a second portion (10). The second portion (10) of the housing (4) has an outer diameter (12) and an inner diameter (14). An exchange means (16) is operatively attached to one end of the first portion (8) of the housing (4) and a retaining means (18) is attached at the opposite end of the first portion (8), between the first portion (8), and the outer diameter (12) and inner diameter (14) of the second portion (10). The exchange means (16) and retaining means (18) are attached in a manner that prevents fleas from escaping. Means of attaching an exchange means (16) and a retaining means (18) to the first portion (8) of the housing (4) include, but are not limited to, rubber cement, glue, tape, solder and araldite. A preferred means of attachment is rubber cement.

The chamber (6) of the saliva collection apparatus (2) has an open ended cylinder having a top end (20) and a bottom end (22). The top end (20) has a suitable diameter to enable the attachment of the chamber (6) to an artificial feeding system such as that described in detail in the Examples. The bottom end (22) has a suitable diameter such that the bottom end (22) can be reversibly attached to the housing (4) in such a manner as to provide a sliding fit. The bottom end (22) is covered by a collection means (24). The collection means (24) has a larger diameter than the inner circumference of the bottom end (22) of the chamber (6), thereby preventing the collection means (24) from passing into the inner space (26) of the chamber (6). Preferably, the diameter of the collection means (24) is not greater than the outer circumference of the bottom end (22) of the chamber (6). The collection means (24) can be connected to the bottom end (22) in order to provide a detachable connection, thereby facilitating removal of the collection means (24) from the saliva collecting apparatus (2) to recover saliva products from the collection means (24).

A collection means (24) attached to the bottom end (22) of a chamber (6) is covered by a barrier means (28). The barrier means (28) is operatively connected to a chamber (6) in such a manner that a seal is formed preventing contact of the collection means (24) by contaminating material deposited by fleas. The barrier means (28) can be connected to the chamber (6) in order to provide a detachable connection. Preferably, the barrier means (28) comprises a stretchable plastic material, such as Parafilm™, which is stretched as thin as possible across a collection means (24) contacting the bottom end (22) of a chamber (6) and further stretched along the sidewall (30) of the chamber (6) towards the top end (20) of the chamber (6). The barrier means (28) can be further secured to the sidewall (30) of the chamber (6) using a rubber seal (32). The rubber seal (32) detachably connects the portion of the barrier means (28) which meets the sidewall (30) of the chamber (6), thereby further securing the collection means (24) to the chamber (6) and seal in the chamber (6) environment.

Blotting (absorbent) material can be placed in the inner space (26) at the bottom end (22) of a chamber (6) to form a blotting means (34). The blotting means (34) can comprise one or more individual blotting pads (e.g., pieces of blotting material). Preferably, the blotting means (34) is from about 2.0 mm thick to about 15.0 mm thick (when dry) when placed in a 47 cm high chamber (6), more preferably is from about 2.2 mm thick to about 12.5 mm thick (when dry) when placed in a 47 mm high chamber (6), and even more preferably is from about 2.45 mm thick to about 10.0 mm thick (when dry) when placed in a 47 mm high chamber (6). In a particularly preferred embodiment, the blotting means (34) comprises from about 2 to 6 pieces of VWR Blotting Pads #320, and preferably from about 3 to 5 pieces of VWR Blotting Pads #320. The diameter of the blotting means (34) is selected to contact the inner sidewall (36) of the chamber (6). The blotting means (34) is preferably sufficiently pre-wetted to provide humidity to the chamber (6) but not so wet that liquid drips from the blotting means (34). The blotting means (34) is juxtaposed to the side of the collection means (24) facing the top end (20) of the chamber (6). The blotting means (34) can directly contact the collection means (24) in a detachable manner.

The chamber (6) is reversibly separable from the housing (4). The chamber (6) can be interconnected to the housing (4) in any reversibly secure manner such as sliding, snapping or screwing together. Preferably, the chamber (6) slides into the housing (4) and is secured using rubber bands.

The relative height dimensions of the chamber (6) can vary relative to the housing (4). Typically, the height dimension of the chamber (6) is greater than the housing (4). Preferably, the height of the chamber (6) ranges from about 1.0 cm to about 7.0 cm, more preferably from about 2.0 cm to about 6.0 cm, and even more preferably the from about 3.0 cm to about 5.0 cm. The height of the housing (4) preferably ranges from about 1.0 cm to about 3.0 cm, more preferably from about 1.5 cm to about 2.5 cm, and even more preferably from about 1.8 cm to about 2.2 cm.

One embodiment of the present invention is a method to collect saliva products from ectoparasites using an apparatus of the present invention. Such a method is particularly advantageous because it enables isolation of ectoparasite saliva, including saliva proteins, substantially free of contaminating material. As such, the method can be used, for example, to characterize ectoparasite saliva proteins and to isolate ectoparasite saliva proteins for diagnostic and therapeutic use.

One embodiment of the present method includes the steps of: (a) collecting ectoparasite saliva products on a collection means within a saliva collection apparatus which contains ectoparasites in the housing of the apparatus; and (b) extracting (i.e., eluting) the collected ectoparasite saliva products from the collection means with a solution to form an extracted product-containing solution. Such an extracted solution can be used directly as a formulation of the present invention or can be submitted to further steps of fractionation and/or purification as described in detail herein, to form additional formulations of the present invention. Examples of such extracted solutions include FS-1, FS-2 and FS-3.

In accordance with the present invention, a saliva collection apparatus containing the ectoparasites has an interface between the chamber and the housing comprising a collection means capable of collecting at least a portion of saliva products deposited by ectoparasite retained in the apparatus and a barrier means capable of substantially preventing contaminating material from contacting the collection means. The ectoparasites contained in the apparatus are maintained under conditions such that there is a temperature differential between the chamber and the housing; that is, the chamber of the apparatus has a temperature warmer than the temperature of the housing containing the ectoparasite, such that the warmer temperature in the chamber attracts the ectoparasites retained in the housing to attempt to penetrate the barrier means and collection means, thereby depositing saliva products on the collection means.

In one embodiment, the method of collecting saliva products includes pre-wetting a collection means of the present invention prior to positioning the collection means in an apparatus of the present invention. A pre-wetting solution suitable for the present invention is capable of facilitating the adsorption (i.e., collection) of saliva products in such a manner that the products can also be extracted during an extraction step (i.e., when exposed to an appropriate solvent). A suitable pre-wetting solution of the present invention includes any buffer that is non-toxic to ectoparasites and has a physiological pH. Examples of suitable buffers include, phosphate buffered saline, water, phosphate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). A preferred prewetting solution includes sterile water containing 50 U/ml penicillin and 50 $\mu$g/ml streptomycin.

When an apparatus used to collect saliva products includes a blotting means, that blotting means should be moistened either prior to or following placement of the blotting means into the chamber. Preferred moistening solutions include, but are not limited to, water, phosphate buffered saline, phosphate buffer, tris buffer, HEPES buffer, TEA buffer and TES buffer. More preferred moistening solutions include water and 50 U/ml penicillin and 50 $\mu$g/ml streptomycin. According to the present invention, a blotting means is sufficiently moistened to produce humidity in a chamber but not to drip liquid from which ectoparasites retained in the apparatus can drink. In a preferred embodiment, a blotting means which is about 4.0 cm in diameter and about 2.5 mm thick is moistened with about 2.3 milliliters (ml) of moistening solution.

In one embodiment, a pre-determined number of ectoparasites are introduced into the housing of an apparatus of the present invention. The number of ectoparasites to be introduced into a housing can vary with the size of the housing and should be a number that will not hinder the ability of an ectoparasite to deposit saliva on a collection means of the present invention.

In a preferred embodiment of the present invention, fleas are added to an apparatus of the present invention. Suitable and preferred numbers of fleas to introduce into a housing are heretofore disclosed. In particular, fleas newly emerged from the pupal stage are used. Such fleas can be raised as described in Wade et al., pp 186–190, 1988, *J. Med Entomol.*, vol 25. Preferably, such fleas have not had a blood meal. Fleas can be loaded into an apparatus by placing the fleas in an aquarium and aspirating them into the housing under vacuum. Additional optional components suitable for the maintenance of fleas can be added to the container, such as animal hair, and dry tissue.

In a preferred embodiment, at least one apparatus of the present invention having fleas contained in the housing of the apparatus is attached to an artificial feeding system such as disclosed herein. The apparatus can remain attached to the feeding system as long as fleas continue to release saliva while penetrating a collection means. Preferably, fleas are maintained in the apparatus attached to the feeding system from about 12 hours to about 120 hours, more preferably from about 24 hours to about 96 hours, and even more preferably for about 72 hours since fleas essentially stop secreting saliva by about that time. In accordance with the method of the present invention, preferably at least about 80 micrograms ($\mu$g), more preferably at least about 90 $\mu$g and even more preferably at least about 200 $\mu$g, of flea saliva protein can be collected from about $10^6$ flea-hour when measured using a Bio-Rad Bradford assay (available from Bio-Rad, Hercules, Calif.).

According to the present invention, ectoparasite saliva products can be extracted using a solvent capable of extracting saliva products from a collection means of the present invention, preferably in a form such that the functional activities of the eluted products are maintained. If functional activity of flea saliva proteins, for example is not maintained, it is within the scope of the invention to refold proteins to regain functionality using techniques known to those of skill in the art. Suitable extraction solvents include, but are not limited to, phosphate buffered saline, phosphate buffered saline containing sodium chloride, TFA in acetonitrile, chaotropic agents, detergents, organics, salts or combinations thereof. Preferred extraction solvents include phosphate buffered saline, phosphate buffered saline containing sodium chloride, acetonitrile and TFA in acetonitrile. More preferred extraction solvents include 1 M NaCl in phosphate buffered saline, 0.1% TFA in 50% acetonitrile, 1% TFA in 50% acetonitrile, 12.8% acetonitrile and 50% acetonitrile. Suitable extraction times for eluting proteins and other products from a collection means are described in detail in the Examples.

Further purifications of saliva proteins extracted from a collection means of the present invention can be performed by fractionating the extracted product-containing solution to obtain separated peak fractions and recovering at least one of the peak fractions substantially free of the remaining fractions to obtain a formulation of ectoparasite saliva proteins. In a preferred embodiment, proteins contained in extracted saliva products of the present invention are further resolved by submitting the extract to HPLC purification to obtain peak fractions. In a particularly preferred embodiment, extracted saliva proteins of the present invention are further resolved by HPLC to obtain the peak fractions shown in FIG. 2. Details regarding the extraction and resolution of such proteins are presented in the Examples.

According to the present invention, a formulation comprising at least one ectoparasite saliva product of the present invention or a mimetope thereof, can be used to identify animals that are susceptible to or have allergic dermatitis.

In accordance with the present invention, a "mimetope" refers to any compound that is able to mimic the ability of an isolated ectoparasite saliva product of the present invention to carry out its function (e.g., anti-coagulation, anti-complement, vasodialators, proteases, acid phosphatases or detecting and/or treating the hypersensitivity of an animal susceptible to or having allergic dermatitis). A mimetope can be a peptide that has been modified to decrease its susceptibility to degradation but that still retains the desired activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. Mimetopes of the present invention can also include non-proteinaceous portions of ectoparasite saliva products having allergenic and/or antigenic activity (e.g., carbohydrate moieties associated with ectoparasite saliva proteins). A mimetope can be obtained by, for example, screening libraries of synthetic compounds for compounds capable of altering the ability of ectoparasites to feed, or of detecting and/or treating allergic dermatitis resulting from the bites of ectoparasites. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

One embodiment of the present invention is an in vivo test that is capable of detecting whether an animal is hypersensitive to ectoparasite saliva products. An in vivo test of the present invention can initially be used to determine if an animal is hypersensitive to ectoparasite saliva products and then used to determine if an animal is hypersensitive to a particular ectoparasite saliva component, in particular to an ectoparasite saliva protein. An in vivo hypersensitivity test of the present invention is particularly useful for identifying animals susceptible to or having allergic dermatitis. An in vivo hypersensitivity test of the present invention is even more useful for identifying animals susceptible to or having FAD. A suitable in vivo hypersensitivity test of the present invention can be, but is not limited to, a skin test comprising administering (e.g., intradermally injecting or superficial scratching) an effective amount of a formulation containing at least one ectoparasite saliva product, or a mimetope thereof. Methods to conduct skin tests of the present invention are known to those of skill in the art and are briefly disclosed herein.

Suitable formulations to use in an in vivo skin test include ectoparasite saliva components (i.e., saliva products collected on, and remaining absorbed to, a collection means of the present invention, ectoparasite saliva extracts, and one or more isolated ectoparasite saliva proteins). A preferred formulation includes extracts and one or more isolated proteins.

A suitable amount of ectoparasite saliva product for use in a skin test of the present invention can vary widely depending on the allergenicity of the product used in the test and on the site at which the product is delivered. Suitable amounts of ectoparasite saliva products for use in a skin test of the present invention include an amount capable of forming reaction, such as a detectable wheal or induration (hardness) resulting from an allergic reaction to the product. Preferred amounts of ectoparasite saliva extracts or proteins for use in a skin test of the present invention range from about 1 nanogram (ng) to about 500 micrograms ($\mu$g), more preferably from about 5 ng to about 300 $\mu$g, and even more preferably from about 10 ng to about 50 $\mu$g of ectoparasite saliva extracts or proteins. It is to be appreciated by those of skill in the art that such amounts will vary depending upon the allergenicity of the extracts and/or protein(s) being administered.

According to the present invention, ectoparasite saliva products of the present invention can be combined with an immunopotentiator (e.g., carriers or adjuvants of the present invention as defined in detail below). A novel aspect, however, of the present invention is that an ectoparasite saliva product of the present invention can induce a hypersensitive response in the absence of an immunopotentiator.

A skin test of the present invention further comprises administering a control solution to an animal. A control solution can include a negative control solution and/or a positive control solution. A positive control solution of the present invention contains an effective amount of at least one compound known to induce a hypersensitive response when administered to an animal. A preferred compound for use as positive control solution includes, but is not limited to, histamine. A negative control solution of the present invention can comprise a solution that is known not to induce a hypersensitive response when administered to an animal. As such, a negative control solution can comprise a solution having compounds essentially incapable of inducing a hypersensitive response or simply a buffer used to prepare the formulation, such as saline. An example of a preferred negative control solution is phenolated phosphate buffered saline (available from Greer Laboratories, Inc., Lenoir, N.C.).

Hypersensitivity of an animal to one or more formulations of the present invention can be evaluated by measuring reactions (e.g., wheal size, induration or hardness; using techniques known to those skilled in the art) resulting from administration of one or more experimental sample(s) and control sample(s) into an animal and comparing the reactions to the experimental sample(s) with reactions resulting from administration of one or more control solution. Preferred devices for intradermal injections include individual syringes. Preferred devices for scratching include devices that permit the administration of a number of samples at one time. The hypersensitivity of an animal can be evaluated by determining if the reaction resulting from administration of a formulation of the present invention is larger than the reaction resulting from administration of a negative control, and/or by determining if the reaction resulting from administration of the formulation is at least about the same size as the reaction resulting from administration of a positive control solution. As such, if an experimental sample produces a reaction greater than or equal to the size of a wheal produced by administration of a positive control sample to an animal, then that animal is hypersensitive to the experimental sample. Conversely, if an experimental sample produces a reaction similar to the reaction produced by administration of a negative control sample to an animal, then that animal is not hypersensitive to the experimental sample.

Preferred wheal sizes for evaluation of the hypersensitivity of an animal range from about 16 mm to about 8 mm, more preferably from about 15 mm to about 9 mm, and even more preferably from about 14 mm to about 10 mm in diameter.

Preferably, the ability or inability of an animal to exhibit an immediate hypersensitive response to a formulation of the present invention is determined by measuring wheal sizes from about 2 minutes to about 30 minutes after administration of a sample, more preferably from about 10 minutes to about 25 minutes after administration of a sample, and even more preferably about 15 minutes after administration of a sample.

Preferably, the ability or inability of an animal to exhibit a delayed hypersensitive response to a formulation of the present invention is determined by measuring induration and/or erythema from about 18 hours to about 30 hours after administration of a sample, more preferably from about 20 hours to about 28 hours after administration of a sample, and even more preferably at about 24 hours after administration of a sample. A delayed hypersensitivity response can also be measured using other techniques such as by determining, using techniques known to those of skill in the art, the extent of cell infiltrate at the site of administration during the time periods defined directly above.

In a preferred embodiment, a skin test of the present invention comprises intradermally injecting into an animal at a given site an effective amount of a formulation that includes flea saliva extracts (i.e., flea saliva products extracted from a collection means of the present invention) or at least one flea saliva protein of the present invention, and intradermally injecting an effective amount of a control solution into the same animal at a different site. It is within the scope of one of skill in the art to use devices capable of delivering multiple samples simultaneously at a number of sites, preferably enabling concurrent evaluation of numerous formulations. One preferred formulation comprises flea saliva products collected in accordance with the present invention. Also preferred are formulations comprising one or more recombinantly produced flea saliva proteins.

Suitable flea saliva products for use with a skin test of the present invention include FS-1, FS-2 and/or FS-3 as well as at least a portion of at least one flea saliva product that can be isolated from FS-1, FS-2 and/or FS-3. A preferred flea saliva product for use with a skin test includes FS-1, FS-2, FS-3 and/or at least a portion of one or more of the proteins fspA, fspB, fspc1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM (F), fspM(G), fspM(H), fspM(I), fspM(J), fspM(K), fspM (L), fspM(M), fspN(B), fspN(C), fspN(D), fspN(E), fspN (F), fspN(G), fspN(H), fspN(I), fspN(J), fspN(K), fspN(L), fspN(M), fspN(N) and fspN(O), or homologues thereof. A more preferred flea saliva product for use with a skin test includes FS-1, FS-2, FS-3 and/or at least a portion of one or more of the proteins fspE, fspF, fspG1, fspG2, fspG3, fspG4, fspH, fspI, fspJ1, fspJ2, fspK, fspL1, fspL2, fspM1, fspM2, fspN1, fspN2 and fspN3. A yet more preferred flea saliva product for use with a skin test includes FS-1, FS-2, FS-3 and/or at least a portion of one or more of the proteins fspG1, fspG2, fspG3, fspG4, fspH, fspM1, fspM2, fspN1, fspN2 and fspN3. Such formulations are shown in the Examples section as being able to induce FAD in dogs. A preferred positive control sample can be a sample comprising histamine. A preferred negative control sample can be a sample comprising diluent.

Animals suitable and preferred to test for hypersensitivity to ectoparasite saliva proteins using a skin test of the present invention are disclosed herein. Particularly preferred animals to test with a skin test of the present invention include dogs, cats and horses, with dogs and cats being even more preferred.

Another embodiment of the present invention is an in vitro immunoabsorbent test that is capable of detecting the presence of an antibody capable of binding to one or more ectoparasite saliva products of the present invention by contacting a putative antibody-containing solution with a solution containing ectoparasite saliva products in such a manner that immunocomplexes can form and be detected. Thus, an in vitro immunoabsorbent test of the present invention is particularly useful for identifying animals susceptible to or having allergic dermatitis by demonstrating that an animal has been previously exposed to an ectoparasite saliva antigen and, therefore may be hypersensitive to further exposure to an ectoparasite saliva antigen.

According to the present invention, an in vitro hypersensitivity test of the present invention can be, but is not limited to, an immunoabsorbent test comprising: (a) contacting a formulation of the present invention with a body fluid from an animal under conditions sufficient for formation of an immunocomplex between the formulation and antibodies, if present, in the body fluid; and (b) determining the amount of immunocomplex formed, wherein formation of the immunocomplex indicates that the animal is susceptible to or has allergic dermatitis. The immunoabsorbent test is particularly useful for the detection of IgE antibodies in the body fluid, thereby indicating immediate hypersensitivity in the animal. Determining the amount of iminmunocomplex formed can include the step of separating depending on the mode of detection. Immunoabsorbent assays can be a variety of protocols and can be set-up by those of skill in the art.

A preferred immunoabsorbent test of the present invention comprises a first step of coating one or more portions of a solid substrate with a suitable amount of one or more ectoparasite saliva products of the present invention or a mimetope thereof, and of coating one or more other portions of the (or another) solid substrate with a suitable amount of positive and/or negative control solutions of the present invention. A preferred solid substrate of the present invention can include, but is not limited to, an ELISA plate, a dipstick, a radioimmunoassay plate, agarose beads, plastic beads, immunoblot membranes and paper; a more preferred solid substrate includes an ELISA plate, a dipstick or a radioimmunoassay plate, with an ELISA plate and a dipstick being even more preferred. As used herein, a dipstick refers to any solid material having a surface to which antibodies can be bound, such solid material having a stick-like shape capable if being inserted into a test tube. Suitable and preferred flea saliva products for use with an in vitro hypersensitivity test of the present invention are as disclosed for a skin test of the present invention.

A second step of a preferred in vitro hypersensitivity test of the present invention comprises contacting the coated substrate with a body fluid, such as serum, plasma or whole blood, from an animal susceptible to allergic dermatitis in such a manner as to allow antibodies contained in the body fluid that are capable of binding to ectoparasite saliva products to bind to such products bound to the substrate to form immunocomplexes. Excess body fluid and antibodies are then washed from the substrate. In a preferred embodiment in which IgE antibodies in the body fluid are to be measured, the body fluid can be pretreated to remove at least some of the other isotypes of immunoglobulin and/or other proteins, such as albumin, present in the fluid. Such removal can include, but is not limited to, contacting the body fluid with a material, such a Protein G, to remove IgG antibodies and/or affinity purifying the IgE antibodies from other components of the body fluid by exposing the fluid to, for example, Concanavalin A (Con-A).

A third step of a preferred in vitro hypersensitivity test of the present invention comprises contacting the immunocomplexes bound to the substrate with a compound capable of binding to the immunocomplexes, such as a secondary antibody or other compound that is capable of binding to the heavy chain of allergy-related antibodies produced by animals allergic to ectoparasites, in such a manner that the compound(s) can bind to the immunocomplexes. Preferred binding compounds include, but are not limited to, secondary antibodies capable of binding to the heavy chain of IgE antibodies and Fc receptors (FcR) that bind to IgE antibodies (i.e., epsilon FcR), including single chains of an FcR (e.g., the alpha chain of an epsilon FcR), as well as truncated forms with or without transmembrane domains. Preferred animals to test are disclosed herein. Compounds capable of binding to immunocomplexes are usually tagged with a label which enables the amount of compound bound to the antibody from the body fluid to be measured. Such labels include, but are not limited to, a radioactive label, an enzyme capable of producing a color reaction upon contact with a substrate, a fluorescent label, a chemiluminescent label, a chromophoric label or a compound capable of being bound by another compound. Preferred labels include, but are not limited to, fluorescein, radioisotopes, alkaline phosphatases, biotin, avidin, or peroxidases.

A fourth step of a preferred in vitro hypersensitivity test of the present invention comprises measuring the amount of detectable label bound to the solid substrate using techniques known to those of skill in the art. It is within the scope of the present invention that the amount of antibody from the body fluid bound to the substrate can be determined using one or more layers of secondary antibodies or other binding compounds. For example, an untagged secondary antibody can be bound to a serum antibody and the untagged secondary antibody can then be bound by a tagged tertiary antibody.

A hypersensitive animal is identified by comparing the level of immunocomplex formation using samples of body fluid with the level of immunocomplex formation using control samples. An immunocomplex refers to a complex comprising an antibody and its ligand (i.e., antigen). As such, immunocomplexes form using positive control samples and do not form using negative control samples. As such, if a body fluid sample results in immunocomplex formation greater than or equal to immunocomplex formation using a positive control sample, then the animal from which the fluid was taken is hypersensitive to the ectoparasite saliva product bound to the substrate. Conversely, if a body fluid sample results in immunocomplex formation similar to immunocomplex formation using a negative control sample, then the animal from which the fluid was taken is not hypersensitive to the ectoparasite saliva product bound to the substrate.

A preferred embodiment of an in vitro hypersensitivity test of the present invention comprises the steps of: (a) contacting an ELISA plate, which is coated with a suitable amount of flea saliva extract, including FS-1, FS-2, FS-3 and/or one or more flea saliva proteins, with serum, plasma or whole blood from an animal being tested for susceptibility to allergic dermatitis; and (b) identifying whether immunocomplexes are formed by step (a) by assaying for the presence of such immunocomplexes by (i) contacting the plate with an antibody that specifically binds to IgE or other compounds capable of binding to such immunocomplexes, such as an epsilon Fc receptor, and (ii) determining whether such an antibody or other compound is bound thereto. It should be noted that citing of specific embodiments does not preclude the use of a variety of other immunoassay protocols, including those in which a compound that binds IgE is coated onto a substrate; the substrate is then contacted with serum, plasma or whole blood; and binding of IgE by the compound is detected by the ability to bind flea saliva extracts or proteins of the present invention.

One embodiment of the present invention is a kit useful for identification of an animal susceptible to or having allergic dermatitis. As used herein, a suspect animal is an animal to be tested. A kit of the present invention comprises a formulation of the present invention and a means for determining if an animal is susceptible to or has allergic dermatitis, in which the formulation is used to identify animals susceptible to or having allergic dermatitis. A means for determining if an animal is susceptible to or has allergic dermatitis can include an in vivo or in vitro hypersensitivity test of the present invention as described in detail above. A kit of the present invention further comprises at least one control solution such as those disclosed herein.

A preferred kit of the present invention comprises the elements useful for performing an immunoassay. A kit of the present invention can comprise one or more experimental samples (i.e., formulations of the present invention) and one or more control samples bound to at least one pre-packed dipstick or ELISA plate, and the necessary means for detecting immunocomplex formation (e.g., labelled secondary antibodies or other binding compounds and any necessary solutions needed to resolve such labels, as described in detail above) between antibodies contained in the bodily fluid of the animal being tested and the proteins bound to the dipstick or ELISA plate. It is within the scope of the invention that the kit can comprise simply a formulation of the present invention and that the detecting means can be provided in another way.

An alternative preferred kit of the present invention comprises elements useful for performing a skin test. A kit of the present invention can comprise at least one pre-packed syringe and needle apparatus containing one or more experimental samples and/or one or more control samples.

It is within the scope of the present invention that two or more different in vivo and/or in vitro tests can be used in combination for diagnostic purposes. For example, the immediate hypersensitivity of an animal to an ectoparasite saliva allergen can be tested using an in vitro immunoabsorbent test capable of detecting IgE antibodies specific for an ectoparasite saliva allergen in the animal's bodily fluid. While most animals that display delayed hypersensitivity to an ectoparasite saliva allergen also display immediate hypersensitivity to the allergen, a small number of animals that display delayed hypersensitivity to an allergen do not display immediate hypersensitivity to the allergen. In such cases, following negative results from the IgE-specific in vitro test, the delayed hypersensitivity of the animal to an ectoparasite saliva allergen can be tested using an in vivo test of the present invention.

Another aspect of the present invention includes treating animals susceptible to or having allergic dermatitis, with a formulation of the present invention. According to the present invention, the term treatment can refer to the regulation of a hypersensitive response by an animal to bites from ectoparasites. Regulation can include, for example, immunomodulation of cells involved in the animal's hypersensitive response or alteration of the ability of an ectoparasite to introduce allergens into an animal, for example by inhibiting the anti-coagulation activity of a saliva enzyme, thereby impairing the ability of the arthropod to penetrate the dermis of an animal and feed. Immunomodulation can include modulating the activity of molecules typically involved in an immune response (e.g., antibodies, antigens, major histocompatibility molecules (MHC) and molecules co-reactive with MHC molecules). In particular, immunomodulation refers to modulation of antigen:antibody interactions resulting in inflammatory responses, immunosuppression, and immunotolerization of cells involved in a hypersensitive response. Immunosuppression refers to inhibiting an immune response by, for example, killing particular cells involved in the immune response. Immunotolerization refers to inhibiting an immune response by anergizing (i.e., diminishing reactivity of a T cell to an antigen) particular cells involved in the immune response. Suitable and preferred ectoparasites against which to treat an animal are disclosed herein. A particularly preferred formulation of the present invention is used to treat FAD.

One embodiment of the present invention is a therapeutic composition that, when administered to an animal in an effective manner, is useful for immunomodulating the immune response of the animal (i.e., immunomodulating the animal) so as to block (i.e., to inhibit, reduce or substantially prevent) a hypersensitive response by the animal upon subsequent exposure to allergenic components transmitted through bites from ectoparasites. Such a therapeutic composition is useful for immunomodulating animals known to be hypersensitive to ectoparasite saliva products and animals susceptible to hypersensitive responses against ectoparasite saliva products.

One embodiment of the present invention is a therapeutic composition that includes de-sensitizing compounds capable of inhibiting an immune response to an ectoparasite saliva product of the present invention. Such de-sensitizing compounds include blocking compounds, toleragens and/or suppressor compounds. Blocking compounds comprise compounds capable of modulating antigen:antibody interactions that can result in inflammatory responses, toleragens are compounds capable of immunotolerizing an animal, and suppressor compounds are capable of immunosuppressing an animal. A de-sensitizing compound of the present invention can be soluble or membrane-bound. Membrane-bound de-sensitizing compounds can be associated with biomembranes, including cells, liposomes, planar membranes, cochleates or micelles. A soluble de-sensitizing compound of the present invention is useful for: (1) inhibiting a Type I hypersensitivity reaction by blocking IgE:antigen mediated de-granulation of mast cells; (2) inhibiting a Type III hypersensitivity reaction by blocking IgG:antigen complex formation leading to complement destruction of cells; and (3) inhibiting a Type IV hypersensitivity reaction by blocking T helper cell stimulation of cytokine secretion by macrophages. A membrane-bound de-sensitizing compound of the present invention is useful for: (1) inhibiting a Type II hypersensitivity reaction by blocking IgG:antigen complex formation on the surface of cells leading to complement destruction of cells; (2) inhibiting a Type II hypersensitivity reaction by blocking IgG regulated signal transduction in immune cells; and (3) inhibiting a Type IV hypersensitivity reaction by blocking T cytotoxic cell killing of antigen-bearing cells.

A de-sensitizing compound of the present invention can also be covalently linked to a ligand molecule capable of targeting the de-sensitizing compound to a specific cell involved in a hypersensitive response to ectoparasite saliva products. Appropriate ligands with which to link a de-sensitizing compound include, for example, at least a portion of an immunoglobulin molecule, cytokines, lectins, heterologous allergens, CD8 molecules, CD4 molecules or major histocompatibility molecules (e.g., MHC class I or MHC class II molecules). Preferred portions of immunoglobulin molecules to link to a de-sensitizing compound include variable regions capable of binding to immune cell specific surface molecules and constant regions capable of binding to Fc receptors on immune cells, in particular IgE constant regions. Preferred CD8 molecules include at least the extracellular functional domains of the β chain of CD8. Preferred CD4 molecules include at least the extracellular functional domains of CD4. An immune cell refers to a cell involved in an immune response, in particular, cells having MHC class I or MHC class II molecules. Preferred immune cells include antigen presenting cells, T cells and B cells.

In one embodiment, a therapeutic composition of the present invention includes ectoparasite saliva products of the present invention, or mimetopes thereof. Preferred therapeutic compositions include formulations comprising ectoparasite saliva extracts or at least one ectoparasite saliva product (preferably protein) of the present invention or mimetopes thereof.

Suitable therapeutic compositions of the present invention for treating flea allergy dermatitis include flea saliva extracts and other formulations including at least one flea saliva product, preferably a protein, or a mimetope thereof. Preferred therapeutic compositions include FS-1, FS2 and/or FS-3 as well as at least a portion of at least one flea saliva product that can be isolated from FS-1, FS-2 and/or FS-3. As such, preferred formulations for use as therapeutic compositions include FS-1, FS-2, FS-3, and/or at least a portion of one or more of the proteins fspA, fspB, fspc1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM (I), fspM(J), fspM(K), fspM(L), fspM(M), fspN(B), fspN (C), fspN(D), fspN(E), fspN(F), fspN(G), fspN(H), fspN(I), fspN(J), fspN(K), fspN(L), fspN(M), fspN(N) and fspN(O), or homologues thereof. A more preferred flea saliva extract for use as a therapeutic compositions includes FS-1, FS-2, FS-3, and/or at least a portion of one or more of the proteins fspE, fspF, fspG1, fspG2, fspG3, fspG4, fspH, fspI, fspJ1, fspJ2, fspK, fspL1, fspL2, fspM1, fspM2, fspN1, fspN2 and fspN3. A yet more preferred flea saliva extract for use as a therapeutic compositions includes FS-1, FS-2, and/or at least a portion of one or more of the proteins fspG1, fspG2, fspG3, fspG4, fspH, fspM1, fspM2, fspN1, fspN2 and fspN3.

In another embodiment, a therapeutic composition can include ectoparasite products of the present invention associated with a suitable excipient. A therapeutic composition of the present invention can be formulated in an excipient that the animal to be treated can tolerate. Preferred excipients are capable of maintaining a product of the present invention in a form that is capable of being bound by cells involved in an allergic response in an animal such that the cells are stimulated to initiate or enhance an immune response. Examples of such excipients include water, saline, Ringer's solution, dextrose solution, Hank's solution, and other aqueous physiologically balanced salt solutions. ion-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition of the present invention can also comprise a carrier or adjuvant, although it is to be appreciated that an advantage of saliva products of the present invention is that adjuvants and/or carriers are not required for administration. Adjuvants are typically substances that generally enhance the immune response of an animal to a specific antigen. Suitable adjuvants include, but are not limited to, cytokines, chemokines, and compounds that induce the production of cytokines and chemokines (e.g., granulocyte macrophage colony stimulating factor [GM-CSF], macrophage colony stimulating factor [M-CSF], granulocyte colony stimulating factor [G-CSF], colony stimulating factor [CSF], erythropoietin [EPO], interleukin-2 [IL-2], interleukin-3 [IL-3], interleukin-5 [IL-5], interleukin-6 [IL-6], interleukin-7 [IL-7], interleukin-8 [IL-8], interleukin-10 [IL-10], interleukin-12 [IL-12], gamma interferon [IFN-γ], interferon gamma inducing factor [IGIF], transforming growth factor beta, RANTES [regulated upon activation, normal T cell expressed and presumably secreted], macrophage inflammatory proteins [e.g., MIP1α and MIP1β], and Leishmania elongation initiating factor [LeIF]; bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant [Vaxcel™, Inc. Norcross, Ga.], Ribi adjuvants [Ribi ImmunoChem Research, Inc., Hamilton, Mont.]; and saponins and their derivatives (e.g., Quil A [Superfos Biosector A/S, Denmark]. Protein adjuvants of the present invention can be delivered in the form of the protein themselves or of nucleic acid molecules encoding such proteins using the methods described herein.

Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a therapeutic composition of the present invention into the bloodstream of an animal. Suitable controlled release formulations include, but are not limited to, biocompatible (including biodegradable) polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ.

The present invention also includes a recombinant virus particle therapeutic composition. Such a composition includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015/414, filed Feb. 8, 1993, entitled "Recombinant Virus Particle Vaccines", U.S. Pat. No. 5,266,313, by Esposito et al., issued Nov. 30, 1993 and U.S. patent application Ser. No. 08/602,010, by Haanes et al., filed Jan. 15, 1996, entitled "Recombinant Canine Herpesvirus", each of the patents and patent application referred to in this section is incorporated by reference herein in its entirety.

When administered to an animal, a recombinant virus particle therapeutic composition of the present invention infects cells within the immunized animal and directs the production of a protective protein or RNA nucleic acid molecule that is capable of protecting the animal from allergic dermatitis caused by the bites of ectoparasites. For example, a recombinant virus particle comprising a nucleic acid molecule encoding one or more ectoparasite saliva protein of the present invention is administered according to a protocol that results in the tolerization of an animal against ectoparasite saliva allergens.

According to one embodiment, a nucleic acid molecule of the present invention can be delivered to an animal as a naked (i.e., not packaged in a viral coat or cellular membrane) nucleic acid vaccine (e.g., as naked DNA or RNA molecules, such as is taught, for example in Wolff et al., 1990, Science 247, 1465–1468). A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a dicistronic recombinant molecule. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. An example of one embodiment is disclosed in PCT Patent Publication No. WO 95/05853, published Mar. 2, 1995. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized, oral and/or topical. Naked DNA of the present invention can be contained in an aqueous excipient (e.g., phosphate buffered saline) alone or a carrier (e.g., lipid-based vehicles).

Therapeutic compositions of the present invention can be sterilized by conventional methods which do not result in protein degradation (e.g., filtration) and/or lyophilized.

A therapeutic composition of the present invention can be administered to any animal susceptible to ectoparasite infestation as herein described. Acceptable protocols by which to administer therapeutic compositions of the present invention in an effective manner can vary according to individual dose size, number of doses, frequency of dose administration, and mode of administration. Determination of such protocols can be accomplished by those skilled in the art. An effective dose refers to a dose capable of treating an animal against hypersensitivity to ectoparasite saliva allergens. Effective doses can vary depending upon, for example, the therapeutic composition used, the arthropod from which the composition was derived, and the size and type of the recipient animal. Effective doses to immunomodulate an animal against ectoparasite saliva allergens include doses administered over time that are capable of alleviating a hypersensitive response by an animal to ectoparasite saliva allergens. For example, a first tolerizing dose can comprise an amount of a therapeutic composition of the present invention that causes a minimal hypersensitive response when administered to a hypersensitive animal. A second tolerizing dose can comprise a greater amount of the same therapeutic composition than the first dose. Effective tolerizing doses can comprise increasing concentrations of the therapeutic composition necessary to tolerize an animal such that the animal does not have a hypersensitive response to the bite of an ectoparasite. An effective dose to desensitize an animal can comprise a concentration of a therapeutic composition of the present invention sufficient to block an animal from having a hypersensitive response to the bite of an ectoparasite. Effective desensitizing doses can include repeated doses having concentrations of a therapeutic composition that cause a minimal hypersensitive response when administered to a hypersensitive animal.

A suitable single dose is a dose that is capable of treating an animal against hypersensitivity to ectoparasite saliva allergens when administered one or more times over a suitable time period. For example, a preferred single dose of an ectoparasite saliva product, or mimetope therapeutic composition is from about 0.5 ng to about 1 g of the therapeutic composition per kilogram body weight of the animal. Further treatments with the therapeutic composition can be administered from about 1 hour to 1 year after the original administration. Further treatments with the therapeutic composition preferably are administered when the animal is no longer protected from hypersensitive responses to ectoparasite. Particular administration doses and schedules can be developed by one of skill in the art based upon the parameters discussed above. Modes of administration can include, but are not limited to, subcutaneous, intradermal, intravenous, nasal, oral, transdermal and intramuscular routes.

A therapeutic composition of the present invention can be used in conjunction with other compounds capable of modifying an animal's hypersensitivity to ectoparasite bites. For example, an animal can be treated with compounds capable of modifying the function of a cell involved in a hypersensitive response, compounds that reduce allergic reactions, such as by systemic agents or anti-inflammatory agents (e.g., anti-histamines, anti-steroid reagents, anti-inflammatory reagents and reagents that drive immunoglobulin heavy chain class switching from IgE to IgG). Suitable compounds useful for modifying the function of a cell involved in a hypersensitive response include, but are not limited to, antihistamines, cromolyn sodium, theophylline, cyclosporin A, adrenalin, cortisone, compounds capable of regulating cellular signal transduction, compounds capable of regulating adenosine 3',5'-cyclic phosphate (cAMP) activity, and compounds that block IgE activity, such as peptides from IgE or IgE specific Fc receptors, antibodies specific for peptides from IgE or IgE-specific Fc receptors, or antibodies capable of blocking binding of IgE to Fc receptors.

Another aspect of the present invention includes a method for prescribing treatment for animals susceptible to or having allergic dermatitis, using a formulation of the present invention. A preferred method for prescribing treatment for flea allergy dermatitis, for example, comprises: (1) intradermally injecting into an animal at one site an effective amount of a formulation containing at least one flea saliva antigen of the present invention, or a mimetope thereof (suitable and preferred formulations are disclosed herein); (2) intradermally injecting into the animal at a second site an effective amount of a control solution; (3) evaluating if the animal has flea allergy dermatitis by measuring and comparing the wheal size resulting from injection of the formulation with the wheal size resulting from injection of the control solution; and (4) prescribing a treatment for the flea allergy dermatitis.

An alternative preferred method for prescribing treatment for flea allergy dermatitis comprises: (1) contacting a first portion of a sample of bodily fluid obtained from an animal to be tested with an effective amount of a formulation containing at least one flea saliva antigen, or a mimetope thereof (suitable and preferred formulations are disclosed herein) to form a first immunocomplex solution; (2) contacting a positive control antibody to form a second immunocomplex solution; (3) evaluating if the animal has flea allergy dermatitis by measuring and comparing the amount of immunocomplex formation in the first and second immunocomplex solutions; and (4) prescribing a treatment for the flea allergy dermatitis. It is to be noted that similar methods can be used to prescribe treatment for allergies caused by other ectoparasites using ectoparasite saliva product formulations as disclosed herein.

Another aspect of the present invention includes a method for monitoring animals susceptible to or having allergic dermatitis, using a formulation of the present invention. In vivo and in vitro tests of the present invention can be used to test animals for allergic dermatitis prior to and following any treatment for allergic dermatitis. A preferred method to monitor treatment of flea allergy dermatitis (which can also be adapted to monitor treatment of other ectoparasite allergies) comprises: (1) intradermally injecting an animal at one site with an effective amount of a formulation containing at least one flea saliva product, or a mimetope thereof (suitable and preferred formulations are disclosed herein); (2) intradermally injecting an effective amount of a control solution into the animal at a second site; and (3) determining if the animal is desensitized to flea saliva antigens by measuring and comparing the wheal size resulting from injection of the formulation with the wheal size resulting from injection of the control solution.

An alternative preferred method to monitor treatment of flea allergy dermatitis (which can be adapted to monitor treatments of other ectoparasite allergies) comprises: (1) contacting a first portion of a sample of bodily fluid obtained from an animal to be tested with an effective amount of a formulation containing at least one flea saliva product or mimetope thereof (suitable and preferred formulations are disclosed herein) to form a first immunocomplex solution; (2) contacting a positive control antibody to form a second immunocomplex solution; and (3) determining if the animal is desensitized to flea saliva antigens by measuring and comparing the amount of immunocomplex formation in the first and second immunocomplex solutions.

The present invention also includes antibodies capable of selectively binding to an ectoparasite saliva product, or mimetope thereof. Such an antibody is herein referred to as an anti-ectoparasite saliva product antibody. As used herein, the term "selectively binds to" refers to the ability of such an antibody to preferentially bind to ectoparasite saliva products and mimetopes thereof. In particular, the present invention includes antibodies capable of selectively binding to flea saliva products. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies. including single chain antibodies, that are capable of selectively binding to at least one of the epitopes of the protein or mimetope used to obtain the antibodies. Preferred antibodies are raised in response to ectoparasite saliva proteins, or mimetopes thereof. More preferred antibodies are raised in response to at least one ectoparasite saliva protein, or mimetope thereof, having at least a portion of an ectoparasite saliva protein eluted from a collection means of the present invention. Even more preferred antibodies are raised in response to at least one flea saliva product, or homologues thereof (e.g., saliva products of other ectoparasites), contained in the saliva extracts FS-1, FS-2 and/or FS-3. More preferred ectoparasite saliva proteins against which to raise an antibody includes at least a portion of one or more of the proteins fspA, fspB, fspC1, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, as well as fspM(A), fspM(B), fspM(C), fspM(D), fspM(E), and fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN (L), fspN(M), fspN(N) and fspN(O), or homologues thereof. Preferably, an antibody of the present invention has a single site binding affinity of from about $10^3$ $M^{-1}$ to about $10^{12}$ $M^{-1}$ for a flea saliva product of the present invention.

A preferred method to produce antibodies of the present invention includes administering to an animal an effective amount of an ectoparasite saliva product or mimetope thereof to produce the antibody and recovering the antibodies. Antibodies raised against defined products or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from allergic dermatitis, (b) as positive controls in test kits, and/or (c) as tools to recover desired ectoparasite saliva products from a mixture of proteins and other contaminants.

The following examples are provided for the purposes of illustration and are not intended to limit the scope of the present invention.

EXAMPLES

Example 1

This example describes the collection of flea saliva proteins using a saliva collection apparatus of the present invention.

A saliva collection apparatus was prepared as follows. Referring to FIG. 4A and 4B, a humidifying means (34) comprising about 4 pieces of VWR blotting pads #320 (VWR, Denver, Colo.) was prepared that fit the inner diameter (about 47 mm in diameter) of a chamber (6) of a saliva collection apparatus (2). The blotting pads were pre-wetted using a sufficient amount of pre-wetting solution (sterile water containing 50 units/ml penicillin and 50 μg/ml streptomycin, available from Sigma, St. Louis, Mo.) such that the blotting pads were damp but not dripping wet. The pre-wetted filters (34) were placed inside the bottom end (22) of the chamber (6) of the saliva collection apparatus (2) such that the filter paper sat immediately inside the bottom end (22) of the chamber (6).

A collection means (24) comprising a Durapore™ membrane (available from Millipore, Bedford, Mass.) was cut to fit the outer diameter (about 48 mm in diameter) of the chamber (6) of the saliva collection apparatus (2). The Durapore™ membrane was pre-wetted using the pre-wetting solution described above. The Durapore™ membrane (24) was placed immediately outside the bottom end (22) of the chamber (6) such that the Durapore™ membrane (24) contacted the outer rim of the bottom end (22) of the chamber (6) and also contacted the damp filter paper. A barrier means comprising a piece of stretched Parafilm™ (28) (available from American National Can™, Greenwich, Conn.) was stretched over the collection means (24) and bottom end (22) of the chamber (6) and up the outer wall (30) of the chamber (6). A rubber seal (32) (i.e., an O-ring) was placed over the Parafilm™ (28) thereby further securing the Parafilm™ (28) across the collection means (24) and to the outer wall (30) and to seal in the chamber (6) environment.

The collection apparatus (2) was preassembled and then the top end (20) of the chamber (6) was attached to an artificial feeding system capable of acting as a source of heat and humidity such as that described by Wade et al., (ibid.). The artificial feeding system comprised a large plexiglass box (40 cm×40 cm×40 cm) divided horizontally into an upper compartment and a lower compartment by a plexiglass shelf having holes drilled through. A collection apparatus (2) was inserted into a hole such that the chamber (6) of the apparatus (2) was located above the shelf in the upper compartment and the housing (4) was located below the shelf in the lower compartment. The apparatus (2) was secured to the shelf by attaching a rubber band attached to metal hooks placed in the shelf. Any open holes in the shelf were closed off using rubber stoppers to isolate the environment within the upper compartment from the environment within the lower compartment. The upper compartment contained two trays of water, a fan and a heating block. The trays of water were placed such that the fan faced the trays. While the apparatus (2) was maintained in the artificial feeding system, the fan was blown continuously thereby circulating heat and humidity throughout the upper compartment and the chamber (6) of the collection apparatus (2). As such, the relative humidity within the chamber (6) was maintained at about 94% humidity and the temperature was maintained at about 37° C.

About 3,000 to 5,000 newly emerged unfed *Ctenocephalides felis* fleas were added to the housing (4) of the collection apparatus (2). The fleas were first collected in a 20 gallon glass aquarium. The fleas were then transferred to the housing (4) of a collection apparatus (2) by placing the end of the housing (4) having the nylon mesh of the exchange means (16) on top of a vacuum chamber and aspirating the fleas from the aquarium into the housing (4) through a tygon tubing. The housing (4) was then covered with the nylon mesh of the retaining means (18) to secure the fleas within the housing (4). The bottom end (22) of the chamber (6) was then placed on the housing (4) such that the Parafilm™ (28) and the nylon mesh of the retaining means (18) were juxtaposed. When the collection apparatus (2) was attached to the artificial feeding system, the ambient temperature within the housing (4) was maintained at about 27° C. while the ambient temperature of the chamber (6) was maintained at about 37° C. The relative humidity of the housing (4) was maintained at about 50% by closing the lower compartment with the plexiglass shelving.

In one experiment, flea saliva products were collected on a Durapore™ membrane (24) and visualized by immersing the membrane in 0.1% Coomassie blue stain for 20 minutes, destaining the membrane in 50% methanol and air drying the membrane. Proteins deposited on the membrane were detected by their blue color.

In another experiment, flea saliva products were collected for 0 through 24 hours, 24 through 72 hours, and 72 through 120 hours after loading fleas into the collection apparatus. At 24 hours, 72 hours and 120 hours, the Durapore™ membrane (24) attached to the collection apparatus (2) was removed and a new pre-wetted Durapore™ membrane (24) was attached to the same apparatus. The blotting pads were re-wetted using the pre-wetting solution described above when the new Durapore™ membrane (24) was replaced. Flea saliva products were extracted from the Duraporew membrane (24) by soaking each membrane from each time point separately in a solvent comprising 50% acetonitrile with 1% TFA overnight at room temperature with stirring to obtain a flea saliva product mixture comprising flea saliva products that had eluted into the solvent. The mixture containing the flea saliva products was recovered and lyophilized until dry to form a pellet. The amount and characteristics of flea saliva proteins eluted from each Durapore™ membrane from each time point was determined by reducing 14% Tris-glycine SDS-PAGE using techniques similar to those described by Sambrook et al., ibid. The resultant protein pattern was visualized by staining the gel with Coomassie blue stain using techniques as described above. The amount of saliva proteins collected on the membranes decreased when the fleas had been in the collection apparatus for more than 72 hours.

Example 2

Standard procedures to collect FS-1, FS-2 and FS-3 flea saliva extracts of the present invention were performed as follows. Flea saliva products were collected for 72 hours on collection membranes using the method described in Example 1, except that for flea saliva extract FS-3, the collection membrane was DE-81 chromatography paper, available from Whatman, Inc., Clifton, N.J.

A. Flea Saliva Extracts FS-1 and FS-2

Flea saliva products were extracted from the Durapore™ membrane (24) by soaking each membrane from each time point separately in a first solvent comprising 50% acetonitrile with 0.1% TFA for 8 hours. The first mixture containing the eluted flea saliva products was recovered and lyophilized until dry, thereby forming a first pellet. The same membranes were then soaked in a second solvent comprising 50% acetonitrile with 1% TFA overnight at room temperature with stirring to obtain a flea saliva product mixture comprising flea saliva products that had eluted into the second solvent. The second mixture was recovered from this second extraction and lyophilized until dry to form a second pellet.

The two pellets recovered from the two lyophilization steps were mixed with a third solvent comprising 12.8% acetonitrile and flea saliva products solubilized in the solvent were recovered. The non-solubilized material was mixed again with 12.8% acetonitrile and additional flea saliva products solubilized in the solvent were recovered. The two mixtures were combined to obtain the extract FS-1.

The non-solubilized material remaining after the second solubilization step was then mixed with 50% acetonitrile which solubilized the remaining material to obtain the extract FS-2.

The amount and characteristics of flea saliva proteins contained in the FS-1 and FS-2 flea saliva extracts obtained in at least one experiment were determined according to the following method. Each extract was concentrated by evaporation under vacuum and evaluated by reducing 16% Tris-glycine SDS-PAGE using techniques similar to those described by Sambrook et al., ibid. Using such standard procedures, about 10 $\mu$g of FS-1 or FS-2 eluted from the Durapore™ membrane was loaded onto a 16% Tris-glycine polyacrylamide gel and subjected to electrophoresis under reducing conditions. The gel was stained with Coomassie blue and dried.

The results are shown in FIG. 1B. FS-1 is shown in lane 13 of FIG. 1B and FS-2 is shown in lanes 14 and 15 of FIG. 1B. FS-1 was found to contain proteins estimated to have the following molecular weights: 9 kD, 11 kD, 12 kD, 15 kD, 22 kD, 48 kD, 50 kD, 53 kD, 80 kD, 124 kD, 130 kD, 189 kD and 201 kD. Those proteins of 80 kD and above were much fainter than the lower molecular weight bands. FS-2 was found to contain proteins having the following molecular weights: 47 kD, 49 kD, 52 kD, 57 kD, 64 kD, 71 kD, 88 kD, 96 kD, 97 kD, 130 kD, 161 kD, 175 kD, 189 kD, 222 kD, 235 kD and 302 kD. The bands at 47 kD, 49 kD and 52 kD were more prominent than the bands having higher molecular weights. The results suggest that a substantial portion of the protein contained in FS-2 is fspN1, fspN2 and/or fspN3.

Protein concentrations were measured using a Bio-Rad Bradford assay (available from Bio-Rad, Hercules, Calif.). The results indicate that about 750 μg of protein can be collected in about $3.66 \times 10^7$ flea hours ($5.08 \times 10^5$ fleas for 72 hours) in an FS-1 extract and about 2.35 mg of protein can be collected in about $3.66 \times 10^7$ flea hours in an FS-2 extract.

B. Flea Saliva Extract FS-3

Flea saliva products to produce FS-3 flea saliva extract were collected in a manner similar to the method by which FS-1 and FS-2 were collected, except that the collection membrane (24) was DE-81 chromatography paper. Flea saliva products were extracted from the DE-81 membrane by soaking each membrane from each time point separately in a solvent comprising 1 M NaCl in phosphate buffered saline for about 8 hours. The products were recovered from the solvent using standard techniques, such as disclosed for FS-1 and FS-2.

Analysis of an FS-3 flea saliva extract indicated that FS-3 appeared to contain proteins such as those found in FS-1 and FS-2, at least based on 1-dimensional gel electrophoresis. The SDS-PAGE pattern of FS-3, for example, was very similar to that of FS-1 except that there appeared to be increased quantities of the higher molecular weight proteins in the FS-3 extract. FS-3 flea saliva extract was also shown to have anti-coagulation activity, using techniques standard in the art; see, for example, Dunwiddle et al., 1991, *Thrombosis Research* 64, 787–794; Ribeiro et al., 1990, *Comp. Biochem. Physiol.* 95, 215–218; Ribeiro et al., 1990, Br. *J. Pharmacol.* 101, 932–936; Ribeiro et al., 1987, *Exper. Parasitol.* 64, 347–353; Cupp et al., 1994, *Am. J. Trop. Med. Hyg.* 50, 241–246; Garcia et al., 1994, *Exper. Parasitol.* 78, 287–293. The FS-3 extract was also shown to exhibit acid phosphatase activity, using techniques standard in the art, such as those supplied by Sigma, St. Louis, Mo., with the Sigma acid phosphatase assay kit.

Example 3

This example describes the characterization by HPLC of flea saliva proteins collected using a saliva collection apparatus of the present invention.

An FS-1 flea saliva extract was collected as described in Example 2 from about 140,000 fleas for 72 hours. Proteins contained in FS-1 were resolved using standard procedures of high pressure liquid chromatography (HPLC). Specifically, the proteins were passed over a 15 cm×0.46 cm C4 column using a gradient from 0.1% TFA in water (Solvent A) to 0.085% TFA in 90% CH$_3$CN (Solvent B) at a flow rate of 0.8 ml per minute. Thus, the gradient was about 5.6% Solvent B at 15 minutes and about 100% Solvent B at 75 minutes.

The results are shown in FIG. 2. About 14 major protein fractions were resolved. The recovery for each peak was about 5 μg to 10 μg of protein per peak. The peaks were labelled peak A, peak B, peak C, peak D, peak E, peak F, peak G, peak H, peak I, peak J, peak K, peak L, peak M and peak N, as shown in FIG. 2, and represent, respectively, protein formulations fspA, fspB, fspC1 and fspC2, fspD1 and fspD2, fspE, fspF, fspG1, fspG2, fspG3, fspH, fspI, fspJ1 and fspJ2, fspK, fspL1 and fspL2, fspM1 and fspM2, and fspN1, fspN2 and fspN3.

Figure 1C:
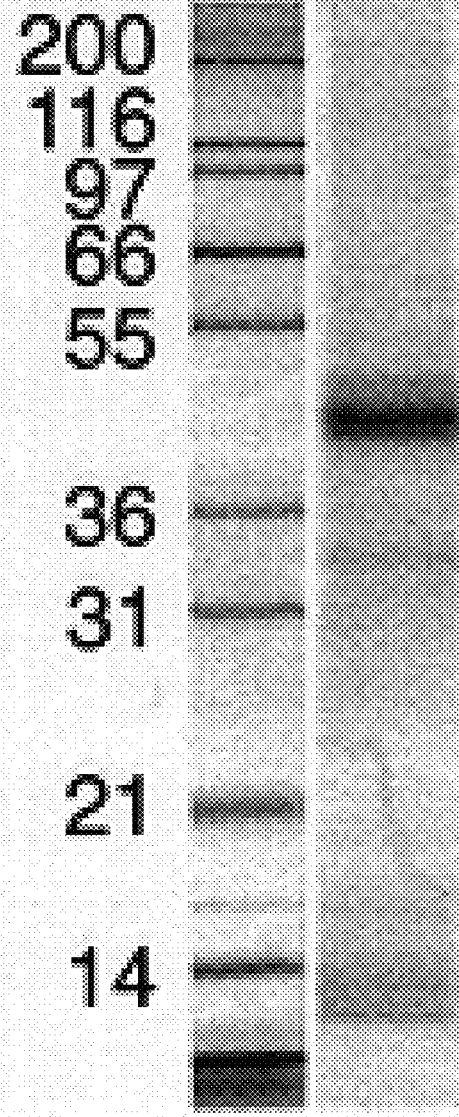
FIG. 1C illustrates the resolution of fspN by reducing 16% Tris glycine SDS-PAGE.

Samples from each HPLC peak were resolved by Tris Glycine SDS-PAGE gels using the method described in Example 1. The results are shown in FIGS. 1A, 1B and 1C. The proteins shown in FIGS. 1A and 1B were resolved on 16% Tris Glycine SDS-PAGE gels and the proteins shown in FIG. 1C were resolved on a 14% Tris Glycine SDS-PAGE gel. Protein markers are shown in lane 1 of FIG. 1A, lane 2 of FIG. 1B and lane 1 of FIG. 1C. The additional lanes show saliva formulation samples as follows:

| FIG. 1A | | |
|---|---|---|
| Lane | Fraction (s) | Fs-() |
| 1) | — | Mol. Wt. Std. |
| 2) | 10 | — |
| 3) | 11–13 | A |
| 4) | 14 | B |
| 5) | 15 | B |
| 6) | 16 | C1 |
| 7) | 17 | C2 |
| 8) | 18 | D1 |
| 9) | 19 | D1 |
| 10) | 20 | D2 |
| 11) | 21 | D2 |
| 12) | 22 | E |
| 13) | 23 | F |
| 14) | 24 | G |
| 15) | 25 | G |

| FIG. 1B | | |
|---|---|---|
| Lane | Fraction (s) | Fs-() |
| 1) | 26–27 | G |
| 2) | — | Mol. Wt. Std. |
| 3) | 28 | H |
| 4) | 29–30 | I |
| 5) | 31 | J |
| 6) | 32 | K |
| 7) | 33 | K |
| 8) | 34 | L |
| 9) | 35 | M1 |
| 10) | 36–37 | M1 |
| 11) | 38 | M1 |
| 12) | 39–50 | M2 |
| 13) | — | FS-1 |
| 14) | — | FS-2 |
| 15) | — | FS-2 |

| FIG. 1C | | |
|---|---|---|
| Lane | Fraction (s) | Fs-() |
| 1) | — | Mol. Wt. Std. |
| 2) | 56-68 | N |

Referring to FIG. 1A, the following flea saliva proteins (referred to as bands) were observed: a prominent band of about 10 kD in peak A and peak B samples; a prominent band of about 6 kD and a less prominent band of 9 kD in a peak C sample referred to as C1; a prominent band of about 7 kD in a peak C sample referred to as C2; a prominent band of about 7 kD and a less prominent band of 8 kD in a peak D sample referred to as D1; a prominent band of about 8 kD and a less prominent band of 9 kD in a peak D sample referred to as D2; a prominent band of 8 kD and a less prominent band of about 7 kD in peaks E and F samples; and a prominent band of about 9 kD, and less prominent bands of about 7 kD and 10 kD in a peak G sample. Referring to FIG. 1B, the following flea saliva proteins were observed: a prominent band of about 9 kD and a less prominent band of about 12 kD in a peak H sample; a prominent band of about 21 kD, and less prominent bands of about 7 kD, 9 kD, 12 kD, 14 kD, and 70 kD in a peak I sample; prominent bands of about 14 kD and 21 kD, and less prominent bands of about 11 kD and 17 kD in a peak J sample; prominent bands of about 14 kD and 15 kD and less prominent bands of about 12 kD, 18 kD and 21 kD in a peak K sample; a prominent band of about 15 kD in a peak L sample; prominent bands of about 11 kD, 12 kD and 21 kD and less prominent bands of about 15 kD, 17 kD, 22 kD and 37 kD in a peak M sample referred to as M1; and a prominent band of about 36 kD and less prominent bands of about 11 kD, 21 kD and 22 kD in a peak M sample referred to as M2. Referring to FIG. 1C, prominent bands of about 42 kD, 43 kD and 44 kD and a less prominent band of about 32 kD were detected in a peak N sample.

Example 4

This example describes the amino acid sequence analysis of the isolated and HPLC purified flea saliva proteins.

Amino (N-) terminal amino acid sequencing analysis was performed on several of the HPLC-separated flea saliva proteins described in Example 3 using standard procedures known to those in the art (see, for example, Geisow et al., 1989, in *Protein Sequencing: A Practical Approach*, JBC Findlay and MJ Geisow (eds.), IRL Press, Oxford, England, pp. 85–98; Hewick et al., 1981, *J. Biol. Chem.*, Vol. 256, pp. 7990–7997).

The N-terminal partial amino acid sequence of flea saliva protein fspA, which migrated as Peak A in FIG. 2, was determined to be

```
Y G K Q Y S E K G G R G Q R H Q I L K K G K
  Q Y S         S K       I     L   D   L
  S
  R
``` as represented in standard single letter code. This N-terminal partial amino acid sequence of fspA is denoted SEQ ID NO:1. It should be noted that there was heterogeneity in several positions which may represent sequence errors (i.e., misidentification of amino acids) or allelic variations in the flea population from which the saliva proteins were collected. There was an apparently equal likelihood of finding any one of the alternative amino acids at the indicated positions.

The N-terminal partial amino acid sequence of flea saliva protein fspB, which migrated as Peak B in FIG. 2, was determined to be S/Q G K Q Y S E X G/S K, denoted SEQ ID NO:27. This amino acid sequence was essentially the same, or at least a subset of, the N-terminal amino acid sequence obtained from flea saliva protein fspA.

Sequence analysis of Peak G proteins indicated the presence of three proteins in that peak, referred to herein as fspG1, fspG2 and fspG3. Flea saliva protein fspG1, having a molecular weight of about 9 kD, had an N-terminal partial amino acid sequence of D R R V S K, denoted SEQ ID NO:28. This N-terminal amino acid sequence is the same as that for fspH, as shown in SEQ ID NO:2, SEQ ID NO:3, SEQ ID NO:4, SEQ ID NO:5 and SEQ ID NO:14. Flea saliva protein fspG2, having a molecular weight of about 7 kD, had an N-terminal partial amino acid sequence of S K M V T E K X K S G G N N P S T K E V S I P, denoted SEQ ID NO:29. Flea saliva protein fspG3, having a molecular weight of about 6 kD, had an N-terminal partial amino acid sequence of E V S I P S G K L T I E D F X I G N H Q, denoted SEQ ID NO:30. A comparison of SEQ ID NO:30 with SEQ ID NO:29 indicates that fspG3 may be a proteolytic degradation product of fspG2, as the last five amino acids of fspG2 are identical with those at the N-terminus of fspG3.

The N-terminal partial amino acid sequence of flea saliva protein fspH, which migrated as Peak H in FIG. 2, was determined to be D R R V S K T X Q S G G K I Q S E X Q V V I K S G Q H/Y I L E N Y X S D G R, denoted herein as SEQ ID NO:14. Histidine and tyrosine were equally likely at amino acid position 27.

Flea saliva protein fspH was also subjected to proteolytic cleavage in order to obtain internal amino acid sequence data. Specifically, fspH was cleaved with Endoproteinase Asp-N (available from Boehringer Mannheim Biochemica, Indianapolis, Ind.) using methods standard in the art. The digested protein was then resolved by HPLC using the method described by Stone et al. (ibid.). The resultant HPLC profile is shown in FIG. 3. Three proteolytic fragments were isolated, that are referred to herein as fspHe, fspHh and fspHj.

The N-terminal partial amino acid sequence of fspHe was determined to be D S K H C Y C E A P Y S, also denoted SEQ ID NO:3. The N-terminal partial amino acid sequence of fspHh was determined to be D G R N N N N P C H L F C M R E C R S G N G G C G N G G R T R P D S K H C, also denoted SEQ ID NO:4. The N-terminal partial amino acid sequence of fspHj was determined to be D R R V S K T C Q S G, also denoted SEQ ID NO:5. Comparison of SEQ ID NO:5 to SEQ ID NO:14 indicated that fspHj was the N-terminal fragment of fspH.

By aligning SEQ ID NO:14, SEQ ID NO:3, SEQ ID NO:4 and SEQ ID NO:5, the following amino acid sequence was deduced, starting at the N-terminus of fspH: D R R V S K T C Q S G G K I Q S E X Q V V I K S G Q H/Y I L E N Y X S D G R N N N N P C H L F C M R E C R S G N G G C G N G G R T R P D S K H C Y C E A P Y S. This amino acid sequence is denoted SEQ ID NO:2 and is believed to represent most of fspH since the molecular weight of a protein having this sequence is about 8600 kD.

The N-terminal partial amino acid sequence of flea saliva protein fspI, which migrated as Peak I in FIG. 2, was determined to be E D I W K V N K K X T S G G K N Q D R K L D Q I I Q K G Q Q V X X Q N X X K, denoted herein as SEQ ID NO:6.

Sequence analysis of Peak J proteins indicated the presence of two proteins in that peak, referred to herein as fspJ1 and fspJ2. The N-terminal partial amino acid sequence of flea saliva protein fspJ1 was determined to be N S H E P G N T R K I R E V M D K L R K Q H P, denoted herein as SEQ ID NO:7. The N-terminal partial amino acid sequence of flea saliva protein fspJ2 was determined to be E I K R N S H E P G N T R K I R E V M D K L R K Q H P, denoted herein as SEQ ID NO:8. The proteins represented by SEQ ID NO:7 and SEQ ID NO:8 were not separately resolved by SDS-PAGE as described in Example 1. Comparison of SEQ ID NO:7 and SEQ ID NO:8 suggest that fspj1 may be a truncated version of fspJ2, in that the N-terminal partial amino acid sequence of fspJl appears to be very similar to that of fspJ2 except that fspJ1 lacks the first 4 amino acids found at the N-terminus of fspJ2.

Sequence analysis of Peak L proteins indicated the presence of two proteins in that peak, referred to herein as fspL1 and fspL2. That there were two proteins, namely fspL1 and fspL2, was shown by subjecting peak L to C4 reverse phase chromatography using 0.13% heptafluorobutyric acid (Solvent A) and 0.1% heptafluorobutyric acid in 90% acetonitrile (Solvent B) in the following gradient format: an 80 minute gradient from 30% Solvent B to 70% Solvent B. The N-terminal partial amino acid sequence of the HPLC-separated fspL1 was determined to be N D K E P G N T R K I R E V M D K L R K Q A Q P R T D G Q R P K T X I M, also denoted SEQ ID NO:9. The N-terminal partial amino acid sequence for fspL2 was determined to be X L X R N D K E P G N T R K I R E V M D K, also denoted SEQ ID NO:10. A comparison of SEQ ID NO:9 and SEQ ID NO:10 indicates that fspL1 and fspL2 are similar proteins, except that fspL1 is 4 amino acids shorter than fspL2 at the N-terminus.

Resolution of proteins contained in Peak N by SDS-PAGE as described in Example 3 revealed 3 distinct bands. The bands were denoted flea saliva proteins fspN1, fspN2 and fspN3. The N-terminal partial amino acid sequence of fspN1 was determined to be N D E L K F V F V M A K, also denoted SEQ ID NO:11. The N-terminal partial amino acid sequence of fspN2 was determined to be X D E L K F V F V M A K G P S X Q A X D Y P C, also denoted SEQ ID NO:12. The N-terminal partial amino acid sequence of fspN3 was determined to be E L K F V F A T A R G M S H T P C D Y P, also denoted SEQ ID NO:13. Comparison of SEQ ID NO:11 and SEQ ID NO:12 suggests that fspN1 and fspN2 share the same N-terminal sequence. Since fspN1 and fspN2 migrate differently when subjected to SDS-PAGE, however, the two proteins are likely to be different homologues, possibly due to one protein having a longer C-terminal domain and/or due to post-translational modification(s). Comparison of SEQ ID NO:13 to SEQ ID NO:11 and SEQ ID NO:12 suggests that fspN3 may be a homologue of fspN1 and fspN2 with internal sequence variations.

Flea saliva proteins in Peak N were also subjected to proteolytic cleavage in order to obtain internal amino acid sequence data. Specifically, the proteins in Peak N were cleaved with Endoproteinase Asp-N (available from Boehringer Mannheim Biochemica, Indianapolis, Ind.) using methods standard in the art. The digested protein was then resolved by HPLC using the method described by Stone et al. (ibid.) and sequenced as previously described. A partial amino acid sequence of flea saliva proteins in Peak N, named fragment pfspN(100–101), was determined to be D I E N I K K G E G Q P G A P G G K E N N L S/L V L, denoted herein as SEQ ID NO:31.

Example 5

This example describes the further characterization of proteins contained in Peak H.

To determine the isoelectric pH of the proteins contained in Peak H, proteins present in that peak were resolved using standard isoelectric focusing techniques known to those of skill in the art; see, for example, O'Farrell, 1975, *J. Biol. Chem.*, Vol. 250, pp. 4007–4021. The pI value for proteins contained in Peak H is about pI 9, ranging from about pI 8.5 to about pI 9.6.

The molecular weight of proteins contained in Peak H was determined by ESMS. The ESMS procedure was performed on a Fisons VG quattro-SQ mass spectrometer. The mass range was calibrated for 100–2000 m/z. The injection rate was performed at 4 μl per minute. The cone voltage was set at 45 volts. The injection sample contained 0.1% formic acid in 50% acetonitrile at a protein concentration of about 100 pmole per μl. The results indicate that Peak H apparently contains a population of proteins all having a molecular weight of 8613±6 daltons.

Example 6

This example describes the isolation of nucleic acid sequences encoding at least portions of flea saliva proteins fspH and fspi.

A. Description of Flea libraries

Fed flea and unfed flea cDNA libraries were prepared using standard procedures. Briefly, about 3000 to 4000 fed fleas and about the same number of unfed fleas were collected separately, placed into a dry-ice cooled mortar/pestle and ground to a fine powder. RNA from the ground-up fleas was prepared by direct extraction using the guanidinium thiocyanate procedure followed by centrifugation in cesium chloride gradients (see, for example, Sambrook et al., ibid.). Cesium chloride-purified gelatinous RNA pellets were collected and dissolved in sterile TE buffer (10 mM Tris-HCl, pH 7.6 and 1 mM EDTA) containing 0.1% sodium dodecyl sulfate. The dissolved pellet was precipitated with addition of 3 M sodium acetate, pH 5.2 to a final concentration of 0.2 mM and two volumes of absolute ethanol to remove residual CsCl. Total RNA was fractionated for enrichment of the mRNA fraction using a FastTrack™ kit (available, with procedures, from InVitrogen Corp., San Diego, Calif.).

Isolated whole flea mRNA was used directly for cDNA synthesis and molecular cloning. The methods of cDNA synthesis and molecular cloning were those provided with the Lambda Zap-cDNA synthesis kit™ (available from Stratagene, Inc., La Jolla, Calif.). Following is a list of flea cDNA libraries prepared having the indicated number of total plaque forming units (PFU) packaged: (a) two whole fed flea cDNA expression libraries referred to as Library C (about $2.5 \times 10^6$ PFU) and Library H (about $1.3 \times 10^6$ PFU); (b) a whole unfed flea cDNA expression library (about $1.3 \times 10^6$ PFU); (c) a flea salivary gland cDNA expression library prepared from approximately 6000 salivary glands collected from fed and unfed fleas (about $1.5 \times 10^6$ PFU); and (d) a flea fed midgut cDNA expression library prepared from approximately 5000 isolated midguts (about $2.3 \times 10^6$ PFU).

B. Isolation of a Nucleic Acid Molecule encoding fspH

A nucleic acid molecule encoding a portion of flea saliva protein fspH was identified using the flea salivary gland cDNA expression library described in Example 6A.

Degenerate synthetic oligonucleotide primers were designed from the amino acid sequence deduced for fspH (see Example 4). Three synthetic oligonucleotides were synthesized that corresponded to the region of fspH spanning from about residues 38 through 51 of SEQ ID NO:2: Primer 1, a "sense" primer corresponding to amino acid residues from about 38 through about 44 of SEQ ID NO:2, has the nucleic acid sequence 5' AAT(C) AAT(C) AAT(C) AAT(C) CCT(GAC) TGT(C) CA 3', and is denoted SEQ ID NO:15. Primer 2, an "antisense" primer corresponding to amino acid residues from about 46 through about 51 of SEQ ID NO:2, has the nucleic acid sequence 5' CA C (T) TC C (TAG) CT (G) CAT G (A) CA G (A) AA 3' and is denoted SEQ ID NO:16. Primer 3, a sense primer corresponding to amino acid residues from about 43 through about 48 of SEQ ID NO:2, has the nucleic acid sequence 5' TGT(C) CAT(C)

T(C)TG(ATC) TTT(C) TGC(T) ATG-3' and is denoted SEQ ID NO:17. A fourth primer, Primer 4, was synthesized that corresponded to the carboxyl region of fspH, namely spanning from about amino residue 69 through 76 of SEQ ID NO:2. Primer 4, an antisense primer, has the nucleic acid sequence 5' GGA(CGA) GCT(C) TCA(G) CAA(G) TAA (G) CAA(G) TGT(C) TT' 3', denoted SEQ ID NO:18.

PCR amplification of fragments from the flea salivary gland library was conducted using standard techniques. PCR amplification products were generated using the combination of Primer 1 and the M13 forward universal standard primer 5' GTAAAACGACGGCCAGT 3', denoted SEQ ID NO:19. The resultant PCR amplification products were used for a nested PCR amplification using Primer 3 and Primer 4. The resultant PCR product, a fragment of 101 nucleotides denoted nfspH$_{101}$, was cloned into the InVitrogen, Corp., TA™ cloning vector (procedures provided by InVitrogen, Corp.) and subjected to DNA sequence analysis using standard techniques. The resulting nucleic acid sequence is presented as SEQ ID NO:20: T TGT CAC TTT TTT TGT ATG AGA GAA TGC AGG TCA GGA AAC GGC GGT TGC GGA AAC GGA GGA AGG ACA AGA CCT GAT TCG AAG CAC TGC TAT GC (primer-derived sequences are in bold). The 60 nucleotides of internal non-primer-derived sequence codes for 20 amino acids of fspH, spanning from residue about 48 through about 68, as numbered in SEQ ID NO:2.

Using standard techniques, nucleic acid molecule nfspH$_{101}$ can be used as a probe to isolate a nucleic acid molecule that encodes a protein corresponding to a full-length, or larger partial, fspH protein.

C. Isolation of a Nucleic Acid Molecule encoding fspI

The amino acid sequence for fspI (SEQ ID NO:6) disclosed in Example 4 was used to design a set of synthetic degenerate oligonucleotide PCR amplification primers. Degenerate Primer 5, a sense primer corresponding to residues from about 1 through about 8 of SEQ ID NO;6, has the nucleic acid sequence 5' GAA(G) GAT(C) ATT(CA) TGG AAA(G) GTT(CAG) AAT(C) AA 3', denoted SEQ ID NO:21. Degenerate Primer 6, a sense primer corresponding to residues from about 11 through about 18 of SEQ ID NO:6, has the nucleic acid sequence 5' ACT(CGA) TCT(CGA) GGT(CGA) GGT(CGA) AAA(G) AAT(C) CAA(G) GA 3', denoted SEQ ID NO:22.

Primers 5 and 6 were used in combination with the vector primers BSKX (5' TTGGGTACCGGGCCCCCCCT 3', SEQ ID NO:23) and the M13 primer denoted by SEQ ID NO:19 in order to generate PCR amplification products. The PCR products were cloned into the InVitrogen TA™ vector and subjected to DNA sequence analysis. One cloned product analyzed, called nfspI$_{573}$ contained a 573-nucleotide product that corresponded, at least in part, to the partial amino acid sequence determined for fspi. The nucleotide sequence of nfspI$_{573}$ is presented as SEQ ID NO:24. Translation of SEQ ID NO:24 yields the following longest open reading frame, denoted as SEQ ID NO:25.

By combining the partial N-terminal sequence of fspI (SEQ ID NO:6) with the protein sequence SEQ ID NO:25 deduced from the nucleic acid sequence SEQ ID NO:24, it is possible to obtain an apparent full-length amino acid sequence for fspI, denoted SEQ ID NO:26.

Example 7

This example further describes the isolation of nucleic acid sequences encoding at least portions of flea saliva proteins fspH and fspi.

A. Amplification of a Nucleic Acid Molecule Encoding fspH

The DNA sequence determined from the carboxyl-terminal PCR product (SEQ ID NO:20) in Example 6B was used to synthesize two non-degenerate synthetic homologous primers: Primer 7, 5' CCT GAC CTG CAT TCT CTC ATA C 3', denoted SEQ ID NO:38, and Primer 8, 5' AGG TCT TGT CCT TCC TCC GTT TCC GCA 3', denoted SEQ ID NO:39. Primer 8 was used in combination with the M13 reverse primer 5' GGAAACAGCTATGACCATG 3', denoted SEQ ID NO:40, to amplify the 5'-terminal portion of the fspH gene from a fraction of the salivary gland cDNA expression library described above in Example 6A using standard techniques. The resultant PCR product, although not clearly visible on a gel, was identified as a single product by Southern hybridization using Primer 7 as a [$^{32}$P]-radio-labeled probe. A clearly visible ethidium bromide stained PCR product was obtained by performing a nested PCR reaction utilizing Primer 7 and the vector T3 primer, 5' ATTAACCCTCACTAAAG 3', denoted SEQ ID NO:41. The approximately 400-bp product was clearly visible on a 1% agarose gel and was hybridization-positive with [$^{32}$p]-labeled degenerate Primer 1 (SEQ ID NO:15).

A partial, 242-bp, nucleotide sequence of the 400-bp product of fspH, named nfspH$_{242}$ is presented as SEQ ID NO:32. Translation of SEQ ID NO:32 yields the amino acid sequence, named PfspH$_{80}$ denoted as SEQ ID NO:33.

B. AmDlification of a Nucleic Acid Molecule Encoding fspI

Two additional primers were made for isolating the fspi protein cDNA sequence from the flea salivary gland library prepared as described in Example 6A. The isolation procedure used PCR reiteration of the flea salivary gland library and probe hybridization to the PCR generated products. Repeating the PCR on fractions of the flea salivary gland library (mini-libraries) narrowed the occurrence frequency of the cloned fspi protein cDNA to approximately 1 in 200 plaque forming units (PFU) before a final plaque lift and identification by hybridization with a [$^{32}$P]-labeled probe.

Two primers based on SEQ ID NO:24 were used: Primer 9, 5' GCA AAG GTT ATA GAG GAG CTT G 3', denoted as SEQ ID NO:42, and Primer 10, 5' AGC TTT CCA TCA CAT CCA GC 3', denoted as SEQ ID NO:43. The primers generated an internal PCR DNA sequence of 268 bp (including primers) which was used as a marker sequence for screening the salivary gland mini-libraries. The final screening of the salivary gland mini-libraries was done with a pool of the four [$^{32}$P]-labeled primers; Primer 5, SEQ ID NO:21, Primer 6, SEQ ID NO:22, Primer 8, SEQ ID NO:42 and Primer 10, SEQ ID NO:43, using standard techniques. A nucleic acid molecule, named nfspI$_{591}$, identified by this technique was sequenced using standard techniques to give SEQ ID NO:34. The translation of SEQ ID NO:34 yielded yields the amino acid sequence, denoted as SEQ ID NO:35, for a protein named PfspI$_{155}$. This amino acid sequence is similar to SEQ ID NO:26, except that SEQ ID NO:35 does not contain the amino acid sequence E D I at the amino terminus, and SEQ ID NO:35 contains a "C" at position 7, whereas SEQ ID NO:26 has an "L" at the corresponding position.

Example 8

This example demonstrates the ability of a formulation of the present invention to induce flea allergy dermatitis in an animal susceptible to flea allergy dermatitis.

To determine whether the isolated flea saliva proteins described in Examples 2 and 3 were capable of inducing an allergic response in animals susceptible to flea allergy dermatitis, skin tests were performed on sensitized dogs. Six dogs were sensitized to fleas using the method of Gross, et al., 1985, Veterinary Pathology, Vol. 22, pp. 78–71. Briefly, each dog was exposed to about 25 C. felis fleas contained in chambers by allowing the contained fleas to feed on the experimental dogs for about 15-minute periods at weekly intervals. The six dogs were sensitized over the following periods: Dog 2080109 was exposed to fleas 38 times over a period spanning Aug. 31, 1993 through Jun. 7, 1994. Dog 2082101 was exposed to fleas 22 times over a period spanning Dec. 14, 1993 through Jun. 7, 1994. Dog 2082128 was exposed to fleas 20 times over a period spanning Aug. 31, 1993 through May 24, 1994. Dog BFQ2 was exposed to fleas 17 times over a period spanning Mar. 15, 1994 through Jul. 12, 1994. Dog CPO2 was exposed to fleas 12 times over a period spanning Mar. 15, 1994 through Jun. 7, 1994. Dog CQQ2 was exposed to fleas 1 time on Mar. 15, 1994.

Skin testing was performed the morning of Jul. 21, 1994. The dogs were shaved in the lateral thorax/abdominal area and intradermally injected in that area with a variety of formulations of the present invention as well as with control solutions. The total volume per injection was 50 microliters ($\mu$l), with the formulations and controls being diluted in phenolated saline. Each dog received the injections listed in Table 1.

TABLE 1

Samples administered to dogs.

| SAMPLE | REPLICATES | $\mu$g/inj | FLEA-HOUR |
|---|---|---|---|
| DILUENT | 2 | N/A* | N/A |
| HISTAMINE | 2 | 1.38 | N/A |
| GREER | 3 | 50 (W/V) | N/A |
| FS-1 | 3 | 1.88 | 4,660 |
| A | 3 | 0.23 | 23,000 |
| B | 3 | 0.32 | 23,000 |
| C1 | 3 | 1.10** | 23,000 |
| C2 | 3 | 0.42 | 23,000 |
| D1 | 3 | 0.24 | 23,000 |
| D2 | 3 | 0.29 | 23,000 |
| E | 3 | 0.16 | 23,000 |
| F | 3 | 0.10 | 23,000 |
| G | 3 | 0.21 | 23,000 |
| H | 3 | 0.20 | 23,000 |
| I | 3 | 0.12 | 23,000 |
| J | 3 | 0.08 | 23,000 |
| K | 3 | 0.12 | 23,000 |
| L | 3 | 0.08 | 23,000 |
| M1 | 3 | 0.16 | 23,000 |
| M2 | 3 | 0.27 | 23,000 |
| N | 3 | 0.20 | 23,000 |
| FS-2 | 3 | 0.71 | 4,660 |

*N/A is not applicable
**Apparent amount, probably artificially high due to assay interference Note that in these studies, fspJ1 and fspJ2 were administered together as fspJ; fspL1 and fspL2 were administered together as fspL; fspN1, fspN2 and fspN3 were administered together as fspN. It is also to be noted that A, B, C1, C2, D1, D2, E, F, G, H, I, J, K, L, M1, M2 and N refer, respectively to flea saliva proteins fspA, fspB, fspC1, fspC2, fspD1, fspD2, fspE, fspF, fspG, fspH, fspI, fspJ, fspK, fspL, fspM1, fspM2 and fspN. The negative control comprised diluent (NC) and the positive controls comprised Greer antigen (GR) and histamine (HIS). The amount of Greer antigen used was determined by weight per volume (w/v) according to the information provided by the manufacturers (Greer Laboratories, Inc., Lenoir, N.C.). The amount of histamine used was determined by information provided on the supplier's label (available from Greer Laboratories, Inc., Lenoir, N.C.).

A. Comparison of Wheal Sizes at Sites of Injection

All injection sites were objectively (Obj) measured in millimeters (mm) at 15 min and subjectively (Sub) scored on a scale of 0 to 4. The subjective scoring was performed by Kenneth W. Kwochka, D. V. M., Diplomat ACVD, (American College of Veterinary Dermatologists) at Ohio State University, Columbus, Ohio. Tables 2 through 7 indicate the results obtained for each dog. # refers to the number designation given to each sample; antigen refers to the sample. Inj 1, Inj 2 and Inj 3 refer to triplicate injections and NA refers to "not applicable."

TABLE 2

DOG ID: 2082101

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 3 | 10 | 3 | 10 | 3 | 10 |
| 4 | FS-1 | 3 | 10 | 4 | 12 | 4 | 12 |
| 5 | A | 1 | 8 | 0 | 8 | 0 | 8 |
| 6 | B | 0 | 6 | 0 | 6 | 0 | 6 |
| 7 | C1 | 0 | 6 | 0 | 6 | 0 | 6 |
| 8 | C2 | 0 | 6 | 0 | 6 | 0 | 6 |
| 9 | D1 | 0 | 8 | 0 | 8 | 0 | 6 |
| 10 | D2 | 0 | 6 | 0 | 6 | 0 | 8 |
| 11 | E | 3 | 12 | 3 | 12 | 3 | 12 |
| 12 | F | 3 | 14 | 3 | 12 | 3 | 12 |
| 13 | G | 3 | 12 | 3 | 12 | 3 | 12 |
| 14 | H | 3 | 11 | 2 | 12 | 3 | 12 |
| 15 | I | 3 | 12 | 2 | 12 | 3 | 11 |
| 16 | J | 2 | 10 | 2 | 11 | 2 | 10 |
| 17 | K | 2 | 11 | 2 | 10 | 2 | 9 |
| 18 | L | 2 | 9 | 1 | 10. | 1 | 10 |
| 19 | M1 | 2 | 12 | 2 | 11 | 2 | 11 |
| 20 | M2 | 3 | 12 | 3 | 11 | 3 | 12 |
| 21 | N | 3 | 11 | 3 | 10 | 2 | 11 |
| 22 | FS-2 | 2 | 11 | 3 | 12 | 2 | 10 |
| 23 | Neg Cntl | 0 | 8 | NA | NA | NA | NA |
| 24 | Histamine | 4 | 14 | NA | NA | NA | NA |

TABLE 3

DOG ID: 2080109

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg. Cntl | 0 | 7 | NA | NA | NA | NA |
| 2 | Histamine | 4 | 14 | NA | NA | NA | NA |
| 3 | Greer | 0 | 8 | 0 | 8 | 0 | 8 |
| 4 | FS-1 | 4 | 13 | 4 | 13 | 4 | 13 |
| 5 | A | 0 | 9 | 0 | 8 | 0 | 8 |
| 6 | B | 0 | 7 | 0 | 7 | 0 | 7 |
| 7 | C1 | 0 | 8 | 0 | 7 | 0 | 7 |
| 8 | C2 | 0 | 8 | 0 | 7 | 0 | 8 |
| 9 | D1 | 1 | 9 | 1 | 9 | 1 | 9 |
| 10 | D2 | 1 | 9 | 1 | 8 | 1 | 8 |
| 11 | E | 3 | 11 | 3 | 11 | 2 | 10 |
| 12 | F | 3 | 11 | 3 | 13 | 4 | 13 |
| 13 | G | 3 | 14 | 3 | 13 | 3 | 13 |
| 14 | H | 2 | 12 | 2 | 11 | 2 | 10 |
| 15 | I | 2 | 10 | 3 | 10 | 3 | 10 |
| 16 | J | 2 | 10 | 3 | 10 | 3 | 10 |
| 17 | K | 2 | 9 | 2 | 9 | 2 | 9 |
| 18 | L | 1 | 9 | 1 | 6 | 1 | 7 |
| 19 | M1 | 3 | 11 | 3 | 13 | 3 | 13 |
| 20 | M2 | 3 | 14 | 3 | 13 | 3 | 14 |
| 21 | N | 3 | 13 | 3 | 14 | 2 | 10 |
| 22 | FS-2 | 2 | 9 | 1 | 7 | 1 | 8 |
| 23 | Neg Cntl | 0 | 6 | NA | NA | NA | NA |
| 24 | Histamine | 4 | 16 | NA | NA | NA | NA |

TABLE 4

DOG ID: 2082128

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 0 | 6 | 0 | 6 | 0 | 6 |
| 4 | FS-1 | 3 | 12 | 3 | 12 | 3 | 12 |
| 5 | A | 0 | 7 | 0 | 7 | 0 | 6 |
| 6 | B | 0 | 7 | 0 | 7 | 0 | 6 |
| 7 | C1 | 0 | 7 | 0 | 6 | 0 | 7 |
| 8 | C2 | 0 | 6 | 0 | 7 | 0 | 7 |
| 9 | D1 | 0 | 7 | 0 | 7 | 0 | 7 |
| 10 | D2 | 0 | 7 | 0 | 7 | 0 | 7 |
| 11 | E | 0 | 7 | 0 | 6 | 0 | 7 |
| 12 | F | 0 | 6 | 0 | 6 | 0 | 6 |
| 13 | G | 1 | 10 | 1 | 9 | 1 | 9 |
| 14 | H | 2 | 10 | 2 | 10 | 2 | 11 |
| 15 | I | 3 | 12 | 3 | 12 | 3 | 11 |
| 16 | J | 3 | 12 | 3 | 11 | 3 | 11 |
| 17 | K | 3 | 11 | 3 | 12 | 3 | 12 |
| 18 | L | 3 | 11 | 3 | 10 | 3 | 11 |
| 19 | M1 | 3 | 11 | 3 | 11 | 3 | 12 |
| 20 | M2 | 3 | 12 | 3 | 12 | 3 | 12 |
| 21 | N | 3 | 12 | 3 | 12 | 3 | 12 |
| 22 | FS-2 | 3 | 12 | 3 | 11 | 3 | 12 |
| 23 | Neg Cntl | 0 | 6 | NA | NA | NA | NA |
| 24 | Histamine | 4 | 14 | NA | NA | NA | NA |

TABLE 5

DOG ID: BFQ2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 12 | NA | NA | NA | NA |
| 3 | Greer | 0 | 6 | 0 | 6 | 0 | 6 |
| 4 | FS-1 | 1 | 9 | 1 | 9 | 1 | 9 |
| 5 | A | 0 | 7 | 0 | 7 | 0 | 7 |
| 6 | B | 0 | 7 | 0 | 7 | 0 | 7 |
| 7 | C1 | 0 | 7 | 1 | 7 | 1 | 7 |
| 8 | C2 | 0 | 7 | 0 | 7 | 0 | 6 |
| 9 | D1 | 0 | 8 | 1 | 7 | 1 | 8 |
| 10 | D2 | 0 | 7 | 0 | 6 | 1 | 7 |
| 11 | E | 1 | 7 | 0 | 6 | 0 | 6 |
| 12 | F | 1 | 6 | 1 | 7 | 0 | 7 |
| 13 | G | 0 | 8 | 1 | 8 | 1 | 8 |
| 14 | H | 0 | 8 | 0 | 7 | 0 | 7 |
| 15 | I | 1 | 7 | 0 | 7 | 0 | 8 |
| 16 | J | 0 | 7 | 0 | 7 | 0 | 7 |
| 17 | K | 0 | 7 | 0 | 7 | 0 | 6 |
| 18 | L | 0 | 8 | 0 | 7 | 0 | 7 |
| 19 | M1 | 0 | 7 | 0 | 7 | 0 | 7 |
| 20 | M2 | 0 | 7 | 0 | 7 | 1 | 8 |
| 21 | N | 3 | 12 | 3 | 11 | 3 | 11 |
| 22 | FS-2 | 3 | 11 | 3 | 11 | 3 | 11 |
| 23 | Neg Cntl | 0 | 7 | NA | NA | NA | NA |
| 24 | Histamine | 4 | 15 | NA | NA | NA | NA |

TABLE 6

DOG ID: CPO2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 3 | NA | NA | NA | NA |
| 2 | Histamine | 4 | 13 | NA | NA | NA | NA |
| 3 | Greer | 0 | 7 | 0 | 7 | 0 | 6 |
| 4 | FS-1 | 4 | 12 | 4 | 12 | 4 | 12 |
| 5 | A | 0 | 7 | 0 | 6 | 0 | 6 |

TABLE 6-continued

DOG ID: CPO2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 6 | B | 0 | 6 | 0 | 7 | 0 | 7 |
| 7 | C1 | 0 | 7 | 0 | 6 | 0 | 7 |
| 8 | C2 | 0 | 6 | 0 | 6 | 0 | 6 |
| 9 | D1 | 0 | 7 | 1 | 7 | 0 | 7 |
| 10 | D2 | 1 | 6 | 0 | 6 | 0 | 5 |
| 11 | E | 0 | 6 | 0 | 6 | 0 | 6 |
| 12 | F | 0 | 6 | 0 | 6 | 2 | 7 |
| 13 | G | 2 | 9 | 2 | 8 | 2 | 8 |
| 14 | H | 4 | 11 | 4 | 12 | 4 | 11 |
| 15 | I | 3 | 12 | 3 | 11 | 3 | 10 |
| 16 | J | 3 | 10 | 3 | 11 | 3 | 10 |
| 17 | K | 2 | 8 | 2 | 8 | 2 | 8 |
| 18 | L | 1 | 8 | 1 | 7 | 1 | 7 |
| 19 | M1 | 3 | 11 | 3 | 11 | 3 | 11 |
| 20 | M2 | 3 | 11 | 4 | 12 | 4 | 12 |
| 21 | N | 4 | 12 | 3 | 10 | 3 | 11 |
| 22 | FS-2 | 3 | 11 | 3 | 12 | 3 | 12 |
| 23 | Neg Cntl | 0 | 6 | NA | NA | NA | NA |
| 24 | Histamine | 4 | 13 | NA | NA | NA | NA |

TABLE 7

DOG ID: CQQ2

| # | Antigen | Inj 1 Sub | Inj 1 Obj | Inj 2 Sub | Inj 2 Obj | Inj 3 Sub | Inj 3 Obj |
|---|---|---|---|---|---|---|---|
| 1 | Neg Cntl | 0 | 6 | NA | NA | NA | NA |
| 2 | Histamine | 4 | 13 | NA | NA | NA | NA |
| 3 | Greer | 0 | 7 | 0 | 7 | 0 | 7 |
| 4 | FS-1 | 2 | 8 | 2 | 8 | 2 | 8 |
| 5 | A | 0 | 6 | 0 | 6 | 0 | 7 |
| 6 | B | 0 | 7 | 0 | 7 | 0 | 6 |
| 7 | C1 | 0 | 7 | 0 | 6 | 0 | 6 |
| 8 | C2 | 0 | 7 | 0 | 7 | 0 | 6 |
| 9 | D1 | 0 | 6 | 0 | 6 | 0 | 6 |
| 10 | D2 | 0 | 6 | 0 | 6 | 0 | 7 |
| 11 | E | 0 | 6 | 0 | 6 | 0 | 6 |
| 12 | F | 0 | 6 | 0 | 7 | 0 | 7 |
| 13 | G | 0 | 7 | 0 | 7 | 0 | 6 |
| 14 | H | 1 | 7 | 1 | 7 | 1 | 7 |
| 15 | I | 2 | 8 | 2 | 9 | 2 | 8 |
| 16 | J | 2 | 8 | 2 | 8 | 2 | 8 |
| 17 | K | 1 | 7 | 1 | 7 | 1 | 7 |
| 18 | L | 1 | 6 | 0 | 6 | 0 | 6 |
| 19 | M1 | 2 | 7 | 2 | 8 | 2 | 8 |
| 20 | M2 | 2 | 8 | 2 | 8 | 2 | 9 |
| 21 | N | 3 | 11 | 3 | 12 | 3 | 11 |
| 22 | FS-2 | 3 | 11 | 3 | 11 | 3 | 10 |
| 23 | Neg Cntl | 0 | 7 | NA | NA | NA | NA |
| 24 | Histamine | 4 | 14 | NA | NA | NA | NA |

As a control, 2 flea naive dogs (i.e., dogs that had never been exposed to fleas) were also tested with single replicates of the same samples that were injected into the sensitized dogs. These dogs are referred to as WANU and WBCE. Objective and subjective wheal size measurements 15 minutes after injection of the samples are shown in Tables 8 and 9.

TABLE 8

DOG ID: WANU

| # | Antigen | Inj 1 Sub | Inj 1 Obj |
|---|---|---|---|
| 1 | Neg Cntl | 0 | 7 |
| 2 | Histamine | 4 | 10 |

TABLE 8-continued

DOG ID: WANU

| # Antigen | Inj 1 Sub | Inj 1 Obj |
|---|---|---|
| 3 Greer | 0 | 6 |
| 4 FS-1 | 0 | 6 |
| 5 A | 0 | 7 |
| 6 B | 0 | 6 |
| 7 C1 | 0 | 6 |
| 8 C2 | 0 | 6 |
| 9 D1 | 0 | 7 |
| 10 D2 | 0 | 6 |
| 11 E | 0 | 6 |
| 12 F | 0 | 6 |
| 13 G | 0 | 7 |
| 14 H | 0 | 7 |
| 15 I | 0 | 7 |
| 16 J | 0 | 7 |
| 17 K | 0 | 6 |
| 18 L | 0 | 7 |
| 19 M1 | 0 | 6 |
| 20 M2 | 0 | 6 |
| 21 N | 1 | 8 |
| 22 FS-2 | 1 | 8 |
| 23 Neg Cntl | NA | NA |
| 24 Histamine | NA | NA |

TABLE 9

DOG ID: WBCE

| # Antigen | Inj 1 Sub | Inj 1 Obj |
|---|---|---|
| 1 Neg Cntl | 0 | 6 |
| 2 Histamine | 4 | 12 |
| 3 Greer | 0 | 7 |
| 4 FS-1 | 0 | 7 |
| 5 A | 0 | 7 |
| 6 B | 0 | 7 |
| 7 C1 | 0 | 7 |
| 8 C2 | 0 | 7 |
| 9 D1 | 0 | 7 |
| 10 D2 | 0 | 6 |
| 11 E | 0 | 7 |
| 12 F | 0 | 7 |
| 13 G | 0 | 8 |
| 14 H | 0 | 7 |
| 15 I | 0 | 7 |
| 16 J | 0 | 7 |
| 17 K | 0 | 7 |
| 18 L | 0 | 6 |
| 19 M1 | 0 | 7 |
| 20 M2 | 0 | 7 |
| 21 N | 0 | 7 |
| 22 FS-2 | 0 | 7 |
| 23 Neg Cntl | NA | NA |
| 24 Histamine | NA | NA |

The average subjective score obtained for each flea saliva antigen from the 6 sensitized dogs tested was calculated and is summarized in FIG. 5. The results indicate that the flea saliva products produced as described in Examples 2 and 3 include at least one allergenic protein capable of inducing an immediate hypersensitive response in a sensitized dog. In particular, injection of the mixtures of flea saliva antigens referred to as FS-1 and FS-2 resulted in substantial wheal formation. Flea saliva proteins fspE, fspF, fspG, fspH, fspI, fspJ, fspK, fspL, fspM1, fspM2 and fspN also resulted in substantial wheal formation. Flea saliva proteins fspA, fspB, fspc1, fspC2, fspD1 and fspD2 produced minimal, if any, allergic response, depending on the dog being tested. The sample containing fspH produced the largest wheal formation when compared with the other flea saliva proteins.

*B. Comparison of Levels of Induration and Erythema at the Injection Sites

In addition to wheal size, the amount of induration and erythema were also measured at each site of injection. Induration produced by the injection of the flea saliva antigens was measured at 6 hours and 24 hours by subjective scoring. Such subjective induration measurements were performed by Kenneth W. Kwochka, D. V. M. In addition, the amount of erythema at each site of injection were subjectively scored by Kenneth W. Kwochka, D. V. M.

The amounts of induration and erythema measured by subjective scoring at 6 hours were negative for each of the sensitized and control dogs except for the following formulations in the following sensitized dogs. Administration of FS-1 to Dog 2082101 produced an average induration score of 1 at 2 sites of injection but no erythema score. Administration of fspL to Dog 2082101 produced no induration but an erythema score of 1 at 1 site of injection. Administration of fspM1 to Dog 2082101 produced no induration but an erythema score of 3 at 1 site of injection. Administration of FS-2 to Dog 2082101 produced no induration but an average erythema score of 1.33 at 3 sites of injection.

Administration of fspH to Dog 2082128 produced no induration but an average erythema score of 2 at 3 sites of injection. Administration of fspi to Dog 2082128 produced an average induration score of 1 and an average erythera score of 1 at 2 sites of injection. Administration of fspJ to Dog 2082128 produced an average induration score of 1 and an average erythema score of 1 at 3 sites of injection. Administration of FS-2 to Dog 2082128 produced no induration but an average erythema score of 2 at 3 sites of injection.

Administration of FS-1 to Dog BFQ2 produced an average induration score of 2 and an average erythema score of 2 at 3 sites of injection. Administration of fspN to Dog BFQ2 produced an average induration score of 1 and an average erythema score of 2 at 2 sites of injection. Administration of FS-2 to Dog BFQ2 produced an average induration score of 1 and an average erythema score of 2 at 2 sites of injection. Administration of FS-1 to Dog CPO2 produced an average induration score of 2.5 but no erythema at 2 sites of injection. Administration of fspG to Dog CPO2 produced no induration but an average erythema score of 2 at 3 sites of injection. Administration of fspH to Dog CPO2 produced no induration but an average erythema score of 1 at 2 sites of injection. Administration of FS-2 to Dog CPO2 produced no induration but an average erythema score of 2 at 3 sites of injection.

Figure 6:
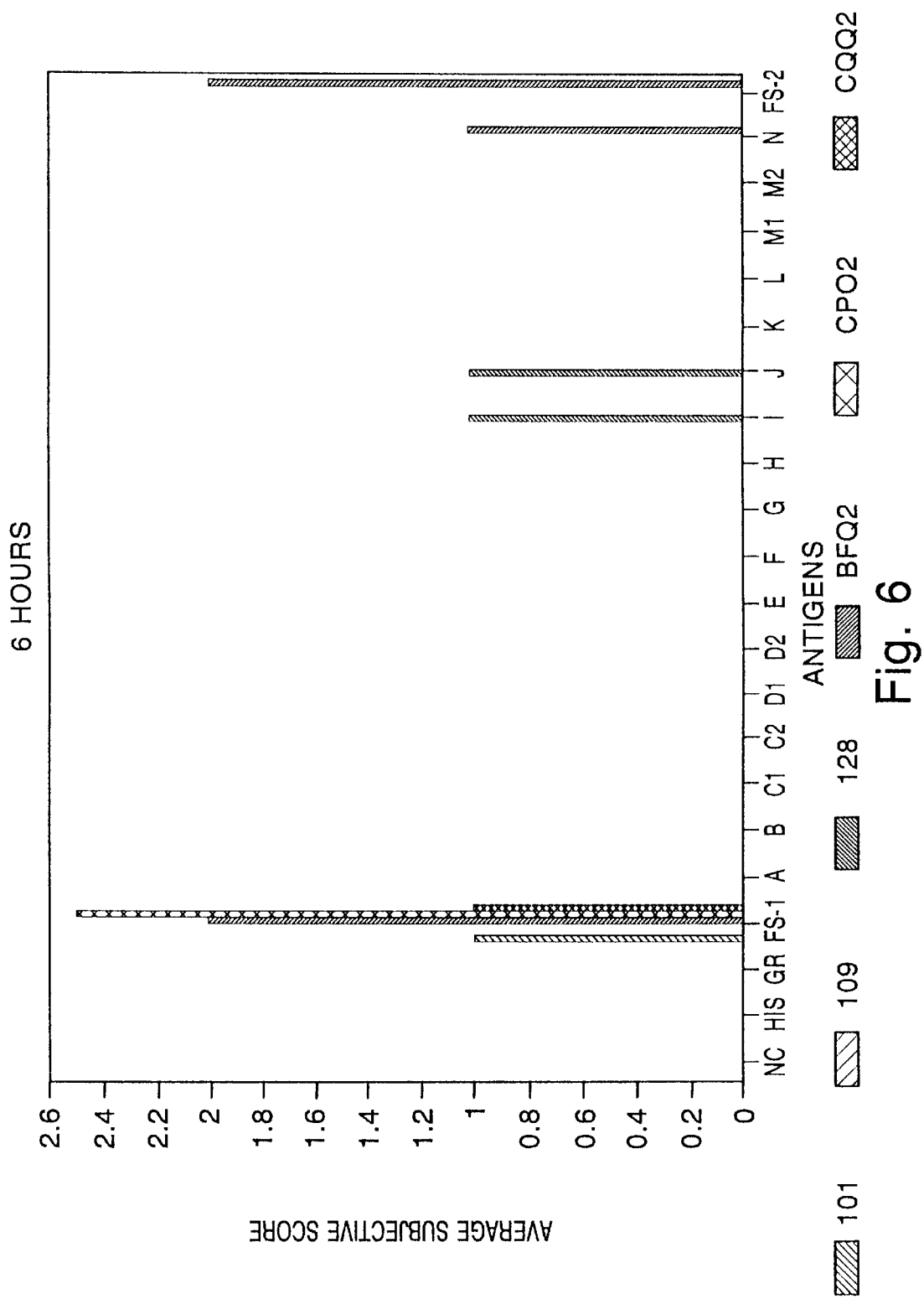
FIG. 6 illustrates the relative induration of wheals 6 hours after injection of various flea saliva protein formulations into flea-sensitized dogs.
Figure 7:
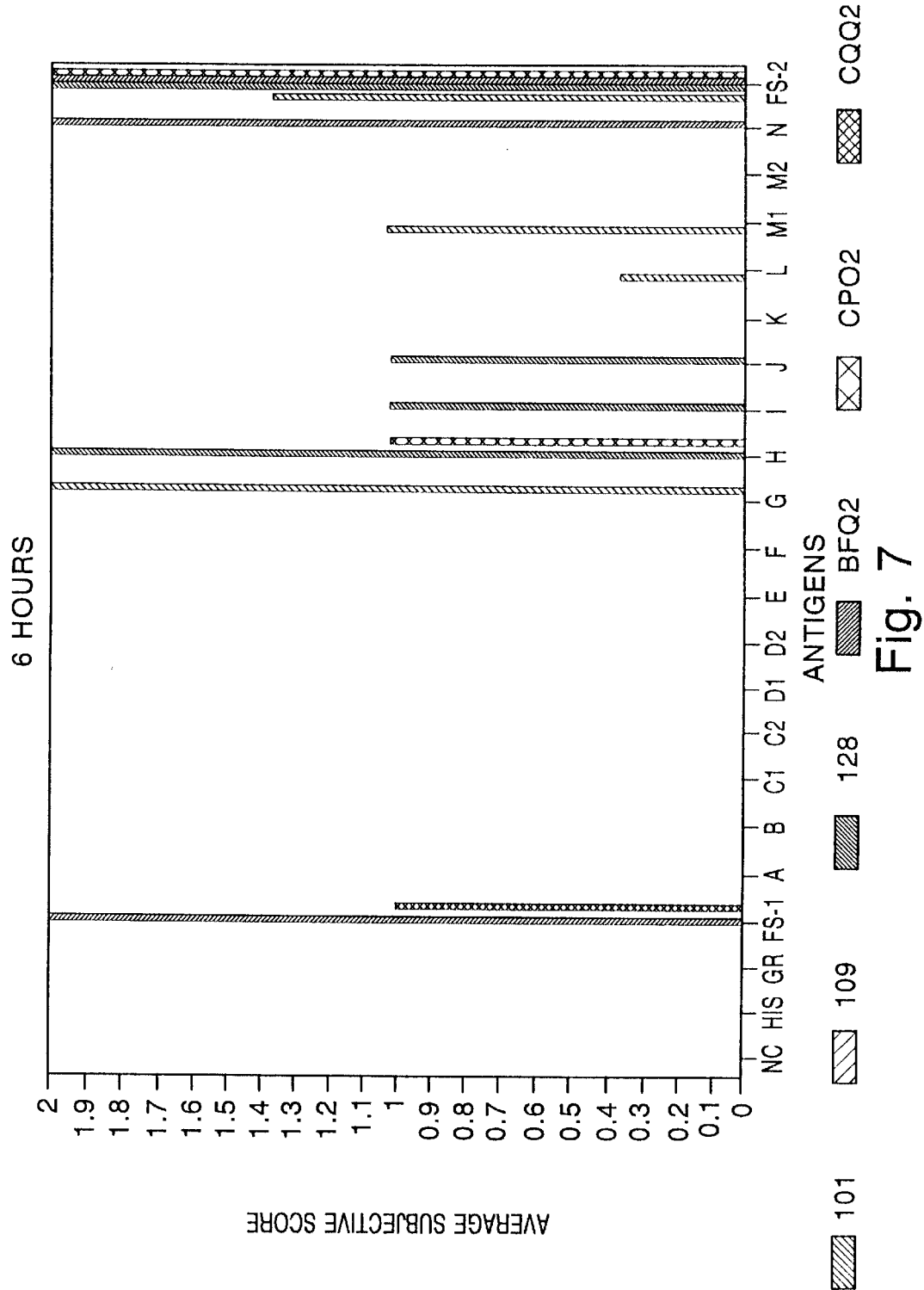
FIG. 7 illustrates the relative erythema of wheals 6 hours after injection of various flea saliva protein formulations into flea-sensitized dogs.

The average subjective score for induration obtained for each flea saliva antigen from the 6 sensitized dogs tested was calculated and is summarized in FIG. 6. The average subjective score for erythema obtained for each flea saliva antigen from the 6 sensitized dogs tested was calculated and is summarized in FIG. 7.

The amounts of induration and erythema measured by subjective scoring at 24 hours results for five of the flea-sensitized dogs and the two control dogs were negative except for the following formulations in the following sensitized dogs.

Administration of fspi to Dog 2082101 produced an average induration score of 1 and an average erythema score of 1 at 3 sites of injection. Administration of fspj to Dog 2082101 produced an average induration score of 1 and an average erythema score of 1 at 3 sites of injection. Administration of fspM1 to Dog 2082101 produced an average induration score of 1 and an average erythema score of 3 at 3 sites of injection. Administration of fspN to Dog 2082101 produced an average induration score of 1 and an average erythema score of 2 at 3 sites of injection. Administration of FS-2 to Dog 2082101 produced an average induration score of 3 and an average erythema score of 4 at 3 sites of injection.

Administration of FS-1 to Dog BFQ2 produced an average induration score of 1 and an average erythema score of 1 at 3 sites of injection. Administration of FS-2 to Dog BFQ2 produced an induration score of 1 and an erythema score of 1 at 1 site of injection.

Administration of FS-1 to Dog CPO2 produced an induration score of 2 and an erythema score of 1 at 1 site of injection. Administration of fspi to Dog CPO2 produced an average induration score of 1 and an average erythema score of 1 at 3 sites of injection. Administration of FS-2 to Dog CPO2 produced an average induration score of 1 and an average erythema score of 2 at 3 sites of injection.

Administration of Greer antigen to Dog CQQ2 produced no induration but an average erythema score of 1 at 3 sites of injection. Administration of FS-1 to Dog CQQ2 produced an induration score of 1 and an erythema score of 1 at 1 site of injection. Administration of fspI, fspJ, fspM1 or fspM2 to Dog CQQ2 produced no induration but an average erythema score of 1 at 3 sites of injection. Administration of fspN to Dog CQQ2 produced an induration score of 1 and an erythema score of 1 at 1 site of injection. Administration of FS-2 to Dog CQQ2 produced an average induration score of 1 and an average erythema score of 2 at 3 sites of injection.

Figure 8:
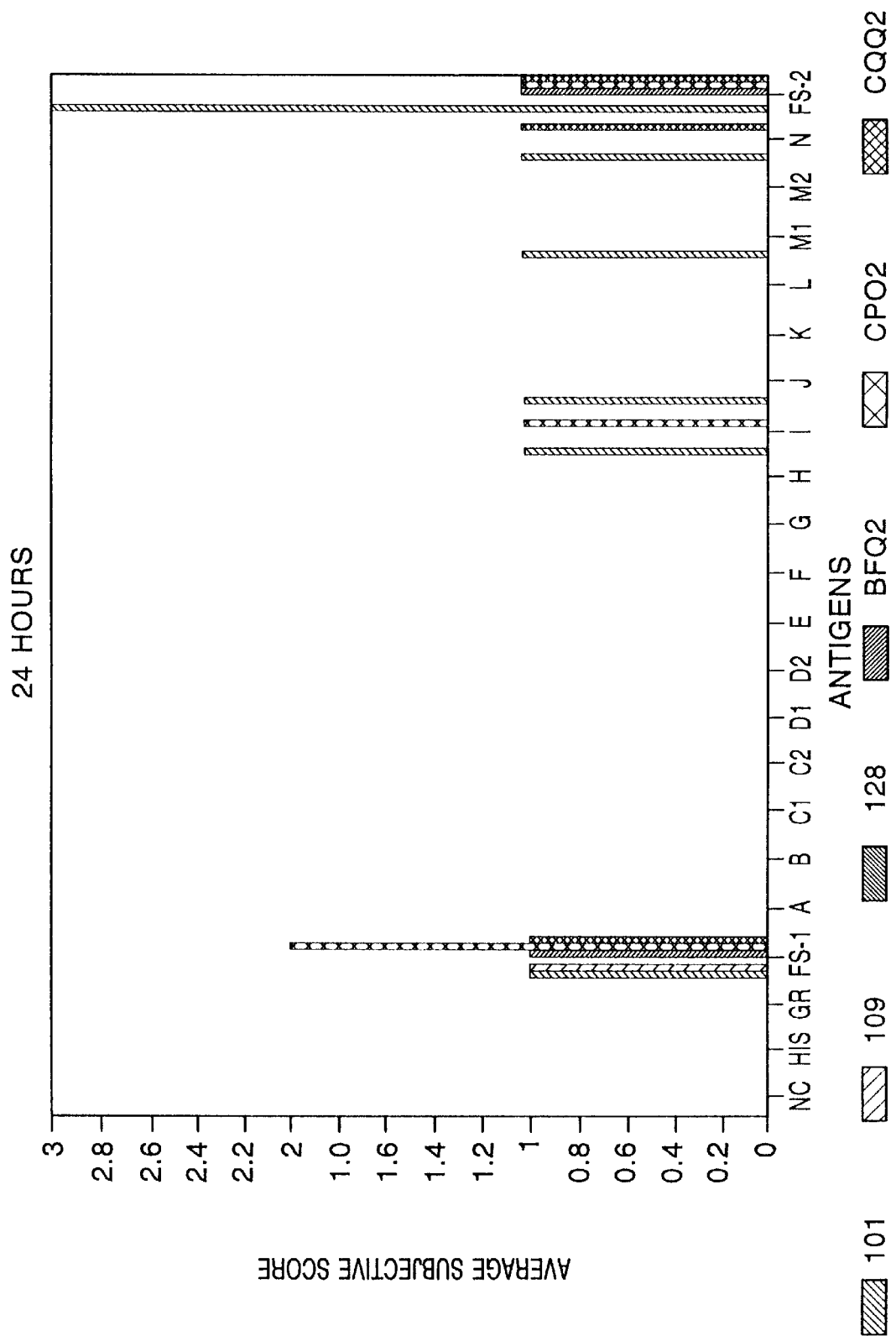
FIG. 8 illustrates the relative induration of wheals 24 hours after injection of various flea saliva protein formulations into flea-sensitized dogs.
Figure 9:
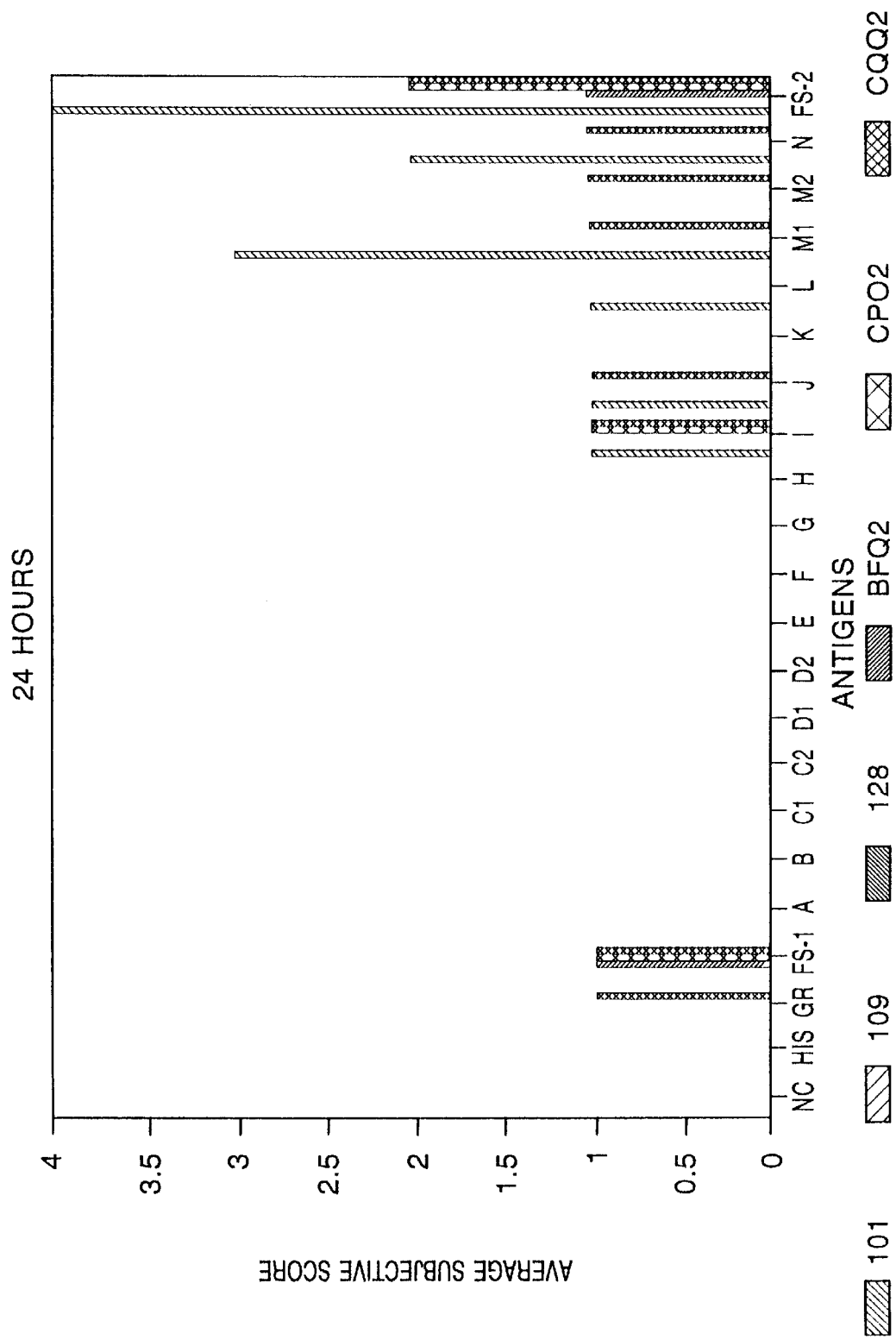
FIG. 9 illustrates the relative erythema of wheals 24 hours after injection of various flea saliva protein formulations into flea-sensitized dogs.

The average subjective score for induration obtained for each flea saliva antigen from the 6 sensitized dogs tested was calculated and is summarized in FIG. 8. The average subjective score for erythema obtained for each flea saliva antigen from the 6 sensitized dogs tested was calculated and is summarized in FIG. 9.

The results indicate that at least some of the flea saliva protein formulations produced as described in Examples 2 and 3 include at least one allergenic protein capable of inducing a delayed hypersensitive response in a sensitized dog. Injection of the mixtures of flea saliva proteins referred to as FS-1 and FS-2 induced substantial induration and erythema for at least 24 hours. In addition, the flea saliva protein samples fspI, fspJ, M1 and fspN were sufficiently allergenic to induce induration and erythema for at least 24 hours. The flea saliva protein sample fspL and fspM2 induced substantial levels of induration but not substantial levels of erythema at 24 hours.

Taken together, the results shown indicated above and shown in FIG. 5 through 9, indicate that saliva protein formulations of the present invention are sufficiently allergenic to induce a hypersensitive response in a sensitized dog. Numerous samples induced both an immediate hypersensitive response and a delayed hypersensitive response.

Example 9

This example demonstrates the ability of numerous flea saliva protein samples isolated in Examples 2 and 3 to induce a hypersensitive response by histopathology of tissue removed from selected lesions on the dogs described in Example 8.

Two tissue samples per dog were removed from each sensitized dog described in Example 8. No biopsies were taken from the two naive dogs. The selected sites from which the tissue samples were removed are indicated in Table 10 below. Biopsies were taken with a 4 mm biopsy punch after subcutaneous injections of Lidocaine. Biopsies were processed and read by Dr. David M. Getzy, DVM, Diplomat ACVP (American College of Veterinary Pathologists) at the Colorado Veterinary Diagnostic Laboratory (College of Veterinary Medicine and Biomedical Sciences, Colorado State University, Fort Collins, Colo.).

TABLE 10

Histopathology

| Dog | Antigen | Time | No. | Slide | Lesion Type | Grade |
|---|---|---|---|---|---|---|
| 101 | FS-1 | 15 min. | 1 | A | A | 1 |
|  |  | 6 hr. | 2 | B | A | 2.5 |
|  |  | 24 hr. | 3 | C | A | 3 |
| 109 | FS-1 | 15 min. | 4 | D | A | 1 |
|  |  | 6 hr. | 5 | E | C | 2 |
|  |  | 24 hr. | 6 | F | C | 3 |
| 128 | FS-1 | 15 min. | 7 | G | A | 1.5 |
|  |  | 6 hr. | 8 | H | C | 1.5 |
|  |  | 24 hr. | 9 | I | C | 3 |
| CPO2 | FS-1 | 15 min. | 10 | J | A | 1.5 |
|  |  | 6 hr. | 11 | K | C | 3 |
|  |  | 24 hr. | 12 | L | C | 4 |
| CQQ2 | FS-1 | 15 min. | 13 | M | A | 1.5 |
|  |  | 6 hr. | 14 | N | C | 2.5 |
|  |  | 24 hr. | 15 | O | C | 2.5 |
| 101 | fspE | 15 min. | 16 | P | A | 1 |
|  |  | 6 hr. | 17 | Q | C | 1.5 |
|  |  | 24 hr. | 18 | R | A | 1.5 |
| 109 | fspF | 15 min. | 19 | S | A | 1 |
|  |  | 6 hr. | 20 | T | A | 1.5 |
|  |  | 24 hr. | 21 | U | A | 1.5 |
| 128 | fspI | 15 min. | 22 | V | A | 1 |
|  |  | 6 hr. | 23 | W | C | 2.5 |
|  |  | 24 hr. | 24 | X | C | 2.5 |
| BFQ2 | fspN | 15 min. | 25 | Y | A | 1.5 |
|  |  | 6 hr. | 26 | Z | C | 2 |
|  |  | 24 hr. | 27 | AA | C | 3.5 |
| BFQ2 | fspO | 15 min. | 28 | BB | A | 1 |
|  |  | 6 hr. | 29 | CC | C | 3 |
|  |  | 24 hr. | 30 | DD | C | 2.5 |
| CPO2 | fspH | 15 min. | 31 | EE | A | 1.5 |
|  |  | 6 hr. | 32 | FF | C | 1.5 |
|  |  | 24 hr. | 33 | GG | A | 1.5 |
| CQQ2 | fspN | 15 min. | 34 | HH | A | 1 |
|  |  | 6 hr. | 35 | II | C | 2.5 |
|  |  | 24 hr. | 36 | JJ | C | 2.5 |

Two types of lesions were found in the tissue samples tested. Lesion Type A refers to a moderate superficial dermal edema having mild numbers of mast cells in a perivascular orientation within the superficial dermis. Vascular endothelium exhibited mild reactive hypertrophy. Minimal numbers of neutrophils were noted in this region as well. Lesion Type C refers to lesions that were similar to those described in Lesion Type A except that the eosinophils were mild to moderate in severity, while neutrophils and mast cells were mild in severity.

On a scale of 0 to 5, lesions ranged from grade 1 to grade 4 in severity. Some of the specimens had predominantly mastocytic inflammatory perivascular infiltrates, edema, and minimal numbers of other cellular components. Other sections showed a predominance of eosinophilic inflammatory infiltrates, with lesser numbers of mast cells and neutrophils. The severity of these lesions was variable, however, in some areas, it progressed to intraepidermal eosinophilic pustulation and collagen necrobiosis within the superficial dermis.

Taken together, the tissue samples indicated the presence of superficial perivascular/periadnexal, mastocytic and eosinophilic, subacute dermatitis. Lesions noted in all the slide specimens examined are consistent with an allergic Type I hypersensitivity reaction.

Example 10

This example further demonstrates the ability of proteins described in Examples 2 and 3 to induce an allergic response in animals naturally susceptible to flea allergy dermatitis through skin tests performed on dogs. These reactions were compared to those obtained using the current standard for diagnosis of flea allergy dermatitis, Greer Whole Flea Extract (Greer Laboratories, Inc., Lenoir, N.C.). In addition, in order to determine specificity of the reactions, test results were compared to those obtained from a population of control dogs with normal skin and a population of dogs with pruritic skin disorders other than flea allergy dermatitis.

Three groups of dogs were used in the study: (1) 10 dogs with naturally occurring flea allergy dermatitis as determined by clinical signs, presence of fleas at the time of diagnosis, and a positive immediate or delayed reaction to Greer Whole Flea Extract; (2) 10 dogs with non-flea-related pruritic dermatoses including, but not limited to, atopy, food allergy dermatitis, pyoderma, seborrhea, and other parasitic hypersensitivity reactions; and (3) 10 dogs with normal skin and no history of chronic skin diseases. The dogs were of any breed, age or sex. They were recruited from the hospital population of the Ohio State University Veterinary Teaching Hospital, Columbus, Ohio. All dogs had written owner consent to participate in the study.

All tests and subjective scoring were performed by Kenneth W. Kwochka, D. V. M., Diplomat ACVD, (American College of Veterinary Dermatologists), in the Dermatology Examination Room at the Veterinary Teaching Hospital, College of Veterinary Medicine, The Ohio State University, Columbus, Ohio. All dogs were tested on the anterior-ventral-lateral aspect of the chest on the left side. Dogs were sedated for testing using standard dosages of xylazine and atropine administered intravenously immediately before the skin test. No glucocorticoids, antihistamines, or other non-steroidal antiinflamatory medications were allowed for at least 3 weeks prior to testing. The area for testing was gently clipped with a #40 electric clipper blade and the njection sites marked with an indelible black felt-tipped marking pen. Twenty-two sites were marked: two rows of ten dots and one row of two dots. Intradermal injections were placed both above and below each mark for a total of forty-four injections that were administered in the following order:

Row 1: Neg. cont.-Histamine-Greer-Greer-Flea saliva-Flea saliva-A-A-B-B

Row 2: C1-C1-C2-C2-D1-D1-D2-D2-E-E

Row 3: F-F-G-G-H-H-I-I-J-J-

Row 4: K-K-L-L-M1-M1-M2-M2-N-N

Row 5: FS2—FS2

Row 6: Neg. cont.-Histamine

Each site was injected intradermally with 50 µl of sterile diluent (Neg. cont.), 1/100,000 w/v histamine phosphate (Histamine), Greer Whole Flea Extract (Greer), whole flea saliva (Flea saliva), or individual salivary protein fractions (fspA,(A); fspB, (B); fspC1, (C1); fspC2, (C2); fspD1, (D1); fspD2, (D2); fspE, (E); fspF, (F) ; fspG, (G); fspH, (H); fspI, (I) ; fspJ, (J) ; fspK, (K) ; fspL, (L) ; fspM1, (M1); fspM2, (M2); fspN, (N); and FS-2 (FS2). All injections were diluted in the same sterile diluent as the Neg. cont.

Skin reactions were read subjectively and objectively at 15 minutes and 24 hours after injections. Owners were required to return their dogs to the Veterinary Teaching Hospital for the 24 hour readings. Subjective assessments were basted on a scale of 0, 1+, 2+, 3+ and 4+ based on wheal size, amount of erythema and amount of induration. Objective assessment was based on wheal diameter measured in millimeters.

Comparison of Skin Reactions

A. FAD Dogs

Of the 10 dogs positive to Greer, 7 (70%) were positive the Flea Saliva (FS). None of the 3 FS-negative dogs reacted to any of the salivary protein fractions. Additionally, the 3 dogs negative to FS at 15 minutes were negative to everything at 24 hours. The 7 FS-positive dogs were used to summarize the 15 minute reactions, shown below in Table 11.

TABLE 11

Immediate (15 min) subjective scores of 7 FS-positive dogs to test antigens

| % Positive | Scores ≧2+ | Scores ≧3+ |
|---|---|---|
| 0 | | I |
| 14 | B, I, J, L | B, D1, J, L |
| 29 | A, C1, C2, D1 | A, C1, C2, K |
| 43 | E, F, K | D2, E, F, H, M2 |
| 57 | D2, H, M2 | G, N, FS2 |
| 71 | G, M1 | M1 |
| 86 | N, FS2 | Greer |
| 100 | Greer, FS | FS |

Four of the 7 FS-positive dogs could not be evaluated at 24 hours because the severity of the immediate reactions warranted antiinflammatory therapy. The remaining 3 FS-positive dogs were used to summarize the 24 hour reactions, shown below in Table 12.

TABLE 12

Delayed (24 hr) subjective scores of 3 FS-positive dogs to test antigens

| % Positive | Scores ≧2+ | Scores ≧3+ |
|---|---|---|
| 0 | | |
| 33 | M2 | |
| 67 | Greer, FS, N, FS2 | FS, N, FS2 |
| 100 | | |

B. Normal Dogs

Three dogs had an immediate reaction to the skin test antigens to some extent. None had a positive delayed reaction at 24 hours. A summary of the immediate (15 min) subjective results is shown below in Table 13.

TABLE 13

Immediate (15 min) subjective scores of 10 normal dogs to test antigens

| % Positive | Scores ≧2+ | Scores ≧3+ |
|---|---|---|
| 0 | | |
| 10 | N, FS2 | FS2 |
| 20 | Greer, FS | Greer, FS |
| 30 | | |
| 40 | | |
| 50 | | |
| 60 | | |
| 70 | | |
| 80 | | |
| 90 | | |
| 100 | | |

Individual dog comments:
Dog #1: Greer 3+, FS 3+, N 2+, FS2 4+
Dog #2: Greer 3+
Dog #3: FS 3+
C. Non-FAD Pruritis Dogs Six dogs had an immediate reaction to the skin test antigens to some extent. A summary of the immediate (15 min) subjective results is shown below in Table 14.

TABLE 14

Immediate (15 min) subjective scores of 10 Non-FAD pruritis dogs to test antigens

| % Positive | Scores ≥2+ | Scores ≥3+ |
|---|---|---|
| 0 | | |
| 10 | G, O | G, O |
| 20 | Greer, M1 | Greer, FS, M1, M2 |
| 30 | FS, M2, N | N |
| 40 | | |
| 50 | | |
| 60 | | |
| 70 | | |
| 80 | | |
| 90 | | |
| 100 | | |

Individual dog comments:
 Dog #1: FS 2+, M1 3+, M2 3+, N 3+, FS2 3+
  Atopic dog under chronic flea exposure
 Dog #2: FS 4+, G 4+, M1 4+, M2 3+, N 3+
  Atopic dog under chronic flea exposure
 Dog #3: FS 4+, M2 2+
  Atopic dog under chronic flea exposure
 Dog #4: N 3+
  Atopic dog under chronic flea exposure
 Dog #5: Greer 4+
  Chronic otitis externa
 Dog #6: Greer 4+
  Generalized demodicosis (mange)

Dogs #1, #2 and #3 all came back to the clinic subsequently and were diagnosed with FAD and were Greer positive.

Three dogs had a delayed reaction to the skin test antigens to some extent. A summary of the delayed (24 hr) subjective results is shown below in Table 15.

TABLE 15

Delayed (24 hr) subjective scores of 10 Non-FAD pruritis dogs to test antigens

| % Positive | Scores ≥2+ | Scores ≥3+ |
|---|---|---|
| 0 | | |
| 10 | FS, N, FS2 | Greer, FS, N, FS2 |
| 20 | | |
| 30 | Greer | |
| 40 | | |
| 50 | | |
| 60 | | |
| 70 | | |
| 80 | | |
| 90 | | |
| 100 | | |

Individual dog comments:
 Dog #3: Greer 2+
  Atopic dog under chronic flea exposure
 Dog #4: Greer 2+
  Atopic dog under chronic flea exposure
 Dog #6: Greer 3+, FS 3+, N 3+, FS2 3+
  Generalized demodicosis (mange)

As an aid in determining the fraction(s) of flea saliva that correlate best with a positive skin test result, all the data for the artificially sensitized and clinically diagnosed FAD dogs that were 2+ or greater to FS (12 dogs total; 5 artificially sensitized and 7 clinically diagnosed as FAD positive) were tabulated according to the responses to the test antigens. The immediate (15 min) subjective results are shown below in Table 16, and the delayed (24 h) subjective results are shown below in Table 17.

TABLE 16

PERCENT RESPONDING
(15 min subjective score)

| | Artificially Sensitized (5) | | Clinical Diagnosis (7) | | Combined (12) | |
|---|---|---|---|---|---|---|
| Antigen | Score ≥2+ | Score ≥3+ | Score ≥2+ | Score ≥3+ | Score ≥2+ | Score ≥3+ |
| Greer | 20 | 20 | 100 | 86 | 67 | 58 |
| FS | 100 | 80 | 100 | 100 | 100 | 92 |
| A | 0 | 0 | 29 | 29 | 17 | 17 |
| B | 0 | 0 | 14 | 14 | 8 | 8 |
| C | 0 | 0 | 29 | 29 | 17 | 17 |
| D1 | 0 | 0 | 29 | 14 | 17 | 8 |
| D2 | 0 | 0 | 57 | 43 | 33 | 25 |
| E | 40 | 20 | 43 | 43 | 42 | 33 |
| F | 40 | 40 | 43 | 43 | 42 | 42 |
| G | 60 | 40 | 71 | 57 | 67 | 50 |
| H | 80 | 20 | 57 | 43 | 67 | 33 |
| I | 100 | 40 | 14 | 0 | 50 | 17 |
| J | 100 | 40 | 14 | 14 | 50 | 25 |
| K | 80 | 20 | 43 | 29 | 58 | 25 |
| L | 20 | 20 | 14 | 14 | 17 | 17 |
| M1 | 100 | 60 | 71 | 71 | 83 | 67 |
| M2 | 100 | 80 | 57 | 43 | 75 | 58 |
| N | 100 | 60 | 86 | 57 | 92 | 58 |
| FS2 | 80 | 60 | 86 | 57 | 83 | 58 |

TABLE 17

PERCENT RESPONDING
(24 hr subjective score)

| | Artificially Sensitized (5) | | Clinical Diagnosis (7) | | Combined (12) | |
|---|---|---|---|---|---|---|
| Antigen | Score ≥2+ | Score ≥3+ | Score ≥2+ | Score ≥3+ | Score ≥2+ | Score ≥3+ |
| Greer | 0 | 0 | 67 | 0 | 25 | 0 |
| FS | 0 | 0 | 67 | 67 | 25 | 25 |
| A | 0 | 0 | 0 | 0 | 0 | 0 |
| B | 0 | 0 | 0 | 0 | 0 | 0 |
| C | 0 | 0 | 0 | 0 | 0 | 0 |
| D1 | 0 | 0 | 0 | 0 | 0 | 0 |
| D2 | 0 | 0 | 0 | 0 | 0 | 0 |
| E | 0 | 0 | 0 | 0 | 0 | 0 |
| F | 0 | 0 | 0 | 0 | 0 | 0 |
| G | 0 | 0 | 0 | 0 | 0 | 0 |
| H | 0 | 0 | 0 | 0 | 0 | 0 |
| I | 0 | 0 | 0 | 0 | 0 | 0 |
| J | 0 | 0 | 0 | 0 | 0 | 0 |
| K | 0 | 0 | 0 | 0 | 0 | 0 |
| L | 0 | 0 | 0 | 0 | 0 | 0 |
| M1 | 20 | 0 | 0 | 0 | 13 | 0 |
| M2 | 0 | 0 | 33 | 0 | 13 | 0 |
| N | 20 | 0 | 67 | 67 | 38 | 25 |
| FS2 | 60 | 20 | 67 | 67 | 63 | 38 |

The results of these studies indicate that the most substantial responses were obtained for fractions fspG, fspH, fspM1, fspM2 and fspN.

Example 11

The following example illustrates the expression of fspI proteins in bacteria and in insect cells.

A. Expression of Flea Protein fspi in E. coli

A 500 bp DNA fragment of fspi was PCR amplified from nucleic acid molecule nfspI$_{591}$, using: Primer 11, a sense primer having the nucleic acid sequence 5' ATTCGGATC-CATGGAAAGTTAATAAAAAATGTAC 3' (BamHI site in bold), denoted as SEQ ID NO:36; and Primer 12, an antisense primer having the nucleic acid sequence 5' TAATGGATCCTTATTTTTTGGTCGACAATAAC 3', denoted SEQ ID NO:37. The PCR product, a fragment of about 535 nucleotides, denoted nfspI$_{535}$, was digested with BamHI restriction endonuclease, gel purified, and subcloned into expression vector pTrcHisB (available from InVitrogen Corp.) that had been digested with BamHI and CIP treated to produce recombinant molecule pHis-nfspI$_{535}$.

The recombinant molecule was transformed into both HB101 (available from BRL, Gaithersburg, Md.) and BL21 (available from Novagen, Madison, Wis.) competent cells to form recombinant cells E.coliHB:pHis-nfspI$_{535}$ and E.coliBL:pHis-nfspI$_{535}$. The recombinant cells were cultured in an enriched bacterial growth medium containing 0.1 mg/ml ampicillin and 0.1% glucose at 32° C. When the cells reached an OD$_{600}$ of about 0.4–0.5, expression was induced by the addition of 0.5 mM isopropyl B-D-thiogalactoside (IPTG), and the cells were cultured for 2 hours at 32° C.

SDS-polyacrylamide gel electrophoresis and western immunoblot analyses of recombinant cell lysates containing the fusion protein PHIS-PfspI$_{155}$ were accomplished by standard procedures using either a T7 Tag monoclonal antibody (available from InVitrogen Corp.) or rabbit anti-FAD antiserum (#A3381) generated by Paravax, Inc. in Fort Collins, Col., produced by immunizing rabbits with nitrocellulose membranes containing flea saliva, produced as described in Example 2. Antigen/antibody reactions were detected by colorimetric enzyme reactions using alkaline phosphatase-conjugated anti-mouse or anti-rabbit antibodies. A 28 kD protein was detected on the immunoblots of induced lysates with both primary antibodies.

B. Expression of Flea Protein fspi in Insect Cells

Nucleic acid molecule nfspI$_{475}$ was PCR amplified from an fspi nucleic acid molecule using the following primers, which were designed to facilitate expression in insect cells using a baculovirus vector: sense Primer 13, with the BamHI site in bold, is 5' CGC GGA TCC TAT AAA TAT GGA GGA CAT CTG GAA AGT TAA TAA AAA ATG TAC ATC 3', denoted as SEQ ID NO:44; and antisense Primer 14, with the XbaI site in bold, is 5' GCT CTA GAG CAT TTA TTT TTT GGT CGA CAA TAA CAA AAC 3', denoted as SEQ ID NO:45. The PCR product was digested with BamHI and XbaI and an about 475 bp DNA fragment was excised and purified from an agarose gel.

Nucleic acid molecule nfspI$_{475}$ was ligated into a pVL1393 vector (available from InVitrogen Corp.) digested with BamHI and XbaI to produce recombinant molecule pVL-nfspI$_{475}$.

The recombinant molecule was transfected into S. frugiperda Sf9 cells with linearized Baculovirus DNA to form recombinant cell S. frugiperda:pVL-nfspI$_{475}$. The recombinant cells were cultured using standard conditions to produce recombinant virus. The transfection supernatant was also found to contain a 23 kD protein which reacted with a rabbit anti-FAD antiserum (#A3381) by Western blot analysis.

Example 12

This example describes the isolation of nucleic acid sequences encoding at least portions of flea saliva proteins in fspN, and their characterization relative to human prostatic acid phosphatase.

The flea salivary gland and the whole fed flea CDNA libraries described previously in Example 6A were immunoscreened using New Zealand White rabbit antiserum developed against a collected mixture of flea salivary proteins (e.g., the rabbit was immunized one or more times with a ground up nitrocellulose filter used as collection membrane to collect flea saliva proteins, followed by one or more immunization with a flea saliva protein extract eluted from a Duropore filter). The immunoscreening protocols used are those described in the picoBlue™ Immunoscreening Kit instruction manual, available from Stratagene, Inc. The methods for preparation of the cDNA expression libraries for immunoscreening, i.e., expression of the cDNA clones and procedures for transferring lambda phage plaques to membranes for immunoscreening, are described in the ZAP-CDNA Synthesis Kit instruction manual, also available from Stratagene, Inc., La Jolla, Calif.

Forty immunopositive clones were selected from the screening. One immunopositive clone was derived from the salivary gland CDNA library and 39 other immunopositive clones were derived from the whole fed flea cDNA library. The initial fspN-protein CDNA sequences, termed nfspN(A) and nfspN(B) were isolated from the whole fed flea cDNA library and came from this initial immunoscreening.

Partial nucleotide sequences for nfspN(A) and nfspN(B) are represented by SEQ ID NO's. Each sequence represents approximately the carboxyl terminal half of the cDNA gene coding region as well as the 3' untranslated region through the poly (A) region. The nucleotide sequence for a nfspN(A) nucleic acid molecule named nfspN(A)$_{646}$ is denoted as SEQ ID NO:50. Translation of SEQ ID NO:50 yields a protein named PfspN(A)$_{172}$ having an amino acid sequence denoted SEQ ID NO:51. The nucleotide sequences for a nfspN(B) nucleic acid molecule named nfspN(B)$_{612}$ is denoted SEQ ID NO:52. Translation of SEQ ID NO:52 yields a protein named PfspN(B)$_{153}$ having an amino acid sequence denoted SEQ ID NO:53.

In addition, an apparent N-terminal amino acid sequence deduced from nucleic acid sequence of nfspN(A), named PfspN(A)$_{56}$ and denoted SEQ ID NO:54, was determined. The amino acid sequence of PfspN(A)$_{56}$ (i.e., SEQ ID NO:54) is similar, but not identical, to the N-terminal amino acid sequences obtained for fspN1 (SEQ ID NO:11), fspN2 (SEQ ID NO:12) and fspN3 (SEQ ID NO:13). While not being bound by theory, it is believed that there is a family of fspN proteins that are found in flea saliva, which may be due to allelic variation or multiple genes in the flea genome. Nucleic acid molecules nfspN(A)$_{646}$ and nfspN(B)$_{612}$ are about 76% identical, and the translated products are about 65% identical.

In a second immunoscreening experiment in which antiserum collected from a rabbit that was immunized with the proteins in peak N of the HPLC separation of flea saliva extract described in Example 4 (i.e., fspN proteins) was used to probe a flea salivary gland cDNA library (prepared as described in Example 6), approximately 20 positive clones were isolated. The nucleic acid sequence of one of the recovered nucleic acid molecules appears to be identical to that of nfspN(A). At least two of the other nucleic acid molecules have nucleic acid sequences that are similar, but not identical, to that of nfspN(A), again supporting the likelihood of a family of fspN proteins in flea saliva. Yet another nucleic acid molecule appears to have a nucleic acid sequence that is similar to myosin gene sequences.

The nucleic acid and amino acid sequences of the fspN(A) and fspN(B) nucleic acid molecules and proteins, respectively, were compared to known nucleic acid and amino acid sequences using a Genbank homology search. Both nucleic acid sequences were found to be similar to the corresponding (i.e., carboxyl-terminal) region of the nucleic acid sequence of human prostatic acid phosphatase. The most highly conserved region of continuous similarity between flea and human amino acid sequences spans from about amino acid 272 through about amino acid 333 of the human enzyme. Comparison of the nucleic acid sequence encoding amino acids from about 268 through about 333 of the human enzyme with the corresponding regions of nfspN (A) and nfspN(B) nucleic acid sequences indicate that nfspN(A) is about 40% identical, and nfspN(B) is about 43% identical, to that region of the human prostatic acid phosphatase gene. Comparison of the region spanning from about amino acid 268 through about amino acid 333 of the human enzyme with the corresponding regions of PfspN(A) and PfspN(B) indicate that PfspN(A) is about 28% identical, and PfspN(B) is about 30% identical, to that region of the human prostatic acid phosphatase gene. The possibility that at least some fspN proteins encode an active acid phosphatase is supported by the finding that flea saliva extract FS-3 has been shown to have acid phosphatase activity, as described in Example 3.

The apparent complete nucleic acid sequence of the coding region of nucleic acid molecule nfspN(A), referred to herein as nfspN(A)$_{1197}$, is denoted herein as SEQ ID NO:55. Translation of SEQ ID NO:55 yields an apparent full-length fspN protein named PfspN(A)$_{398}$ having an amino acid sequence denoted herein as SEQ ID NO:56. (It should be noted that although nucleic acid sequence SEQ ID NO:55 and amino acid sequence SEQ ID NO:56 do not exactly match nucleic acid sequence SEQ ID NO:50 or amino acid sequences SEQ ID NO:51 or SEQ ID NO:54 in the corresponding regions, the mismatches are likely due to sequencing errors in SEQ ID NO:50, SEQ ID NO:51 and SEQ ID NO:54.)

Comparison of SEQ ID NO:56 with the N-terminal amino acid sequences obtained for fspN1 (SEQ ID NO:11), fspN2 (SEQ ID NO:12) and fspN3 (SEQ ID NO:13) indicates that the amino terminal amino acids of fspN1 and fspN2 correspond to amino acid position 18 of SEQ ID NO:56, while the amino terminal amino acid of fspN3 corresponds to amino acid position 20 of SEQ ID NO:56. SEQ ID NO:13 appears to be identical to the region of SEQ ID NO:56 spanning amino acid positions from 20 through 39, suggesting that nfspN(A) encodes fspN3. SEQ ID NO:11 is about 67% identical to the corresponding region of SEQ ID NO:56, and SEQ ID NO:12 is about 60% identical (discounting the 3 unknown amino acids in SEQ ID NO:12) to the corresponding region of SEQ ID NO:56, supporting the suggestion that fspN1 and fspN2 are members of the same flea saliva protein family as fspN3.

Comparison of SEQ ID NO:56 with the amino acid sequence of human prostatic acid phosphatase indicates that the two sequences share about 30% identity at the amino acid level.

Example 13

This Example demonstrates the production of a bacterial recombinant cell including an fspN protein and use of that cell to produce the fspN protein.

An about 1000 bp DNA fragment, denoted nfspN$_{1000}$, was PCR amplified from a nucleic acid molecule encoding an fspN protein using the following primers: F7 sense, having nucleic acid sequence 5' GGCGTCTCGAGAGAAT-TGAAATTTGTGTTTGCG 3' (XhoI site in bold), denoted SEQ ID NO:46; and F7 antisense, having nucleic acid sequence 5' AGACGAGAATTCCAATTTATCAT-GAGCGG 3' (EcoRI site in bold), denoted SEQ ID NO:47. The PCR product was digested with XhoI and EcoRI restriction endonucleases, gel purified and subcloned into expression vector pTrcHisB (available from InVitrogen, Corp.) that had been digested with XhoI and EcoRI to form recombinant molecule pHis-nfspN$_{1000}$. The recombinant molecule was transformed into E. coli BL21 competent cells (available from Novagen) to form recombinant cell E. coli:pHis-nfspN$_{1000}$.

Recombinant cell E. coli:pHis-nfspN$_{1000}$ was cultured and induced as described in Example 11A to produce fusion protein PHIS-PfspN3. The recombinant fusion protein was detected by immunoblot analysis using the T7 Tag monoclonal antibody as described in Example 11A. PHIS-PfspN3 was Ni purified using Ni-NTA spin kit (available from Qiagen, Chatsworth, Calif.) and the purification verified using T7 Tag monoclonal antibody as described above.

Example 14

The Example demonstrates the expression of an fspN protein in insect cells.

Recombinant molecule pVL-nfspN$_{1000}$ containing the nfspN$_{1000}$ nucleic acid molecule operatively linked to baculovirus polyhedrin transcription control sequences was produced in the following manner. An about 1000 bp DNA fragment, denoted nfspN$_{1000}$, was PCR amplified from a nucleic acid molecule encoding an fspN protein using the following primers: sense primer 17, having nucleic acid sequence 5' CCG GAA TTC CGG TAT AAA TAT GTG GCG TCT ACT G 3' (EcoRI site in bold), denoted SEQ ID NO:48, and designed to enhance expression in insect cells; and antisense primer 18, having nucleic acid sequence 5' CCG GAA TTC TTA AGA CGA TTT ACA CAA TTT ATC 3' (EcoRI site in bold), denoted SEQ ID NO:49. The PCR product was digested with EcoRI and non-directionally cloned into the baculovirus shuttle vector pVL1393 (available from InVitrogen, Corp.). Orientation was determined by restriction digest with the enzyme EcoRV. The resultant recombinant molecule, i.e., pVL-nfspN$_{1000}$, was co-transfected into S. frugiperda cells (donated by the Colorado Bioprocessing Center, Fort Collins, Col.) with wild type linear baculovirus DNA (AcMNPV) and insectin cationic liposome according to manufacturer's specifications (available from InVitrogen Corp.) to produce recombinant cell S. frugiperda:pVL-nfspN$_{1000}$. The supernatant was tested five days post-transfection by Western blot analysis using rabbit antiserum against flea fspN proteins (as described in Example 12; denoted B2237) and a protein approximately 40 kD was detected. The recombinant virus, vBV-nfspN$_{1000}$ was recovered from the supernatant and plaque purified.

Example 15

This Example demonstrates that use of ELISAs to detect anti-flea saliva IgE antibodies in the sera of dogs sensitized to fleas or flea saliva.

A. In a first study, sera collected from three dogs that had been artificially sensitized to flea bites were pooled and pretreated by contacting the pooled sera with Protein G to remove at least some of the non-IgE immunoglobulins present in the sera. IgE antibodies were then affinity-purified from the pretreated sera using Con-A chromatography.

The affinity-purified IgE antibodies were exposed to the following flea saliva products and proteins: FS-1 saliva extract at 2 mg/ml (23,300 flea-hours per μl); fspA, fspB, fspC1, fspC2, fspD1, fspD2, fspE, fspF, fspG, fspH, fspI, fspJ, fspK, fspL, fspM1, fspM2, and fspN (from a 233,000 flea-hours per μl sample applied to HPLC chromatography as described in Example 3). The flea saliva products and proteins were suspended in 0.1 M sodium carbonate, pH 9.6, and 100 μl samples of each were placed in microtiter dish wells. The samples were incubated overnight at room temperature, washed 5 times with PBS/Tween, blocked with a solution of PBS, 2% BSA, 0.02% NaN$_3$, for 1 hour at 37° C., and washed 5 times with PBS/Tween. The washed wells were each exposed to 100 μl aliquots of the affinity-purified dog IgE antibodies for 1 hour at 37° C. The wells were washed 5 times with PBS/Tween and exposed for 1 hour, at 37° C., to 100 μl of a monoclonal mouse anti-canine IgE antibody preparation diluted 1:000 in PBS, 2% BSA, 0.05% Triton X-100. The wells were washed 5 times with PBS/Tween, exposed for 1 hour, at 37° C., to 100 μl donkey anti-mouse IgG (H+L)-HRP, and washed 5 times with PBS/Tween. The wells were developed with 100 μl KPL TMB:H$_2$O$_2$, 1:1, for 10 minutes, the reaction being stopped with 50 μl 2.5 N hydrogen sulfate. The wells were read at 450 nm.

Figure 10:
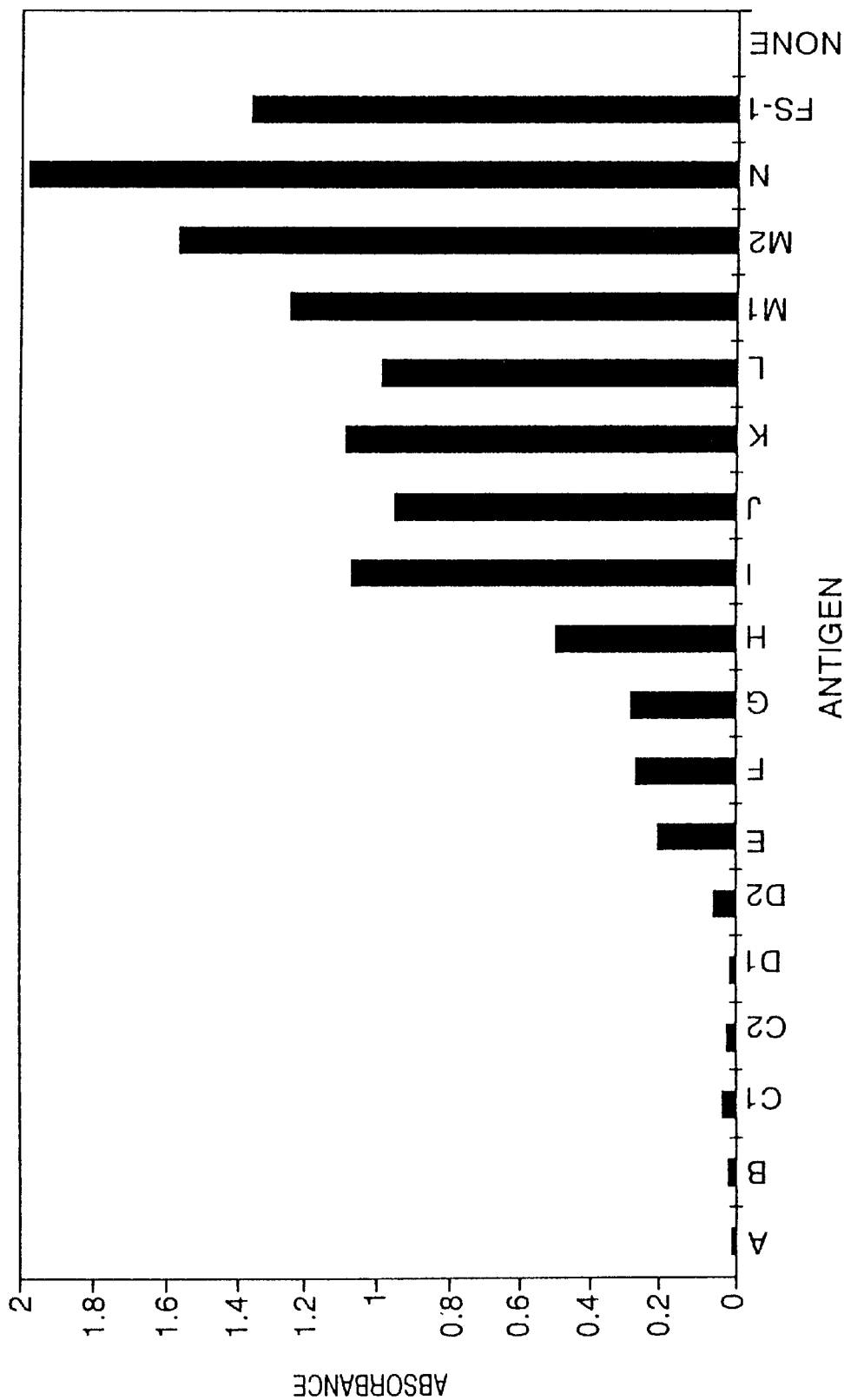
FIG. 10 depicts ELISA results measuring anti-flea saliva IgE antibodies in the sera of flea sensitized dogs.
Figure 12:
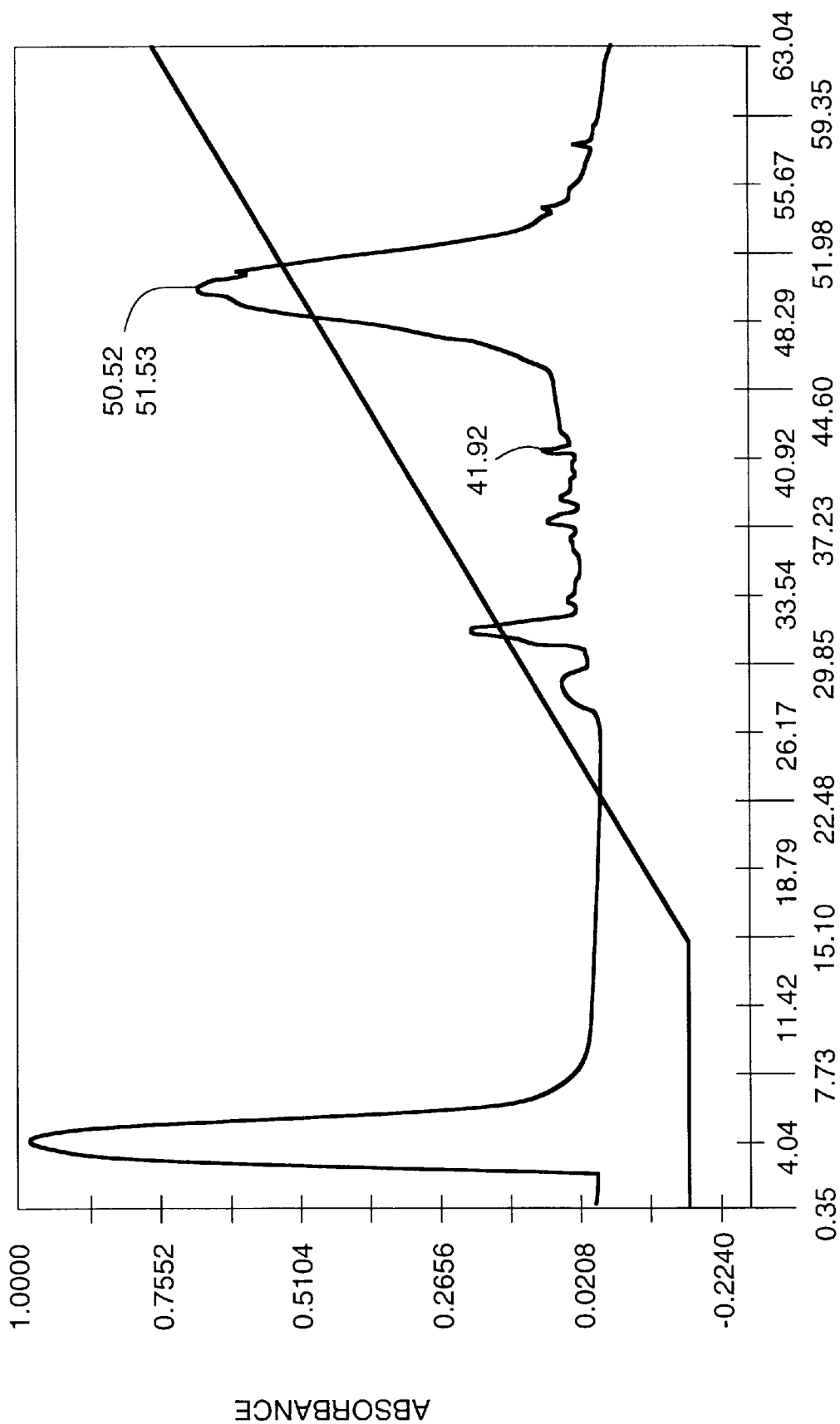
FIG. 12 illustrates the resolution of a FS-2 extract using high pressure liquid chromatography.

The results, shown in Table 18 and FIG. 10, indicate that FAD+ dogs have in their sera IgE antibodies that react in a sensitive and specific manner with FS-1 flea saliva extract as well as with flea saliva proteins fspE, fspF, fspG, fspH, fspI, fspJ, fspK, fspL, fspM1, fspM2 and fspN. The IgE antibody preparation reacted minimally, if at all, with flea saliva proteins fspA, fspB, fspC1, fspC2, fspD1 and fspD2. Thus, the IgE reactivity closely followed the skin test results of Example 8 in the artificially sensitized dogs with the same flea saliva products and proteins.

TABLE 18

| | Volume of Antigen | | | |
|---|---|---|---|---|
| Fraction | 0.5 μl | 0.25 μl | 0.125 μl | 0.063 μl |
| A | 0.007 | 0.008 | 0.012 | 0.018 |
| B | 0.016 | 0.010 | 0.013 | 0.052 |
| C1 | 0.035 | 0.008 | 0.035 | 0.020 |
| C2 | 0.022 | 0.009 | 0.002 | 0.005 |
| D1 | 0.013 | 0.025 | 0.004 | 0.005 |
| D2 | 0.059 | 0.018 | 0.017 | 0.012 |
| E | 0.214 | 0.263 | 0.206 | 0.092 |
| F | 0.276 | 0.393 | 0.217 | 0.114 |
| G | 0.288 | 0.217 | −0.010 | −0.010 |
| H | 0.503 | 0.336 | 0.203 | 0.062 |
| I | 1.076 | 0.997 | 0.917 | 0.637 |
| J | 0.955 | 0.816 | 0.673 | 0.456 |
| K | 1.095 | 0.898 | 0.815 | 0.690 |
| L | 0.991 | 0.721 | 0.485 | 0.162 |
| M1 | 1.251 | 1.190 | 0.840 | 0.454 |
| M2 | 1.561 | 1.105 | 0.902 | 0.558 |
| N | 1.989 | 1.887 | 1.819 | 1.435 |
| FS-1 | 1.367 | 1.246 | 0.982 | 0.604 |
| none | 0.002 | 0.005 | 0.008 | 0.121 |

B. In a second study, serum collected from a dog that had been artificially sensitized to flea bites was pretreated by contacting the serum with Protein G to remove at least some of the non-IgE immunoglobulins present in the serum. The reactivity of the pretreated serum to FS-1 flea saliva extract was determined as described in Example 15A. Also tested was the reactivity to FS-1 flea saliva extract of sera collected from dogs infected with heartworm, pooled and pretreated by contacting the serum with Protein G. The results, shown in Table 19 and FIGS. 11A and 11B, demonstrate a dose dependent reactivity of IgE from the FAD+ dog while IgE from heartworm infected dogs had no reactivity against FS-1 flea saliva extract.

TABLE 19

| | Sera dil. | | | | | | | |
|---|---|---|---|---|---|---|---|---|
| | 1:2 | 1:4 | 1:8 | 1:16 | 1:32 | 1:64 | 1:128 | none |
| DOG 2082128 | | | | | | | | |
| 2 μg | 1.67 | 1.20 | 0.85 | 0.57 | 0.34 | 0.19 | 0.11 | 0.01 |
| 1 μg | 1.43 | 1.16 | 0.80 | 0.49 | 0.30 | 0.17 | 0.10 | 0.00 |
| 0.5 μg | 1.32 | 1.02 | 0.71 | 0.46 | 0.28 | 0.14 | 0.08 | 0.00 |
| 0.25 μg | 1.18 | 0.92 | 0.59 | 0.38 | 0.22 | 0.12 | 0.06 | 0.00 |
| 0.13 μg | 0.95 | 0.80 | 0.52 | 0.30 | 0.19 | 0.11 | 0.06 | 0.00 |
| none | 0.00 | 0.01 | 0.00 | 0.00 | 0.00 | 0.00 | 0.00 | 0.01 |
| HEART-WORM POOL | | | | | | | | |
| 2 μg | 0.00 | 0.00 | 0.00 | 0.00 | 0.00 | 0.00 | 0.00 | 0.00 |
| 1 μg | 0.00 | 0.00 | 0.00 | 0.00 | 0.00 | 0.00 | 0.00 | 0.00 |
| 0.5 μg | 0.00 | 0.00 | 0.00 | 0.00 | 0.00 | 0.00 | 0.00 | 0.00 |
| 0.25 μg | 0.00 | 0.01 | 0.01 | 0.00 | 0.00 | 0.00 | 0.00 | 0.00 |
| 0.13 μg | 0.01 | 0.00 | 0.00 | 0.00 | 0.00 | 0.00 | 0.00 | 0.00 |
| none | 0.01 | 0.01 | 0.01 | 0.00 | 0.00 | 0.00 | 0.01 | 0.00 |

EXAMPLE 16

This example demonstrates the ability of formulations of the present invention, including formulations comprising flea saliva extract FS-1, *E. coli*-produced fspH, *E. coli*-produced fspN3 or insect cell *S. frugiperda*-produced fspN3 to identify animals susceptible to flea allergy dermatitis (i.e., to induce flea allergy dermatitis in an animal susceptible to flea allergy dermatitis).

The formulations were produced as follows. FS-1 was produced as described in Example 2. *E. coli*-produced fspH was produced by an *E. coli* cell transformed with a nucleic acid molecule encoding fspH operatively linked to expression vector λP$_R$/T$^2$ori/S10HIS-RSET-A9, the production of which is described in PCT/US95/02941, Example 7; the resultant PHIS-fspH fusion protein was purified as described in Example 13. *E. coli*-produced fspN3 and *S. frugiperda*-produced fspN3 were produced as described in Examples 13 and 14, respectively; *E. coil*-produced produced fspN3 was purified as described in Example 11A; *S. frugiperda*-produced fspN3 was purified by anion/cation exchange chromatography.

The formulations were tested in artificially sensitized dogs 2080109, 2082101, 2082128, BFQ2, CPO2, CQQ2, as described in Example 8. The injected samples were as follows: (a) saline negative control; (b) histamine positive control; (c) 2 μg FS-1; (d) 0.1 μg *E. coli*-produced fspH; (e) 1.0 μg *E. coli*-produced fspH; (f) 0.2 μg *E. coli*-produced fspN3; (g) 2.0 μg *E. coli*-produced fspN3; (h) 0.2 μg *S. frugiperda*-produced fspN3; and (i) 2.0 μg *S. frugiperda*-produced fspN3. The immediate hypersensitivity results are shown in Table 20, and the delayed hypersensitivity results are shown in Table 21. Scoring was as described in Example 8; NA indicates a bad injection.

TABLE 20 a) Immediate (15 min.) subjective score (1 – 4+) (NA was a bad injection)

| Dog | Sa-line | Hista-mine | FS-1 | E. coli FS-H 0.1 | E. coli FS-H 1.0 | E. coli fspN3 0.2 | E. coli fspN3 2.0 | S. frugiperda fspN3 0.2 | S. frugiperda fspN3 2.0 |
|---|---|---|---|---|---|---|---|---|---|
| 109 | 0 | 4 | 4 | NA | 4 | 1 | 1 | 1 | 1 |
| 101 | 0 | 4 | 4 | 4 | 4 | 1 | 2 | 0 | 1 |
| 128 | 0 | 4 | 4 | 2 | 4 | 1 | 2 | 1 | 3 |
| BFQ2 | 0 | 4 | 3 | 0 | 3 | 0 | 0 | 0 | 2 |
| CPO2 | 0 | 4 | 4 | 4 | 4 | 1 | 4 | 1 | 2 |
| CQQ2 | 0 | 4 | 4 | 4 | 4 | 0 | 0 | 0 | 2 |

TABLE 21 b) Delayed (24 hr.) subjective score (1 – 4+) (NA was a bad injection)

| Dog | Sa-line | Hista-mine | FS-1 | E. coli FS-H 0.1 | E. coli FS-H 1.0 | E. coli fspN3 0.2 | E. coli fspN3 2.0 | S. frugiperda fspN3 0.2 | S. frugiperda fspN3 2.0 |
|---|---|---|---|---|---|---|---|---|---|
| 109 | 0 | 0 | 0 | NA | 0 | 0 | 0 | 0 | 0 |
| 101 | 0 | 0 | 3 | 0 | 2 | 2 | 3 | 2 | 3 |
| 128 | 0 | 0 | 3 | 0 | 2 | 2 | 2 | 2 | 3 |
| BFQ2 | 0 | 0 | 1 | 0 | 0 | 0 | 0 | 0 | 0 |
| CPO2 | 0 | 0 | 0 | 0 | 0 | 0 | 0 | 0 | 0 |
| CQQ2 | 0 | 0 | 0 | 0 | 0 | 0 | 0 | 0 | 0 |

In summary, these results indicate that E. coli-produced fspH exhibited a strong positive immediate reaction in all dogs, the reaction being proportional to the dogs' reaction to flea saliva. E. coli-produced and S. frugiperda-produced fspN3 proteins also exhibited a positive immediate reaction in 4 and all dogs, respectively. The two dogs that showed a strong delayed hypersensitive response reaction to FS-1 showed similar delayed hypersensitive response reactions to recombinantly produced fspH and fspN3.

EXAMPLE 17

This example describes the amino acid sequence analysis of additional isolated flea saliva proteins from FS-1 extract and eluted from DE-81 filters.

FS-1 flea saliva extract and flea saliva product eluted from DE-81 filters were collected using standard techniques. Using standard purification techniques (e.g., C4 reverse phase chromatography; SDS-PAGE gel electrophoresis and blotting; and/or flow through electrophoresis), several proteins were isolated from peak M and partial amino acid sequences were determined as described in Example 4. Partial N-terminal amino acid sequencing indicated that peak M contained fspJ, fspL and fspN proteins as well as newly identified proteins referred to herein as fspM(G), fspM(H), fspM(I), fspM(J), fspM(K), fspM(L) and fspM(M). Flea saliva protein fspM(G), having a molecular weight of about 37 kD, had an N-terminal partial amino acid sequence of M R G N H V F L E D G M A D M T G G Q Q M G R D L Y, denoted SEQ ID NO:72. Flea saliva protein fspM(H), having a molecular weight of about 34 kD, had an N-terminal partial amino acid sequence of K Y R N (Y/D) X T N D P Q Y, denoted SEQ ID NO:73. Flea saliva protein fspM(I), having a molecular weight of about 10 kD had an N-terminal partial amino acid sequence of E I K R N D R E P G N L S K I R T V M D K V I K Q T Q, denoted SEQ ID NO:74. Flea saliva protein fspM(J), having a molecular weight of about 25 kD, had an N-terminal partial amino acid sequence of L K D N D I Y (A/H) (A/H) R D I N E I L R V L D P S K, denoted SEQ ID NO:75. Flea saliva protein fspM(K), having a molecular weight of about 30 kD, had an N-terminal partial amino acid sequence of N Y G R V Q I E D Y T X S N H K D X E E K D Q I N G L, denoted SEQ ID NO:76. Flea saliva protein fspM(L), having a molecular weight of about 37 kD, had an N-terminal partial amino acid sequence of K Y R N X Y T N D P Q L K L L D E G, denoted SEQ ID NO:77. Flea saliva protein fspM(M) was recovered from peak M and subjected to amino acid sequence analysis as described in Example 4. Flea saliva protein fsp(M), having a molecular weight of about 31 kD, had an N-terminal partial amino acid sequence of Y F N D Q I K S V M E P X V F K Y P X A X L, denoted SEQ ID NO:78. A Genbank homology search revealed no significant homology between known amino acid sequences and those determined for fspM(G), fspM(H), fspM(I), fspM(J), fspM(K), fspM(L) and fspM(M).

EXAMPLE 18

This example describes the isolation of nucleic acid molecules encoding at least a portion of a fspG flea saliva protein. This example also describes expression of a fspG protein by bacteria.

A. Isolation of fspG4 nucleic acid molecules

The partial N-terminal amino acid sequence of fspG2 (i.e., SEQ ID NO:29) was used to synthesize degenerate antisense Primer G2-2, having the nucleic acid sequence 5' TGR TTT CCW ATR AAR TCT TC 3', denoted SEQ ID NO:103. Primer G2-2 was used in combination with the M13 reverse primer (SEQ ID NO:40), to PCR amplify, using standard techniques, the 5'-terminal portion of the fspG4 gene from a salivary gland CDNA expression library as described above in Example 6A. The resulting PCR product was approximately 225-bp when visualized on a 1% agarose gel. The nucleotide sequence of the 225-bp PCR fragment was obtained, named nfspG4$_{225}$ is presented as SEQ ID NO:104.

The nucleic acid sequence of nfspG4$_{225}$ was used to synthesize sense Primer G5, having nucleic acid sequence 5' AAT TCG GCA CGA GTG 3', denoted SEQ ID NO:105. Primer G5 was used in combination with the M13 universal primer (SEQ ID NO:19), to PCR amplify, as described above, the 3'-terminal portion of the fspG4 gene from the salivary gland cDNA expression library described above in Example 6A. The resulting PCR product, denoted nfspG4$_{610}$, was approximately 610-bp when visualized on a 1% agarose gel. The nucleotide sequence of the 610-bp PCR fragment was obtained, 565 nucleotides of which are presented as SEQ ID NO:57. The nucleic acid molecule containing nucleic acid sequence SEQ ID NO:57 is referred to herein as nfspG4$_{565}$. Translation of SEQ ID NO:57 suggests that nucleic acid molecule nfspG4$_{565}$ encodes a full-length fspG protein of about 90 amino acids, referred to herein as PfspG4$_{90}$, assuming an open reading frame having a start codon spanning from about nucleotide 45 through about nucleotide 47 of SEQ ID NO:57 and a stop codon spanning from about nucleotide 315 through about nucleotide 317 of SEQ ID NO:57. This open reading frame, excluding the stop codon, comprises nucleic acid molecule nfspG4$_{270}$ of the present invention, the nucleic acid sequence of which is represented herein by SEQ ID NO:79. PfspG4$_{90}$ is denoted herein as SEQ ID NO:58. Residues 20–42 of SEQ ID NO:58 appear to be identical to SEQ ID NO:29 (N-terminal partial amino acid sequence of fspG2), except that residue 37 of SEQ ID NO:58 is a glutamic acid rather than a lysine. In addition, residues 38–57 of SEQ ID NO:58 appear to be identical to SEQ ID NO:30 (N-terminal partial amino acid sequence of fspG3). These similarities support the likelihood of a family of fspG proteins in flea saliva.

Analysis of SEQ ID NO:57 suggests that the sequence includes a leader segment of about 19 amino acids followed by a mature protein. The leader sequence is apparently cleaved to form a mature protein termed PfspG4$_{71}$, denoted SEQ ID NO:80. PfspG4$_{71}$ has a calculated molecular weight of 7536 daltons and calculated pI of about 9.0. PfspG4 has a calculated molecular weight of 9657 daltons and calculated pI of about 9.26. A Genbank homology search revealed no significant homology between SEQ ID NO:57 or SEQ ID NO:58 and known nucleic acid sequences or known amino acid sequences, respectively.

B. Expression

An about 216-bp DNA fragment of nfspG4 was PCR amplified from nucleic acid molecule nfspG4, using: Primer G7: a sense primer having the nucleic acid sequence 5' AGT GGA TCC GTC AAA AAT GGT CAC TG 3', denoted as SEQ ID NO:106 (BamHI site in bold); and Primer G8, an antisense primer having the nucleic acid sequence 5' CCG GAA TTC GGT TAT TCG CAA TAA CAG T 3' (EcoRI site in bold), denoted SEQ ID NO:107. The PCR product, a fragment of about 216 nucleotides, denoted nfspG4$_{2161}$, was digested with BamHI and EcoRI restriction endonucleases, gel purified, and subcloned into expression vector λPR/T$^2$ori/S10HIS-RSET-A9 (described in Example 16) that had been digested with BamHI and EcoRI to produce recombinant molecule pHis-nfspG4$_{216}$.

The recombinant molecule was transformed into *E. coli* to form recombinant cell *E.coli*:pHis-nfspG4$_{216}$. The recombinant cell was cultured and induced as described in Example 11A to produce fusion protein PHIS-fspG4$_{72}$. The recombinant fusion protein was detected by immunoblot analysis using the T7 Tag monoclonal antibody as described in Example 11A.

EXAMPLE 19

This example describes the isolation of nucleic acid sequences encoding at least a portion of flea saliva proteins fspM(A), fspM(B), fspM(C), fspM(D), fspM(E), and fspM(F).

A. nfspM(A)$_{897}$ and nfspM(B)$_{2706}$

A flea salivary gland cDNA library (prepared as described in Example 6) was immunoscreened with antiserum collected from a rabbit that was immunized with the proteins in peak M2 of the HPLC separation of flea saliva extract described in Example 3 (i.e., fspM2 proteins). Immunoscreening was performed as described in Example 12.

A nucleotide sequence for a nfspM nucleic acid molecule named nfspM(A)$_{897}$ is denoted as SEQ ID NO:59. Translation of SEQ ID NO:59 suggests that nucleic acid molecule nfspM(A)$_{897}$ encodes a full-length fspM protein of about 157 amino acids, referred to herein as PfspM(A)$_{157}$, assuming an open reading frame having a start codon spanning from about nucleotide 97 through about nucleotide 99 of SEQ ID NO:59 and a stop codon spanning from about nucleotide 568 through about nucleotide 570 of SEQ ID NO:59. This open reading frame, excluding the stop codon, comprises nucleic acid molecule nfspM(A)$_{471}$ of the present invention, the nucleic acid sequence of which is represented herein by SEQ ID NO:81. The amino acid sequence of PfspM(A)$_{157}$ is denoted SEQ ID NO:60. PfspM(A)$_{157}$ has a calculated molecular weight of about 18,291.68 daltons and calculated pI of about 10.3. A Genbank homology search revealed no significant homology between SEQ ID NO:59 or SEQ ID NO:60 and known nucleic acid or amino acid sequences, respectively.

A nucleotide sequence for another nfspM nucleic acid molecule named nfspM(B)$_{2706}$ is denoted as SEQ ID NO:61. Translation of SEQ ID NO:61 suggests that nucleic acid molecule nfspM(B)$_{2706}$ encodes a non-full-length fspM protein of about 900 amino acids, referred to herein as PfspM(B)g$_{900}$, assuming an open reading frame having a start codon spanning from about nucleotide 5 through about nucleotide 7 of SEQ ID NO:61. The amino acid sequence of PfspM(B)900 is denoted SEQ ID NO:62. PfspM(B)900 has a calculated molecular weight of about 104,647 daltons and calculated pI of about 5.8.

The nucleic acid and amino acid sequences of the nfspM (B)$_{2706}$ nucleic acid molecule and PfspM(B)$_{900}$ protein, respectively, were compared to known nucleic acid and amino acid sequences using a Genbank homology search. SEQ ID NO:62 was found to be similar to the amino acid sequence of RhoA-binding alpha kinase (ROK). The most highly conserved region of continuous similarity between SEQ ID NO:62 and ROK amino acid sequences spans from about amino acid 32 through about amino acid 351 of SEQ ID NO:62 and from about amino acid 1 through about amino acid 900 of the ROK, there being about 75% identity between the two regions. Comparison of the nucleic acid sequence encoding amino acids from about 326 through about 1285 of the ROK kinase with the corresponding regions, spanning nucleotides from about 98 through about 1075 of nfspM(B)$_{2706}$ indicate that those regions are about 71% identical.

B. nfspM(C)$_{414}$ and nfspM(D)$_{273}$

A flea salivary gland cDNA library (prepared as described in Example 6) was immunoscreened with antiserum collected from a rabbit that was immunized with the proteins in peak M1 of the HPLC separation of flea saliva extract described in Example 3 (i.e., fspM1 proteins). Immunoscreening was performed as described in Example 12.

Nucleotide sequence for a nfspM nucleic acid molecule named nfspM(C)$_{414}$ is denoted as SEQ ID NO:63. Translation of SEQ ID NO:63 suggests that nucleic acid molecule nfspM(C)$_{414}$ encodes a non-full-length fspM protein of about 137 amino acids, referred to herein as PfspM(C)$_{137}$, assuming the first residue spans from about nucleotide 2 through about nucleotide 4 of SEQ ID NO:64. The amino acid sequence of PfspM(C)$_{138}$ is denoted SEQ ID NO:64. PfspM(C) $_{137}$ has a calculated molecular weight of about 14,452 daltons and calculated pI of about 2.81. A Genbank homology search revealed no significant homology between SEQ ID NO:63 or SEQ ID NO:64 and known nucleic acid sequences or known amino acid sequences, respectively.

A nucleotide sequence for another nfspM nucleic acid molecule named nfspM(D)$_{273}$ is denoted as SEQ ID NO:65. Translation of SEQ ID NO:65 suggests that nucleic acid molecule nfspM(D)$_{273}$ encodes a non-full-length fspM protein of about 90 amino acids, referred to herein as PfspM (D)$_{90}$, assuming the first residue spans from about nucleotide 3 through about nucleotide 5 of SEQ ID NO:65. The amino acid sequence of PfspM(D)$_{90}$ denoted SEQ ID NO:66. PfspM(D)$_{90}$ has a calculated molecular weight of about 9,503 daltons and calculated pI of about 3.01. SEQ ID NO:65 and SEQ ID NO:66 appear to be substantially similar to SEQ ID NO:63 and SEQ ID NO:64, respectively, suggesting a family of fspM proteins in flea saliva.

C. nfspM(E)$_{1704}$ and nfspM(F)$_{1758}$

A flea salivary gland cDNA library (prepared as described in Example 6) was immunoscreened with antiserum collected from a rabbit that was immunized with the proteins in peak M2 of the HPLC separation of flea saliva extract described in Example 3 (i.e., fspM2 proteins). Immunoscreening was performed as described in Example 12.

A nucleotide sequence for another nfspM nucleic acid molecule named nfspM(E)$_{1704}$ is denoted as SEQ ID NO:67. Translation of SEQ ID NO:67 suggests that nucleic acid molecule nfspM(E)$_{1704}$, encodes a full-length fspM protein of about 461 amino acids, referred to herein as PfspM(E)$_{461}$, assuming the first residue spans from about nucleotide 24 through about nucleotide 26 of SEQ ID NO:67 and a stop codon spanning from about nucleotide 1407 through about nucleotide 1409 of SEQ ID NO:67. This open reading frame, excluding the stop codon, comprises nucleic acid molecule nfspM(E)$_{1383}$ of the present invention, the nucleic acid sequence of which is represented herein by SEQ ID NO:82. The amino acid sequence of PfspM(E)$_{461}$ is denoted SEQ ID NO:68. PfspM(E)$_{461}$ has a calculated molecular weight of about 54,139 daltons and calculated pI of about 7.00. A Genbank homology search revealed no significant homology between SEQ ID NO:67 or SEQ ID NO:68 and known nucleic acid sequences or known amino acid sequences, respectively.

A nucleotide sequence for another nfspm nucleic acid molecule named nfspM(F)$_{1758}$ is denoted as SEQ ID NO:69. Translation of SEQ ID NO:69 suggests that nucleic acid molecule nfspM(F)$_{1758}$ encodes a non-full-length fspM protein of about 586 amino acids, referred to herein as PfspM (F)$_{586}$, assuming an open reading frame having a start codon spanning from about nucleotide 1 through about nucleotide 3 of SEQ ID NO:69. The amino acid sequence of PfspM (F)$_{586}$ is denoted SEQ ID NO:70. PfspM(F)$_{586}$ has a calculated molecular weight of about 66,547 daltons and calculated pI of about 4.80. A Genbank homology search revealed no significant homology between SEQ ID NO:69 or SEQ ID NO:70 and known nucleic acid sequences or known amino acid sequences, respectively.

EXAMPLE 20

This Example demonstrates the expression of a fspM protein in E. Coli cells.

Flea saliva protein PHIS-PfspM(D)$_{90}$ fusion protein was produced in the following manner. An about 305-bp DNA fragment, referred to herein as nfspM(D)$_{305}$ (denoted SEQ ID NO:71), was isolated from nfspM(D)$_{273}$ subcloned into pBluescript plasmid by digesting the nfspM(D)-containing plasmid with BamH1 and XhoI restriction endonucleases. The digestion product was gel purified and subcloned into expression vector pTrcHisB that had been digested with BamH1 and XhoI, and dephosphorylated. The resultant recombinant molecule, referred to herein as pHis-nfspM(D)$_{305}$, was transformed into E. coli HB101 competent cells (available from Gibco BRL, Gaithersburg, Md.) to form recombinant cell E. coli:pHis-nfspM(D)$_{305}$. The recombinant cell was cultured and expression of nfspM$_{305}$ induced using conditions described in Example 11. Immunoblot analysis of recombinant cell E. coli:pHis-nfspM(D)$_{305}$ lysates using a T7 tag monoclonal antibody (Novagen, Inc) directed against the fusion portion of the recombinant PHis-nfspM(D)$_{305}$ fusion protein identified a protein of the appropriate size, namely an about 15,851 kD protein.

EXAMPLE 21

This example describes the isolation of nucleic acid sequences encoding at least a portion of flea saliva proteins fspN(C), fspN(D), fspN(E), fspN(F), fspN(G), fspN(H), fspN(I), fspN(J), fspN(K), fspN(L), fspN(M), fspN(N) and fspN(O).

A. Preparation of IgE enriched antiserum

Serum was obtained from the artificially sensitized dog CQQ2 (described in Example 8). About 10 ml of antiserum was incubated with protein G-Sepharose (5 ml) over night at 4° C.

B. Immunoscreening with IgE enriched antiserum

About 2.4 ml of Escherichia coli (XL1 Blue, O.D.$_{.600}$= 0.5) was incubated with 6.48×10$^5$ pfu of phage from a flea salivary gland ZAP-cDNA library (1.8×10$^7$pfu/ml), at 37° C. for 15 min and plated in 12 Luria-Bertani (LB) medium agar plates (150 mm). The plates were incubated at 37° C. over night. Each plate was then overlaid with an IPTG (10 mM) treated nitrocellulose filters for about 4 hours at 37° C. The filters were then removed and washed with TBST (20 mM Tris-HCl pH 7.5, 150 mM NaCl, 0.05% Tween-20). The filters were blocked with 5% dry milk in TBST for 2 hours at room temperature. Different filters were then incubated first with either IgE enriched CQQ2 antiserum or antiserum obtained from dogs infected with Dirofilaria immitis) at 4° C., overnight, then with a monoclonal anti-canine IgE antibody (D-9; gift from the laboratory of Dr. D. J. DeBoer, School of Veterinary Medicine, University of Wisconsin, Madison, Wis.), and then with a donkey anti-mouse IgG antibody conjugated to horseradish peroxidase (obtained from Jackson ImmunoResearch, West Grove, Pa.) for 2 hours at room temperature at each step. All of the filters were washed with TBST (3×15 min/wash) between each incubation. All of the filters were then treated to a final wash in TBS. Immunocomplexed plaques were identified by immersing the filters into the developing solution (TMB Peroxidase Substrate/TMB Peroxidase Solution/TMB Membrane Enhancer from Kirkegaard & Perry Laboratories) at 1/1/0.1 volume ratio to produce a color reaction. Eighteen plaques were identified and further plaque purified under the same immunoscreening condition as described above.

C. nfspN(C) $_{335}$, nfspN(D) $_{396}$, nfspN(E) $_{285}$, nfspN(F)$_{228}$, nfspN(G)$_{339}$, nfspN(G)$_{493}$, nfspN(H)$_{306}$, nfspN(I)$_{490}$, nfspN(J)$_{616}$, nfspN(K)$_{475}$, nfspN(L)$_{295}$, nfspN(M)$_{372}$, nfspN (N)$_{252}$, nfspN(N)$_{613}$, nfspN(O)$_{538}$, nfspN(O)$_{432}$.

Single plaque of purified clones were isolated and stored in SM phage buffer (50 mM Tris, pH 7.4, 0.58% NaCl, 0.2% MgCl$_2$·7H$_2$O and 0.01% Gelatin). The in vivo excision of the pBluescript phagemid from each positive clone was prepared by using ExAssist™/SOLR™ system (Stratagene). The pBluescript plasmid was purified by plasmid midi kit (Qiagen), and denatured with NaOH (0.4 N) at 37° C. for 15 min. The denatured plasmid was precipitated by ethanol and nucleic acid sequence obtained.

A nucleotide sequence for a nfspN nucleic acid molecule named nfspN(C)$_{335}$ is denoted as SEQ ID NO:83. A Genbank homology search revealed some similarity between SEQ ID NO:83 and ribosomal protein S6.

A nucleotide sequence for another nfspN nucleic acid molecule named nfspN(D)$_{396}$ is denoted as SEQ ID NO:84. A Genbank homology search revealed some similarity between SEQ ID NO:84 and erythropoietin.

A nucleotide sequence for another nfspN nucleic acid molecule named nfspN(E)$_{285}$ is denoted as SEQ ID NO:85. A Genbank homology search revealed some similarity between SEQ ID NO:85 and glutamic acid-rich protein or heat-shock protein, HSP81.

A nucleotide sequence for another nfspN nucleic acid molecule named nfspN(F)$_{228}$is denoted as SEQ ID NO:86.

Nucleic acid sequence for portions of another nfspN nucleic acid molecule, denoted herein as nfspN(G), were obtained. The nucleic acid molecule representing a 5' portion of nfspN(G) named nfspN(G)$_{339}$ is denoted as SEQ ID NO:87. Translation of SEQ ID NO:87 suggests that nucleic acid molecule nfspN(G)$_{339}$ encodes a non-full-length fspN (G) protein of about 113 amino acids, referred to herein as PfspN(G)$_{113}$, assuming the first residue spans from about nucleotide 1 through about nucleotide 3 of SEQ ID NO:87. The amino acid sequence of PfspN(G)$_{113}$ is denoted SEQ ID NO:88.

The nucleic acid molecule representing a 3' portion of nfspN(G) named nfspN(G)$_{493}$ is denoted as SEQ ID NO:89. Translation of SEQ ID NO:89 suggests that nucleic acid molecule nfspN(G)$_{493}$encodes a non-full-length fspN(G) protein of about 130 amino acids, referred to herein as PfspN(G)$_{130}$, assuming the first residue spans from about nucleotide 1 through about nucleotide 3 of SEQ ID NO:89 and a stop codon spanning from about nucleotide 391 through about nucleotide 393 of SEQ ID NO:89. The amino acid sequence of PfspN(G)$_{130}$ is denoted SEQ ID NO:90. A Genbank homology search revealed some similarity between SEQ ID NO:87 and SEQ ID NO:89 and vitellogenin.

A nucleotide sequence for another nfspN nucleic acid molecule named nfspN(H)$_{306}$ is denoted as SEQ ID NO:91.

A nucleotide sequence for another nfspN nucleic acid molecule named nfspN(I)$_{490}$ is denoted as SEQ ID NO:92.

A nucleotide sequence for another nfspN nucleic acid molecule named nfspN(J)$_{616}$ is denoted as SEQ ID NO:93.

A nucleotide sequence for another nfspN nucleic acid molecule named nfspN(K)$_{475}$ is denoted as SEQ ID NO:94.

A nucleotide sequence for another nfspN nucleic acid molecule named nfspN(L)$_{295}$ is denoted as SEQ ID NO:95.

A nucleotide sequence for another nfspN nucleic acid molecule named nfspN(M)$_{372}$ is denoted as SEQ ID NO:96.

Nucleic acid sequence for portions of another nfspN nucleic acid molecule, denoted herein as nfspN(N), were obtained. The nucleic acid molecule representing a 5' portion of nfspN(N) named nfspN(N)$_{252}$ is denoted as SEQ ID NO:97. The nucleic acid molecule representing a 3' portion of nfspN(N) named nfspN(N)$_{613}$ is denoted as SEQ ID NO:98.

Nucleic acid sequence for portions of another nfspN nucleic acid molecule, denoted herein as nfspN(O), were obtained. The nucleic acid molecule representing a 5' portion of nfspN(O) named nfspN(O)$_{538}$ is denoted as SEQ ID NO:99. Translation of SEQ ID NO:99 suggests that nucleic acid molecule nfspN(0)$_{538}$ encodes a non-full-length fspN (O) protein of about 178 amino acids, referred to herein as PfspN(O)$_{178}$, assuming the first residue spans from about nucleotide 1 through about nucleotide 3 of SEQ ID NO:99. The amino acid sequence of PfspN(N)$_{178}$is denoted SEQ ID NO:100.

The nucleic acid molecule representing a 3' portion of nfspN(O) named nfspN(0)$_{432}$ is denoted as SEQ ID NO:101. Translation of SEQ ID NO:101 suggests that nucleic acid molecule nfspN(O)$_{432}$encodes a non-full-length fspN(O) protein of about 129 amino acids, referred to herein as PfspN(O)$_{129}$, assuming the first residue spans from about nucleotide 1 through about nucleotide 3 of SEQ ID NO:101 and a stop codon spanning from about nucleotide 388 through about nucleotide 390 of SEQ ID NO:101. The amino acid sequence of PfspN(O)$_{129}$ is denoted SEQ ID NO:102.

EXAMPLE 22

This example describes studies confirming the specificity of IgE enriched antiserum from CQQ2 to fspN protein.

Three different petri dishes (100 mm) were overlaid with 300 microliter per plate of E.coli (XL1 Blue, O.D.$_{600}$32 500). A drop (about 100 pfu/drop) of each of the eighteen isolated phage clones was dropped onto each plate (18 phage clones/plate). Using the methods described in Example 22, the plates were incubated, filter lifted and the filters immunoscreened with IgE enriched antiserum from CQQ2, antiserum from a D. Immitis infected dog and antiserum from rabbits injected with flea saliva product from peak N.

The results of the experiment indicate that both the IgE enriched CQQ2 antiserum and the antiserum specific for peak N flea saliva product bind to the products of the purified phage clones significantly better than the antiserum from a D. Immitis infected dog.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 through SEQ ID NO:107 submitted herewith are the same.

What is claimed is:

1. An isolated nucleic acid molecule encoding an ectoparasite saliva protein in a formulation comprising at least one isolated ectoparasite saliva product substantially free of contaminating material, said formulation being produced by a process comprising:
   (a) collecting ectoparasite saliva products on a collection means within a saliva collection apparatus containing ectoparasites, said apparatus comprising:
      (i) a housing operatively connected to a chamber, said chamber having an ambient temperature warmer than said housing thereby forming a temperature differential between said housing and said chamber, said housing being capable of retaining ectoparasites; and
      (ii) an interface between said housing and said chamber, said interface comprising ((a)) a means capable of collecting at least a portion of saliva products deposited by ectoparasites retained in said apparatus and ((b)) a barrier means capable of substantially preventing contaminating material from contacting said collection means, wherein said temperature differential attracts ectoparasites retained in said housing to attempt to feed through said barrier means and collection means and, thereby, deposit saliva products on said collection means; and
   (b) extracting said saliva products from said collection means to obtain said formulation.

2. An isolated nucleic acid molecule capable of hybridizing under stringent conditions with a gene encoding a flea saliva protein present in a flea saliva extract selected from the group consisting of FS-1 and FS-2 flea saliva extracts.

3. The nucleic acid molecule of claim 2, wherein said flea saliva protein is selected from the group consisting of fspA, fspB, fspCl, fspC2, fspD1, fspD2, fspE, fspF, fspG1, fspG2, fspG3, fspG4, fspH, fspI, fspJ1, fspJ2, fspK, fspL1, fspL2, fspM1, fspM2, fspN1, fspN2, fspN3, fspM(A), fspM(B), fspM(C), fspM(D), fspM(E), fspM(F), fspM(G), fspM(H), fspM(I), fspM(J), fspM(K), fspM(L), fspM(M), fspN(B), fspN(C), fspN(D), fspN(E), fspN(F), fspN(G), fspN(H), fspN(I), fspN(J), fspN(K), fspN(L), fspN(M), fspN(N), and fspN(O).

4. The nucleic acid molecule of claim 2, wherein said nucleic acid molecule is capable of hybridizing under stringent conditions with a nucleic acid sequence selected from the group consisting of SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:79; SEQ ID NO:81; SEQ ID NO:82; SEQ ID NO:83; SEQ ID NO:84; SEQ ID NO:85; SEQ ID NO:86; SEQ ID NO:87; SEQ ID NO:89; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:101; or with a complement of any of said nucleic acid sequences.

5. The nucleic acid molecule of claim 2, wherein said nucleic acid molecule comprises a nucleic acid sequence selected from the group consisting of SEQ ID NO:20, SEQ ID:24, SEQ ID NO:32, SEQ ID NO:34, SEQ ID NO:50, SEQ ID NO:52, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71; SEQ ID NO:79; SEQ ID NO:81; SEQ ID NO:82; SEQ ID NO:83; SEQ ID NO:84; SEQ ID NO:85; SEQ ID NO:86; SEQ ID NO:87; SEQ ID NO:89; SEQ ID NO:91; SEQ ID NO:92; SEQ ID NO:93; SEQ ID NO:94; SEQ ID NO:95; SEQ ID NO:96; SEQ ID NO:97; SEQ ID NO:98; SEQ ID NO:99; SEQ ID NO:101, SEQ ID NO:104, a complement of any of said nucleic acid sequences, or an allelic variant of any of said nucleic acid sequences.

6. A recombinant molecule comprising at least one isolated nucleic acid molecule as set forth in claim 2 operatively linked to at least one transcription control sequence.

7. A recombinant cell comprising a cell having at least one nucleic acid molecule as set forth in claim 2, said cell being capable of expressing said nucleic acid molecule.

8. A therapeutic composition comprising at least one isolated nucleic acid molecule as set forth in claim 2.

9. An isolated nucleic acid molecule capable of hybridizing under stringent conditions with a gene encoding a flea saliva protein selected from the group consisting of fspA, fspB, fspG1, fspG2, fspG3, fspG4, fspH, fspI, fspJ1, fspJ2, fspL1, fspL2, fspM(A), fspM(B), fspM(C), fspM(D), fspM (E), fspM(F), fspM(G), fspM(H), fspM(I), fspM(J), fspM (K), fspM(L), fspM(M), fspN1, fspN2, fspN3, fspN(B), fspN(C), fspN(D), fspN(E), fspN(F), fspN(G), fspN(H), fspN(I), fspN(J), fspN(K), fspN(L), fspN(M), fspN(N), and fspN(O).

\* \* \* \* \*

SEQUENCE LISTING (1) GENERAL INFORMATION:

(iii) NUMBER OF SEQUENCES: 107

(2) INFORMATION FOR SEQ ID NO:1:

(i) SEQUENCE CHARACTERISTICS:
      (A) LENGTH: 22 amino acids
      (B) TYPE: amino acid
      (D) TOPOLOGY: linear (ii) MOLECULE TYPE: protein (ix) FEATURE:
            (A) NAME/KEY: Xaa = Tyr, Gln, Ser or Arg
            (B) LOCATION: 1

(ix) FEATURE:
            (A) NAME/KEY: Xaa = Gly or Tyr
            (B) LOCATION: 2

(ix) FEATURE:
            (A) NAME/KEY: Xaa = Lys or Ser
            (B) LOCATION: 3

(ix) FEATURE:
            (A) NAME/KEY: Xaa = Gly or Ser
            (B) LOCATION: 9

(ix) FEATURE:
            (A) NAME/KEY: Xaa = Gly or Lys
            (B) LOCATION: 10

(ix) FEATURE:
            (A) NAME/KEY: Xaa = Arg or Ile
            (B) LOCATION: 14

(ix) FEATURE:
            (A) NAME/KEY: Xaa = Ile or Leu
            (B) LOCATION: 17

(ix) FEATURE:
            (A) NAME/KEY: Xaa = Lys or Asp
            (B) LOCATION: 19

(ix) FEATURE:
            (A) NAME/KEY: Xaa = Gly or Leu
            (B) LOCATION: 21

(xi) SEQUENCE DESCRIPTION: SEQ ID NO:1:

Xaa Xaa Xaa Gln Tyr Ser Glu Lys Xaa Xaa Arg Gly Gln Xaa His Gln
1               5                   10                  15

Xaa Leu Xaa Lys Xaa Lys
            20

(2) INFORMATION FOR SEQ ID NO:2:

(i) SEQUENCE CHARACTERISTICS:
            (A) LENGTH: 78 amino acids
            (B) TYPE: amino acid
            (D) TOPOLOGY: linear (ii) MOLECULE TYPE: protein (ix) FEATURE:
            (A) NAME/KEY: Xaa = His or Tyr
            (B) LOCATION: 27

(xi) SEQUENCE DESCRIPTION: SEQ ID NO:2:

Asp Arg Arg Val Ser Lys Thr Cys Gln Ser Gly Gly Lys Ile Gln Ser
1               5                   10                  15

Glu Xaa Gln Val Val Ile Lys Ser Gly Gln Xaa Ile Leu Glu Asn Tyr
            20                  25                  30

Xaa Ser Asp Gly Arg Asn Asn Asn Pro Cys His Leu Phe Cys Met
            35                  40                  45

Arg Glu Cys Arg Ser Gly Asn Gly Gly Cys Gly Asn Gly Gly Arg Thr
50                  55                  60

Arg Pro Asp Ser Lys His Cys Tyr Cys Glu Ala Pro Tyr Ser
65                  70                  75

(2) INFORMATION FOR SEQ ID NO:3:

(i) SEQUENCE CHARACTERISTICS:
            (A) LENGTH: 12 amino acids (B) TYPE: amino acid
        (D) TOPOLOGY: linear (ii) MOLECULE TYPE: protein (xi) SEQUENCE DESCRIPTION: SEQ ID NO:3:

Asp Ser Lys His Cys Tyr Cys Glu Ala Pro Tyr Ser
1               5                   10

(2) INFORMATION FOR SEQ ID NO:4:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:4:

Asp Gly Arg Asn Asn Asn Pro Cys His Leu Phe Cys Met Arg Glu
1               5                   10                  15

Cys Arg Ser Gly Asn Gly Gly Cys Gly Asn Gly Gly Arg Thr Arg Pro
                20                  25                  30

Asp Ser Lys His Cys
            35

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:5:

Asp Arg Arg Val Ser Lys Thr Cys Gln Ser Gly
1               5                   10

(2) INFORMATION FOR SEQ ID NO:6:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:6:

Glu Asp Ile Trp Lys Val Asn Lys Lys Xaa Thr Ser Gly Gly Lys Asn
1               5                   10                  15

Gln Asp Arg Lys Leu Asp Gln Ile Ile Gln Lys Gly Gln Gln Val Xaa
                20                  25                  30

Xaa Gln Asn Xaa Xaa Lys
            35

(2) INFORMATION FOR SEQ ID NO:7:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:7:

Asn Ser His Glu Pro Gly Asn Thr Arg Lys Ile Arg Glu Val Met Asp

```
                 1               5              10              15
Lys Leu Arg Lys Gln His Pro
                20

(2) INFORMATION FOR SEQ ID NO:8:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:8:

Glu Ile Lys Arg Asn Ser His Glu Pro Gly Asn Thr Arg Lys Ile Arg
1               5                  10                  15
Glu Val Met Asp Lys Leu Arg Lys Gln His Pro
                20                  25

(2) INFORMATION FOR SEQ ID NO:9:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:9:

Asn Asp Lys Glu Pro Gly Asn Thr Arg Lys Ile Arg Glu Val Met Asp
1               5                  10                  15
Lys Leu Arg Lys Gln Ala Gln Pro Arg Thr Asp Gly Gln Arg Pro Lys
                20                  25                  30
Thr Xaa Ile Met
        35

(2) INFORMATION FOR SEQ ID NO:10:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:10:

Xaa Leu Xaa Arg Asn Asp Lys Glu Pro Gly Asn Thr Arg Lys Ile Arg
1               5                  10                  15
Glu Val Met Asp Lys
                20

(2) INFORMATION FOR SEQ ID NO:11:

(i) SEQUENCE CHARACTERISTICS:
        (A) LENGTH: 12 amino acids
        (B) TYPE: amino acid
        (D) TOPOLOGY: linear (ii) MOLECULE TYPE: DNA (genomic)

(xi) SEQUENCE DESCRIPTION: SEQ ID NO:11:

Asn Asp Glu Leu Lys Phe Val Phe Val Met Ala Lys
1               5                  10

(2) INFORMATION FOR SEQ ID NO:12:
```

(i) SEQUENCE CHARACTERISTICS:
              (A) LENGTH: 23 amino acids
              (B) TYPE: amino acid
              (D) TOPOLOGY: linear (ii) MOLECULE TYPE: protein (xi) SEQUENCE DESCRIPTION: SEQ ID NO:12:

Xaa Asp Glu Leu Lys Phe Val Phe Val Met Ala Lys Gly Pro Ser Xaa
1               5                   10                  15

Gln Ala Xaa Asp Tyr Pro Cys
            20

(2) INFORMATION FOR SEQ ID NO:13:

(i) SEQUENCE CHARACTERISTICS:
              (A) LENGTH: 20 amino acids
              (B) TYPE: amino acid
              (D) TOPOLOGY: linear (ii) MOLECULE TYPE: protein (xi) SEQUENCE DESCRIPTION: SEQ ID NO:13:

Glu Leu Lys Phe Val Phe Ala Thr Ala Arg Gly Met Ser His Thr Pro
1               5                   10                  15

Cys Asp Tyr Pro
            20

(2) INFORMATION FOR SEQ ID NO:14:

(i) SEQUENCE CHARACTERISTICS:
              (A) LENGTH: 37 amino acids
              (B) TYPE: amino acid
              (D) TOPOLOGY: linear (ii) MOLECULE TYPE: protein (ix) FEATURE:
              (A) NAME/KEY: Xaa = His or Tyr
              (B) LOCATION: 27

(xi) SEQUENCE DESCRIPTION: SEQ ID NO:14:

Asp Arg Arg Val Ser Lys Thr Xaa Gln Ser Gly Gly Lys Ile Gln Ser
1               5                   10                  15

Glu Xaa Gln Val Val Ile Lys Ser Gly Gln Xaa Ile Leu Glu Asn Tyr
            20                  25                  30

Xaa Ser Asp Gly Arg
            35

(2) INFORMATION FOR SEQ ID NO:15:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (primer)

(xi) SEQUENCE DESCRIPTION: SEQ ID NO:15:

AAYAAYAAYA AYCCNTGYCA                                                           20

(2) INFORMATION FOR SEQ ID NO:16:

(i) SEQUENCE CHARACTERISTICS:
              (A) LENGTH: 17 base pairs
              (B) TYPE: nucleic acid
              (C) STRANDEDNESS: single (D) TOPOLOGY: linear (ii) MOLECULE TYPE: DNA (primer)

(xi) SEQUENCE DESCRIPTION: SEQ ID NO:16:

CAYTCNCKCA TRCARAA                                                         17

(2) INFORMATION FOR SEQ ID NO:17:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (ii) MOLECULE TYPE: DNA (primer)

(xi) SEQUENCE DESCRIPTION: SEQ ID NO:17:

TGYCAYYTNT TYTGYATG                                                        18

(2) INFORMATION FOR SEQ ID NO:18:

(i) SEQUENCE CHARACTERISTICS:
                    (A) LENGTH: 23 base pairs
                    (B) TYPE: nucleic acid
                    (C) STRANDEDNESS: single
                    (D) TOPOLOGY: linear (ii) MOLECULE TYPE: DNA (primer)

(xi) SEQUENCE DESCRIPTION: SEQ ID NO:18:

GGNGCYTCRC ARTARCARTG YTT                                                  23

(2) INFORMATION FOR SEQ ID NO:19:

(i) SEQUENCE CHARACTERISTICS:
                    (A) LENGTH: 17 base pairs
                    (B) TYPE: nucleic acid
                    (C) STRANDEDNESS: single
                    (D) TOPOLOGY: linear (ii) MOLECULE TYPE: DNA (primer)

(xi) SEQUENCE DESCRIPTION: SEQ ID NO:19:

GTAAAACGAC GGCCAGT                                                         17

(2) INFORMATION FOR SEQ ID NO:20:

(i) SEQUENCE CHARACTERISTICS:
                    (A) LENGTH: 93 base pairs
                    (B) TYPE: nucleic acid
                    (C) STRANDEDNESS: single
                    (D) TOPOLOGY: linear (ii) MOLECULE TYPE: cDNA (xi) SEQUENCE DESCRIPTION: SEQ ID NO:20:

TTGTCACTTT TTTTGTATGA GAGAATGCAG GTCAGGAAAC GGCGGTTGCG GAAACGGAGG           60

AAGGACAAGA CCTGATTCGA AGCACTGCTA TGC                                       93

(2) INFORMATION FOR SEQ ID NO:21:

(i) SEQUENCE CHARACTERISTICS:
                    (A) LENGTH: 23 base pairs
                    (B) TYPE: nucleic acid
                    (C) STRANDEDNESS: single
                    (D) TOPOLOGY: linear (ii) MOLECULE TYPE: DNA (primer)

(xi) SEQUENCE DESCRIPTION: SEQ ID NO:21:

GARGAYATHT GGAARGTNAA YAA                                              23

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:22:

ACNTCNGGNG GNAARAAYCA RGA                                              23

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:23:

TTGGGTACCG GGCCCCCCCT                                                  20

(2) INFORMATION FOR SEQ ID NO:24:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CTTACGTCCG GGGGTAAGAA TCAGGATAGA AAACTCGATC AAATAATTCA AAAAGGCCAA       60

CAAGTTAAAA TCCAAAATAT TTGCAAATTA ATACGAGATA AACCACATAC AAATCAAGAG      120

AAAGAAAAAT GTATGAAATT TTGCACAAAA AACGTTTGCA AAGGTTATAG AGGAGCTTGT      180

GATGGCAATA TTTGCTACTG CAGCAGGCCA AGTAATTTAG GTCCTGATTG GAAAGTCAAC      240

GAAAGAATCG AAAGACTCCC AATAACAAAG ATTCTCGTCT CAGGAAATAG TTCCATATCG      300

ACAACAATTA CGAATTCCAA ATATTTCGAA ACTAAAAATT CAGAGACCAA TGAAGATTCC      360

AAATCGAAAA AACATTCGAA AGAAAAATGT CGTGGTGGAA ATGATGCTGG ATGTGATGGA      420

AACGTTTTGT TATTGTCGAC CAAAAAATAA ATAATAATTA TAATAAATAA ATTGTTATAG      480

TTATTAGTTA TCCCGTCACA TATTAGAAAA GTGGCTTATA ATTTATGAAC AATATAACAC      540

ATAAATTAGT TGTGTAAAAA AAAAAAAAAA AAA                                  573

(2) INFORMATION FOR SEQ ID NO:25:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO:25:

```
Leu Thr Ser Gly Gly Lys Asn Gln Asp Arg Lys Leu Asp Gln Ile Ile
1               5                   10                  15

Gln Lys Gly Gln Gln Val Lys Ile Gln Asn Ile Cys Lys Leu Ile Arg
                20                  25                  30

Asp Lys Pro His Thr Asn Gln Glu Lys Glu Lys Cys Met Lys Phe Cys
            35                  40                  45

Thr Lys Asn Val Cys Lys Gly Tyr Arg Gly Ala Cys Asp Gly Asn Ile
        50                  55                  60

Cys Tyr Cys Ser Arg Pro Ser Asn Leu Gly Pro Asp Trp Lys Val Asn
65                  70                  75                  80

Glu Arg Ile Glu Arg Leu Pro Ile Thr Lys Ile Leu Val Ser Gly Asn
                85                  90                  95

Ser Ser Ile Ser Thr Thr Ile Thr Asn Ser Lys Tyr Phe Glu Thr Lys
            100                 105                 110

Asn Ser Glu Thr Asn Glu Asp Ser Lys Ser Lys Lys His Ser Lys Glu
            115                 120                 125

Lys Cys Arg Gly Gly Asn Asp Arg Gly Cys Asp Gly Asn Val Leu Leu
130                 135                 140

Leu Ser Thr Lys Lys
145
```

(2) INFORMATION FOR SEQ ID NO:26:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:26:

```
Glu Asp Ile Trp Lys Val Asn Lys Lys Leu Thr Ser Gly Gly Lys Asn
1               5                   10                  15

Gln Asp Arg Lys Leu Asp Gln Ile Ile Gln Lys Gly Gln Gln Val Lys
                20                  25                  30

Ile Gln Asn Ile Cys Lys Leu Ile Arg Asp Lys Pro His Thr Asn Gln
                35                  40                  45

Glu Lys Glu Lys Cys Met Lys Phe Cys Thr Lys Asn Val Cys Lys Gly
50                  55                  60

Tyr Arg Gly Ala Cys Asp Gly Asn Ile Cys Tyr Cys Ser Arg Pro Ser
65                  70                  75                  80

Asn Leu Gly Pro Asp Trp Lys Val Asn Glu Arg Ile Glu Arg Leu Pro
                85                  90                  95

Ile Thr Lys Ile Leu Val Ser Gly Asn Ser Ser Ile Ser Thr Thr Ile
            100                 105                 110

Thr Asn Ser Lys Tyr Phe Glu Thr Lys Asn Ser Glu Thr Asn Glu Asp
            115                 120                 125

Ser Lys Ser Lys Lys His Ser Lys Glu Lys Cys Arg Gly Gly Asn Asp
130                 135                 140

Arg Gly Cys Asp Gly Asn Val Leu Leu Leu Ser Thr Lys Lys
145                 150                 155
```

(2) INFORMATION FOR SEQ ID NO:27:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
            (A) NAME/KEY: Xaa = Ser or Gln
            (B) LOCATION: 1

(ix) FEATURE:
            (A) NAME/KEY: Xaa = any amino acid
            (B) LOCATION: 8

(ix) FEATURE:
            (A) NAME/KEY: Xaa = Gly or Lys
            (B) LOCATION: 9

(xi) SEQUENCE DESCRIPTION: SEQ ID NO:27:

Xaa Gly Lys Gln Tyr Ser Glu Xaa Xaa Lys
1               5                   10

(2) INFORMATION FOR SEQ ID NO:28:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO:28:

Asp Arg Arg Val Ser Lys
1               5

(2) INFORMATION FOR SEQ ID NO:29:

(i) SEQUENCE CHARACTERISTICS:
            (A) LENGTH: 23 amino acids
            (B) TYPE: amino acid
            (D) TOPOLOGY: linear (ii) MOLECULE TYPE: protein (ix) FEATURE:
            (A) NAME/KEY: Xaa = any amino acid
            (B) LOCATION: 8

(xi) SEQUENCE DESCRIPTION: SEQ ID NO:29:

Ser Lys Met Val Thr Glu Lys Xaa Lys Ser Gly Gly Asn Asn Pro Ser
1               5                   10                  15

Thr Lys Glu Val Ser Ile Pro
            20

(2) INFORMATION FOR SEQ ID NO:30:

(i) SEQUENCE CHARACTERISTICS:
            (A) LENGTH: 20 amino acids
            (B) TYPE: amino acid
            (D) TOPOLOGY: linear (ii) MOLECULE TYPE: protein (ix) FEATURE:
            (A) NAME/KEY: Xaa = any amino acid
            (B) LOCATION: 15

(xi) SEQUENCE DESCRIPTION: SEQ ID NO:30:

Glu Val Ser Ile Pro Ser Gly Lys Leu Thr Ile Glu Asp Phe Xaa Ile
1               5                   10                  15

Gly Asn His Gln
            20

(2) INFORMATION FOR SEQ ID NO:31:

(i) SEQUENCE CHARACTERISTICS:
    (A) LENGTH: 25 amino acids
    (B) TYPE: amino acid
    (D) TOPOLOGY: linear (ii) MOLECULE TYPE: protein (xi) SEQUENCE DESCRIPTION: SEQ ID NO:31:

Asp Ile Glu Asn Ile Lys Lys Gly Glu Gly Gln Pro Gly Ala Pro Gly
1               5                  10                  15

Gly Lys Glu Asn Asn Leu Ser Val Leu
            20                  25

(2) INFORMATION FOR SEQ ID NO:32:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..242

(xi) SEQUENCE DESCRIPTION: SEQ ID NO:32:

AT TTT TCC CTT TGT GTT TTA TAC CAA ATT GTG GTT GCT GAT AGA AGA        47
   Phe Ser Leu Cys Val Leu Tyr Gln Ile Val Val Ala Asp Arg Arg
     1           5                  10                  15

GTT TCC AAA ACA TGT CAA AGT GGA GGA AAG ATA CAA AGT GAG GAG CAA       95
Val Ser Lys Thr Cys Gln Ser Gly Gly Lys Ile Gln Ser Glu Glu Gln
            20                  25                  30

GTG GTA ATT AAA TCT GGA CAA CAT ATT CTT GAA AAT TAT TGC TCA GAT      143
Val Val Ile Lys Ser Gly Gln His Ile Leu Glu Asn Tyr Cys Ser Asp
            35                  40                  45

GGG AGA AAT AAT AAT AAT CCA TGC CAC TTG TTT TGT ATG AGA GAA TGC      191
Gly Arg Asn Asn Asn Asn Pro Cys His Leu Phe Cys Met Arg Glu Cys
            50                  55                  60

AGG TCA GGA AAC GGC GGT TGC GGA AAC GGA GGA AGG ACA AGA CCT GAT      239
Arg Ser Gly Asn Gly Gly Cys Gly Asn Gly Gly Arg Thr Arg Pro Asp
            65                  70                  75

TCG                                                                   242
Ser
80

(2) INFORMATION FOR SEQ ID NO:33:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO:33:

Phe Ser Leu Cys Val Leu Tyr Gln Ile Val Val Ala Asp Arg Arg Val
1               5                  10                  15

Ser Lys Thr Cys Gln Ser Gly Gly Lys Ile Gln Ser Glu Glu Gln Val
            20                  25                  30

Val Ile Lys Ser Gly Gln His Ile Leu Glu Asn Tyr Cys Ser Asp Gly
            35                  40                  45

Arg Asn Asn Asn Asn Pro Cys His Leu Phe Cys Met Arg Glu Cys Arg
    50                  55                  60

```
                  5,932,470
       103                              104
                  -continued Ser Gly Asn Gly Gly Cys Gly Asn Gly Gly Arg Thr Arg Pro Asp Ser
 65                  70                  75                  80

(2) INFORMATION FOR SEQ ID NO:34:

(i) SEQUENCE CHARACTERISTICS:
          (A) LENGTH: 591 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..466

(xi) SEQUENCE DESCRIPTION: SEQ ID NO:34:

TGG AAA GTT AAT AAA AAA TGT ACA TCA GGT GGA AAA AAT CAA GAT AGA        48
Trp Lys Val Asn Lys Lys Cys Thr Ser Gly Gly Lys Asn Gln Asp Arg
  1               5                  10                  15

AAA CTC GAT CAA ATA ATT CAA AAA GGC CAA CAA GTT AAA ATC CAA AAT        96
Lys Leu Asp Gln Ile Ile Gln Lys Gly Gln Gln Val Lys Ile Gln Asn
                 20                  25                  30

ATT TGC AAA TTA ATA CGA GAT AAA CCA CAT ACA AAT CAA GAG AAA GAA       144
Ile Cys Lys Leu Ile Arg Asp Lys Pro His Thr Asn Gln Glu Lys Glu
         35                  40                  45

AAA TGT ATG AAA TTT TGC ACA AAA AAC GTT TGC AAA GGT TAT AGA GGA       192
Lys Cys Met Lys Phe Cys Thr Lys Asn Val Cys Lys Gly Tyr Arg Gly
     50                  55                  60

GCT TGT GAT GGC AAT ATT TGC TAC TGC AGC AGG CCA AGT AAT TTA GGT       240
Ala Cys Asp Gly Asn Ile Cys Tyr Cys Ser Arg Pro Ser Asn Leu Gly
 65                  70                  75                  80

CCT GAT TGG AAA GTC AAC GAA AGA ATC GAA AGA CTC CCA ATA ACA AAG       288
Pro Asp Trp Lys Val Asn Glu Arg Ile Glu Arg Leu Pro Ile Thr Lys
                 85                  90                  95

ATT CTC GTC TCA GGA AAT AGT TCC ATA TCG ACA ACA ATT ACG AAT TCC       336
Ile Leu Val Ser Gly Asn Ser Ser Ile Ser Thr Thr Ile Thr Asn Ser
            100                 105                 110

AAA TAT TTC GAA ACT AAA AAT TCA GAG ACC AAT GAA GAT TCC AAA TCG       384
Lys Tyr Phe Glu Thr Lys Asn Ser Glu Thr Asn Glu Asp Ser Lys Ser
        115                 120                 125

AAA AAA CAT TCG AAA GAA AAA TGT CGT GGT GGA AAT GAT CGT GGA TGT       432
Lys Lys His Ser Lys Glu Lys Cys Arg Gly Gly Asn Asp Arg Gly Cys
    130                 135                 140

GAT GGA AAC GTT TTG TTA TTG TCG ACC AAA AAA T AAATAATAAT              476
Asp Gly Asn Val Leu Leu Leu Ser Thr Lys Lys
145                 150                 155

TATAATAAAT AAATTGTTAT AGTTATTAGT TATCCCGTCA CATATTAGAA AAGTGGCTTA     536

TAATTTATGA ACAATATAAC ACATAAATTA GTTGTGTAAA AAAAAAAAAA AAAAA          591

(2) INFORMATION FOR SEQ ID NO:35:

(i) SEQUENCE CHARACTERISTICS:
          (A) LENGTH: 155 amino acids
          (B) TYPE: amino acid
          (D) TOPOLOGY: linear (ii) MOLECULE TYPE: protein (xi) SEQUENCE DESCRIPTION: SEQ ID NO:35:

Trp Lys Val Asn Lys Lys Cys Thr Ser Gly Gly Lys Asn Gln Asp Arg
  1               5                  10                  15
```

```
Lys Leu Asp Gln Ile Ile Gln Lys Gly Gln Gln Val Lys Ile Gln Asn
             20                  25                  30

Ile Cys Lys Leu Ile Arg Asp Lys Pro His Thr Asn Gln Glu Lys Glu
         35                  40                  45

Lys Cys Met Lys Phe Cys Thr Lys Asn Val Cys Lys Gly Tyr Arg Gly
 50                  55                  60

Ala Cys Asp Gly Asn Ile Cys Tyr Cys Ser Arg Pro Ser Asn Leu Gly
 65                  70                  75                  80

Pro Asp Trp Lys Val Asn Glu Arg Ile Glu Arg Leu Pro Ile Thr Lys
                 85                  90                  95

Ile Leu Val Ser Gly Asn Ser Ser Ile Ser Thr Thr Ile Thr Asn Ser
            100                 105                 110

Lys Tyr Phe Glu Thr Lys Asn Ser Glu Thr Asn Glu Asp Ser Lys Ser
            115                 120                 125

Lys Lys His Ser Lys Glu Lys Cys Arg Gly Gly Asn Asp Arg Gly Cys
        130                 135                 140

Asp Gly Asn Val Leu Leu Leu Ser Thr Lys Lys
145                 150                 155
```

(2) INFORMATION FOR SEQ ID NO:36:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:36:

ATTCGGATCC ATGGAAAGTT AATAAAAAAT GTAC                    34

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:37:

TAATGGATCC TTATTTTTTG GTCGACAATA AC                      32

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:38:

CCTGACCTGC ATTCTCTCAT AC                                22

(2) INFORMATION FOR SEQ ID NO:39:

(i) SEQUENCE CHARACTERISTICS:
        (A) LENGTH: 27 base pairs
        (B) TYPE: nucleic acid
        (C) STRANDEDNESS: single
        (D) TOPOLOGY: linear -continued (ii) MOLECULE TYPE: primer (xi) SEQUENCE DESCRIPTION: SEQ ID NO:39:

AGGTCTTGTC CTTCCTCCGT TTCCGCA                                        27

(2) INFORMATION FOR SEQ ID NO:40:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: primer (xi) SEQUENCE DESCRIPTION: SEQ ID NO:40:

GGAAACAGCT ATGACCATG                                                 19

(2) INFORMATION FOR SEQ ID NO:41:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: primer (xi) SEQUENCE DESCRIPTION: SEQ ID NO:41:

ATTAACCCTC ACTAAAG                                                   17

(2) INFORMATION FOR SEQ ID NO:42:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: primer (xi) SEQUENCE DESCRIPTION: SEQ ID NO:42:

GCAAAGGTTA TAGAGGAGCT TG                                             22

(2) INFORMATION FOR SEQ ID NO:43:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: primer (xi) SEQUENCE DESCRIPTION: SEQ ID NO:43:

AGCTTTCCAT CACATCCAGC                                                20

(2) INFORMATION FOR SEQ ID NO:44:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (ii) MOLECULE TYPE: primer (xi) SEQUENCE DESCRIPTION: SEQ ID NO:44:

CGCGGATCCT ATAAATATGG AGGACATCTG GAAAGTTAAT AAAAAATGTA CATC        54

(2) INFORMATION FOR SEQ ID NO:45:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:45:

GCTCTAGAGC ATTTATTTTT TGGTCGACAA TAACAAAAC        39

(2) INFORMATION FOR SEQ ID NO:46:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:46:

GGCGTCTCGA GAGAATTGAA ATTTGTGTTT GCG        33

(2) INFORMATION FOR SEQ ID NO:47:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:47:

AGACGAGAAT TCCAATTTAT CATGAGCGG        29

(2) INFORMATION FOR SEQ ID NO:48:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:48:

CCGGAATTCC GGTATAAATA TGTGGCGTCT ACTG        34

(2) INFORMATION FOR SEQ ID NO:49:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:49:

CCGGAATTCT TAAGACGATT TACACAATTT ATC        33

(2) INFORMATION FOR SEQ ID NO:50:

(i) SEQUENCE CHARACTERISTICS:
    (A) LENGTH: 646 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 3..519

(xi) SEQUENCE DESCRIPTION: SEQ ID NO:50:

```
CG GCA CGA GCT CGG TCT GTT GGA AGT ATG AAA AAC AAA TTG AAA AGT         47
   Ala Arg Ala Arg Ser Val Gly Ser Met Lys Asn Lys Leu Lys Ser
    1               5                  10                  15

TTT TCC GAG AAA TAT GTA TGG GCG GCT TTA ACT TCT AAC GAC AAT CTT        95
Phe Ser Glu Lys Tyr Val Trp Ala Ala Leu Thr Ser Asn Asp Asn Leu
                20                  25                  30

AGG AAA ATG TCT GGA GGT CGT ATG ATT AAC GAT ATA TTG AAC GAT ATC       143
Arg Lys Met Ser Gly Gly Arg Met Ile Asn Asp Ile Leu Asn Asp Ile
            35                  40                  45

GAT AAT ATA AAG AAA GGA AAT GGA CAA CCG AAT GCT CCT GGA AAA ACT       191
Asp Asn Ile Lys Lys Gly Asn Gly Gln Pro Asn Ala Pro Gly Lys Thr
        50                  55                  60

GAA AAT AAA TTA TCG GTG TCT GAC CGT TCC TCA AGG TAT CTT AGC AGC       239
Glu Asn Lys Leu Ser Val Ser Asp Arg Ser Ser Arg Tyr Leu Ser Ser
 65                  70                  75

ATT CGT TTC AGC CTT TTT CGT CCA AGG TAC AAA ATT GAA AAT CAG GAC       287
Ile Arg Phe Ser Leu Phe Arg Pro Arg Tyr Lys Ile Glu Asn Gln Asp
 80                  85                  90                  95

CTT GAA CCG TCT AGT TTA TAT CCT GGC CAA GGA GCC CTC CAT GTT ATT       335
Leu Glu Pro Ser Ser Leu Tyr Pro Gly Gln Gly Ala Leu His Val Ile
                100                 105                 110

GAA CTG CAC AAA GAT AAG AAT CAG TGG AAT GTA AAA ACC CTC TAT AGA       383
Glu Leu His Lys Asp Lys Asn Gln Trp Asn Val Lys Thr Leu Tyr Arg
            115                 120                 125

AAC AAT GAC CAA CAG GAA CTC AAA CCT ATG AAA CTT GCA AAA TGC GGT       431
Asn Asn Asp Gln Gln Glu Leu Lys Pro Met Lys Leu Ala Lys Cys Gly
        130                 135                 140

GAC ACA TGT TCT TAT GAA ACT TTC AAA TCA ACT CTA CAA TCC TAT AAC       479
Asp Thr Cys Ser Tyr Glu Thr Phe Lys Ser Thr Leu Gln Ser Tyr Asn
    145                 150                 155

ATG GAT AAG ACC GCT CAT GAT AAA TTG TGT AAA TCG TCT T AAAAATTATT      529
Met Asp Lys Thr Ala His Asp Lys Leu Cys Lys Ser Ser
160                 165                 170

CGTGAAAAAT AGAATTTTAT TGCTATTTTC TGTAAAACCA TATAAAGCTA TTTTAATACT     589

TTGTACAGTA TATACATAAT AAATTGCTAC ATTTGCTCTA AAAAAAAAAA AAAAAAA        646
```

(2) INFORMATION FOR SEQ ID NO:51:

(i) SEQUENCE CHARACTERISTICS:
    (A) LENGTH: 172 amino acids
    (B) TYPE: amino acid
    (D) TOPOLOGY: linear (ii) MOLECULE TYPE: protein (xi) SEQUENCE DESCRIPTION: SEQ ID NO:51:

```
Ala Arg Ala Arg Ser Val Gly Ser Met Lys Asn Lys Leu Lys Ser Phe
 1               5                  10                  15

Ser Glu Lys Tyr Val Trp Ala Ala Leu Thr Ser Asn Asp Asn Leu Arg
            20                  25                  30
```

```
Lys Met Ser Gly Gly Arg Met Ile Asn Asp Ile Leu Asn Asp Ile Asp
         35                  40                  45

Asn Ile Lys Lys Gly Asn Gly Gln Pro Asn Ala Pro Gly Lys Thr Glu
     50                  55                  60

Asn Lys Leu Ser Val Ser Asp Arg Ser Ser Arg Tyr Leu Ser Ser Ile
 65                  70                  75                  80

Arg Phe Ser Leu Phe Arg Pro Arg Tyr Lys Ile Glu Asn Gln Asp Leu
                 85                  90                  95

Glu Pro Ser Ser Leu Tyr Pro Gly Gln Gly Ala Leu His Val Ile Glu
                100                 105                 110

Leu His Lys Asp Lys Asn Gln Trp Asn Val Lys Thr Leu Tyr Arg Asn
             115                 120                 125

Asn Asp Gln Gln Glu Leu Lys Pro Met Lys Leu Ala Lys Cys Gly Asp
         130                 135                 140

Thr Cys Ser Tyr Glu Thr Phe Lys Ser Thr Leu Gln Ser Tyr Asn Met
145                 150                 155                 160

Asp Lys Thr Ala His Asp Lys Leu Cys Lys Ser Ser
                 165                 170
```

(2) INFORMATION FOR SEQ ID NO:52:

(i) SEQUENCE CHARACTERISTICS:
        (A) LENGTH: 612 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..461

(xi) SEQUENCE DESCRIPTION: SEQ ID NO:52:

```
C GGC ACG AGG AAA AAC GAG CTG AAA AGT TTT TCC GAA GAA TAT TTA        46
  Gly Thr Arg Lys Asn Glu Leu Lys Ser Phe Ser Glu Glu Tyr Leu
   1               5                  10                  15

TGG AGG GCT CTA ACT TCT AAT GAG AAT CTT AGA AAG ATG TCA GGA GGC      94
Trp Arg Ala Leu Thr Ser Asn Glu Asn Leu Arg Lys Met Ser Gly Gly
                 20                  25                  30

CGT ATG ATT AAC GAT ATA TTG AAC GAT ATC GAT AGT ATA AAA GAA GAA     142
Arg Met Ile Asn Asp Ile Leu Asn Asp Ile Asp Ser Ile Lys Glu Glu
                     35                  40                  45

AGG GAC AAC CGG GTG CTC CTG GAA AAA CAG GAA ATT AAA TTA TCA ATG     190
Arg Asp Asn Arg Val Leu Leu Glu Lys Gln Glu Ile Lys Leu Ser Met
         50                  55                  60

CTG ACC GTT CCT CAA GCT ATC TTA GCA GCA TTT GTT TCA GCT TTT GCT     238
Leu Thr Val Pro Gln Ala Ile Leu Ala Ala Phe Val Ser Ala Phe Ala
 65                  70                  75

CCC AAA GGT ACA AAA ATT GAA AAT CAG GAC CTT GGT CCG TCT AGT TTA     286
Pro Lys Gly Thr Lys Ile Glu Asn Gln Asp Leu Gly Pro Ser Ser Leu
 80                  85                  90                  95

TAT CCT GGC CAA GGA GCA CTC CAC GTT ATT GAA CTG CAC AAG GAT AAC     334
Tyr Pro Gly Gln Gly Ala Leu His Val Ile Glu Leu His Lys Asp Asn
                100                 105                 110

AAC CAA TGG AGT GTG AAA GTT CTC TAT AGA AAC AAT GAC AAA ATG GAA     382
Asn Gln Trp Ser Val Lys Val Leu Tyr Arg Asn Asn Asp Lys Met Glu
             115                 120                 125

CTG GAA CCT ATG AAA CTT CCA TCA TGC GAT GAC AAA TGT CCT TGT GAA     430
Leu Glu Pro Met Lys Leu Pro Ser Cys Asp Asp Lys Cys Pro Cys Glu
         130                 135                 140
```

-continued

```
CTT TTA AAT CAA CTC TAC AAT CCT ATG ATA T GAAAAAGCAG TCATGTAAAT      481
Leu Leu Asn Gln Leu Tyr Asn Pro Met Ile
    145                 150

TATGTAAAAA GCAATAAAAC TGTTGGCAAA ACATACACTT GAACATATTC TGCAAAATTA    541

TATGACGTTA TTTTTAATAT CACGAAATAA ACTACAAACA AACATATACA AATAAAAAAA    601

AAAAAAAAA A                                                          612
```

(2) INFORMATION FOR SEQ ID NO:53:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:53:

```
Gly Thr Arg Lys Asn Glu Leu Lys Ser Phe Ser Glu Glu Tyr Leu Trp
 1               5                  10                  15

Arg Ala Leu Thr Ser Asn Glu Asn Leu Arg Lys Met Ser Gly Gly Arg
            20                  25                  30

Met Ile Asn Asp Ile Leu Asn Asp Ile Asp Ser Ile Lys Glu Glu Arg
        35                  40                  45

Asp Asn Arg Val Leu Leu Glu Lys Gln Glu Ile Lys Leu Ser Met Leu
 50                  55                  60

Thr Val Pro Gln Ala Ile Leu Ala Ala Phe Val Ser Ala Phe Ala Pro
65                  70                  75                  80

Lys Gly Thr Lys Ile Glu Asn Gln Asp Leu Gly Pro Ser Ser Leu Tyr
                85                  90                  95

Pro Gly Gln Gly Ala Leu His Val Ile Glu Leu His Lys Asp Asn Asn
            100                 105                 110

Gln Trp Ser Val Lys Val Leu Tyr Arg Asn Asn Asp Lys Met Glu Leu
        115                 120                 125

Glu Pro Met Lys Leu Pro Ser Cys Asp Asp Lys Cys Pro Cys Glu Leu
    130                 135                 140

Leu Asn Gln Leu Tyr Asn Pro Met Ile
145                 150
```

(2) INFORMATION FOR SEQ ID NO:54:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:54:

```
Met Trp Arg Leu Leu Val Ile Ser Ser Ala Leu Ile Ile Gln Asn
 1               5                  10                  15

Val Asn Ala Glu Leu Lys Phe Val Phe Ala Thr Ala Thr Arg Tyr Val
            20                  25                  30

Ser His Thr Pro Ser Pro Cys Asp Pro Gly Gly Pro Lys Ile Thr Asn
        35                  40                  45

Lys Pro Gly Asp Phe Gln Arg Val
 50                  55
```

(2) INFORMATION FOR SEQ ID NO:55:

(i) SEQUENCE CHARACTERISTICS:

```
            (A) LENGTH: 1197 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..1196

(xi) SEQUENCE DESCRIPTION: SEQ ID NO:55:

ATG TGG CGT CTA CTG TTA GTT ATT TCA AGT GCA CTT ATC ATT CAA AAT        48
Met Trp Arg Leu Leu Leu Val Ile Ser Ser Ala Leu Ile Ile Gln Asn
1               5                   10                  15

GTT AAT GCA GAA TTG AAA TTT GTG TTT GCG ACT GCA CGA GGT ATG TCA        96
Val Asn Ala Glu Leu Lys Phe Val Phe Ala Thr Ala Arg Gly Met Ser
                20                  25                  30

CAT ACA CCT TGT GAT TAT CCA GGC GGT CCA AAA ATT ACT AAC AAG CCT       144
His Thr Pro Cys Asp Tyr Pro Gly Gly Pro Lys Ile Thr Asn Lys Pro
            35                  40                  45

GAG ACT TCA AGC GTG TTG ACA ACA GCT GGT AAA AAT GAG GCA CTA GAA       192
Glu Thr Ser Ser Val Leu Thr Thr Ala Gly Lys Asn Glu Ala Leu Glu
        50                  55                  60

ATT GGC AAA CTA TTA TCT GAC CAT TAC AAA AGT AAT TTA ACA GTT AAG       240
Ile Gly Lys Leu Leu Ser Asp His Tyr Lys Ser Asn Leu Thr Val Lys
65              70                  75                  80

GAA TGG GAC TCA AGT AAA AAT TAT TGG ACA TTA GCT AGT AAT ACA AGA       288
Glu Trp Asp Ser Ser Lys Asn Tyr Trp Thr Leu Ala Ser Asn Thr Arg
                85                  90                  95

AGA TCT CAA GAA GGA ACA CTT ATT ATT GGT TCT GGA CTA GAA GGA AAG       336
Arg Ser Gln Glu Gly Thr Leu Ile Ile Gly Ser Gly Leu Glu Gly Lys
            100                 105                 110

AGT AGA GCA GCA GAG TGG TCA CAA GAG ATA GGA AAG AAA ACC ACA TTT       384
Ser Arg Ala Ala Glu Trp Ser Gln Glu Ile Gly Lys Lys Thr Thr Phe
        115                 120                 125

TCA GGA TTT TCT GAG TAT GCT AAA TTT TAT AGT CAA AAA GAA TGC CCA       432
Ser Gly Phe Ser Glu Tyr Ala Lys Phe Tyr Ser Gln Lys Glu Cys Pro
130             135                 140

AAC TTC ATA AAA CAA CAG TTG GAT GCA GTG AAG GAC TTG TTA AAG AGT       480
Asn Phe Ile Lys Gln Gln Leu Asp Ala Val Lys Asp Leu Leu Lys Ser
145                 150                 155                 160

GCA AAA GAA TAT AAT ACA GAA TTT GAC AAA TTA AAG AAA GTG TAT AAT       528
Ala Lys Glu Tyr Asn Thr Glu Phe Asp Lys Leu Lys Lys Val Tyr Asn
                165                 170                 175

ATT GAT GCA ATG AAG GGC CCA CAA AAT GTT TGG CTG GCA TAC GAG ACT       576
Ile Asp Ala Met Lys Gly Pro Gln Asn Val Trp Leu Ala Tyr Glu Thr
            180                 185                 190

TTA AAT TTA CAA AGC AAG CTC GAT CAG ATT GGT TTG GGA AGT ATG AAA       624
Leu Asn Leu Gln Ser Lys Leu Asp Gln Ile Gly Leu Gly Ser Met Lys
        195                 200                 205

AAC AAA TTG AAA AGT TTT TCC GAG AAA TAT GTA TGG GCG GGT TTA ACT       672
Asn Lys Leu Lys Ser Phe Ser Glu Lys Tyr Val Trp Ala Gly Leu Thr
    210                 215                 220

TCT AAC GAC AAT CTT AGG AAA ATG TCT GGA GGT CGT ATG ATT AAC GAT       720
Ser Asn Asp Asn Leu Arg Lys Met Ser Gly Gly Arg Met Ile Asn Asp
225                 230                 235                 240

ATA TTG AAC GAT ATC GAT AAT ATA AAG AAA GGA AAT GGA CAA CCG AAT       768
Ile Leu Asn Asp Ile Asp Asn Ile Lys Lys Gly Asn Gly Gln Pro Asn
                245                 250                 255

GCT CCT GGA AAA CTG AAA ATA ATT ATC GGG CTG ACC GCC CCA AGG TTC       816
Ala Pro Gly Lys Leu Lys Ile Ile Ile Gly Leu Thr Ala Pro Arg Phe
            260                 265                 270
```

-continued

```
TTA GCA GAA TCC GTT CAG CTT GGG TCC AAG GGT ACA AAA TTG AAT CAG     864
Leu Ala Glu Ser Val Gln Leu Gly Ser Lys Gly Thr Lys Leu Asn Gln
        275                 280                 285

GAC CAA AAT AAA TTA TCG GTG CTG ACC GTT CCT CAA GGT ATC TTA GCA     912
Asp Gln Asn Lys Leu Ser Val Leu Thr Val Pro Gln Gly Ile Leu Ala
    290                 295                 300

GCA TTC GTT TCA GCT TTT GCT CCC AAA GGT ACA AAA ATT GAA AAT CAG     960
Ala Phe Val Ser Ala Phe Ala Pro Lys Gly Thr Lys Ile Glu Asn Gln
305                 310                 315                 320

GAC CTT GAT CCG TCT AGT TTA TAT CCT GGC CAA GGA GCA CTC CAT GTT    1008
Asp Leu Asp Pro Ser Ser Leu Tyr Pro Gly Gln Gly Ala Leu His Val
                325                 330                 335

ATT GAA CTG CAC AAA GAT AAG AAC CAG TGG AAT GTA AAA ATC CTC TAT    1056
Ile Glu Leu His Lys Asp Lys Asn Gln Trp Asn Val Lys Ile Leu Tyr
            340                 345                 350

AGA AAC AAT GAC CAA TCG GAA CTC AAA CCT ATG AAA CTT GCA AAA TGC    1104
Arg Asn Asn Asp Gln Ser Glu Leu Lys Pro Met Lys Leu Ala Lys Cys
                355                 360                 365

GGT GAC ACA TGT TCT TAT GAA ACT TTC AAA TCA ACT CTA CAA TCC TAT    1152
Gly Asp Thr Cys Ser Tyr Glu Thr Phe Lys Ser Thr Leu Gln Ser Tyr
370                 375                 380

AAC ATG GAT AAG ACC GCT CAT GAT AAA TTG TGT AAA TCG TCT TAA        1197
Asn Met Asp Lys Thr Ala His Asp Lys Leu Cys Lys Ser Ser
385                 390                 395
```

(2) INFORMATION FOR SEQ ID NO:56:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:56:

```
Met Trp Arg Leu Leu Leu Val Ile Ser Ser Ala Leu Ile Ile Gln Asn
 1               5                  10                  15

Val Asn Ala Glu Leu Lys Phe Val Phe Ala Thr Ala Arg Gly Met Ser
                20                  25                  30

His Thr Pro Cys Asp Tyr Pro Gly Gly Pro Lys Ile Thr Asn Lys Pro
            35                  40                  45

Glu Thr Ser Ser Val Leu Thr Thr Ala Gly Lys Asn Glu Ala Leu Glu
        50                  55                  60

Ile Gly Lys Leu Leu Ser Asp His Tyr Lys Ser Asn Leu Thr Val Lys
65                  70                  75                  80

Glu Trp Asp Ser Ser Lys Asn Tyr Trp Thr Leu Ala Ser Asn Thr Arg
                85                  90                  95

Arg Ser Gln Glu Gly Thr Leu Ile Ile Gly Ser Gly Leu Glu Gly Lys
            100                 105                 110

Ser Arg Ala Ala Glu Trp Ser Gln Glu Ile Gly Lys Lys Thr Thr Phe
        115                 120                 125

Ser Gly Phe Ser Glu Tyr Ala Lys Phe Tyr Ser Gln Lys Glu Cys Pro
    130                 135                 140

Asn Phe Ile Lys Gln Gln Leu Asp Ala Val Lys Asp Leu Leu Lys Ser
145                 150                 155                 160

Ala Lys Glu Tyr Asn Thr Glu Phe Asp Lys Leu Lys Lys Val Tyr Asn
                165                 170                 175

Ile Asp Ala Met Lys Gly Pro Gln Asn Val Trp Leu Ala Tyr Glu Thr
            180                 185                 190
```

```
Leu Asn Leu Gln Ser Lys Leu Asp Gln Ile Gly Leu Gly Ser Met Lys
        195                 200                 205

Asn Lys Leu Lys Ser Phe Ser Glu Lys Tyr Val Trp Ala Gly Leu Thr
    210                 215                 220

Ser Asn Asp Asn Leu Arg Lys Met Ser Gly Gly Arg Met Ile Asn Asp
225                 230                 235                 240

Ile Leu Asn Asp Ile Asp Asn Ile Lys Lys Gly Asn Gly Gln Pro Asn
                245                 250                 255

Ala Pro Gly Lys Leu Lys Ile Ile Gly Leu Thr Ala Pro Arg Phe
            260                 265                 270

Leu Ala Glu Ser Val Gln Leu Gly Ser Lys Gly Thr Lys Leu Asn Gln
        275                 280                 285

Asp Gln Asn Lys Leu Ser Val Leu Thr Val Pro Gln Gly Ile Leu Ala
    290                 295                 300

Ala Phe Val Ser Ala Phe Ala Pro Lys Gly Thr Lys Ile Glu Asn Gln
305                 310                 315                 320

Asp Leu Asp Pro Ser Ser Leu Tyr Pro Gly Gln Gly Ala Leu His Val
                325                 330                 335

Ile Glu Leu His Lys Asp Lys Asn Gln Trp Asn Val Lys Ile Leu Tyr
            340                 345                 350

Arg Asn Asn Asp Gln Ser Glu Leu Lys Pro Met Lys Leu Ala Lys Cys
        355                 360                 365

Gly Asp Thr Cys Ser Tyr Glu Thr Phe Lys Ser Thr Leu Gln Ser Tyr
370                 375                 380

Asn Met Asp Lys Thr Ala His Asp Lys Leu Cys Lys Ser Ser
385                 390                 395

(2) INFORMATION FOR SEQ ID NO:57:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 45..317

(xi) SEQUENCE DESCRIPTION: SEQ ID NO:57:

TGAAATTCAA TATTTTGTTT TACATTAAAT TTTTCAAATT CGAT ATG AAA TTT TTA      56
                                                 Met Lys Phe Leu
                                                   1

CTG GCA ATT TGC GTG TTG TGT GTT TTA TTA AAT CAA GTA TCT ATG TCA     104
Leu Ala Ile Cys Val Leu Cys Val Leu Leu Asn Gln Val Ser Met Ser
  5                  10                  15                  20

AAA ATG GTC ACT GAA AAG TGT AAG TCA GGT GGA AAT AAT CCA AGT ACA     152
Lys Met Val Thr Glu Lys Cys Lys Ser Gly Gly Asn Asn Pro Ser Thr
             25                  30                  35

GAA GAG GTG TCA ATA CCA TCT GGG AAG CTT ACT ATT GAA GAT TTT TGT     200
Glu Glu Val Ser Ile Pro Ser Gly Lys Leu Thr Ile Glu Asp Phe Cys
         40                  45                  50

ATT GGA AAT CAT CAA AGT TGC AAA ATA TTT TAC AAA AGT CAA TGT GGA     248
Ile Gly Asn His Gln Ser Cys Lys Ile Phe Tyr Lys Ser Gln Cys Gly
     55                  60                  65

TTT GGA GGT GGT GCT TGT GGA AAC GGT GGT TCA ACA CGA CCA AAT CAA     296
Phe Gly Gly Gly Ala Cys Gly Asn Gly Gly Ser Thr Arg Pro Asn Gln
 70                  75                  80
```

```
AAA CAC TGT TAT TGC GAA TAACCATATT CCGGATGAAA GACCAAATTG              344
Lys His Cys Tyr Cys Glu
 85              90

ATATAAATTA CTAAAATTAT GCTAGATAGC AATCATAAAA TTTTGAAGTT TTCAATGATC      404

CTAACATGTT TTGCCTCCAA TTTATTTTAA CAGCAAATTG CTGGAACTTA CCGTACCGTA      464

ACTAAATGTT CAAGAAATAC TGAATGTTTA CAAATAGATT ATTATAAATA TTGTAACATT      524

GTCTAATATT TATAAGAATT ATATAAACTG AATTGCAAAA A                          565

(2) INFORMATION FOR SEQ ID NO:58:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:58:

Met Lys Phe Leu Leu Ala Ile Cys Val Leu Cys Val Leu Leu Asn Gln
 1               5                  10                  15

Val Ser Met Ser Lys Met Val Thr Glu Lys Cys Lys Ser Gly Gly Asn
                20                  25                  30

Asn Pro Ser Thr Glu Val Ser Ile Pro Ser Gly Lys Leu Thr Ile
            35                  40                  45

Glu Asp Phe Cys Ile Gly Asn His Gln Ser Cys Lys Ile Phe Tyr Lys
 50                  55                  60

Ser Gln Cys Gly Phe Gly Gly Ala Cys Gly Asn Gly Gly Ser Thr
 65                  70                  75              80

Arg Pro Asn Gln Lys His Cys Tyr Cys Glu
                85                  90

(2) INFORMATION FOR SEQ ID NO:59:

(i) SEQUENCE CHARACTERISTICS:
        (A) LENGTH: 897 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 97..568

(xi) SEQUENCE DESCRIPTION: SEQ ID NO:59:

CCGAAATCTC CTATCACAGT GTACGGAGTG TAAAATATTG TTGAAGTATT TTGAAATTTA       60

TTAATTTATT CGAAAGGAG ATTTCATTAA ATAAAA ATG GTT TAC GAA AGT GAC         114
                                        Met Val Tyr Glu Ser Asp
                                         1               5

TTT TAC ACG ACC CGT CGG CCC TAC AGT CGT CCG GCT TTG TCT TCA TAC        162
Phe Tyr Thr Thr Arg Arg Pro Tyr Ser Arg Pro Ala Leu Ser Ser Tyr
             10                  15                  20

TCC GTA ACG GCA CGT CCA GAG CCG GTT CCT TGG GAC AAA TTG CCG TTC        210
Ser Val Thr Ala Arg Pro Glu Pro Val Pro Trp Asp Lys Leu Pro Phe
        25                  30                  35

GTC CCC CGT CCA AGT TTG GTA GCA GAT CCC ATA ACA GCA TTT TGC AAG        258
Val Pro Arg Pro Ser Leu Val Ala Asp Pro Ile Thr Ala Phe Cys Lys
    40                  45                  50

CGA AAA CCT CGC CGA GAA GAA GTT GTT CAA AAA GAG TCC ATT GTT CGA        306
Arg Lys Pro Arg Arg Glu Glu Val Val Gln Lys Glu Ser Ile Val Arg
```

```
                55                  60                  65                  70

AGG ATC AAT TCT GCA GGA ATT AAA CCC AGC CAG AGA GTT TTA TCG GCT          354
Arg Ile Asn Ser Ala Gly Ile Lys Pro Ser Gln Arg Val Leu Ser Ala
                        75                  80                  85

CCA ATA AGA GAA TAC GAA TCC CCA AGG GAC CAG ACC AGG CGT AAA GTT          402
Pro Ile Arg Glu Tyr Glu Ser Pro Arg Asp Gln Thr Arg Arg Lys Val
                90                  95                  100

TTG GAA AGC GTC AGA AGA CAA GAA GCT TTT CTG AAC CAA GGA GGA ATT          450
Leu Glu Ser Val Arg Arg Gln Glu Ala Phe Leu Asn Gln Gly Gly Ile
            105                 110                 115

TGT CCA TTG ACC ACC AGA AAT GAT GAC ATG GAT AGA CTT CTA CCC CGT          498
Cys Pro Leu Thr Thr Arg Asn Asp Asp Met Asp Arg Leu Leu Pro Arg
        120                 125                 130

CTC CAC AGT TCA CAC ACA ACA CCT TCT GCG GAT AGG AAA GTT TTG TTG          546
Leu His Ser Ser His Thr Thr Pro Ser Ala Asp Arg Lys Val Leu Leu
135                 140                 145                 150

ACC ACT TTT CAC AGA AGA TAC T GATTAAAAAT GAAAGTTAAG AAATTTGTTG           598
Thr Thr Phe His Arg Arg Tyr
                        155

AAGTCATGTG GTGTTTTTTA TACATTCTTT ATTAATCGAT ATTCCTAACG AACGATACGA        658

TAACTTTCGA TAACTTTTTC TGGTTAATTT TGACAAAATA TGCATTTGCA AGCATAACAT        718

TCATTTTCAA GGCAAACGCT TTCTGATGAT TATCTTGTTA AAAGTGTGGA AACAAGCGTA        778

GTGTTAACAA ATGCATTGCT TGTTTTGATT ATTTATTTAT CTATTATATA TTCCATATTG        838

TATTGTAGGT GGTGTACTTG GTATTACTAA TACACGTACT TTGTGAAAAA AAAAAAAA         897

(2) INFORMATION FOR SEQ ID NO:60:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO:60:

Met Val Tyr Glu Ser Asp Phe Tyr Thr Thr Arg Arg Pro Tyr Ser Arg
 1               5                  10                  15

Pro Ala Leu Ser Ser Tyr Ser Val Thr Ala Arg Pro Glu Pro Val Pro
             20                  25                  30

Trp Asp Lys Leu Pro Phe Val Pro Arg Pro Ser Leu Val Ala Asp Pro
         35                  40                  45

Ile Thr Ala Phe Cys Lys Arg Lys Pro Arg Arg Glu Glu Val Val Gln
     50                  55                  60

Lys Glu Ser Ile Val Arg Arg Ile Asn Ser Ala Gly Ile Lys Pro Ser
 65                  70                  75                  80

Gln Arg Val Leu Ser Ala Pro Ile Arg Glu Tyr Glu Ser Pro Arg Asp
                 85                  90                  95

Gln Thr Arg Arg Lys Val Leu Glu Ser Val Arg Arg Gln Glu Ala Phe
            100                 105                 110

Leu Asn Gln Gly Gly Ile Cys Pro Leu Thr Thr Arg Asn Asp Asp Met
        115                 120                 125

Asp Arg Leu Leu Pro Arg Leu His Ser Ser His Thr Thr Pro Ser Ala
    130                 135                 140

Asp Arg Lys Val Leu Leu Thr Thr Phe His Arg Arg Tyr
145                 150                 155

(2) INFORMATION FOR SEQ ID NO:61:
```

(i) SEQUENCE CHARACTERISTICS:
    (A) LENGTH: 2706 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 5..2706

(xi) SEQUENCE DESCRIPTION: SEQ ID NO:61:

```
GCGG ATG AAG AGC ATC GAG GCT TAT ACA AAC AGA TAT GAA ATC ATA GCT        49
     Met Lys Ser Ile Glu Ala Tyr Thr Asn Arg Tyr Glu Ile Ile Ala
      1               5                  10                  15

TCT GAA ATA GTT AAT CTT CGA ATG AAA CCA GAT GAT TTT AAT TTA ATA         97
Ser Glu Ile Val Asn Leu Arg Met Lys Pro Asp Asp Phe Asn Leu Ile
                 20                  25                  30

AAA GTT ATT GGT CGA GGA GCA TTT GGT GAA GTA CAG TTA GTG CGA CAC        145
Lys Val Ile Gly Arg Gly Ala Phe Gly Glu Val Gln Leu Val Arg His
             35                  40                  45

AAA TCA ACT GCA CAA GTT TTT GCT ATG AAA CGC CTA TCA AAA TTT GAA        193
Lys Ser Thr Ala Gln Val Phe Ala Met Lys Arg Leu Ser Lys Phe Glu
         50                  55                  60

ATG ATT AAG AGA CCA GAC TCT GCA TTT TTT TGG GAA GAA CGT CAT ATA        241
Met Ile Lys Arg Pro Asp Ser Ala Phe Phe Trp Glu Glu Arg His Ile
     65                  70                  75

ATG GCT CAT GCA AAA TCA GAA TGG ATT GTA CAA TTA CAT TTT GCT TTT        289
Met Ala His Ala Lys Ser Glu Trp Ile Val Gln Leu His Phe Ala Phe
 80                  85                  90                  95

CAA GAT CAA AAA TAT CTT TAT ATG GTC ATG GAT TAT ATG CCG GGG GGT        337
Gln Asp Gln Lys Tyr Leu Tyr Met Val Met Asp Tyr Met Pro Gly Gly
                100                 105                 110

GAC TTG GTG AGT CTT ATG TCC GAT TAT GAA ATT CCA GAA AAA TGG GCA        385
Asp Leu Val Ser Leu Met Ser Asp Tyr Glu Ile Pro Glu Lys Trp Ala
            115                 120                 125

ATG TTC TAT ACA ATG GAA GTG GTG CTA GCA CTT GAT ACA ATT CAC TCC        433
Met Phe Tyr Thr Met Glu Val Val Leu Ala Leu Asp Thr Ile His Ser
        130                 135                 140

ATG GGA TTT GTA CAT CGT GAT GTT AAA CCT GAT AAT ATG CTT CTA GAC        481
Met Gly Phe Val His Arg Asp Val Lys Pro Asp Asn Met Leu Leu Asp
    145                 150                 155

AAA TAT GGT CAT TTA AAG TTA GCT GAC TTT GGA ACC TGT ATG AAA ATG        529
Lys Tyr Gly His Leu Lys Leu Ala Asp Phe Gly Thr Cys Met Lys Met
160                 165                 170                 175

GAT ACA GAT GGT TTG GTA CGT TCT AAT AAT GCT GTT GGA ACG CCT GAT        577
Asp Thr Asp Gly Leu Val Arg Ser Asn Asn Ala Val Gly Thr Pro Asp
                180                 185                 190

TAC ATT TCT CCC GAA GTT TTG CAG TCC CAA GGT GGT GAA GGA GTT TAC        625
Tyr Ile Ser Pro Glu Val Leu Gln Ser Gln Gly Gly Glu Gly Val Tyr
            195                 200                 205

GGT CGT GAA TGC GAT TGG TGG TCT GTG GGA ATT TTT TTG TAT GAA ATG        673
Gly Arg Glu Cys Asp Trp Trp Ser Val Gly Ile Phe Leu Tyr Glu Met
        210                 215                 220

TTA TTT GGA GAA ACA CCT TTT TAT GCA GAC AGT TTG GTT GGA ACT TAC        721
Leu Phe Gly Glu Thr Pro Phe Tyr Ala Asp Ser Leu Val Gly Thr Tyr
    225                 230                 235

AGT AAA ATT ATG GAT CAC AGA AAC TCA TTA ACT TTT CCT CCA GAA GTG        769
Ser Lys Ile Met Asp His Arg Asn Ser Leu Thr Phe Pro Pro Glu Val
240                 245                 250                 255

GAA ATA AGC CAA TAT GCC CGA TCT TTG ATA CAA GGA TTT TTA ACA GAC        817
```

-continued

```
Glu Ile Ser Gln Tyr Ala Arg Ser Leu Ile Gln Gly Phe Leu Thr Asp
            260                 265                 270

AGA ACA CAG CGT TTA GGC AGA AAT GAA GTG GAA GAA ATT AAA CGA CAT      865
Arg Thr Gln Arg Leu Gly Arg Asn Glu Val Glu Glu Ile Lys Arg His
            275                 280                 285

CCA TTT TTC ATA AAT GAT CAA TGG ACT TTT GAC AAT TTA AGA GAC TCT      913
Pro Phe Phe Ile Asn Asp Gln Trp Thr Phe Asp Asn Leu Arg Asp Ser
            290                 295                 300

GCC CCA CCT GTA GTG CCA GAG CTG AGT GGT GAT GAT GAT ACA AGG AAC      961
Ala Pro Pro Val Val Pro Glu Leu Ser Gly Asp Asp Asp Thr Arg Asn
305                 310                 315

TTT GAT GAT ATT GAA CGT GAT GAA ACA CCT GAA GAG AAT TTT CCT ATA     1009
Phe Asp Asp Ile Glu Arg Asp Glu Thr Pro Glu Glu Asn Phe Pro Ile
320                 325                 330                 335

CCA AAA ACT TTT GCT GGT AAT CAT CTG CCA TTT GTT GGA TTC ACA TAT     1057
Pro Lys Thr Phe Ala Gly Asn His Leu Pro Phe Val Gly Phe Thr Tyr
                340                 345                 350

AAT GGT GAT TAC CAA TTA TTA ACA AAT GGA GGT GTT AGA AAT AGT GAT     1105
Asn Gly Asp Tyr Gln Leu Leu Thr Asn Gly Gly Val Arg Asn Ser Asp
                355                 360                 365

ATG GTT GAT ACA AAA TTA AAC AAC ATT TGT GTT TCA AGT AAG GAT GAT     1153
Met Val Asp Thr Lys Leu Asn Asn Ile Cys Val Ser Ser Lys Asp Asp
            370                 375                 380

GTG TTA AAT TTA CAA AAT TTA TTA GAA CAA GAG AAA GGT AAC AGT GAA     1201
Val Leu Asn Leu Gln Asn Leu Leu Glu Gln Glu Lys Gly Asn Ser Glu
385                 390                 395

AAT TTG AAA ACA AAC ACC CAA TTA TTA AGT AAT AAA TTA GAT GAA CTA     1249
Asn Leu Lys Thr Asn Thr Gln Leu Leu Ser Asn Lys Leu Asp Glu Leu
400                 405                 410                 415

GGT CAG AGA GAA TGT GAA TTA AGG AAT CAG GCT GGA GAT TAT GAG AAA     1297
Gly Gln Arg Glu Cys Glu Leu Arg Asn Gln Ala Gly Asp Tyr Glu Lys
                420                 425                 430

GAA TTG ACT AAA TTC AAA TTA TCG TGC AAA GAA TTA CAA CGT AAG GCA     1345
Glu Leu Thr Lys Phe Lys Leu Ser Cys Lys Glu Leu Gln Arg Lys Ala
                435                 440                 445

GAA TTT GAG AAT GAA TTA CGG CGT AAA ACT GAG TCC TTA CTA GTT GAA     1393
Glu Phe Glu Asn Glu Leu Arg Arg Lys Thr Glu Ser Leu Leu Val Glu
            450                 455                 460

ACA AAG AAA AGA CTA GAC GAA GAG CAG AAT AAA AGA ACT AGA GAA ATG     1441
Thr Lys Lys Arg Leu Asp Glu Glu Gln Asn Lys Arg Thr Arg Glu Met
465                 470                 475

AAT AAT AAT CAA CAG CAC AAT GAC AAA ATA AAT ATG TTA GAA AAA CAA     1489
Asn Asn Asn Gln Gln His Asn Asp Lys Ile Asn Met Leu Glu Lys Gln
480                 485                 490                 495

ATT AAT GAT TTA CAA GAA AAA TTG AAA GGT GAA TTA GAG CAC AAT CAG     1537
Ile Asn Asp Leu Gln Glu Lys Leu Lys Gly Glu Leu Glu His Asn Gln
                500                 505                 510

AAA TTA AAG AAG CAA GCT GTT GAG CTT AGA GTT GCT CAG TCT GCT ACT     1585
Lys Leu Lys Lys Gln Ala Val Glu Leu Arg Val Ala Gln Ser Ala Thr
                515                 520                 525

GAA CAA CTG AAT AAT GAA TTA CAG GAA ACT ATG CAG GGT TTA CAA ACA     1633
Glu Gln Leu Asn Asn Glu Leu Gln Glu Thr Met Gln Gly Leu Gln Thr
            530                 535                 540

CAA AGA GAT GCT TTA CAA CAA GAA GTA GCA TCT CTC CAA GGC AAA CTT     1681
Gln Arg Asp Ala Leu Gln Gln Glu Val Ala Ser Leu Gln Gly Lys Leu
545                 550                 555

TCT CAA GAG AGG AGC TCT AGA TCA CAG GCT TCT GAT ATG CAG ATA GAA     1729
Ser Gln Glu Arg Ser Ser Arg Ser Gln Ala Ser Asp Met Gln Ile Glu
560                 565                 570                 575

CTA GAA GCA AAA TTG CAG GCT CTC CAT ATT GAA CTG GAG CAT GTC AGA     1777
```

```
            Leu Glu Ala Lys Leu Gln Ala Leu His Ile Glu Leu Glu His Val Arg
                            580                 585                 590

AAT TGT GAA GAC AAA GTT ACC CAA GAC AAC AGA CAA CTA TTG GAA AGG        1825
Asn Cys Glu Asp Lys Val Thr Gln Asp Asn Arg Gln Leu Leu Glu Arg
                595                 600                 605

ATA TCA ACA TTG GAG AAA GAA TGT GCT TCT CTA GAA TTA GAA TTG AAA        1873
Ile Ser Thr Leu Glu Lys Glu Cys Ala Ser Leu Glu Leu Glu Leu Lys
            610                 615                 620

GCA ACA CAA AAC AAA TAT GAG CAA GAG GTC AAA GCA CAT CGC GAA ACT        1921
Ala Thr Gln Asn Lys Tyr Glu Gln Glu Val Lys Ala His Arg Glu Thr
        625                 630                 635

GAA AAA TCA AGA CTG GTC AGT AAA GAA GAA GCA AAT ATG GAG GAA GTT        1969
Glu Lys Ser Arg Leu Val Ser Lys Glu Glu Ala Asn Met Glu Glu Val
640                 645                 650                 655

AAA GCA CTC CAA ATA AAA TTA AAT GAA GAG AAA TCT GCT CGA CAG AAA        2017
Lys Ala Leu Gln Ile Lys Leu Asn Glu Glu Lys Ser Ala Arg Gln Lys
                660                 665                 670

TCT GAT CAG AAT TCT CAA GAA AAG GAA CGA CAA ATT TCT ATG TTA TCT        2065
Ser Asp Gln Asn Ser Gln Glu Lys Glu Arg Gln Ile Ser Met Leu Ser
            675                 680                 685

GTG GAT TAT CGT CAA ATC CAA CAG CGT TTG CAA AAG CTA GAA GGA GAA        2113
Val Asp Tyr Arg Gln Ile Gln Gln Arg Leu Gln Lys Leu Glu Gly Glu
        690                 695                 700

TAT AGG CAA GAG AGT GAA AAA GTT AAA GCT CTC CAC AGT CAG ATT GAG        2161
Tyr Arg Gln Glu Ser Glu Lys Val Lys Ala Leu His Ser Gln Ile Glu
    705                 710                 715

CAA GAG CAA CTA AAA AAA TCA CAA TTA CAA AGC GAA TTG GGT GTT CAA        2209
Gln Glu Gln Leu Lys Lys Ser Gln Leu Gln Ser Glu Leu Gly Val Gln
720                 725                 730                 735

AGG TCT CAG ACT GCA CAT TTA ACA GCC AGG GAA GCT CAG CTA GTT GGA        2257
Arg Ser Gln Thr Ala His Leu Thr Ala Arg Glu Ala Gln Leu Val Gly
                740                 745                 750

GAA GTT GCT CAT CTT AGA GAT GCT AAA AGA AAT GTT GAA GAA GAG TTA        2305
Glu Val Ala His Leu Arg Asp Ala Lys Arg Asn Val Glu Glu Glu Leu
            755                 760                 765

CAC AAG TTA AAA ACT GCT CGA TCA GTG GAT AAT GCT CAG ATG AAA GAG        2353
His Lys Leu Lys Thr Ala Arg Ser Val Asp Asn Ala Gln Met Lys Glu
        770                 775                 780

CTT CAA GAA CAA GTT GAA GCC GAG CAA GTT TTC TCG ACT CTT TAT AAA        2401
Leu Gln Glu Gln Val Glu Ala Glu Gln Val Phe Ser Thr Leu Tyr Lys
    785                 790                 795

ACA CAT TCT AAT GAA CTT AAG GAA GAA CTT GAG GAA AAA TCT CGT CAT        2449
Thr His Ser Asn Glu Leu Lys Glu Glu Leu Glu Glu Lys Ser Arg His
800                 805                 810                 815

ATT CAA GAA ATG GAA GAA GAA AGA GAA AGT TTG GTT CAT CAG CTA CAA        2497
Ile Gln Glu Met Glu Glu Glu Arg Glu Ser Leu Val His Gln Leu Gln
                820                 825                 830

ATT GCA TTA GCT AGA GCT GAT TCA GAG GCA TTG GCG AGA TCA ATA GCT        2545
Ile Ala Leu Ala Arg Ala Asp Ser Glu Ala Leu Ala Arg Ser Ile Ala
            835                 840                 845

GAT GAA AGT ATA GCT GAT TTA GAA AAG GAA AAG ACT ATG AAG GAA TTA        2593
Asp Glu Ser Ile Ala Asp Leu Glu Lys Glu Lys Thr Met Lys Glu Leu
        850                 855                 860

GAA CTA AAA GAA TTA TTA AAC AAA AAT CGT ACT GAA CTT TCC CAG AAA        2641
Glu Leu Lys Glu Leu Leu Asn Lys Asn Arg Thr Glu Leu Ser Gln Lys
    865                 870                 875

GAC ATT TCA ATA AGT GCA TTG CGT GAA CGA GAA AAT GAA CAG AAG AAA        2689
Asp Ile Ser Ile Ser Ala Leu Arg Glu Arg Glu Asn Glu Gln Lys Lys
880                 885                 890                 895

CTT TTA GAA CAA ATC TC                                                 2706
```

Leu Leu Glu Gln Ile
                900

(2) INFORMATION FOR SEQ ID NO:62:

(i) SEQUENCE CHARACTERISTICS:
        (A) LENGTH: 900 amino acids
        (B) TYPE: amino acid
        (D) TOPOLOGY: linear (ii) MOLECULE TYPE: protein (xi) SEQUENCE DESCRIPTION: SEQ ID NO:62:

Met Lys Ser Ile Glu Ala Tyr Thr Asn Arg Tyr Glu Ile Ile Ala Ser
  1               5                  10                  15

Glu Ile Val Asn Leu Arg Met Lys Pro Asp Asp Phe Asn Leu Ile Lys
                 20                  25                  30

Val Ile Gly Arg Gly Ala Phe Gly Glu Val Gln Leu Val Arg His Lys
             35                  40                  45

Ser Thr Ala Gln Val Phe Ala Met Lys Arg Leu Ser Lys Phe Glu Met
 50                  55                  60

Ile Lys Arg Pro Asp Ser Ala Phe Phe Trp Glu Arg His Ile Met
 65                  70                  75                  80

Ala His Ala Lys Ser Glu Trp Ile Val Gln Leu His Phe Ala Phe Gln
                 85                  90                  95

Asp Gln Lys Tyr Leu Tyr Met Val Met Asp Tyr Met Pro Gly Gly Asp
                100                 105                 110

Leu Val Ser Leu Met Ser Asp Tyr Glu Ile Pro Glu Lys Trp Ala Met
            115                 120                 125

Phe Tyr Thr Met Glu Val Val Leu Ala Leu Asp Thr Ile His Ser Met
130                 135                 140

Gly Phe Val His Arg Asp Val Lys Pro Asp Asn Met Leu Leu Asp Lys
145                 150                 155                 160

Tyr Gly His Leu Lys Leu Ala Asp Phe Gly Thr Cys Met Lys Met Asp
                165                 170                 175

Thr Asp Gly Leu Val Arg Ser Asn Asn Ala Val Gly Thr Pro Asp Tyr
            180                 185                 190

Ile Ser Pro Glu Val Leu Gln Ser Gln Gly Gly Glu Gly Val Tyr Gly
            195                 200                 205

Arg Glu Cys Asp Trp Trp Ser Val Gly Ile Phe Leu Tyr Glu Met Leu
210                 215                 220

Phe Gly Glu Thr Pro Phe Tyr Ala Asp Ser Leu Val Gly Thr Tyr Ser
225                 230                 235                 240

Lys Ile Met Asp His Arg Asn Ser Leu Thr Phe Pro Pro Glu Val Glu
                245                 250                 255

Ile Ser Gln Tyr Ala Arg Ser Leu Ile Gln Gly Phe Leu Thr Asp Arg
            260                 265                 270

Thr Gln Arg Leu Gly Arg Asn Glu Val Glu Glu Ile Lys Arg His Pro
            275                 280                 285

Phe Phe Ile Asn Asp Gln Trp Thr Phe Asp Asn Leu Arg Asp Ser Ala
290                 295                 300

Pro Pro Val Val Pro Glu Leu Ser Gly Asp Asp Thr Arg Asn Phe
305                 310                 315                 320

Asp Asp Ile Glu Arg Asp Glu Thr Pro Glu Glu Asn Phe Pro Ile Pro
                325                 330                 335

Lys Thr Phe Ala Gly Asn His Leu Pro Phe Val Gly Phe Thr Tyr Asn
            340                 345                 350

```
Gly Asp Tyr Gln Leu Leu Thr Asn Gly Val Arg Asn Ser Asp Met
        355                 360                 365
Val Asp Thr Lys Leu Asn Asn Ile Cys Val Ser Ser Lys Asp Asp Val
    370                 375                 380
Leu Asn Leu Gln Asn Leu Leu Glu Gln Glu Lys Gly Asn Ser Glu Asn
385                 390                 395                 400
Leu Lys Thr Asn Thr Gln Leu Leu Ser Asn Lys Leu Asp Glu Leu Gly
                405                 410                 415
Gln Arg Glu Cys Glu Leu Arg Asn Gln Ala Gly Asp Tyr Glu Lys Glu
            420                 425                 430
Leu Thr Lys Phe Lys Leu Ser Cys Lys Glu Leu Gln Arg Lys Ala Glu
        435                 440                 445
Phe Glu Asn Glu Leu Arg Arg Lys Thr Glu Ser Leu Leu Val Glu Thr
    450                 455                 460
Lys Lys Arg Leu Asp Glu Glu Gln Asn Lys Arg Thr Arg Glu Met Asn
465                 470                 475                 480
Asn Asn Gln Gln His Asn Asp Lys Ile Asn Met Leu Glu Lys Gln Ile
                485                 490                 495
Asn Asp Leu Gln Glu Lys Leu Lys Gly Glu Leu Glu His Asn Gln Lys
            500                 505                 510
Leu Lys Lys Gln Ala Val Glu Leu Arg Val Ala Gln Ser Ala Thr Glu
        515                 520                 525
Gln Leu Asn Asn Glu Leu Gln Glu Thr Met Gln Gly Leu Gln Thr Gln
    530                 535                 540
Arg Asp Ala Leu Gln Gln Glu Val Ala Ser Leu Gln Gly Lys Leu Ser
545                 550                 555                 560
Gln Glu Arg Ser Ser Arg Ser Gln Ala Ser Asp Met Gln Ile Glu Leu
                565                 570                 575
Glu Ala Lys Leu Gln Ala Leu His Ile Glu Leu Glu His Val Arg Asn
            580                 585                 590
Cys Glu Asp Lys Val Thr Gln Asp Asn Arg Gln Leu Leu Glu Arg Ile
        595                 600                 605
Ser Thr Leu Glu Lys Glu Cys Ala Ser Leu Glu Leu Glu Leu Lys Ala
    610                 615                 620
Thr Gln Asn Lys Tyr Glu Gln Glu Val Lys Ala His Arg Glu Thr Glu
625                 630                 635                 640
Lys Ser Arg Leu Val Ser Lys Glu Glu Ala Asn Met Glu Glu Val Lys
                645                 650                 655
Ala Leu Gln Ile Lys Leu Asn Glu Glu Lys Ser Ala Arg Gln Lys Ser
            660                 665                 670
Asp Gln Asn Ser Gln Glu Lys Glu Arg Gln Ile Ser Met Leu Ser Val
        675                 680                 685
Asp Tyr Arg Gln Ile Gln Gln Arg Leu Gln Lys Leu Glu Gly Glu Tyr
    690                 695                 700
Arg Gln Glu Ser Glu Lys Val Lys Ala Leu His Ser Gln Ile Glu Gln
705                 710                 715                 720
Glu Gln Leu Lys Lys Ser Gln Leu Gln Ser Glu Leu Gly Val Gln Arg
                725                 730                 735
Ser Gln Thr Ala His Leu Thr Ala Arg Glu Ala Gln Leu Val Gly Glu
            740                 745                 750
Val Ala His Leu Arg Asp Ala Lys Arg Asn Val Glu Glu Glu Leu His
        755                 760                 765
Lys Leu Lys Thr Ala Arg Ser Val Asp Asn Ala Gln Met Lys Glu Leu
```

```
                770                775                780
Gln Glu Gln Val Glu Ala Glu Gln Val Phe Ser Thr Leu Tyr Lys Thr
785                 790                 795                 800

His Ser Asn Glu Leu Lys Glu Glu Leu Glu Glu Lys Ser Arg His Ile
                805                 810                 815

Gln Glu Met Glu Glu Arg Glu Ser Leu Val His Gln Leu Gln Ile
            820                 825                 830

Ala Leu Ala Arg Ala Asp Ser Glu Ala Leu Ala Arg Ser Ile Ala Asp
                835                 840                 845

Glu Ser Ile Ala Asp Leu Glu Lys Glu Lys Thr Met Lys Glu Leu Glu
            850                 855                 860

Leu Lys Glu Leu Leu Asn Lys Asn Arg Thr Glu Leu Ser Gln Lys Asp
865                 870                 875                 880

Ile Ser Ile Ser Ala Leu Arg Glu Arg Glu Asn Glu Gln Lys Lys Leu
                885                 890                 895

Leu Glu Gln Ile
            900

(2) INFORMATION FOR SEQ ID NO:63:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..414

(xi) SEQUENCE DESCRIPTION: SEQ ID NO:63:

GA GCT GAT GAG AAT GGA AAT GTG ATT AGC ATT ACT GAT GAA AAT GGA        47
   Ala Asp Glu Asn Gly Asn Val Ile Ser Ile Thr Asp Glu Asn Gly
   1               5                   10                  15

AAC ATT ATT AGT ACT ACT GAT GAG AAT GGA AAT GTG ATT AGC ATT ACT       95
Asn Ile Ile Ser Thr Thr Asp Glu Asn Gly Asn Val Ile Ser Ile Thr
                    20                  25                  30

GAT GAG AAT GGA AAC ATT ATT AGT ACT ACT GAT GAG AAT GGA AAT GTG      143
Asp Glu Asn Gly Asn Ile Ile Ser Thr Thr Asp Glu Asn Gly Asn Val
                35                  40                  45

ATT AGC ATT ACT GAT GAA AAT GGA AAC ATT ATT AGT ACT ACT GAT GAG      191
Ile Ser Ile Thr Asp Glu Asn Gly Asn Ile Ile Ser Thr Thr Asp Glu
            50                  55                  60

AAT GGA AAT GTG ATT AGC ATT ACT GAT GAG AAT GGA AAT GTG ATT AGC      239
Asn Gly Asn Val Ile Ser Ile Thr Asp Glu Asn Gly Asn Val Ile Ser
65                  70                  75

ATT ACT GAT GAA AAT GGA AAC TCG AAT AGC ACT ACT AGT GTT TTC AAT      287
Ile Thr Asp Glu Asn Gly Asn Ser Asn Ser Thr Thr Ser Val Phe Asn
80                  85                  90                  95

GAA ACT GAA AAT ATG ACT GGT GCT GCT GAT ACA AAT GAA TAT TCA ATT      335
Glu Thr Glu Asn Met Thr Gly Ala Ala Asp Thr Asn Glu Tyr Ser Ile
                    100                 105                 110

GGT TCT ACT GAC GGA AAT GGA AAT TTT ATA AGT ACT TTT AGT GAT CAT      383
Gly Ser Thr Asp Gly Asn Gly Asn Phe Ile Ser Thr Phe Ser Asp His
                115                 120                 125

GAT TAC GTA AGT AAT ACT GAA GAA AAT GAA A                            414
Asp Tyr Val Ser Asn Thr Glu Glu Asn Glu
            130                 135
```

(2) INFORMATION FOR SEQ ID NO:64:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:64:

```
Ala Asp Glu Asn Gly Asn Val Ile Ser Ile Thr Asp Glu Asn Gly Asn
 1               5                  10                  15

Ile Ile Ser Thr Thr Asp Glu Asn Gly Asn Val Ile Ser Ile Thr Asp
                20                  25                  30

Glu Asn Gly Asn Ile Ile Ser Thr Thr Asp Glu Asn Gly Asn Val Ile
            35                  40                  45

Ser Ile Thr Asp Glu Asn Gly Asn Ile Ile Ser Thr Thr Asp Glu Asn
        50                  55                  60

Gly Asn Val Ile Ser Ile Thr Asp Glu Asn Gly Asn Val Ile Ser Ile
65                  70                  75                  80

Thr Asp Glu Asn Gly Asn Ser Asn Ser Thr Thr Ser Val Phe Asn Glu
                85                  90                  95

Thr Glu Asn Met Thr Gly Ala Ala Asp Thr Asn Glu Tyr Ser Ile Gly
               100                 105                 110

Ser Thr Asp Gly Asn Gly Asn Phe Ile Ser Thr Phe Ser Asp His Asp
           115                 120                 125

Tyr Val Ser Asn Thr Glu Glu Asn Glu
           130                 135
```

(2) INFORMATION FOR SEQ ID NO:65:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..273

(xi) SEQUENCE DESCRIPTION: SEQ ID NO:65:

```
AT GAG AAT GGA AAT GTG ATT AGC TAT ACT GAT GAA AAT GGA AAC ATT        47
   Glu Asn Gly Asn Val Ile Ser Tyr Thr Asp Glu Asn Gly Asn Ile
    1               5                  10                  15

ATC AGT ACT ACT GAT GAG AAT GGA AAT GTG ATT AGC ATT ACT GAT GAA       95
Ile Ser Thr Thr Asp Glu Asn Gly Asn Val Ile Ser Ile Thr Asp Glu
                20                  25                  30

AAT GGA AAT GTG ATT AGC ATT ACT GAT GAA AAT GGA AAC ATT ATC AGT      143
Asn Gly Asn Val Ile Ser Ile Thr Asp Glu Asn Gly Asn Ile Ile Ser
            35                  40                  45

ACT ACT GAT GAG AAT GGA AAT GTG ATT AGC ATT ACT GAT GAA AAT GGA      191
Thr Thr Asp Glu Asn Gly Asn Val Ile Ser Ile Thr Asp Glu Asn Gly
        50                  55                  60

AAT GTG ATT AGC ATT ACT GAT GAA AAT GGA AAC ATT ATT AGT ACT ACT      239
Asn Val Ile Ser Ile Thr Asp Glu Asn Gly Asn Ile Ile Ser Thr Thr
65                  70                  75

GAT GAG AAT GGA AAT GTG ATT AGC AAT ACT CGA G                        273
Asp Glu Asn Gly Asn Val Ile Ser Asn Thr Arg
80                  85                  90
```

(2) INFORMATION FOR SEQ ID NO:66:

(i) SEQUENCE CHARACTERISTICS:
       (A) LENGTH: 90 amino acids
       (B) TYPE: amino acid
       (D) TOPOLOGY: linear (ii) MOLECULE TYPE: protein (xi) SEQUENCE DESCRIPTION: SEQ ID NO:66:

```
Glu Asn Gly Asn Val Ile Ser Tyr Thr Asp Glu Asn Gly Asn Ile Ile
 1               5                  10                  15

Ser Thr Thr Asp Glu Asn Gly Asn Val Ile Ser Ile Thr Asp Glu Asn
             20                  25                  30

Gly Asn Val Ile Ser Ile Thr Asp Glu Asn Gly Asn Ile Ile Ser Thr
         35                  40                  45

Thr Asp Glu Asn Gly Asn Val Ile Ser Ile Thr Asp Glu Asn Gly Asn
     50                  55                  60

Val Ile Ser Ile Thr Asp Glu Asn Gly Asn Ile Ile Ser Thr Thr Asp
 65                  70                  75                  80

Glu Asn Gly Asn Val Ile Ser Asn Thr Arg
             85                  90
```

(2) INFORMATION FOR SEQ ID NO:67:

(i) SEQUENCE CHARACTERISTICS:
       (A) LENGTH: 1704 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 24..1409

(xi) SEQUENCE DESCRIPTION: SEQ ID NO:67:

```
CAGAAACCCG ACATTCTCAA AAT ATG GAA CCT CAA TCG CTG TCT TGG CAA        50
                         Met Glu Pro Gln Ser Leu Ser Trp Gln
                           1               5

CTT CCG ACT CAA GTA GTT CAG CCA GTT TTT GAA CAA CAA ATG CAG ATT      98
Leu Pro Thr Gln Val Val Gln Pro Val Phe Glu Gln Gln Met Gln Ile
 10              15                  20                  25

CCT GGA TAT AAT ATG CAA ATT CAA TCT AAT TAT TAT CAA ATT CAC CCA     146
Pro Gly Tyr Asn Met Gln Ile Gln Ser Asn Tyr Tyr Gln Ile His Pro
             30                  35                  40

GAA ATG TTG GAT CCA AAT TTG AAC AAT CCT CAG CAG TTA ATG TTT AAT     194
Glu Met Leu Asp Pro Asn Leu Asn Asn Pro Gln Gln Leu Met Phe Asn
         45                  50                  55

TAT ATG CAA TTA CAA CAA TTG CAG GAA CTA CAA CAT TTA AGT CAA CAA     242
Tyr Met Gln Leu Gln Gln Leu Gln Glu Leu Gln His Leu Ser Gln Gln
     60                  65                  70

CAG CCA ATG CAT CAT GAA TTT GAA CAT CAT ATC CCC ATT CCA CAA GAA     290
Gln Pro Met His His Glu Phe Glu His His Ile Pro Ile Pro Gln Glu
 75                  80                  85

GCA ACT TCA ACT AAT TAC GGT CCA TCC GGA CAG TAT ATT ACT AGT GAC     338
Ala Thr Ser Thr Asn Tyr Gly Pro Ser Gly Gln Tyr Ile Thr Ser Asp
 90                  95                 100                 105

GCA ACA TCT TAT CAA TCA ATT GCC CAA CAA TTT GTA CCA CAA CCA CCA     386
Ala Thr Ser Tyr Gln Ser Ile Ala Gln Gln Phe Val Pro Gln Pro Pro
             110                 115                 120

ATT GAA ACT ACC ACC ACG AAA ATA CCT GAA ACT GAA ATT CAA ATT GGC     434
Ile Glu Thr Thr Thr Thr Lys Ile Pro Glu Thr Glu Ile Gln Ile Gly
```

-continued

|  | 125 | 130 | 135 |  |
|---|---|---|---|---|
| GTT TCG AAT CAA TAT GCC CAA AAT ATA ACT TAT AAT TCA AAT ATC AGT | | | | 482 |
| Val Ser Asn Gln Tyr Ala Gln Asn Ile Thr Tyr Asn Ser Asn Ile Ser | | | | |
| 140 145 150 | | | | |
| CCT GAA GTG ATT GGA TTC CGA GAA CAT TAT GTT GCG GAA CAG CCT TCT | | | | 530 |
| Pro Glu Val Ile Gly Phe Arg Glu His Tyr Val Ala Glu Gln Pro Ser | | | | |
| 155 160 165 | | | | |
| GGT GAC GTG CTT CAC AAA AGT CAT TTA ACA GAA CAA CCA GCA GAT AAA | | | | 578 |
| Gly Asp Val Leu His Lys Ser His Leu Thr Glu Gln Pro Ala Asp Lys | | | | |
| 170 175 180 185 | | | | |
| AGC ACA CGT GGT GAT CAG GAA CCT GTT AGT GAG ACA GGC TCT GGT TTT | | | | 626 |
| Ser Thr Arg Gly Asp Gln Glu Pro Val Ser Glu Thr Gly Ser Gly Phe | | | | |
| 190 195 200 | | | | |
| TCG TAT GCA CAA ATT TTA TCA CAG GGA CTT AAG CCT ACC CAG CCA TCC | | | | 674 |
| Ser Tyr Ala Gln Ile Leu Ser Gln Gly Leu Lys Pro Thr Gln Pro Ser | | | | |
| 205 210 215 | | | | |
| AAC TCA GTT AAT TTG CTT GCA GAT CGA TCG AGA TCA CCT CTA GAT ACG | | | | 722 |
| Asn Ser Val Asn Leu Leu Ala Asp Arg Ser Arg Ser Pro Leu Asp Thr | | | | |
| 220 225 230 | | | | |
| AAA ACG AAA GAA AAT TAT AAA TCT CCT GGT CGT GTG CAG GAT ATC ACG | | | | 770 |
| Lys Thr Lys Glu Asn Tyr Lys Ser Pro Gly Arg Val Gln Asp Ile Thr | | | | |
| 235 240 245 | | | | |
| AAA ATA ATA GAT GAG AAA CAA AAG TCG TCA AAA GAC ACA GAG TGG CAT | | | | 818 |
| Lys Ile Ile Asp Glu Lys Gln Lys Ser Ser Lys Asp Thr Glu Trp His | | | | |
| 250 255 260 265 | | | | |
| AAT AAG AAA GTG AAA GAA CAT AAA AAA GTG AAA GAT ATC AAA CCT GAT | | | | 866 |
| Asn Lys Lys Val Lys Glu His Lys Lys Val Lys Asp Ile Lys Pro Asp | | | | |
| 270 275 280 | | | | |
| TTC GAA TCT TCT CAA AGG AAT AAG AAA AGC AAG AAT ATT CCT AAG CAA | | | | 914 |
| Phe Glu Ser Ser Gln Arg Asn Lys Lys Ser Lys Asn Ile Pro Lys Gln | | | | |
| 285 290 295 | | | | |
| ATT GAA AAT ATC ACA CCT CAA CTT GAC AGC TTA CGA TCA CGA GAT ATA | | | | 962 |
| Ile Glu Asn Ile Thr Pro Gln Leu Asp Ser Leu Arg Ser Arg Asp Ile | | | | |
| 300 305 310 | | | | |
| GTA ATT AAG GGA GAA TTA CTA ACA AAA GAT ACT ACA AAA AGT TTA ACT | | | | 1010 |
| Val Ile Lys Gly Glu Leu Leu Thr Lys Asp Thr Thr Lys Ser Leu Thr | | | | |
| 315 320 325 | | | | |
| ACT GTT AAT GTT GAT AGT GAA TTA GAT AGT GTA AAA CCT AAA GAT GAA | | | | 1058 |
| Thr Val Asn Val Asp Ser Glu Leu Asp Ser Val Lys Pro Lys Asp Glu | | | | |
| 330 335 340 345 | | | | |
| AAA CCT GAA CCT TCT GAA CCT AGT AAA ACG TTT ATT GAT ACT TCA GTT | | | | 1106 |
| Lys Pro Glu Pro Ser Glu Pro Ser Lys Thr Phe Ile Asp Thr Ser Val | | | | |
| 350 355 360 | | | | |
| GCA AAG GAT GTT GAT AAT TCT ACA CAG GCG AAC CAT AAA AAG AAG AAA | | | | 1154 |
| Ala Lys Asp Val Asp Asn Ser Thr Gln Ala Asn His Lys Lys Lys Lys | | | | |
| 365 370 375 | | | | |
| AGT AAA TCT AAG CCG AGG AAA ACG GAA CCG GAA GAT GAA ATT GAA AAA | | | | 1202 |
| Ser Lys Ser Lys Pro Arg Lys Thr Glu Pro Glu Asp Glu Ile Glu Lys | | | | |
| 380 385 390 | | | | |
| GCT TTG AAA GAA ATT CAA GCT AGT GAG AAA AAA CTT ACG AAG TCT ATC | | | | 1250 |
| Ala Leu Lys Glu Ile Gln Ala Ser Glu Lys Lys Leu Thr Lys Ser Ile | | | | |
| 395 400 405 | | | | |
| GAT AAC ATT GTG AAT AAA TTT AAT ACA CCA CTT GCT AGT GTT AAA GCC | | | | 1298 |
| Asp Asn Ile Val Asn Lys Phe Asn Thr Pro Leu Ala Ser Val Lys Ala | | | | |
| 410 415 420 425 | | | | |
| GAT GAT TCC AAT TCT ACC AAG GAT AAT GTA CCA GCA AAG AAG AAA AAA | | | | 1346 |
| Asp Asp Ser Asn Ser Thr Lys Asp Asn Val Pro Ala Lys Lys Lys Lys | | | | |
| 430 435 440 | | | | |
| CCT TCG AAG TCA TCT GTT TCT TTA CCT GAG AAT GTA GTA CAA AAT CTA | | | | 1394 |
| Pro Ser Lys Ser Ser Val Ser Leu Pro Glu Asn Val Val Gln Asn Leu | | | | |

```
                  445            450            455
TTG ATA CTA ACA TAACTACTAG TAGCGACAAG ATTGAAAACA TGCCGCAACC       1446
Leu Ile Leu Thr
        460

GCAACCAAAA AGAGAAGATT TACAAGATGC AGCTAAGGAA GTATTGACTT CAATAGAGTC 1506

AGTAATGATG CAGTCTGTTG AGACTATTCC TATTACGAAG AAAAGAGTAA ATAAGAAAAA 1566

GAATACCACT CAACAGACGA AGGAATTTGT GGAACACGAA ATATGCGATA CATCAAAAAA 1626

TGAAACTTTA AAAATATTG AAAAAGAATC GCATGAGAAT ATGGCTATAT TGCAAACAAG 1686

TCCGAAACCG CCACTAAG                                               1704
```

(2) INFORMATION FOR SEQ ID NO:68:

(i) SEQUENCE CHARACTERISTICS:
        (A) LENGTH: 461 amino acids
        (B) TYPE: amino acid
        (D) TOPOLOGY: linear (ii) MOLECULE TYPE: protein (xi) SEQUENCE DESCRIPTION: SEQ ID NO:68:

```
Met Glu Pro Gln Ser Leu Ser Trp Gln Leu Pro Thr Gln Val Val Gln
 1               5                  10                  15

Pro Val Phe Glu Gln Gln Met Gln Ile Pro Gly Tyr Asn Met Gln Ile
             20                  25                  30

Gln Ser Asn Tyr Tyr Gln Ile His Pro Glu Met Leu Asp Pro Asn Leu
         35                  40                  45

Asn Asn Pro Gln Gln Leu Met Phe Asn Tyr Met Gln Leu Gln Gln Leu
     50                  55                  60

Gln Glu Leu Gln His Leu Ser Gln Gln Pro Met His His Glu Phe
 65                  70                  75                  80

Glu His His Ile Pro Ile Pro Gln Glu Ala Thr Ser Thr Asn Tyr Gly
                 85                  90                  95

Pro Ser Gly Gln Tyr Ile Thr Ser Asp Ala Thr Ser Tyr Gln Ser Ile
             100                 105                 110

Ala Gln Gln Phe Val Pro Gln Pro Ile Glu Thr Thr Thr Thr Lys
         115                 120                 125

Ile Pro Glu Thr Glu Ile Gln Ile Gly Val Ser Asn Gln Tyr Ala Gln
 130                 135                 140

Asn Ile Thr Tyr Asn Ser Asn Ile Ser Pro Glu Val Ile Gly Phe Arg
145                 150                 155                 160

Glu His Tyr Val Ala Glu Gln Pro Ser Gly Asp Val Leu His Lys Ser
                 165                 170                 175

His Leu Thr Glu Gln Pro Ala Asp Lys Ser Thr Arg Gly Asp Gln Glu
             180                 185                 190

Pro Val Ser Glu Thr Gly Ser Gly Phe Ser Tyr Ala Gln Ile Leu Ser
         195                 200                 205

Gln Gly Leu Lys Pro Thr Gln Pro Ser Asn Ser Val Asn Leu Leu Ala
     210                 215                 220

Asp Arg Ser Arg Ser Pro Leu Asp Thr Lys Thr Lys Glu Asn Tyr Lys
225                 230                 235                 240

Ser Pro Gly Arg Val Gln Asp Ile Thr Lys Ile Ile Asp Glu Lys Gln
                 245                 250                 255

Lys Ser Ser Lys Asp Thr Glu Trp His Asn Lys Lys Val Lys Glu His
             260                 265                 270

Lys Lys Val Lys Asp Ile Lys Pro Asp Phe Glu Ser Ser Gln Arg Asn
```

```
                   275                 280                 285
Lys Lys Ser Lys Asn Ile Pro Lys Gln Ile Glu Asn Ile Thr Pro Gln
    290                 295                 300

Leu Asp Ser Leu Arg Ser Arg Asp Ile Val Ile Lys Gly Glu Leu Leu
305                 310                 315                 320

Thr Lys Asp Thr Thr Lys Ser Leu Thr Thr Val Asn Val Asp Ser Glu
                325                 330                 335

Leu Asp Ser Val Lys Pro Lys Asp Glu Lys Pro Glu Pro Ser Glu Pro
                340                 345                 350

Ser Lys Thr Phe Ile Asp Thr Ser Val Ala Lys Asp Val Asp Asn Ser
                355                 360                 365

Thr Gln Ala Asn His Lys Lys Lys Ser Lys Ser Lys Pro Arg Lys
370                 375                 380

Thr Glu Pro Glu Asp Glu Ile Glu Lys Ala Leu Lys Glu Ile Gln Ala
385                 390                 395                 400

Ser Glu Lys Lys Leu Thr Lys Ser Ile Asp Asn Ile Val Asn Lys Phe
                405                 410                 415

Asn Thr Pro Leu Ala Ser Val Lys Ala Asp Asp Ser Asn Ser Thr Lys
                420                 425                 430

Asp Asn Val Pro Ala Lys Lys Lys Pro Ser Lys Ser Ser Val Ser
                435                 440                 445

Leu Pro Glu Asn Val Val Gln Asn Leu Leu Ile Leu Thr
450                 455                 460
```

(2) INFORMATION FOR SEQ ID NO:69:

(i) SEQUENCE CHARACTERISTICS:
      (A) LENGTH: 1758 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1758

(ix) FEATURE:
      (A) NAME/KEY: W = A or T
      (B) LOCATION: 1..1758
      (D) OTHER INFORMATION: /note= "Change A at 1136 to W;
          change Lys to Xaa, any aa (xi) SEQUENCE DESCRIPTION: SEQ ID NO:69:

```
CTA GAG ATG GCT AAA TTT CTG ACG GAA ACA TTA GAC GAC ATG ACT CTA     48
Leu Glu Met Ala Lys Phe Leu Thr Glu Thr Leu Asp Asp Met Thr Leu
 1               5                  10                  15

CAA CAC AAA GAT CAC AGA TCA GAA TTG GCT AAA GAG TTT TCA ATT TGG     96
Gln His Lys Asp His Arg Ser Glu Leu Ala Lys Glu Phe Ser Ile Trp
            20                  25                  30

TTT ACG AAA ATG AGA CAG TCT GGC GCT CAA GCC AGT AAC GAA GAA ATC    144
Phe Thr Lys Met Arg Gln Ser Gly Ala Gln Ala Ser Asn Glu Glu Ile
        35                  40                  45

ATG AAA TTT TCA AAA TTG TTT GAA GAT GAA ATC ACT CTT GAC TCG CTG    192
Met Lys Phe Ser Lys Leu Phe Glu Asp Glu Ile Thr Leu Asp Ser Leu
    50                  55                  60

GCG AGG CCG CAA CTT GTT GCT TTG TGC AGG GTA CTA GAA ATC AGT ACT    240
Ala Arg Pro Gln Leu Val Ala Leu Cys Arg Val Leu Glu Ile Ser Thr
65                  70                  75                  80

TTA GGA ACA ACA AAT TTC TTA AGG TTT CAA CTG CGA ATG AAA CTG CGT    288
Leu Gly Thr Thr Asn Phe Leu Arg Phe Gln Leu Arg Met Lys Leu Arg
```

```
                        85                    90                    95
TCA TTA GCT GCT GAT GAT AAA ATG ATT CAA AAA GAA GGC ATA GTT TCT         336
Ser Leu Ala Ala Asp Asp Lys Met Ile Gln Lys Glu Gly Ile Val Ser
            100                 105                 110

ATG ACT TAT TCG GAG GTG CAA CAG GCC TGC AGA GCT CGT GGA ATG CGA         384
Met Thr Tyr Ser Glu Val Gln Gln Ala Cys Arg Ala Arg Gly Met Arg
            115                 120                 125

GCT TAT GGT ATG CCT GAA CAT AGG TTG AGG AGG CAA TTG GAA GAC TGG         432
Ala Tyr Gly Met Pro Glu His Arg Leu Arg Arg Gln Leu Glu Asp Trp
            130                 135                 140

ATT AAT TTA AGC TTG AAT GAA AAG GTT CCA CCA TCA TTA TTG CTT TTG         480
Ile Asn Leu Ser Leu Asn Glu Lys Val Pro Pro Ser Leu Leu Leu Leu
145                 150                 155                 160

TCA AGG GCG CTG ATG TTG CCC GAG AAT GTT CCA GTG TCT GAT AAA CTT         528
Ser Arg Ala Leu Met Leu Pro Glu Asn Val Pro Val Ser Asp Lys Leu
                165                 170                 175

AAA GCA ACA ATA AAT GCT CTT CCT GAA ACT ATT GTA ACT CAG ACA AAG         576
Lys Ala Thr Ile Asn Ala Leu Pro Glu Thr Ile Val Thr Gln Thr Lys
            180                 185                 190

GCT GCT ATT GGA GAA AGA GAA GGA AAG ATT GAC AAT AAG ACC AAA ATT         624
Ala Ala Ile Gly Glu Arg Glu Gly Lys Ile Asp Asn Lys Thr Lys Ile
            195                 200                 205

GAG GTC ATC AAA GAG GAA GAA CGC AAA ATT CGC GAA GAG CGC CAA GAA         672
Glu Val Ile Lys Glu Glu Glu Arg Lys Ile Arg Glu Glu Arg Gln Glu
            210                 215                 220

GCA CGT GAG GAA GAG GAA CAA CGC AAG CAA GCC GAA CTT GCT CTT AAT         720
Ala Arg Glu Glu Glu Glu Gln Arg Lys Gln Ala Glu Leu Ala Leu Asn
225                 230                 235                 240

GCC AGT TCT GCA GCA GCT GAG GCC TCT TCA GCT CAG GAA CTT TTG ATA         768
Ala Ser Ser Ala Ala Ala Glu Ala Ser Ser Ala Gln Glu Leu Leu Ile
                245                 250                 255

GAT ACA GCT CCT GTA ATA GAT GCA GAA AAG ACA CCA AAG GTG GCA ACA         816
Asp Thr Ala Pro Val Ile Asp Ala Glu Lys Thr Pro Lys Val Ala Thr
            260                 265                 270

TCA CCT GTT GAA TCA CCA TTG GCA CCA CCA GAA GTT CTG ATT ATG GGT         864
Ser Pro Val Glu Ser Pro Leu Ala Pro Pro Glu Val Leu Ile Met Gly
            275                 280                 285

GCT CCT AAA ACA CCT GTT GCA ACC GAA GTG GAT AAG AAT GCT GAT GAG         912
Ala Pro Lys Thr Pro Val Ala Thr Glu Val Asp Lys Asn Ala Asp Glu
290                 295                 300

GTG GAA TTC ACC AAG AAA GAT CTT GAG GTT GTT GAA GAT GCA TTG GAT         960
Val Glu Phe Thr Lys Lys Asp Leu Glu Val Val Glu Asp Ala Leu Asp
305                 310                 315                 320

ACA CTA TCG AAA GAC AAA AAT AAT TTG GTG ATT GAA AAG GAA GTT ATT        1008
Thr Leu Ser Lys Asp Lys Asn Asn Leu Val Ile Glu Lys Glu Val Ile
                325                 330                 335

AAA GAC ATT AAG GAA GAA ATT GCT GAT TAC CAA GAA GAT GTA GAA GAA        1056
Lys Asp Ile Lys Glu Glu Ile Ala Asp Tyr Gln Glu Asp Val Glu Glu
            340                 345                 350

TTG AAA GAA GCC ATA GTT GCT GCT GAG AAA CCA AAG GAT GAG ATA AAA        1104
Leu Lys Glu Ala Ile Val Ala Ala Glu Lys Pro Lys Asp Glu Ile Lys
            355                 360                 365

GAA ACT AAA GGA GCT CAA CGA TTG TTG AAG AWG GTT AAC AAG ATG ATA        1152
Glu Thr Lys Gly Ala Gln Arg Leu Leu Lys Xaa Val Asn Lys Met Ile
            370                 375                 380

ACG AAA ATG GAT ACT GTT GTA CAA GAA ATT GAA AGC AAA GAA TCT GAG        1200
Thr Lys Met Asp Thr Val Val Gln Glu Ile Glu Ser Lys Glu Ser Glu
385                 390                 395                 400

AAG AAA GCC AAA ACA TTG CCA CTT GAA GCT CCT AGG AGC GCT ACT GAA        1248
Lys Lys Ala Lys Thr Leu Pro Leu Glu Ala Pro Arg Ser Ala Thr Glu
```

```
                405             410             415
ACT CAA GAA TTA GAT GTA AGG AAA GAA AGA GGA GAG ATT TTA ATT GAC    1296
Thr Gln Glu Leu Asp Val Arg Lys Glu Arg Gly Glu Ile Leu Ile Asp
            420             425             430

GAA TTA ATG GAC GCT ATT AAG AAA GTT AAA AAT GTG CCA GAC GAA AAT    1344
Glu Leu Met Asp Ala Ile Lys Lys Val Lys Asn Val Pro Asp Glu Asn
            435             440             445

CGC TTG AAA TTA ATT GAG AAC ATT TTG GGC AGG ATC GAT ACT GAC AAA    1392
Arg Leu Lys Leu Ile Glu Asn Ile Leu Gly Arg Ile Asp Thr Asp Lys
            450             455             460

GAT AGG CAT ATC AAA GTT GAA GAT GTA TTG AAG GTT ATT GAC ATT GTG    1440
Asp Arg His Ile Lys Val Glu Asp Val Leu Lys Val Ile Asp Ile Val
465             470             475             480

GAA AAA GAA GAT GGT ATC ATG AGT ACA AAA CAA TTA GAT GAG TTG GTT    1488
Glu Lys Glu Asp Gly Ile Met Ser Thr Lys Gln Leu Asp Glu Leu Val
            485             490             495

CAG CTT TTG AAA AAG GAG GAA GTT ATT GAA TTG GAA GAA AAG AAA GAA    1536
Gln Leu Leu Lys Lys Glu Glu Val Ile Glu Leu Glu Glu Lys Lys Glu
            500             505             510

AAG CAA GAG TCT CAA CAG AAA AGT TTT GTA CCA CCA AGT GAA ACT TTG    1584
Lys Gln Glu Ser Gln Gln Lys Ser Phe Val Pro Pro Ser Glu Thr Leu
            515             520             525

CAT CTT GAA TCA TCA CAG CAG AAG AGT ACA GTT CCT AGC TCG GGA CAT    1632
His Leu Glu Ser Ser Gln Gln Lys Ser Thr Val Pro Ser Ser Gly His
            530             535             540

GAA GCT AAG GTG TCC GAA GAT GAC TTA AAT GTT AAA AAT AAA AAT TTG    1680
Glu Ala Lys Val Ser Glu Asp Asp Leu Asn Val Lys Asn Lys Asn Leu
545             550             555             560

GAA GAA TCG ACC AAA ACT GAA TGT GGA GCA ATT GAC GAA GAG CAC AGA    1728
Glu Glu Ser Thr Lys Thr Glu Cys Gly Ala Ile Asp Glu Glu His Arg
            565             570             575

AGA GAG CAT TGC CAG TAC CCA GAC ATT ACA                            1758
Arg Glu His Cys Gln Tyr Pro Asp Ile Thr
            580             585
```

(2) INFORMATION FOR SEQ ID NO:70:

(i) SEQUENCE CHARACTERISTICS:
        (A) LENGTH: 586 amino acids
        (B) TYPE: amino acid
        (D) TOPOLOGY: linear (ii) MOLECULE TYPE: protein (ix) FEATURE:
        (A) NAME/KEY: Xaa = any amino acid
        (B) LOCATION: 379

(xi) SEQUENCE DESCRIPTION: SEQ ID NO:70:

```
Leu Glu Met Ala Lys Phe Leu Thr Glu Thr Leu Asp Asp Met Thr Leu
1               5               10              15

Gln His Lys Asp His Arg Ser Glu Leu Ala Lys Glu Phe Ser Ile Trp
            20              25              30

Phe Thr Lys Met Arg Gln Ser Gly Ala Gln Ala Ser Asn Glu Glu Ile
        35              40              45

Met Lys Phe Ser Lys Leu Phe Glu Asp Glu Ile Thr Leu Asp Ser Leu
    50              55              60

Ala Arg Pro Gln Leu Val Ala Leu Cys Arg Val Leu Glu Ile Ser Thr
65              70              75              80

Leu Gly Thr Thr Asn Phe Leu Arg Phe Gln Leu Arg Met Lys Leu Arg
            85              90              95
```

-continued

```
Ser Leu Ala Ala Asp Asp Lys Met Ile Gln Lys Glu Gly Ile Val Ser
            100                 105                 110

Met Thr Tyr Ser Glu Val Gln Gln Ala Cys Arg Ala Arg Gly Met Arg
            115                 120                 125

Ala Tyr Gly Met Pro Glu His Arg Leu Arg Arg Gln Leu Glu Asp Trp
            130                 135                 140

Ile Asn Leu Ser Leu Asn Glu Lys Val Pro Pro Ser Leu Leu Leu Leu
145                 150                 155                 160

Ser Arg Ala Leu Met Leu Pro Glu Asn Val Pro Val Ser Asp Lys Leu
                    165                 170                 175

Lys Ala Thr Ile Asn Ala Leu Pro Glu Thr Ile Val Thr Gln Thr Lys
                    180                 185                 190

Ala Ala Ile Gly Glu Arg Glu Gly Lys Ile Asp Asn Lys Thr Lys Ile
            195                 200                 205

Glu Val Ile Lys Glu Glu Arg Lys Ile Arg Glu Arg Gln Glu
            210                 215                 220

Ala Arg Glu Glu Glu Gln Arg Lys Gln Ala Glu Leu Ala Leu Asn
225                 230                 235                 240

Ala Ser Ser Ala Ala Glu Ala Ser Ser Ala Gln Glu Leu Leu Ile
                    245                 250                 255

Asp Thr Ala Pro Val Ile Asp Ala Glu Lys Thr Pro Lys Val Ala Thr
                    260                 265                 270

Ser Pro Val Glu Ser Pro Leu Ala Pro Pro Glu Val Leu Ile Met Gly
            275                 280                 285

Ala Pro Lys Thr Pro Val Ala Thr Glu Val Asp Lys Asn Ala Asp Glu
            290                 295                 300

Val Glu Phe Thr Lys Lys Asp Leu Glu Val Val Glu Asp Ala Leu Asp
305                 310                 315                 320

Thr Leu Ser Lys Asp Lys Asn Asn Leu Val Ile Glu Lys Glu Val Ile
                    325                 330                 335

Lys Asp Ile Lys Glu Glu Ile Ala Asp Tyr Gln Glu Asp Val Glu Glu
                    340                 345                 350

Leu Lys Glu Ala Ile Val Ala Ala Glu Lys Pro Lys Asp Glu Ile Lys
            355                 360                 365

Glu Thr Lys Gly Ala Gln Arg Leu Leu Lys Xaa Val Asn Lys Met Ile
            370                 375                 380

Thr Lys Met Asp Thr Val Val Gln Glu Ile Glu Ser Lys Glu Ser Glu
385                 390                 395                 400

Lys Lys Ala Lys Thr Leu Pro Leu Glu Ala Pro Arg Ser Ala Thr Glu
                    405                 410                 415

Thr Gln Glu Leu Asp Val Arg Lys Glu Arg Gly Glu Ile Leu Ile Asp
                    420                 425                 430

Glu Leu Met Asp Ala Ile Lys Lys Val Lys Asn Val Pro Asp Glu Asn
            435                 440                 445

Arg Leu Lys Leu Ile Glu Asn Ile Leu Gly Arg Ile Asp Thr Asp Lys
450                 455                 460

Asp Arg His Ile Lys Val Glu Asp Val Leu Lys Val Ile Asp Ile Val
465                 470                 475                 480

Glu Lys Glu Asp Gly Ile Met Ser Thr Lys Gln Leu Asp Glu Leu Val
                    485                 490                 495

Gln Leu Leu Lys Lys Glu Glu Val Ile Glu Leu Glu Lys Lys Glu
                    500                 505                 510

Lys Gln Glu Ser Gln Gln Lys Ser Phe Val Pro Pro Ser Glu Thr Leu
            515                 520                 525
```

His Leu Glu Ser Ser Gln Gln Lys Ser Thr Val Pro Ser Ser Gly His
    530                 535                 540

Glu Ala Lys Val Ser Glu Asp Asp Leu Asn Val Lys Asn Lys Asn Leu
545                 550                 555                 560

Glu Glu Ser Thr Lys Thr Glu Cys Gly Ala Ile Asp Glu Glu His Arg
                565                 570                 575

Arg Glu His Cys Gln Tyr Pro Asp Ile Thr
            580                 585

(2) INFORMATION FOR SEQ ID NO:71:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:71:

CCCGGGCTGC AGGAATTCGG CACGAGATGA GAATGGAAAT GTGATTAGCT ATACTGATGA      60

AAATGGAAAC ATTATCAGTA CTACTGATGA GAATGGAAAT GTGATTAGCA TTACTGATGA     120

AAATGGAAAT GTGATTAGCA TTACTGATGA AAATGGAAAC ATTATCAGTA CTACTGATGA     180

GAATGGAAAT GTGATTAGCA TTACTGATGA AAATGGAAAT GTGATTAGCA TTACTGATGA     240

AAATGGAAAC ATTATTAGTA CTACTGATGA GAATGGAAAT GTGATTAGCA ATA            293

(2) INFORMATION FOR SEQ ID NO:72:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:72:

Met Arg Gly Asn His Val Phe Leu Glu Asp Gly Met Ala Asp Met Thr
1               5                   10                  15

Gly Gly Gln Gln Met Gly Arg Asp Leu Tyr
            20                  25

(2) INFORMATION FOR SEQ ID NO:73:

(i) SEQUENCE CHARACTERISTICS:
        (A) LENGTH: 12 amino acids
        (B) TYPE: amino acid
        (D) TOPOLOGY: linear (ii) MOLECULE TYPE: protein (ix) FEATURE:
        (A) NAME/KEY: Xaa = Tyr or Asp
        (B) LOCATION: 5

(xi) SEQUENCE DESCRIPTION: SEQ ID NO:73:

Lys Tyr Arg Asn Xaa Xaa Thr Asn Asp Pro Gln Tyr
1               5                   10

(2) INFORMATION FOR SEQ ID NO:74:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:74:

Glu Ile Lys Arg Asn Asp Arg Glu Pro Gly Asn Leu Ser Lys Ile Arg
1               5                   10                  15

Thr Val Met Asp Lys Val Ile Lys Gln Thr Gln
            20                  25

(2) INFORMATION FOR SEQ ID NO:75:

(i) SEQUENCE CHARACTERISTICS:
        (A) LENGTH: 23 amino acids
        (B) TYPE: amino acid
        (D) TOPOLOGY: linear (ii) MOLECULE TYPE: protein (ix) FEATURE:
        (A) NAME/KEY: Xaa = Ala or His
        (B) LOCATION: 8

(ix) FEATURE:
        (A) NAME/KEY: Xaa = Ala or His
        (B) LOCATION: 9

(xi) SEQUENCE DESCRIPTION: SEQ ID NO:75:

Leu Lys Asp Asn Asp Ile Tyr Xaa Xaa Arg Asp Ile Asn Glu Ile Leu
1               5                   10                  15

Arg Val Leu Asp Pro Ser Lys
            20

(2) INFORMATION FOR SEQ ID NO:76:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:76:

Asn Tyr Gly Arg Val Gln Ile Glu Asp Tyr Thr Xaa Ser Asn His Lys
1               5                   10                  15

Asp Xaa Glu Glu Lys Asp Gln Ile Asn Gly Leu
            20                  25

(2) INFORMATION FOR SEQ ID NO:77:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:77:

Lys Tyr Arg Asn Xaa Tyr Thr Asn Asp Pro Gln Leu Lys Leu Leu Asp
1               5                   10                  15

Glu Gly (2) INFORMATION FOR SEQ ID NO:78:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:78:

```
Tyr Phe Asn Asp Gln Ile Lys Ser Val Met Glu Pro Xaa Val Phe Lys
1               5                  10                  15

Tyr Pro Xaa Ala Xaa Leu
            20
```

(2) INFORMATION FOR SEQ ID NO:79:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..270

(xi) SEQUENCE DESCRIPTION: SEQ ID NO:79:

```
ATG AAA TTT TTA CTG GCA ATT TGC GTG TTG TGT GTT TTA TTA AAT CAA       48
Met Lys Phe Leu Leu Ala Ile Cys Val Leu Cys Val Leu Leu Asn Gln
1               5                  10                  15

GTA TCT ATG TCA AAA ATG GTC ACT GAA AAG TGT AAG TCA GGT GGA AAT       96
Val Ser Met Ser Lys Met Val Thr Glu Lys Cys Lys Ser Gly Gly Asn
                20                  25                  30

AAT CCA AGT ACA GAA GAG GTG TCA ATA CCA TCT GGG AAG CTT ACT ATT      144
Asn Pro Ser Thr Glu Glu Val Ser Ile Pro Ser Gly Lys Leu Thr Ile
            35                  40                  45

GAA GAT TTT TGT ATT GGA AAT CAT CAA AGT TGC AAA ATA TTT TAC AAA      192
Glu Asp Phe Cys Ile Gly Asn His Gln Ser Cys Lys Ile Phe Tyr Lys
        50                  55                  60

AGT CAA TGT GGA TTT GGA GGT GGT GCT TGT GGA AAC GGT GGT TCA ACA      240
Ser Gln Cys Gly Phe Gly Gly Gly Ala Cys Gly Asn Gly Gly Ser Thr
65                  70                  75                  80

CGA CCA AAT CAA AAA CAC TGT TAT TGC GAA                              270
Arg Pro Asn Gln Lys His Cys Tyr Cys Glu
                85                  90
```

(2) INFORMATION FOR SEQ ID NO:80:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:80:

```
Met Lys Phe Leu Leu Ala Ile Cys Val Leu Cys Val Leu Leu Asn Gln
1               5                  10                  15

Val Ser Met Ser Lys Met Val Thr Glu Lys Cys Lys Ser Gly Gly Asn
                20                  25                  30

Asn Pro Ser Thr Glu Glu Val Ser Ile Pro Ser Gly Lys Leu Thr Ile
            35                  40                  45

Glu Asp Phe Cys Ile Gly Asn His Gln Ser Cys Lys Ile Phe Tyr Lys
        50                  55                  60

Ser Gln Cys Gly Phe Gly Gly Gly Ala Cys Gly Asn Gly Gly Ser Thr
65                  70                  75                  80

Arg Pro Asn Gln Lys His Cys Tyr Cys Glu
                85                  90
```

(2) INFORMATION FOR SEQ ID NO:81:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

```
ATGGTTTACG AAAGTGACTT TTACACGACC CGTCGGCCCT ACAGTCGTCC GGCTTTGTCT      60
TCATACTCCG TAACGGCACG TCCAGAGCCG GTTCCTTGGG ACAAATTGCC GTTCGTCCCC     120
CGTCCAAGTT TGGTAGCAGA TCCCATAACA GCATTTTGCA AGCGAAAACC TCGCCGAGAA     180
GAAGTTGTTC AAAAAGAGTC CATTGTTCGA AGGATCAATT CTGCAGGAAT TAAACCCAGC     240
CAGAGAGTTT TATCGGCTCC AATAAGAGAA TACGAATCCC CAAGGGACCA GACCAGGCGT     300
AAAGTTTTGG AAAGCGTCAG AAGACAAGAA GCTTTTCTGA ACCAAGGAGG AATTTGTCCA     360
TTGACCACCA GAAATGATGA CATGGATAGA CTTCTACCCC GTCTCCACAG TTCACACACA     420
ACACCTTCTG CGGATAGGAA AGTTTTGTTG ACCACTTTTC ACAGAAGATA C              471
```

(2) INFORMATION FOR SEQ ID NO:82:

(i) SEQUENCE CHARACTERISTICS:
        (A) LENGTH: 1383 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

```
ATGGAACCTC AATCGCTGTC TTGGCAACTT CCGACTCAAG TAGTTCAGCC AGTTTTTGAA      60
CAACAAATGC AGATTCCTGG ATATAATATG CAAATTCAAT CTAATTATTA TCAAATTCAC     120
CCAGAAATGT TGGATCCAAA TTTGAACAAT CCTCAGCAGT TAATGTTTAA TTATATGCAA     180
TTACAACAAT TGCAGGAACT ACAACATTTA AGTCAACAAC AGCCAATGCA TCATGAATTT     240
GAACATCATA TCCCCATTCC ACAAGAAGCA ACTTCAACTA ATTACGGTCC ATCCGGACAG     300
TATATTACTA GTGACGCAAC ATCTTATCAA TCAATTGCCC AACAATTTGT ACCACAACCA     360
CCAATTGAAA CTACCACCAC GAAAATACCT GAAACTGAAA TTCAAATTGG CGTTTCGAAT     420
CAATATGCCC AAAATATAAC TTATAATTCA AATATCAGTC CTGAAGTGAT TGGATTCCGA     480
GAACATTATG TTGCGGAACA GCCTTCTGGT GACGTGCTTC ACAAAAGTCA TTTAACAGAA     540
CAACCAGCAG ATAAAAGCAC ACGTGGTGAT CAGGAACCTG TTAGTGAGAC AGGCTCTGGT     600
TTTTCGTATG CACAAATTTT ATCACAGGGA CTTAAGCCTA CCCAGCCATC CAACTCAGTT     660
AATTTGCTTG CAGATCGATC GAGATCACCT CTAGATACGA AAACGAAAGA AAATTATAAA     720
TCTCCTGGTC GTGTGCAGGA TATCACGAAA ATAATAGATG AGAAACAAAA GTCGTCAAAA     780
GACACAGAGT GGCATAATAA GAAAGTGAAA GAACATAAAA AGTGAAAGA TATCAAACCT     840
GATTTCGAAT CTTCTCAAAG GAATAAGAAA AGCAAGAATA TTCCTAAGCA AATTGAAAAT     900
ATCACACCTC AACTTGACAG CTTACGATCA CGAGATATAG TAATTAAGGG AGAATTACTA     960
ACAAAAGATA CTACAAAAAG TTTAACTACT GTTAATGTTG ATAGTGAATT AGATAGTGTA    1020
AAACCTAAAG ATGAAAAACC TGAACCTTCT GAACCTAGTA AAACGTTTAT TGATACTTCA    1080
GTTGCAAAGG ATGTTGATAA TTCTACACAG GCGAACCATA AAAAGAAGAA AAGTAAATCT    1140
```

```
AAGCCGAGGA AAACGGAACC GGAAGATGAA ATTGAAAAAG CTTTGAAAGA AATTCAAGCT    1200

AGTGAGAAAA AACTTACGAA GTCTATCGAT AACATTGTGA ATAAATTTAA TACACCACTT    1260

GCTAGTGTTA AAGCCGATGA TTCCAATTCT ACCAAGGATA ATGTACCAGC AAAGAAGAAA    1320

AAACCTTCGA AGTCATCTGT TTCTTTACCT GAGAATGTAG TACAAAATCT ATTGATACTA    1380

ACA                                                                  1383

(2) INFORMATION FOR SEQ ID NO:83:

(i) SEQUENCE CHARACTERISTICS:
        (A) LENGTH: 335 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

TTGGAAACAG CTATGACCAT GATTACCCCA AGCTCGAAAG TTAAVCCCTC ACTHARAGGG     60

GAACAAAAGT CTGGAGCTCC ACCCGCGGAT GGCGGCCGCB TCTAGAACCT AGTGGACTCC    120

CCCGGSGCTG CAGGAATTCG GCACGAGCT CCAGCTAGCC ATATACATTC ATCCAAAATG    180

AAGTTGSAAT GTGTCCTACC CGGCAACGGG ATGCCAGAAA TTGTKTCGAA ATKTGTGGAC    240

GAGCACAAGC TTCGTGTCTK TCTATGAAAA ACGTATGGGA GCAGAAGTCG AGGGCCGACA    300

TCCTCGGCGA TGAATGGARA GGTTATGTGC TCCGA                               335

(2) INFORMATION FOR SEQ ID NO:84:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

ATAGCTTTTA ATATTTTTAA TTGATGTATT GCTCAATGGT GATTTCTGTT TATTAAACTG     60

AGTTACCAAT ATGCTCGCTT CAATAGACAT AGCAAATGAA AGCATTCCGT ATCCTCAAGC    120

GTTACCAAAC TAACATTAAG GAGTTAAATA AATGTTGTTT CCAATAAATA TAATGGGAAA    180

AACATTTAAT ATTTGTTCCA ATTTGTATTT ATTTTTACTA CAATTATATA CAATAAAATA    240

TTTTTATATA TATTTTATAA AGTTTATGAT GCAGGAGAGA AAATAATGTT AAGAATATAG    300

GTAATGTGTA TATATAAATG TTTGACAAGC ATGTTCTAGT TAAATAATAA ATACAATGTT    360

AAATCTACTT AAAAAAAAAA AAAAAAAAA AAAAAA                               396

(2) INFORMATION FOR SEQ ID NO:85:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

GGAAAGCGAA GAATGAAAAG GGGAAACAAA AAAAGAAAAG ACGAAGGAGT GGAGAGATAA     60

AACGGAGGCA AAGAAGAAAA TGAGGATGCA AAAGAAAGGT AATAAAAGAG ATGAAAAGAA    120
```

-continued

```
GGAAAAAGGA AATAAGAAAG AAAGAGTGAG GGAAAAATAA AGACAGAGGC GAAGCAAAAA        180

AGGAGGAGAA ATAGAGATTA AAAAGAAAT ACAGCGAAGA AACCAGGAAA GCGATAAAGA         240

AAAAAAAAGA AAAAAGAGA GCAGTGAAAA AAAAAAAAAA AAAAA                         285
```

(2) INFORMATION FOR SEQ ID NO:86:

(i) SEQUENCE CHARACTERISTICS:
  (A) LENGTH: 228 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:86:

```
CAGATATTTA CTAAAYATTG TGAAAYAAAT CATTTTCAAA ATGGTSTCCA AAGTGTTTGT        60

TGCTCTTGCC ATCAATGGCT TTATAGGGGG CTSCACAAGY CTTTTTTCGA ACAAGATGMC       120

GTCTTAGATA ASATSGTAGA TRACATCTCT GRCTSMATAT GAGAACARCA TTGSMAGAAT       180

TAGCCAAGGR TNGCRAAATT GATATGMTTS CYGCTGTAAT TCGAAAAA                    228
```

(2) INFORMATION FOR SEQ ID NO:87:

(i) SEQUENCE CHARACTERISTICS:
  (A) LENGTH: 339 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 1..339

(xi) SEQUENCE DESCRIPTION: SEQ ID NO:87:

```
CTT CGT GTC AAC CGC TGG GTC AGA CCT GTT ATT GCT ATG CAC CCA ACC          48
Leu Arg Val Asn Arg Trp Val Arg Pro Val Ile Ala Met His Pro Thr
 1               5                  10                  15

ATG ACT CTT GCT GAA CGT CTC GGC AAA AAA GCT TTG CGC GAC CAA TAT          96
Met Thr Leu Ala Glu Arg Leu Gly Lys Lys Ala Leu Arg Asp Gln Tyr
                 20                  25                  30

GCT CCC GTT TGC TCC ATT GGA CAA CGT AAC ATC AAC ACC TTT GAC AAC         144
Ala Pro Val Cys Ser Ile Gly Gln Arg Asn Ile Asn Thr Phe Asp Asn
             35                  40                  45

ATG ACC TTC CCC GCT CAA TTC GGA AAA TGC TGG CAC GCT TTG TTG CAA         192
Met Thr Phe Pro Ala Gln Phe Gly Lys Cys Trp His Ala Leu Leu Gln
         50                  55                  60

ACT GTT CCC CAA AAG TAT TCC GAA GAA CGT GAA TAC AGC GAA GAA CAA         240
Thr Val Pro Gln Lys Tyr Ser Glu Glu Arg Glu Tyr Ser Glu Glu Gln
 65                  70                  75                  80

CAA TAC GAC CGT CAA ATG TCC GTC CTC GTT CGT GAA AAC GGC GAA GAA         288
Gln Tyr Asp Arg Gln Met Ser Val Leu Val Arg Glu Asn Gly Glu Glu
                 85                  90                  95

AAA AGA CGT TAT GAT TGT CTT GGG CAA CCG TTA CAA CAA TTG AAT TGC         336
Lys Arg Arg Tyr Asp Cys Leu Gly Gln Pro Leu Gln Gln Leu Asn Cys
                100                 105                 110

AAT                                                                      339
Asn
```

(2) INFORMATION FOR SEQ ID NO:88:

(i) SEQUENCE CHARACTERISTICS:
  (A) LENGTH: 113 amino acids (B) TYPE: amino acid
(D) TOPOLOGY: linear (ii) MOLECULE TYPE: protein (xi) SEQUENCE DESCRIPTION: SEQ ID NO:88:

```
Leu Arg Val Asn Arg Trp Val Arg Pro Val Ile Ala Met His Pro Thr
 1               5                  10                  15

Met Thr Leu Ala Glu Arg Leu Gly Lys Lys Ala Leu Arg Asp Gln Tyr
            20                  25                  30

Ala Pro Val Cys Ser Ile Gly Gln Arg Asn Ile Asn Thr Phe Asp Asn
        35                  40                  45

Met Thr Phe Pro Ala Gln Phe Gly Lys Cys Trp His Ala Leu Leu Gln
    50                  55                  60

Thr Val Pro Gln Lys Tyr Ser Glu Glu Arg Glu Tyr Ser Glu Glu Gln
65                  70                  75                  80

Gln Tyr Asp Arg Gln Met Ser Val Leu Val Arg Glu Asn Gly Glu Glu
                85                  90                  95

Lys Arg Arg Tyr Asp Cys Leu Gly Gln Pro Leu Gln Gln Leu Asn Cys
            100                 105                 110

Asn
```

(2) INFORMATION FOR SEQ ID NO:89:

(i) SEQUENCE CHARACTERISTICS:
(A) LENGTH: 493 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..390

(xi) SEQUENCE DESCRIPTION: SEQ ID NO:89:

```
TCC AGC TCC TCC AGC TCC AGC AGT GAC TCT TCC AGC TCC AGC AGC TCT        48
Ser Ser Ser Ser Ser Ser Ser Ser Asp Ser Ser Ser Ser Ser Ser Ser
 1               5                  10                  15

TCC TCT TCC AGC TCC AGC AGC TCC TCT TCT GAA TCT TCC GAA GAA AAA        96
Ser Ser Ser Ser Ser Ser Ser Ser Ser Ser Glu Ser Ser Glu Glu Lys
            20                  25                  30

ACC TCC CAC AAA AAA TCC GAA AAG AAG GAA CAC AAA TCC TGC TCC ATC       144
Thr Ser His Lys Lys Ser Glu Lys Lys Glu His Lys Ser Cys Ser Ile
        35                  40                  45

AAG AAG CAA GTA CAA TTC GTA GAA AAA GAC GGT AAA CTC TGC TTC AGC       192
Lys Lys Gln Val Gln Phe Val Glu Lys Asp Gly Lys Leu Cys Phe Ser
    50                  55                  60

ATC CGT CCC TTG GCC GCT TGC CAA AAA CAC TGC AAA GCC ACT GAA ACC       240
Ile Arg Pro Leu Ala Ala Cys Gln Lys His Cys Lys Ala Thr Glu Thr
65                  70                  75                  80

ACT CAA ATG GAA GTC GAA GTA TAC TGC CCC TCT GGC AGC CTT GCT GAA       288
Thr Gln Met Glu Val Glu Val Tyr Cys Pro Ser Gly Ser Leu Ala Glu
                85                  90                  95

CTT TAC AAA CAA AAG ATC CTT AAG GGA GCC AAC CCC GAC TTG AGC GAC       336
Leu Tyr Lys Gln Lys Ile Leu Lys Gly Ala Asn Pro Asp Leu Ser Asp
            100                 105                 110

AAG ACT CCT TCC AGA ATC TTG AAA TTC AAG GTT CCC AAA GCT TGC ACC       384
Lys Thr Pro Ser Arg Ile Leu Lys Phe Lys Val Pro Lys Ala Cys Thr
        115                 120                 125

GCT TAC TAAATCTGAA ATAAATTACA TGGATTAGTT CATTTCTGAT GTAGTGCAAT        440
Ala Tyr
```

Ala Tyr
    130

TAGTTCGATA ATAAATTATT CAATGAGCAT TTAAAAAAAA AAAAAAAAAA AAC        493

(2) INFORMATION FOR SEQ ID NO:90:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:90:

Ser Ser Ser Ser Ser Ser Ser Asp Ser Ser Ser Ser Ser Ser
  1               5                  10                  15

Ser Ser Ser Ser Ser Ser Ser Ser Ser Glu Ser Ser Glu Glu Lys
             20                  25                  30

Thr Ser His Lys Lys Ser Glu Lys Glu His Lys Ser Cys Ser Ile
         35                  40                  45

Lys Lys Gln Val Gln Phe Val Glu Lys Asp Gly Lys Leu Cys Phe Ser
     50                  55                  60

Ile Arg Pro Leu Ala Ala Cys Gln Lys His Cys Lys Ala Thr Glu Thr
 65                  70                  75                  80

Thr Gln Met Glu Val Glu Val Tyr Cys Pro Ser Gly Ser Leu Ala Glu
                 85                  90                  95

Leu Tyr Lys Gln Lys Ile Leu Lys Gly Ala Asn Pro Asp Leu Ser Asp
             100                 105                 110

Lys Thr Pro Ser Arg Ile Leu Lys Phe Lys Val Pro Lys Ala Cys Thr
         115                 120                 125

Ala Tyr
    130

(2) INFORMATION FOR SEQ ID NO:91:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:91:

GTAGTGCCAT CATTCGTAAA CSTTYTGACG GTKGGGCGCT GTATWGGTGC TGCCTGGAAA        60

TTGCATCGAT GCACTWCCGT GTCGGGCGCA WATAGTGCKK TGGSCCCTGT CTGMTTATAG       120

ACATTCAGGG CGCSGGSAKT AGCCATGTTC ATGGCTCMCA AWMTGCATTC ACAGTGGGGT       180

CACATTTCAG TCGCATGATT KMTCAARTTA GTATMWGADA TATATTTTTA TCATACTAAG       240

TAGTGAGCDA ATAACACGCG ARWWACRAAC ACCGAATATC TTKAGTTTTT GCACAGATAT       300

KTGTAA                                                                 306

(2) INFORMATION FOR SEQ ID NO:92:

(i) SEQUENCE CHARACTERISTICS:
        (A) LENGTH: 490 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:92:

| | |
|---|---|
| ACCGGATACG TTGCCAATGA CTACGTCACC ACCAATGTTG TTTCCACTCC AGTTACTGGA | 60 |
| TACACCACCG GACATCTTGC TAATGACTAC GTCACCACCA ATGTTGTATC CACTCCAGTT | 120 |
| ACTGGATACA CCACCGGACA TCTTGCCAAT GACTACGTCA CCACCAACGT AGTTTCCGCA | 180 |
| CCAGTCACCA CTGGATACAC CACTGGCTAT ACCACCGGTA ATGTCGGATA CACCACCGGA | 240 |
| GTTACTGGTT ACACCAACGG AGTTAGTGGA TATACCAATG GACTTAATGG TTATACCACT | 300 |
| GGTAGCTATG TCAGCTCCCC AGGATACACT TCTTCTGGAC TTGTCAACGT TTTCTAGATT | 360 |
| TATGATTTCG TCTGCCCTCA ATGATGATGA CCACACTTTT TACTTTTTAT GATATTTGGA | 420 |
| AAAAATAAAT AACTGGAAGA ATATATAATA ATTTCAAAAT AAAAAAAAAA AAAAAAAAA | 480 |
| CTCGAGGGGG | 490 |

(2) INFORMATION FOR SEQ ID NO:93:

(i) SEQUENCE CHARACTERISTICS:
        (A) LENGTH: 616 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:93:

| | |
|---|---|
| AAAAAATCGA AGAAGGCGT AAAACCAAAA TGGGCACAGA AGGATATTCG GGATTTTAGT | 60 |
| GATGCCGACA TGGAGAGGTT ACTGGATCAA TGGGAAGAAG ATGAAGACCC CCTTCCAGAA | 120 |
| GACGAATTGC CCGAACATCT CAGACCTGAT CCAAAGATCG ACATAAGCAA CATCGATATG | 180 |
| AGCAATCCCB AAAACATACT AAAGGCTTCC AAAAAAGGCA AGACTTTGAT GGCATTCGTA | 240 |
| CAAGTCAGTG GAAATCCAAC ACAAGAAGAA GCCGAAACCA TCACTAAATT GTGGCAAGGC | 300 |
| AGTCTATGGA ATAGTCATAT ACAAGCCGAA AGATATATGG TTAGCGATGA CAGGGCTATA | 360 |
| TTTATGTTTA AAGATGGTTC TCAAGCTTGG CCTGCTAAAG ACTTTTTAGT GGAACAAGAA | 420 |
| AGGTGTAAAG ATGTTACAAT TGAAAATAAA ATATATCCTG GTAAATATTC TTCGACTAAA | 480 |
| GAAGAATTAT AATATAATAT ATTATAATTA TAATCTATAA AATAGATTTG AAATTCTACA | 540 |
| TTCATGATCT ACTATGTATG ATATTAATTT ATTAAAAATA ATGTTTTTTC AAGTAAAAAA | 600 |
| AAAAAAAAAA AAAAAA | 616 |

(2) INFORMATION FOR SEQ ID NO:94:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:94:

| | |
|---|---|
| CTCGTGCGGG ACAGATATAG GACCGGATTC GTTAATTGAT TTGAGTGAAG TGGCTTCTGG | 60 |
| TGGTTCTGAT ATTGACACAA AATTTTCCAA TTTAAAAATA GATAAAAAGC CTGTTGCAAC | 120 |
| TTCACAACAA GGAATTGATG AATTTGATAT GTTTGCACAA TCGAGAAACA TTTCTAGTGA | 180 |
| GGGATCAACC AGTGCTATGA AGGAAGGACA CGGTTTGGAC TTATTATCAA ATACACATAA | 240 |
| AAATGTACCA CCAACAATTC CACAAGCCGG ACAACTTCCA AGGGATTCTG AGTTTGATGA | 300 |
| AATTGCTGCT TGGCTTGATG AAAAGGTTGA AGACAAAGCC CAAGTTCCCG AAGACAGTAT | 360 |

| | |
|---|---|
| TACAAGCAGT GAATTTGATA AATTCCTGGC AGAACGGGCA GCTGTTGCTG AAACTTTGCC | 420 |
| AAATATTCCA CCGACTACAC AAAGTAATCA TTCAAATATT GAAGCAAACG ATAAA | 475 |

(2) INFORMATION FOR SEQ ID NO:95:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:95:

| | |
|---|---|
| CCGGCACGGG AGGTAGTGAC GAAAAATAAC GATACGGGAC TCATCCGAGG CCCCGTAATC | 60 |
| GGAATGAGTA CACTTTAAAT CCTTTAACGA GGATCTATTA GAGGGCCAGT CTGTGTGCCA | 120 |
| GCAGCCGCGG TAATTCCAGC TCTAATAGCG TATATTAAAG TTGTTGCGGT TAAAAAGCTC | 180 |
| GTAGTTGAAT CTGTGTCCCA CACTGTYGGT TCACCGCTCG CGGTGTTCAA CTGGCATGTC | 240 |
| TGTGGGACGT CCTACCGGTG GGCTTAGCCC GTCAAAAGGC GGCCCAACTC AAAAT | 295 |

(2) INFORMATION FOR SEQ ID NO:96:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:96:

| | |
|---|---|
| CTGACTAATC CCAGGACTCC TTTATCCTGT TTGCGCAATG TCGATACCCA TCTCACAATG | 60 |
| GTTAATGATT TATCGGCTAA ACAGAAGAGT CCTAAGAAGG TTGTTAAAGG TGTTTCTAGA | 120 |
| ATACCGACTT TTAGACCCAA GGCTATGAAT GCTGATGTTG AGAATTTTGA TTCGATGAGG | 180 |
| TGCGATGTTT GGRACAAAGA CACCAGTGTT GTTATATAAT TACTAAAGCA ATCCACATGT | 240 |
| AGCTAATTTT TTTTTTACAA TTTTATTTGT AACTATGTGT ATTTATATGA ATTCTTGTGG | 300 |
| AATATAATTT TAAGTTTTTA AATGAAATAT AGATATTATT CTAAAAAAAA AAAACAAAAA | 360 |
| AAAAAAAAAA AA | 372 |

(2) INFORMATION FOR SEQ ID NO:97:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:97:

| | |
|---|---|
| GGATTCGGCA CGAGAATTTA TTAAGCGCAT TATTTGCAAG TGTAATTTGC TCCTTTAACG | 60 |
| CGGAAGTACA AAATCGAATC GTTGGTGGCA ATGATGTAAG TATTTCAAAA ATTGGGTGGC | 120 |
| AAGTATCTAT TCAAAGTAAT AACCAACATT TCTGTGGTGG TTCAATCATT GCTAAAGATT | 180 |
| GGGTACTGAC TTCTTCTCAA TGCGTCGTGG ACAAACAAAG TCCACCGAAG GATTTAACTG | 240 |
| TTCGTGTTGG AA | 252 |

(2) INFORMATION FOR SEQ ID NO:98:

(i) SEQUENCE CHARACTERISTICS:
    (A) LENGTH: 613 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:98:

```
ATTCCTGCTG TTAATAGTAC TAATGCAGTA ATTGCTGCHA GCTGCTGCAC AGAGGTTTTT      60

AAAATGGCAA CAAGTTGTTA CACCCACATG AACAACTACA TGGTATTCAA TGATACCGAT     120

GGGATTTATA CATATACTTA CGAAGCTGAA AGAAAACCTG ACTGTTTAGC TTGTTCACAA     180

ATTCCAAAAA CTATAGAAGT TTCTAATCCT GAAAATATGA CTCTCCAAGA CTTGATTACT     240

TTGTTGTGTG AAGGGGCTGA ATATCAAATG AAGAGCCCAG GTATTGTAGC CTCAATCGAA     300

GGCAAAAACA AAACCTTATA CATGTCAACA GTAGCAAGTA TAGAAGAAAA GACTAAACAG     360

AATCTAACAA AGTCTCTAAA AGAATTAAAT CTAGAAAATG GAATGGAACT GATGGTTGCA     420

GATGTGACGA CACCAAACAC AATATTACTT AAATTAAAAT ATAAGAATGT AATTGAAAAC     480

GATGTTGAGA TGACTTGATA TTTACTTAAA AATGTTATCT TACAATAATT GATAATTTAT     540

ATTTAATACT TTTGGAACTT TGTATTTAAT GATAATAAAT TATTATAAGA ATTAAAAAAA     600

AAAAAAAAAA AAA                                                       613
```

(2) INFORMATION FOR SEQ ID NO:99:

(i) SEQUENCE CHARACTERISTICS:
    (A) LENGTH: 538 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 3..538

(xi) SEQUENCE DESCRIPTION: SEQ ID NO:99:

```
TT GAT ATT TGC TCT GTT GAG GGT GCC TTA GGA TTT TTA GTG GAA ATG         47
   Asp Ile Cys Ser Val Glu Gly Ala Leu Gly Phe Leu Val Glu Met
   1               5                   10                  15

TTA AAA TAT AAG GCC CCA AGT AAA ACT CTA GCT ATT GTA GAG AAT GCT        95
Leu Lys Tyr Lys Ala Pro Ser Lys Thr Leu Ala Ile Val Glu Asn Ala
            20                  25                  30

GGT GGA ATA TTA CGA AAT GTA TCT AGT CAT ATA GCC CTT AGA GAG GAC       143
Gly Gly Ile Leu Arg Asn Val Ser Ser His Ile Ala Leu Arg Glu Asp
        35                  40                  45

TAC AGA GAA ATA CTT CGA CAT CAT AAT TGC TTA ACA ATA TTA CTA CAA       191
Tyr Arg Glu Ile Leu Arg His His Asn Cys Leu Thr Ile Leu Leu Gln
    50                  55                  60

CAA TTA AAA TCA CCA AGC CTC ATA ATT GTC AGT AAT GCT TGT GGG ACA       239
Gln Leu Lys Ser Pro Ser Leu Ile Ile Val Ser Asn Ala Cys Gly Thr
65                  70                  75

TTA TGG AAT TTA TCT GCT AGG AAT TCA ACA GAT CAA CAA TTT TTA TGG       287
Leu Trp Asn Leu Ser Ala Arg Asn Ser Thr Asp Gln Gln Phe Leu Trp
            80                  85                  90                  95

GAG AAT GGT GCT GTC CCT TTA TTA AGA AGT TTG ATA TAT TCT AAG CAT       335
Glu Asn Gly Ala Val Pro Leu Leu Arg Ser Leu Ile Tyr Ser Lys His
                100                 105                 110

AAA ATG ATA TCT ATG GGA TCA AGT GCA GCT CTC AAA AAT TTG TTA AAT       383
Lys Met Ile Ser Met Gly Ser Ser Ala Ala Leu Lys Asn Leu Leu Asn
            115                 120                 125
```

```
GCA AAA CCT GAG TGC ATC AAT TTC TTA AGT GAT TCT TCT TCT AAA GGA        431
Ala Lys Pro Glu Cys Ile Asn Phe Leu Ser Asp Ser Ser Ser Lys Gly
        130                 135                 140

GTT CCA AAT CTA ACT ACA TTG GGT GTA AGA AAA CAA AAA TCT CTA CAT        479
Val Pro Asn Leu Thr Thr Leu Gly Val Arg Lys Gln Lys Ser Leu His
145                 150                 155

GAG TTA ATA GAT CAA AAT CTT TCA GAA ACT TGT GAT AAT ATA GAT AGT        527
Glu Leu Ile Asp Gln Asn Leu Ser Glu Thr Cys Asp Asn Ile Asp Ser
160                 165                 170                 175

GTG GCC GCT AA                                                         538
Val Ala Ala
```

(2) INFORMATION FOR SEQ ID NO:100:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO:100:

```
Asp Ile Cys Ser Val Glu Gly Ala Leu Gly Phe Leu Val Glu Met Leu
1               5                   10                  15

Lys Tyr Lys Ala Pro Ser Lys Thr Leu Ala Ile Val Glu Asn Ala Gly
                20                  25                  30

Gly Ile Leu Arg Asn Val Ser Ser His Ile Ala Leu Arg Glu Asp Tyr
            35                  40                  45

Arg Glu Ile Leu Arg His His Asn Cys Leu Thr Ile Leu Leu Gln Gln
        50                  55                  60

Leu Lys Ser Pro Ser Leu Ile Ile Val Ser Asn Ala Cys Gly Thr Leu
65                  70                  75                  80

Trp Asn Leu Ser Ala Arg Asn Ser Thr Asp Gln Gln Phe Leu Trp Glu
                85                  90                  95

Asn Gly Ala Val Pro Leu Leu Arg Ser Leu Ile Tyr Ser Lys His Lys
            100                 105                 110

Met Ile Ser Met Gly Ser Ser Ala Ala Leu Lys Asn Leu Leu Asn Ala
        115                 120                 125

Lys Pro Glu Cys Ile Asn Phe Leu Ser Asp Ser Ser Ser Lys Gly Val
    130                 135                 140

Pro Asn Leu Thr Thr Leu Gly Val Arg Lys Gln Lys Ser Leu His Glu
145                 150                 155                 160

Leu Ile Asp Gln Asn Leu Ser Glu Thr Cys Asp Asn Ile Asp Ser Val
                165                 170                 175

Ala Ala
```

(2) INFORMATION FOR SEQ ID NO:101:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..388

(xi) SEQUENCE DESCRIPTION: SEQ ID NO:101:

```
GTT CTT CTT AAA CAG TTG GAC TCT GGA TTG TTA CTT GTT ACA GGT CCC     48
Val Leu Leu Lys Gln Leu Asp Ser Gly Leu Leu Leu Val Thr Gly Pro
  1               5                  10                  15

TTC TTA ATC AAT GCA TGC CCA TTG CGT CGC ATT TCC CAA AAC TAT GTC     96
Phe Leu Ile Asn Ala Cys Pro Leu Arg Arg Ile Ser Gln Asn Tyr Val
             20                  25                  30

ATT GCC ACC TCT ACC CGA TTA GAC GTT AGT GGA GTT AAA TTA CCA GAA    144
Ile Ala Thr Ser Thr Arg Leu Asp Val Ser Gly Val Lys Leu Pro Glu
         35                  40                  45

CAC ATC AAT GAT GAT TAT TTC AAA AGG CAA AAG AAC AAG CGT GCA AAG    192
His Ile Asn Asp Asp Tyr Phe Lys Arg Gln Lys Asn Lys Arg Ala Lys
     50                  55                  60

AAA GAG GAA GGT GAT ATT TTT GCT GCC AAG AAA GAG GCT TAT AAA CCA    240
Lys Glu Glu Gly Asp Ile Phe Ala Ala Lys Lys Glu Ala Tyr Lys Pro
 65                  70                  75                  80

ACT GAG CAA AGG AAG AAT GAC CAA AAG CTT GTA GAC AAA ATG GTT TTA    288
Thr Glu Gln Arg Lys Asn Asp Gln Lys Leu Val Asp Lys Met Val Leu
                 85                  90                  95

GGA GTA ATC AAG AAG CAC CCA GAC CAC AAA CTT TTG TAT ACA TAT TTG    336
Gly Val Ile Lys Lys His Pro Asp His Lys Leu Leu Tyr Thr Tyr Leu
            100                 105                 110

TCA GCT ATG TTT GGT TTG AAA TCT TCC CAA TAT CCA CAT CGT ATG AAG    384
Ser Ala Met Phe Gly Leu Lys Ser Ser Gln Tyr Pro His Arg Met Lys
        115                 120                 125

TTC T AAATACTATA TTCATAAAAT AAATTGAACT TCTCAAAAAA AAAA             432
Phe
```

(2) INFORMATION FOR SEQ ID NO:102:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO:102:

```
Val Leu Leu Lys Gln Leu Asp Ser Gly Leu Leu Leu Val Thr Gly Pro
  1               5                  10                  15

Phe Leu Ile Asn Ala Cys Pro Leu Arg Arg Ile Ser Gln Asn Tyr Val
             20                  25                  30

Ile Ala Thr Ser Thr Arg Leu Asp Val Ser Gly Val Lys Leu Pro Glu
         35                  40                  45

His Ile Asn Asp Asp Tyr Phe Lys Arg Gln Lys Asn Lys Arg Ala Lys
     50                  55                  60

Lys Glu Glu Gly Asp Ile Phe Ala Ala Lys Lys Glu Ala Tyr Lys Pro
 65                  70                  75                  80

Thr Glu Gln Arg Lys Asn Asp Gln Lys Leu Val Asp Lys Met Val Leu
                 85                  90                  95

Gly Val Ile Lys Lys His Pro Asp His Lys Leu Leu Tyr Thr Tyr Leu
            100                 105                 110

Ser Ala Met Phe Gly Leu Lys Ser Ser Gln Tyr Pro His Arg Met Lys
        115                 120                 125

Phe
```

(2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (genomic)

(ix) FEATURE:
            (A) NAME/KEY: misc_feature
            (B) LOCATION: 1..20
            (D) OTHER INFORMATION: /label= primer (xi) SEQUENCE DESCRIPTION: SEQ ID NO:103:

TGRTTTCCWA TRAARTCTTC                                                 20

(2) INFORMATION FOR SEQ ID NO:104:

(i) SEQUENCE CHARACTERISTICS:
            (A) LENGTH: 225 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:104:

GAATTCGGCA CGAGTGAAAT TCAATATTTT GTTTTACATT AAATTTTTCA AATTCGATAT      60

GAAATTTTTA CTGGCAATTT GCGTGTTGTG TGTTTTATTA AATCAAGTAT CTATGTCAAA    120

AATGGTCACT GAAAAGTGTA AGTCAGGTGG AAATAATCCA AGTACAGAAG AGGTGTCAAT    180

ACCATCTGGG AAGCTTACTA TTGAAGATTT TTGTATTGGA AATCA                    225

(2) INFORMATION FOR SEQ ID NO:105:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..15
            (D) OTHER INFORMATION: /label= primer (xi) SEQUENCE DESCRIPTION: SEQ ID NO:105:

AATTCGGCAC GAGTG                                                      15

(2) INFORMATION FOR SEQ ID NO:106:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..26
            (D) OTHER INFORMATION: /label= primer (xi) SEQUENCE DESCRIPTION: SEQ ID NO:106:

AGTGGATCCG TCAAAAATGG TCACTG                                          26

(2) INFORMATION FOR SEQ ID NO:107:

(i) SEQUENCE CHARACTERISTICS:
            (A) LENGTH: 28 base pairs
            (B) TYPE: nucleic acid

```
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..28
            (D) OTHER INFORMATION: /label= primer (xi) SEQUENCE DESCRIPTION: SEQ ID NO:107:

CCGGAATTCG GTTATTCGCA ATAACAGT                                                    28
```